United States Patent
Ogata et al.

(10) Patent No.: US 7,973,109 B2
(45) Date of Patent: Jul. 5, 2011

(54) CROSSLINKED TYPE LAYERED METAL PHOSPHONATE COMPOUND, PRODUCTION PROCESS THEREFOR, NON-CROSSLINKED TYPE LAYERED METAL PHOSPHONATE COMPOUND, PRODUCTION PROCESS THEREFOR, AS WELL AS STOCK SOLUTION

(75) Inventors: Shin-ichi Ogata, Aichi-gun (JP);
Yoshiaki Fukushima, Aichi-gun (JP);
Masaya Kawasumi, Anjo (JP)

(73) Assignee: Kabushiki Kaisha Toyota Chuo Kenkyusho, Aichi-Gun (JP)

( * ) Notice: Subject to any disclaimer, the term of this patent is extended or adjusted under 35 U.S.C. 154(b) by 562 days.

(21) Appl. No.: 12/076,829

(22) Filed: Mar. 24, 2008

(65) Prior Publication Data

US 2009/0093607 A1    Apr. 9, 2009

(30) Foreign Application Priority Data

Mar. 29, 2007 (JP) .................. 2007-089950
Sep. 10, 2007 (JP) .................. 2007-233625

(51) Int. Cl.
C08G 79/04 (2006.01)
C08L 85/02 (2006.01)
C08F 283/00 (2006.01)
C07F 9/38 (2006.01)

(52) U.S. Cl. ............... 525/538; 525/330.9; 528/166; 528/167; 528/287; 528/398; 528/487; 524/123; 524/115; 556/19

(58) Field of Classification Search .............. 525/538, 525/330.9; 528/287, 398, 487, 166, 167; 524/123, 115; 556/19
See application file for complete search history.

(56) References Cited

U.S. PATENT DOCUMENTS

| 4,235,991 | A | 11/1980 | DiGiacomo et al. |
| 4,267,308 | A | 5/1981 | Parziale et al. |
| 4,429,111 | A | 1/1984 | Dines et al. |
| 4,436,899 | A | 3/1984 | DiGiacomo et al. |

FOREIGN PATENT DOCUMENTS

| EP | 0 736 539 A2 | 10/1996 |
| JP | A-3-504378 | 9/1991 |
| JP | A-9-20507 | 1/1997 |
| JP | A-2004-217563 | 8/2004 |
| JP | A-2007-262047 | 10/2007 |
| WO | WO 89/11485 A1 | 11/1989 |

OTHER PUBLICATIONS

Clearfield et al. "Highly Porous Zirconium Aryldiphosphonates and Their Conversion to Strong Bronsted Acids;" *J. Solid State Chemistry*; No. 167; pp. 376-385; 2002.

(Continued)

*Primary Examiner* — Duc Truong
(74) *Attorney, Agent, or Firm* — Oliff & Berridge, PLC

(57) ABSTRACT

A process for producing a crosslinked type or non-crosslinked type layered metal phosphonate compound including a reaction step of reacting two or more members selected from organic diphosphonic acids or monophosphonic acids, or derivatives thereof having predetermined conditions and a metal source capable of forming an ion of a hexacoordinate metal atom as a central atom (M) of a metal oxide octahedron upon reaction under the presence of a sulfuric acid catalyst, a crosslinked or non-crosslinked metal phosphonate compound obtained by the process, as well as a stock solution used for the synthesis of the crosslinked or non-crosslinked type layered metal phosphonate compound described above.

12 Claims, 64 Drawing Sheets

OTHER PUBLICATIONS

Yang et al. "The Preparation and Ion-Exchange properties of Zirconium Sulphophosphonates;" *Reactive Polymers*; vol. 5; pp. 13-21; 1987.

Wang et al. "Sulfonated Micropores Organic-Inorganic Hybrids as Strong Bronsted Acids;" *J. Am. Chem. Soc.*; vol. 125 pp. 10375-10385.

Montoneri et al. "Organosulphur Phosphorus Acid Compounds. Part 1. m-Sulphophenylphosphonic Acid;" *J. Chem. Soc. Dalton Trans.*; pp. 1819-1823; 1989.

Segawa et al. "Molecular Design of Layered Zirconium Phosphonates for Fuel Cell Applications;" *Studies in Surface and Catalysis*; vol. 154; pp. 1097-1103; 2004.

Reasons of Rejection for Japanese Application No. 2007-089950, mailed on Mar. 16, 2009 (w/ English translation).

[Zr($O_3$P–$C_6H_4$–$SO_3$H)$_{2x}$($O_3$P–Ph)$_{2-2x}$]:
a) ZP855(Comparative sample: x=0%).
b) ZP823(PS-method: x=100%), c) ZP863(2M-method: x=100%),
d) ZP869(2M-method: x=50%).

ZP969: Zr{(O₃P-C₆H₅)₁.₃(O₃P-CH₃)₀.₇}
ZP972: Zr{(O₃P-C₆H₄-SO₃H)₁.₃(O₃P-CH₃)₀.₇} [Synthesized by post sulfonation]
ZP978: Zr{(O₃P-C₆H₄-SO₃H)₁.₀(O₃P-CH₃)₁.₀} [Synthesized by sulfonated stock solution]

CROSSLINKED TYPE LAYERED METAL PHOSPHONATE COMPOUND, PRODUCTION PROCESS THEREFOR, NON-CROSSLINKED TYPE LAYERED METAL PHOSPHONATE COMPOUND, PRODUCTION PROCESS THEREFOR, AS WELL AS STOCK SOLUTION

BACKGROUND OF THE INVENTION

1. Field of the Invention

The present invention concerns a crosslinked type layered metal phosphonate compound and a production process therefor, a non-crosslinked type layered metal phosphonate compound and a production process therefor, as well as a stock solution. More specifically, the invention relates to a novel multi-ingredient crosslinked type and non-crosslinked type layered metal phosphonate compound that can be used, for example, as adsorption materials, ion exchange materials, electrolyte materials, etc. and a production process therefor, as well as a stock solution used for the production of the crosslinked type and non-crosslinked type layered metal phosphonate compound described above.

2. Description of the Related Art

A crystalline organic hexacoordinate metal phosphonate compound has a two dimensional layered structure in which a metal oxide octahedron having a hexacoordinate metal atom as a central atom (M) and a phosphonic acid tetrahedron are connected by sharing oxygen atoms. Particularly in a case where the central atom (M) is a hexacoordinate metal atom capable of taking a tetravalence, the crystalline organic hexacoordinate metal phosphonate compound has an $\alpha$-type or $\gamma$-type layered structure.

For example, the $\alpha$-type layered structure of the crystalline organic zirconium phosphonate has a layered structure in which zirconium atoms present uniformly on a plane are connected two dimensionally by sharing oxygen atoms with the bottoms of phosphonic acid tetrahedrons present therebetween alternatively above and below. Accordingly, planes in which phosphonic acid tetrahedrons are arranged with the top being directed outward and a plane in which oxide octahedrons formed with zirconium atoms are arranged constitute a 2:1 layered structure. Since organic groups connected by a P—C bond are present at the outer apexes of the tetrahedrons, organic groups derived from phosphonic acid are present on both surfaces of the 2:1 layer.

On the other hand, the $\gamma$-type structure has a composite plane in which two planes where zirconium atoms present uniformly and alternately on two planes are connected alternately by sharing four oxygen atoms of $PO_4$ tetrahedron are connected with a phase being displaced from each other. The zirconium atoms of the composite plane are further connected by sharing two oxygen atoms with phosphonic acid tetrahedrons present on the layer surface, to provide a layered structure forming zirconium oxide octahedrons. Accordingly, organic groups derived from phosphonic acid are present on both surfaces of the layer.

Theoretically, in the $\alpha$-type, three apexes of each of the organic phosphonic acid tetrahedrons are bonded with three different zirconium atoms. Further, each of the zirconium atoms is bonded with oxygen atoms of different six phosphonic groups to form an octahedron.

By optimizing the type of the organic group of the organic phosphonic acid, the layered zirconium phosphonate can be used, for example, as adsorbent materials, ion exchange materials, electrolyte materials, etc.

A phosphoric acid in which the organic group of the phosphonic acid is replaced with an OH group forms a zirconium phosphate by reacting with a metal source such as $ZrOCl_2.8H_2O$. However, it has been known long since that the method of merely reacting starting materials does not form the 2:1 layer but forms an amorphous gel, and the structural stability is low. A layered zirconium phosphate of high structural stability and high crystallinity was obtained for the first time by A. Clearfield in 1964 by refluxing in a 12M phosphoric acid for a long time. In 1978, G. Alberti found that a layered zirconium phosphate of extremely high crystallinity was obtained by using an HF catalyst for the reaction. M. B. Dines applied the HF catalyst to the reaction between the organic phosphonic acid and $ZrOCl_2.8H_2O$ to obtain a layered organic zirconium phosphonate in 1980. Further, a method of carrying out reaction between various types of organic phosphonic acids and $ZrOCl_2.8H_2O$ by a hydrothermic reaction or HCl or HBr catalytic reaction has also been known. A method of using hydrothermic reaction or a method of HCl or HBr as a catalyst has a merit in that the layered structure has crystallinity to some extent and a plurality types of organic phosphonic acids can be introduced uniformly to the 2:1 layer.

Those layered organic zirconium phosphonates in which the organic group has a sulfonic group function as electrolytes. Since the sulfonation product of the layered organic zirconium phosphonate has a two dimensional (layered) structure of inorganic materials as a main chain and sulfonic groups on the side chain ingredient, they have a feature that the durability to hydrogen peroxide by-produced during fuel cell reaction is higher compared with polyperfluoro sulfonation products typically represented by Nafion (registered trade mark), or hydrocarbon type sulfonation products such as crosslinked type polystyrene sulfonic acid, and sulfonated polyether ether ketone (S-PEEK).

For sulfonation products of non-crosslinked type layered zirconium phosphonate, while various proposals have been made so far, sulfonation products of the non-crosslinked type layered organic zirconium phosphonate have a drawback that they are soluble to water.

On the other hand, in a case of using an organic diphosphonic acid for the starting material, a crosslinked type layered zirconium phosphonate in which the 2:1 layers are crosslinked to each other with the organic diphosphonic acid. However, while many examples on the sulfonation products of water soluble non-crosslinked type layered zirconium phosphonate have been reported, there are scarce reports on sulfonation products of crosslinked type layered zirconium phosphonate that are insoluble to water.

For example, Non-Patent Documents 1-3 disclose sulfonation products of crosslinked type layered zirconium phosphonate obtained by reacting $Zr^{4+}$compound, an organic diphosphonic acid (($HO)_2OP$—$C_6H_4$—$C_6H_4$—$PO(OH)_2$, or $(HO)_2OP$—$C_6H_4$—$C_6H_4$—$C_6H_4$—$PO(OH)_2$), or an organic diphosphonic acid and an inorganic monophosphonic acid ($HPO(OH)_2$) as a second ingredient under the presence of an HF catalyst and then sulfonating the organic diphosphonic acid ingredient by a post reaction.

The documents describe that (1) an aromatic sulfonic acid moiety is present only in the organic diphosphonic acid ingredient (crosslinking ingredient), (2) a monophosphonic acid introduced at first as P—H is oxidized to P—OH by the step of sulfonation in the post reaction, and (3) HF as a catalyst is taken as Zr—F in zirconium phosphonate.

Further, Pantet Document 1 discloses a crosslinked type layered zirconium phosphonate obtained by;

(1) reacting $ZrOCl_2.8H_2O$ and 1,4-phenylene diphosphonic acid (($HO)_2OP$—$C_6H_4$—$PO(OH_2)$)), and inorganic phosphonic acid ($H_3PO_3$) under the presence of an HF catalyst, and (2) reacting the resultant product and phenylene-3-sulfo-1-phosphonic acid (($HO)_2OP$—$CH_6H_4$—$SO_3H$).

The document describes that the relative ratio for the phenylene diphosphonic acid, phenylene phosphonic acid-sulfonic acid, and inorganic phosphonic acid in the solid obtained by the method is 1.20:0.56:1.

Non-Patent Document 4 discloses a method of synthesizing phenylene-3-sulfo-1-phosphonic acid (($HO)_2OP$—$CH_6H_4$—$SO_3H$). The document describes
(1) reacting phenyl phosphonic acid (($HO)_2OP$—$C_6H_5$) with 2.4 equivalent amount of $SO_3$ in $CH_2ClCH_2Cl$ at 84° C. for 24 hr,
(2) repeating the procedure of adding $BaCl_2.2H_2O$ to the reaction solution and recovering excess sulfuric acid as $BaSO_4$ by precipitation, and
(3) regenerating products of free acid by an ion exchange resin, thereby capable of isolating phenylene-3-sulfo-1-phosphonic acid.

Patent Document 2 discloses a homopolymer $Zr(O_3$—$P$—$R$—$SO_3H)_2$ of various sulfonated zirconium phosphonates. The document describes that
(1) zirconium 3-sulfopropyl phosphonate is obtained by adding HF to an aqueous solution containing $ZrOCl_2.8H_2O$ dissolved therein and dropping the same to an aqueous solution of 3-sulfopropyl phosphonic acid,
(2) zirconium 2-sulfoethyl phosphonate is obtained by adding an aqueous solution of $ZrOCl_2.8H_2O$ to 2-sulfoethyl phosphonic acid hydrolyzed with HBr and refluxing the same for 1.5 hr and
(3) zirconium 2-(sulfophenyl)ethyl phosphonate is obtained by treating an aqueous solution containing 2-(sulfophenyl)ethyl phosphonic acid with an aqueous solution of $ZrOCl_2.8H_2O$ and HF.

Further, Patent Document 3 describes that zirconium phenyl phosphonate ($Zr(O_3PC_6H_5)_2$) is obtained by adding phenyl phosphonic acid and HCl to an aqueous solution of $ZrOCl_2.8H_2O$ although this is not a sulfonation product.

Further, Patent Document 4 discloses various types of layered metal phosphonate compounds represented by the general formula $M(O_3P$—$R)_2$ obtained by reacting $ZrOCl_2.8H_2O$, $Th(NO_3)_4.4H_2O$, $PbO_2$, $UCl_4$, $TiCl_4$, or $Ce(HSO_4)$, and a phosphonic acid such as chloromethyl phosphonic acid (($HO)_2OPCH_2Cl$), 2-mecarpto ethyl phosphonic acid (($HO)_2OPCH_2CH_2SH$), or 2-sulfoethyl phosphonic acid (($HO)_2OPCH_2CH_2SO_3H$).

Further, Patent Document 5 discloses a copolymer of zirconium phosphonates containing two types of phosphonic acid ingredients.

[Non-Patent Document 1] A. Clearfield, et al., J. Solid State Chem. 167, 376 (2002)

[Non-Patent Document 2] A. Clearfield, et al., Reactive Polymer, 5, 13 (1987)

[Non-Patent Document 3] A. Clearfield, et al., J. Am. Chem. Soc., 2003, 125, 103754.

[Non-Patent Document 4] G. Alberti. et al., J. Chem. Soc. Dalton Trans., 1819 (1989)

[Patent Document 1] G. Alberti, et al., EP0736539/2001 (Japanese Patent Unexamined Publication No. H09-20507)

[Patent Document 2] U.S. Pat. No. 4,235,991

[Patent Document 3] U.S. Pat. No. 4,267,308

[Patent Document 4] U.S. Pat. No. 4,436,899

[Patent document 5] U.S. Pat. No. 4,429,111

In a case of synthesizing a layered zirconium phosphonate, when HF is used as a catalyst, a soluble intermediate reaction product $ZrF_6$ is formed and reaction with an organic phosphonic acid proceeds moderately. Accordingly, this can avoid precipitation of fine particle products caused by violent reaction and provide an advantage of greatly promoting the development of the layered structure. However, the method involves a problem that when reaction is conducted by using various types of phosphonic acids, synthesis of a multi-ingredient type layered zirconium phosphonate with uniform introduction of them is difficult to be synthesized. That is, since the starting composition of the phosphonic acid cannot be reflected on copolymerized composition of the product, the structural design of the copolymer is difficult. It is considered that this is attributable to the large difference of the reactivity of the intermediate reaction product $ZrF_6$ to different types of phosphonic acids. As a result, it tends to form a mixture of a plurality of compounds each containing a single phosphonic acid not a single compound containing the multi-ingredient phosphonic acid. Further, in a case of using HF as the catalyst, a portion of fluorine atoms remains in the form of $Zr$—$F$ in the compound to possibly result in environmental problems.

Further, a method of synthesizing a layered zirconium phosphonate by using hydrothermic reaction, HCl catalytic reaction, or HBr catalytic reaction has an advantage capable of synthesizing a multi-ingredient zirconium phosphonate in which the crystallinity of the layered structure is high to some extent and, in addition, multi-ingredient layered zirconium phosphonate where a plurality types of phosphonic acids are introduced uniformly can be synthesized.

However, such methods involve a problem that the crystallinity of the layered structure cannot be improved so much. The trend is remarkable, particularly, in the case of the hydrothermic reaction. Further, in a case of the HCl catalytic reaction and HBr catalytic reaction, it involves a problem that acid mists are generated during synthesis.

Further, for the method of synthesizing a sulfonation product of a layered zirconium phosphonate, a method of synthesizing a layered zirconium phosphonate not having a sulfonic group and then sulfonating the phosphonic acid ingredient (post-sulfonation) has been known.

However, the post-sulfonation is difficult to control and it may possibly result in corruption of the layered structure if the reaction conditions are severe. Further, in a case of synthesizing the layered zirconium phosphonate, when a monophosphonic acid having a substituent instable to the post-sulfonation is used, the substituent of the monophosphonic acid ingredient is sometimes lost upon post-sulfonation. Accordingly, the degree of freedom for the structure design is low.

For solving the problems, it may be considered to use a sulfonated phosphonic acid as the starting material. For example, since a sulfonation product of an aliphatic phosphonic acid can be purified to a high level, a product of high crystallinity is obtained by synthesizing a zirconium phosphonate using the same.

However, an isolation procedure of a sulfonated phosphonic acid is generally troublesome extremely. Further, the isolation procedure has not yet been established for many sulfonated phosphonic acids. For example, since sulfonation products of aromatic phosphonic acids have high boiling points, isolation by distillation is difficult. Further, since the isolation procedure by an ion exchange is troublesome, it is difficult to obtain a highly pure sulfonation product. Accordingly, when a zirconium phosphonate is synthesized by using the same, only the product of low crystallinity can be obtained. Lowering of the crystallinity causes lowering of stability against hydrolysis.

Further, in the crosslinked type layered zirconium phosphonate disclosed in Patent Document 1, a portion of the organic diphosphonic acid ingredient not consumed in the crosslinking reaction is present at the layer surface. In a case of reacting such a crosslinked type layered zirconium phosphonate and metasulfophenylene phosphonic acid, not-crosslinked organic diphosphonic acid ingredient present at the layer surface is substituted by the metasulfophenylene sulfonic acid ingredient due to the surface exchange reaction. Accordingly, this involves the problem that sulfonic groups cannot be introduced between the layers.

Since the existent synthesis methods involve the various problems as described above, examples on the crosslinked type layered zirconium phosphonate having three or more phosphonic acid ingredients or crosslinked type layered zirconium phosphonate containing two or more types of phosphonic acid ingredients having the sulfonic group have not been reported. Further, examples on the crosslinked type layered metal phosphonate compounds containing two or more types of phosphonic acid ingredients and in which the central atom of the metal oxide octahedron includes other than Zr have not been reported.

In the same manner, due to the problem as described above in the existent synthesis methods, examples on the report on the multi-ingredient non-crosslinked type layered metal phosphonate compound having two or more types of ingredients have not been reported. Further, examples on the non-crosslinked type layered metal phosphonate compounds containing two or more types of phosphonic acid ingredients having a sulfonic group have not been reported.

SUMMARY OF THE INVENTION

The present invention intends to provide a novel crosslinked type layered metal phosphonate compound having a sulfonic group, high crystallinity, uniformly introduced with various types of phosphonic acid ingredients and, in addition, not containing a fluorine atom, as well as a production process therefor.

Further, the invention intends to provide a novel crosslinked type layered metal phosphonate compound introduced with sulfonic groups not only to the crosslinking ingredient but also to the phosphonic acid ingredient other than the crosslinking ingredient, as well as a production process therefor.

The invention further intends to provide a novel crosslinked type layered metal phosphonate compound having a sulfonic group and not soluble to water, as well as a production process therefor.

Further, the invention intends to provide a process for producing a crosslinked type layered metal phosphonate compound that can be introduced with a sulfonic group easily, can reflect a starting composition on a copolymerized composition and, in addition, having high degree of freedom for the structural design.

Further, the invention intends to provide a process for producing a crosslinked type layered metal phosphonate compound that can introduce a sulfonic acid also to the phosphonic acid ingredient other than the crosslinking ingredient and, in addition, an instable substituent is not possibly lost upon introduction of the sulfonic group.

Further, the invention intends to provide a process for producing a crosslinked type layered metal phosphonate compound capable of introducing a plurality types of phosphonic acid ingredients at least one of them having a sulfonic group uniformly, without by way of complicated isolation procedures.

The invention intends to provide a novel non-crosslinked type layered metal phosphonate compound having a sulfonic group, high crystallinity, introduced uniformly with various types of phosphonic acid ingredients and, in addition, not containing a fluorine atom, as well as a process for producing the same.

Further, the invention intends to provide a novel non-crosslinked type layered metal phosphonate compound introduced with sulfonic groups to two or more types of phosphonic acid ingredients, as well as a production process therefor.

Further, the invention intends to provide a process for producing a non-crosslinked type layered metal phosphonate compound in which sulfonic groups can be introduced easily, a starting composition can be reflected on a copolymerized composition, and having high degree of freedom for structural design.

Further, the invention intends to provide a process for producing a non-crosslinked type layered metal phosphonate compound capable of introducing sulfonic groups to two or more types of phosphonic acid ingredients, with no possibility for losing instable substituent upon introduction of sulfonic groups.

Further, the invention intends to provide a process for producing a non-crosslinked type layered metal phosphonate compound capable of introducing a plurality types of phosphonic acid ingredients at least one of them having a sulfonic group uniformly, without by way of a complicated isolation procedure.

Further, the invention intends to provide a stock solution suitable to the production of such a crosslinked type or non-crosslinked type layered metal phosphonate compound.

For attaining the foregoing problems, a crosslinked type layered metal phosphonate compound according to the invention includes, as a first aspect, the following constitutions.

(a) The crosslinked type layered metal phosphonate compound has a two dimensional layered structure in which metal oxide octahedrons having a hexacoordinate metal atom as a central atom (M) and phosphonic acid tetrahedrons are connected by sharing oxygen atoms.

(b) The crosslinked type layered metal phosphonate compound contains at least one organic diphosphonic acid ingredient in which both ends thereof are connected respectively with different hexacoordinate metal atoms in different layered structures by way of at least one P—O—M bond.

(c) The crosslinked type layered metal phosphonate compound contains at least one monophosphonic acid ingredient that is bonded with a different hexacoordinate metal atom in the layered structure by way of at least one P—O—M bond.

(d) One of the organic diphosphonic acid ingredient and the monophosphonic acid ingredient has a sulfonic group or a group that can be converted into the sulfonic group and the rest of them has no such group.

(e) The average molecular cross sectional area for the substituent of the organic diphosphonic acid ingredient and the monophosphonic acid ingredient contained in the crosslinked type layered metal phosphonate compound is equal with or less than the free area of one surface phosphonic acid of the two dimensional layered structure.

(f) The crosslinked type layered metal phosphonate compound does not contain a fluorine atom bonded with the central atom (M).

The central atom (M) is preferably a hexacoordinate metal atom capable of taking a tetra atomic valence.

The crosslinked type layered metal phosphonate compound according to the invention includes, as a second aspect, the following constitutions.

(a) The crosslinked type layered metal phosphonate compound has a two dimensional layered structure in which metal oxide octahedrons having a hexacoordinate metal atom as a central atom (M) and phosphonic acid tetrahedrons are connected by sharing oxygen atoms.

(b) The crosslinked type layered metal phosphonate compound contains at least one organic diphosphonic acid ingredient in which both ends thereof are connected with different hexacoordinate metal atoms in different layered structures by way of at least one P—O-M bond.

(c) The crosslinked type layered metal phosphonate compound contains at least one monophosphonic acid ingredient that is bonded with different hexacoordinate metal atoms in the layered structure by way of at least one P—O-M bond.

(d) At least two or more of the organic diphosphonic acid ingredient and the monophosphonic acid ingredients have a sulfonic group or a group that can be converted into the sulfonic group and the rest of them has no such group.

(e) The average molecular cross sectional area for the substituent of the organic diphosphonic acid ingredient and the monophosphonic acid ingredient contained in the crosslinked type layered metal phosphonate compound is equal with or less than the free area of one surface phosphonic acid of the two dimensional layered structure.

(f) The crosslinked type layered metal phosphonate compound does not contain a fluorine atom bonded with the central atom (M).

The central atom (M) is preferably a hexacoordinate metal atom capable of taking a tetra atomic valence.

A process for producing the crosslinked type layered metal phosphonate compound according to the invention includes a reaction step of reacting at least one organic diphosphonic acid or a derivative thereof and at least one monophosphonic acid or a derivative thereof having the following conditions, and a metal source capable of forming an ion of a hexacoordinate metal atom as a central atom (M) of a metal oxide octahedron in the reaction under the presence of a sulfuric acid catalyst.

(a) The blending ratio of the organic diphosphonic acid or the derivative thereof, the monophosphonic acid or the derivative thereof, and the metal source is such that the molar ratio (M/P ratio) of the central atom (M) to the amount of P contained in the phosphonic group or the derivative thereof is: $1/3 < M/P < 1.0$.

(b) The blending ratio of the organic diphosphonic acid or the derivative thereof and the monophosphonic acid or the derivative thereof is such that the average molecular cross sectional area for the substituent of the organic diphosphonic acid ingredient and the monophosphonic acid ingredient constituting the crosslinked type layered metal phosphonate compound is equal with or less than the free area of one surface phosphonic group of the two dimensional layered structure.

In this case, the organic diphosphonic acid or the derivative thereof and the monophosphonic acid or the derivatives thereof preferably further have the following conditions.

(c) At least one of the organic diphosphonic acids or the derivative thereof and the monophosphonic acids or the derivative thereof has a sulfonic group or a group that can be converted into the sulfonic group.

Further, the reaction step preferably includes a first reaction step of reacting the organic diphosphonic acid or the derivative thereof and the metal source, and a second reaction step of adding the monophosphonic acid or the derivative thereof to the reaction solution obtained by the first reaction step and reacting them under the presence of the sulfuric acid catalyst.

In the first reaction step, sulfuric acid may also be used as the catalyst.

The non-crosslinked type layered metal phosphonate compound according to the invention includes, as a first aspect, the following constitutions.

(a) The non-crosslinked type layered metal phosphonate compound has a two dimensional layered structure in which metal oxide octahedrons having a hexacoordinate metal atom as a central atom (M) and phosphonic acid tetrahedrons are connected by sharing oxygen atoms.

(b) The non-crosslinked type layered metal phosphonate compound contains two or more monophosphonic acid ingredients that are bonded with different hexacoordinate metal atoms in the layered structure by way of at least one P—O-M bond.

(c) One of the monophosphonic acid ingredients has a sulfonic group or a group that can be converted into the sulfonic group and the rest of them has no such group.

(d) The non-crosslinked type layered metal phosphonate compound does not contain a fluorine atom bonded with the central atom (M).

The non-crosslinked type layered metal phosphonate compound is preferably those satisfying the following conditions.

(e) The average molecular cross sectional area for the substituent of the monophosphonic acid ingredient contained in the non-crosslinked type layered metal phosphonate compound is 70% or less of the free area of one surface phosphonic group in the two dimensional layered structure.

Further, the central atom (M) is preferably a hexacoordinate metal atom capable of taking a tetra atomic valence.

The non-crosslinked type layered metal phosphonate compound according to the invention includes, as a second aspect, the following constitutions.

(a) The non-crosslinked type layered metal phosphonate compound has a two dimensional layered structure in which metal oxide octahedrons having a hexacoordinate metal atom as a central atom (M) and phosphonic acid tetrahedrons are connected by sharing oxygen atoms.

(b) The non-crosslinked type layered metal phosphonate compound contains two or more monophosphonic acid ingredients that are bonded with different hexacoordinate metal atoms in the layered structures by way of at least one P—O-M bond.

(c) At least two or more of the monophosphonic acid ingredients have a sulfonic group or a group that can be converted into the sulfonic group and the rest of them has no such group.

(d) The non-crosslinked type layered metal phosphonate compound does not contain a fluorine atom bonded with the central atom (M).

The non-crosslinked type layered metal phosphonate compound is preferably those further satisfying the following conditions.

(e) The average molecular cross sectional area for the substituent of the monophosphonic acid ingredient contained in the non-crosslinked type layered metal phosphonate compound is 70% or less of a free area of one surface phosphonic group in the two dimensional layered structure.

Further, the central atom (M) is preferably a hexacoordinate metal atom capable of taking a tetra atomic valence.

A process for producing the non-crosslinked type layered metal phosphonate compound according to the invention includes a reaction step of reacting two or more monophosphonic acids or derivatives thereof having the following conditions and a metal source capable of forming the ion of a hexacoordinate metal atom as a central atom (M) of the metal oxide octahedron in the reaction under the presence of a sulfuric acid catalyst, in which (a) the blending ratio of the monophosphonic acid or the derivative thereof and the metal source is such that the molar ratio (M/P ratio) of the central atom (M) to the amount of P contained in the phosphonic group or the derivative thereof is: $1/3 < M/P < 1.0$.

In this case, the monophosphonic acid or the derivative thereof preferably has the following conditions (b) and/or (c) further.
(b) The blending ratio of the monophosphonic acid or the derivative thereof is such that an average molecular cross sectional area for the substituent of the monophosphonic acid ingredient constituting the non-crosslinked type layered metal phosphonate compound is 70% or less of a free area of one surface phosphonic group in the two dimensional layered structure.
(c) At least one of the monophosphonic acid or the derivative thereof has a sulfonic acid or a group that can be converted into the sulfonic group.

Further, the reaction step is preferably a reaction step of adding and reacting:
(1) the metal source, and
(2) the remaining ingredient of the monophosphonic acid or the derivative thereof, to a stock solution in which at least one of the monophosphonic acid or the derivative thereof, which has the sulfonic group or a group that can be converted into the sulfonic group is dissolved or dispersed in an aqueous solution of sulfuric acid or a mixed solution of the aqueous solution of sulfuric acid and organic solvent.

Further, in the stock solution according to the invention, one or more members selected from the organic diphosphonic acid and derivatives thereof having a sulfonic group or a group that can be converted into the sulfonic group, and monophosphonic acids and derivatives thereof having a sulfonic group or a group that can be converted into the sulfonic group are dissolved or dispersed in an aqueous solution of sulfuric acid or a mixed solution of an aqueous solution of sulfuric acid and organic solvent.

In a case of synthesizing the crosslinked type layered metal phosphonate compound by using the metal source, the organic diphosphonic acid or the derivative thereof, and the monophosphonic acids or the derivatives thereof, the following effects are obtained by using sulfuric acid as a catalyst:
(1) The crystallinity of the layered structure is improved. Particularly, by using a method of at first reacting the metal source and the organic diphosphonic acid or the derivatives thereof and then reacting the same with the monophosphonic acid or the derivatives thereof, the crystallinity of the layered structure is further improved compared with a case of collectively charging the reactants.
(2) Also a plurality types of phosphonic acids can be introduced uniformly into the layered structure. Further, a copolymerized composition reflecting the starting composition can be obtained easily.
(3) The sulfonic group can be introduced easily not only to the crosslinking ingredient but also to the monophosphonic acid ingredient other than the crosslinking ingredient in the layered structure.
(4) In a case of using the phosphonic acid or the derivatives thereof having a sulfonic group or a group that can be converted into the sulfonic group or derivatives thereof as the starting material, since post-sulfonation is not required, there is less possibility that substituents instable to the post-sulfonation may be lost.
(5) Since there is no requirement of using HF as the catalyst, a crosslinked type layered metal phosphonate compound not containing fluorine bonded with a metal atom can be obtained. Since the fluorine atoms bonded to the metal atoms are instable, this may result in environmental problems.
(6) In a case of using a stock solution of the sulfonated organic phosphonic acid upon synthesis, since not only the isolation is unnecessary but also there is no restriction on the type of the organic diphosphonic acid and the monophosphonic acid used for the synthesis, sulfonation products of crosslinked type layered metal phosphonate compounds of any composition which was difficult to be produced so far by the existent method can be synthesized.

In the same manner, in a case of synthesizing the non-crosslinked type layered metal phosphonate compound by using the metal source, and the monophosphonic acid or the derivative thereof, when sulfuric acid is used as the catalyst, the following effects are obtained.
(1) The crystallinity of the layered structure is improved.
(2) Also a plurality types of phosphonic acids can be introduced uniformly into the layered structure. Further, a copolymerized composition reflecting the starting composition can be obtained easily.
(3) The sulfonic group can be introduced easily also to two or more monophosphonic acid ingredients.
(4) In a case of using the phosphonic acid or the derivatives thereof having the sulfonic group or the group that can be converted into the sulfonic group as the starting material, since post-sulfonation is not required, there is less possibility that substituents instable to the post-sulfonation may be lost.
(5) Since there is no requirement of using HF as the catalyst, a non-crosslinked type layered metal phosphonate compound not containing fluorine bonded with the metal atom can be obtained.
(6) In a case of using a stock solution of the sulfonated organic phosphonic acid upon synthesis, since not only the isolation is unnecessary but also there is no restriction on the type of the monophosphonic acid used for the synthesis, sulfonation products of non-crosslinked type layered metal phosphonate compounds of any composition which were difficult to be produced by the existent method can be synthesized.

DESCRIPTION OF PREFERRED EMBODIMENTS

Figure 1:
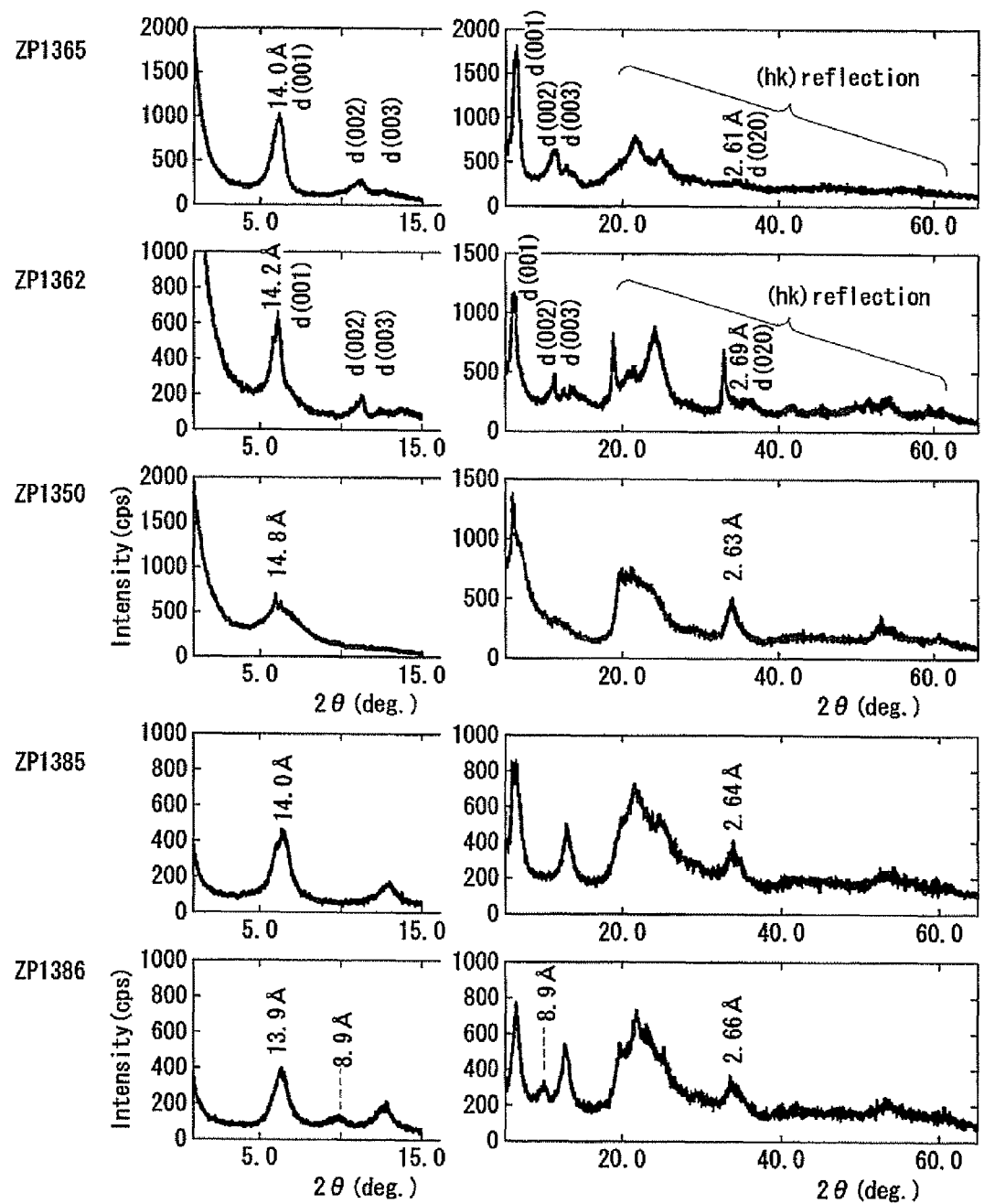
FIG. 1 is XRD patterns for non-sulfonation products and sulfonation products (post-sulfonation) of copolymers of biphenyl bismethylene crosslinked type two ingredient zirconium phosphonates.

[I Crosslinked Type Layered Metal Phosphonate Compound (1)]

The crosslinked type layered metal phosphonate compound according to the first embodiment of the invention contains two or more phosphonic acid ingredients (organic diphosphonic acid ingredient and monophosphonic acid ingredient) in which only one of them has a sulfonic group or a group that can be converted into the sulfonic group and it has, specifically, the following conditions (a)-(f).

[1. Constitution of Crosslinked Type Layered Metal Phosphonate Compound According to the First Embodiment]

[1.1. Condition (a)]

The crosslinked type layered metal phosphonate compound according to the invention has a two dimensional layered structure in which an octahedron metal oxides having a hexacoordinate metal atom as the central atom (M) and phosphonic acid tetrahedrons are connected by sharing oxygen atoms.

Generally, "organic phosphonic acid" means an organic acid compound in which three oxygen atoms (O) are bonded to pentavalent P and "organic phosphoric acid" means an organic acid compound in which four oxygen atoms (O) are bonded to pentavalent P. In the invention, "crosslinked type layered metal phosphonate compound" includes those in which a portion of the monophosphonic acid ingredient to be described later is an ingredient derived from an inorganic phosphoric acid. However, the organic diphosphonic acid ingredient to be described later does not contain organic diphosphoric acid. This is because the organic phosphoric acid bond as C—O—P bond tends to be disconnected by hydrolysis and when the organic diphosphoric acid is contained in the organic diphosphonic acid ingredient, the crosslinked type layered metal phosphonate compound tends to be dissolved in water.

The crosslinked type layered metal phosphonate compound according to the invention is a compound in which a portion of a pair of tetrahedrons present between opposed layers, among tetrahedrons contained in the layered structure where the octahedrons and the tetrahedron are connected, is substituted by an organic diphosphonic acid ingredient.

The hexacoordinate metal atom as the central atom (M) for the octahedron includes, specifically, Zr(IVa), Ti(IVa), Hf(IVa), Th(IVa), Si(IVb), Ge(IVb), Sn(IVb), Pb (IVb), Cu(Ib), Zn(IIb), Al(IIIb), Ga(IIIb), Nb(Va), Fe(III), Co(VIII), La(La), Ce(La), Mo(VIa), W(VIa), Mn(VIIa), etc. The octahedron contained in the layered structure may contain one of such hexacoordinate metal atoms, or may contain two or more hexacoordinate metal atoms. Further, in a case of containing two or more hexacoordinate metal atoms, two or more hexacoordinate metal atoms may be contained in the octahedron within one identical layer, or different hexacoordinate metal atoms may be contained in the octahedron in different layers respectively.

Further, in a case where the central atom (M) of the octahedron is a hexacoordinate metal atom capable of taking a tetra atomic valence, the crosslinked type layered metal phosphonate compound can take an α-type or γ-type layered structure.

Hexacoordinate metal atom capable of taking the tetra atomic valence includes, for example, Zr(IVa), Ti(IVa), Hf(IVa), Th(IVa), Si(IVb), Ge(IVb), Sn(IVb), Pb (IVb), Ce(La), Mo(VIa), W(VIa), and Mn(VIIa).

As to be described later, in a case of using sulfuric acid as the catalyst, a crosslinked type layered metal phosphonate compound of high crystallinity is obtained. The degree of the crystallinity is in proportion with the size of the layered structure and it is shown by a Scherrer's formula that this is in inverse proportion with the half-width value (°) for a d(001) peak obtained by measurement of X-ray powder refraction pattern using $CuK_\alpha$ as an X-ray source.

For improving the durability to hydrolysis, the crystallinity is preferably 7° or less, and more preferably, 3° or less for the half-width value of the d(001) peak.

[1.2. Condition (b)]

The crosslinked type layered metal phosphonate compound includes at least one organic diphosphonic acid ingredient.

"Organic diphosphonic acid ingredient" means those in which two —$PO_3$ groups are bonded to both ends of a bivalent organic group by way of a P—C bond respectively.

The organic diphosphonic acid ingredient is particularly preferably those represented by the following formula (A)

$$(-O)_3P—Z^1(A^1)_r-P(O)_3 \quad (A)$$

In the formula (A), $Z^1$ represents a (2+r) valent organic group having at least one benzene ring, an alkylene chain or an oligo(oxyalkylene) chain. The interlayer distance can be controlled optionally depending on the length of $Z^1$.

$A^1$ represents a sulfonic group or a group that can be converted into the sulfonic group, or an aliphatic group having a sulfonic group or a group that can be converted into the sulfonic group.

"Group that can be converted into the sulfonic group" means a group that can be converted into a sulfonic group by such a moderate reaction as not breaking the layered structure of the layered compound (for example, by hydrolysis). The group that can be converted into the sulfonic group includes, specifically, -Hal (Hal; halogen), —SH, —S—R', (—R': —$CH_3$, or —$C_2H_5$), —$SO_2Cl$, etc.

r represents a number from "0" to "(number of benzene rings in $Z^1$)×2". Since $A^1$ is introduced into the benzene ring, r is 0 in a case where $Z^1$ is an alkylene chain or an oligo (oxyalkylene) chain.

The (2+r) valent organic group, alkylene chain, and oligo (oxyalkylene) chain constituting $Z^1$ are preferably those represented by the following formulas (A. 1) to (A. 3) respectively.

[Chemical formula 1]

—$Z^1$—: —$(CH_2)_l$—$Ar^1$—$(CH_2)_l$— (l=0~3)  (A. 1)

—$(CH_2)_m$— (m=6~24)  (A. 2)

—$(CH_2CH_2O)_p$—$CH_2CH_2$— (p=1~7)  (A. 3)

In the formula (A. 1), $Ar^1$ presents a monocyclic or polycyclic aromatic group. The polycyclic aromatic group includes those in which (1) a plurality of benzene rings are connected by a single bond,
(2) a plurality of benzene rings are connected by way of a bivalent group,
(3) condensed ring (acenes), and
(4) combination of (1) to (3).

$Ar^1$ is particularly preferably those represented by the following formulae (A. 1.1) to (A. 1.7).

[Chemical formula 2]

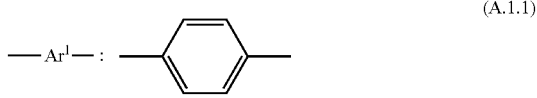 (A.1.1)

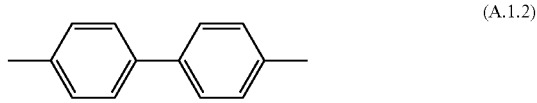 (A.1.2)

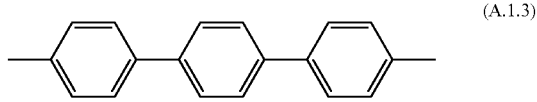 (A.1.3)

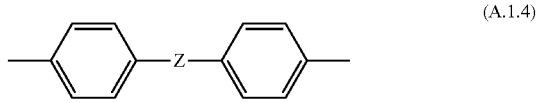 (A.1.4)

 (A.1.5)

 (A.1.6)

 (A.1.7)

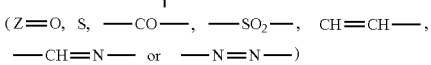

(Z=O, S, —CO—, —$SO_2$—, CH=CH—, —CH=N— or —N=N—)

The organic diphosphonic acid ingredient is bonded at both ends thereof by way of P—O-M bonds with hexacoordinate metal atoms in adjacent layers respectively. In the layered metal phosphonate compound, the phosphonic acid tetrahedron is bonded with the hexacoordinate metal atom by way of the P—O-M bond such that the apex of the tetrahedron is directed to the outside of the layer plane. As a result, the plane where the tetrahedrons are arranged and the plane where the hexacoordinate metal oxide octahedrons are arranged are connected to form a layer. The layered structure is formed so long as the central atom (M) of the metal oxide is a hexacoordinate metal atom and, particularly, in a case where this is the hexacoordinate metal atom capable of taking the tetra atomic valence, it is known that the structure takes an α-type or γ-type.

This is identical also for the crosslinked type layered metal phosphonate compound according to the invention. The bottom of the tetrahedrons on both ends of the organic diphosphonic acid ingredient are directed to the plane where the octahedrons are arranged. That is, oxygen atoms three in total are present on both ends of the organic diphosphonic acid ingredient respectively.

In the crosslinked type layered metal phosphonate compound having the α-type layered structure, the organic diphosphonic acid ingredient may be in a state bonded with the hexacoordinate metal atom by way of three P—O-M bonds (that is, in a state where all three oxygen atoms are shared with different octahedrons) or in a state where it is bonded with the hexacoordinate metal atom by way of one or two P—O-M bonds (that is, in a state where one or two oxygen atoms are shared with different octahedrons). Oxygen atoms having no concerns with the P—O-M bond may be bonded with other substituent such as H, or may be bonded by way of a double bond to P.

Also for the crosslinked type layered metal phosphonate compound having the γ-type layered structure, the way of bonding between the organic diphosphonic acid ingredient and the octahedron is in an identical situation but the number of P—O-M bonds is decreased each by one compared with the case of α-type structure.

The α-type and γ-type can be prepared selectively depending on the type of the starting materials, the starting composition thereof, and control for the reaction conditions.

The crosslinked type layered metal phosphonate compound according to the invention may contain one or more organic diphosphonic acid ingredients. However, in a case of containing two or more organic diphosphonic acid ingredients, when the length for each of the organic diphosphonic acid ingredients differs greatly, the layered structure where the layers are arranged in parallel can no more be maintained. Accordingly, in a case of containing two or more organic diphosphonic acid ingredients, it is necessary that the length of the organic diphosphonic ingredients is substantially identical.

[1.3. Condition (c)]

The crosslinked type layered metal phosphonate compound contains at least one monophosphonic acid ingredient.

"Monophosphonic acid ingredient" means those having one —$PO_3$ group. The monophosphonic acid ingredient includes those where the P atom in the —$PO_3$ group is bonded directly or by way of an O atom with an organic group (organic monophosphonic acid ingredient, organic phosphoric acid ingredient) or the P-atom is bonded with a group other than the organic group (for example, —H, —OH, etc.) (inorganic phosphonic acid ingredient, inorganic phosphoric acid ingredient). That is, "monophosphonic acid ingredient" referred to in the invention includes those having a phosphoric acid bond.

A first specific example of the mono phosphonic acid ingredient includes those represented by the following formula (B):

where $Z^2$ represents a (1+r') valent organic group having at least one benzene ring.

$A^2$ represents a sulfonic group, a group that can be converted into the sulfonic group, or aliphatic group having the sulfonic group or the group that can be converted into the sulfonic group. Since specific examples of the group that can be converted into the sulfonic group are identical with those of $A^1$, explanations are to be omitted.

x is 0 or 1.

r' represents a number from "0" to "(number of benzene rings in $Z^2$)×2".

The (1+r') valent organic group constituting $Z^2$ is preferably those represented by the following formula (B. 1).

[Chemical formula 3]

—$Z^2$—: —$(CH_2)_{l'}$—$Ar^2$— (l'=0 to 3)      (B. 1)

In the formula (B. 1), $Ar^2$ represents a monocyclic or polycyclic aromatic group. The polycyclic aromatic group includes, for example, (1) a plurality of benzene rings connected by a single bond,
(2) a plurality of benzene rings connected by a bivalent group,
(3) condensed ring (acenes), and
(4) combination of (1) to (3).

$Ar^2$ is particularly preferably those represented by the following formulae (B. 1.1) to (B. 1.3).

[Chemical formula 4]

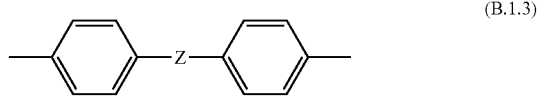

The second specific example of the monophosphonic acid ingredient includes those represented by the following formula (C):

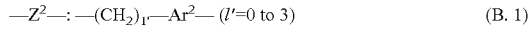

In the formula (C), —Y is not particularly restricted. That is, —Y may be an organic group or a group other than the organic group. In a case where the organic diphosphonic acid ingredient or other phosphonic acid ingredient has a relatively large group such as a sulfophenyl group, —Y is preferably a small-size substituent having a molecular cross sectional area smaller than that of the sulfophenyl group.

The small-size substituent constituting —Y includes, for example,
(1) —H,
(2) —OH,
(3) —$C_\gamma H_{2\gamma+1}$ ($1 \leq \gamma \leq 16$),
(4) —$C_\delta H_{2\delta}$—W ($1 \leq \delta \leq 3$), —$C_\epsilon F_{2\epsilon}$—W ($1 \leq \epsilon \leq 3$) (—W=-Hal (halogen), —OH, —CN, —$CO_2$H, —$SO_3$H, —SH, —S—R' (—R': —$CH_3$ or —$C_2H_5$), —$SO_2$Cl, etc.)

In the crosslinked type layered metal phosphonate compound having the α-type layered structure, tetrahedrons in the layer includes an organic diphosphonic acid ingredient and a monophosphonic acid ingredient such as those represented by the formula (B) or the formula (C) described above.

The monophosphonic acid ingredient may be in a state of bonding by way of three P—O-M bonds with the hexacoordinate metal atom (that is, in a state where all of three oxygen atoms are shared with the different octahedrons), or in a state of bonding by way of one or two P—O-M bonds with the hexacoordinate metal atom (that is, a state where one or two oxygen atoms are shared with different octahedrons). Oxygen atoms having no concerns with the P—O-M bond may be bonded with other substituent such as H. Alternatively, they may be also bonded by way of a double bond to P.

Also for the crosslinked type layered metal phosphonate compound having the γ-type layered structure, the mode of bonding between the monophosphonic acid ingredient and the octahedron is identical but the number of P—O-M bonds is decreased each by one compared with the case of the α-type.

The crosslinked type layered metal phosphonate compound according to the invention may contain one or more monophosphonic acid ingredients. Further, in a case of containing two or more monophosphonic acid ingredients, the length for each of the monophosphonic acid ingredients may be identical or different with each other.

[1.4. Condition (d)]

In the crosslinked type layered metal phosphonate compound according to this embodiment, one of the organic diphosphonic acid ingredients and the monophosphonic acid ingredients has a sulfonic group or a group that can be converted into the sulfonic group. The remaining organic diphosphonic acid ingredients and the monophosphonic acid ingredients have no sulfonic group or the group that can be converted into the sulfonic group.

In a case where the organic diphosphonic acid ingredients and the monophosphonic acid ingredients have a benzene ring, each of them can have a sulfonic group or a group that can be converted into the sulfonic group by the number corresponding to "number of benzene rings×2" at the maximum per one molecule respectively by controlling the reaction conditions.

[1.5. Condition (e)]

The average molecular cross sectional area for the substituent of the organic diphosphonic acid ingredient and the monophosphonic acid ingredient contained in the crosslinked type layered metal phosphonate compound is equal with or less than the free cross sectional area for one surface phosphonic group in the two dimensional layered structure. The average molecular cross sectional area is preferably 70% or less of the free area.

While the free area is determined depending on the type of the hexacoordinate metal atom and the crystal structure, it can be determined experimentally from the lattice constant. The free area has been determined for several hexacoordinate metal atoms on the α-type and the γ-type layered structures ("Intercalation Chemistry" Ed. by M. Stanley, Wittingam, Allan, J. Jacobson, Academic Press 1982, p. 152; G. Alberti, et al., Adv. Mater., 1996, 8, 291). It is reported as α-type: Zr(24 Å$^2$(24×10$^{-2}$ mm$^2$)), Ti(21.6 Å$^2$ (21.6×10$^{-2}$ nm$^2$)), Sn(21.4 Å$^2$ (21.4×10$^{-2}$ nm$^2$)), Hf(23.7 Å$^2$ (23.7×10$^{-2}$ nm$^2$)), Pb(21.5 Å$^2$ (21.5×10$^{-2}$ nm$^2$)), and γ-type: Zr(35.7 Å$^2$ (35.7×10$^{-2}$ Å$^2$)), Ti(33.0 Å$^2$ (33.0×10$^{-2}$ nm$^2$)).

"Substituent" means herein a group connected to the apex of the tetrahedron having P as the central atom.

"Molecular cross sectional area" means a cross sectional area for the largest portion of a substituent as viewed from the direction perpendicular to the bottom of the tetrahedron. "Average molecular cross sectional area" means the total ($\Sigma S_i \times N_i$) for the product of each of the molecular cross sectional areas ($S_i$) of the organic diphosphonic acid ingredient and the monophosphonic acid ingredient connected between the layers and the mole fraction ($N_i$) thereof.

In a case where the average molecule cross section exceeds 70% of the free area (particularly when the average molecular cross sectional area exceeds the free area), steric hindrance of the substituent increases making it difficult to maintain the two dimensional layered structure of high crystallinity.

The molecular cross sectional area can be calculated based on a CPK model drawn by a commercial software (for example, "Chem 3D (registered trade mark)"). For example, the terphenylene group of the organic diphosphonic acid ingredient has a molecular cross sectional area of 24.6 Å$^2$ (26.4×10$^{-2}$ nm$^2$). When the terphenylene group is sulfonated, the molecular cross sectional area increases to about 50 Å$^2$ (50×10$^{-2}$ nm$^2$) for the trisulfonated terphenylene group. This is about 44 Å$^2$ (44×10$^{-2}$ nm$^2$) for the disulfonated terphenylene group. In the monophosphonic acid ingredient, this is 14.6 Å$^2$ (14.6×10$^{-2}$ nm$^2$) for the phenyl group, and 17.2 Å$^2$ (17.2×10$^{-2}$ nm$^2$) for the sulfophenyl group, and the molecular cross sectional area for the hydrogen group is 4.1 Å$^2$ (4.1×10$^{-2}$ nm$^2$). On the other hand, the free area of the α-type crosslinked type layered zirconium phosphonate is 24 Å$^2$ (24×10$^{-2}$ nm$^2$) and 70% of which is 16.8 Å$^2$ (16.8×10$^{-2}$ nm$^2$).

Accordingly, when all tetrahedrons bonded with the hexacoordinate metal atom in the layered structure are derived from 7 mol % of the organic diphosphonic acid ingredient having the trisulfonated terphenylene group, 87×0.5=43 mol % of the monophosphonic acid ingredient having the sulfophenyl group, and 100×0.5=50 mol % of the monophosphonic acid ingredient having the phenyl group, the average molecular cross sectional area (18.3 Å$^2$ (18.3×10$^{-2}$ nm$^2$) is greater than 70% of the free area and the stability of the layered structure is low.

On the other hand, in a case where those derived from the organic diphosphonic acid ingredient having the trisulfonated terphenylene group are 7 mol %, those derived from the monophosphonic acid ingredient having the sulfophenyl group are maintained at 43 mol %, and those derived from the monophosphonic acid ingredient having the hydrogen group are added by 50 mol % instead of the phenyl group in all of the tetrahedrons bonded with the hexacoordinate metal atom in the layered structure, the average molecular cross sectional area (13.0 Å$^2$ (13.0×10$^{-2}$ nm$^2$)) is equal with or less than 70% of the free area. Accordingly, the layered structure is stabilized and the crosslinked type layered metal phosphonate compound of high crystallinity can be obtained.

[1.6. Condition (f)]

The crosslinked type layered metal phosphonate compound does not contain a fluorine atom bonded with the central atom (M).

In a case of synthesizing the crosslinked type layered metal phosphonate compound, when HF is used as the catalyst, a portion of the F atoms is bonded with the central atom (M) of the metal oxide octahedron. On the contrary, since the crosslinked type layered metal phosphonate compound according to the invention is synthesized under the presence of the sulfuric catalyst as will be described later, it does not substantially contain the F atoms bonded with the central atom (M).

[2. Specific Example of the Crosslinked Type Layered Metal Phosphonate Compound According to the First Embodiment]

[2.1. First Specific Example]

The first specific example of the crosslinked type layered metal phosphonate compound according to this invention includes those having the α-type layered structure and the composition represented by the following formula (1). The crosslinked type layered metal phosphonate compound represented by the formula (1) contains three ingredients of an organic diphosphonic acid ingredient, an organic monophosphonic acid ingredient having a benzene ring (containing phosphoric acid ingredient), and a third monophosphonic acid ingredient having a small-size substituent (—Y) in which one of the three types of the phosphonic acid ingredients has a sulfonic group or a group that can be converted into the sulfonic group. In the formula (1), since details for —Z$^1$— and —Z$^2$— are as has been described above, descriptions therefor are to be omitted.

[Chemical formula 5]

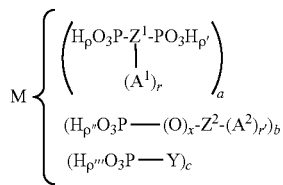
(1)

in which

M: hexacoordinate metal atom capable of taking a tetra atomic valence,

—$Z^1$—: (2+r) valent organic group having at least one benzene ring, alkylene chain, or oligo (oxyalkylene) chain, -$A^1$: —$(CH_2)_\alpha$—$SO_3H$, —$(CH_2)_\alpha$-Hal, —$(CH_2)_\alpha$—SH, —$(CH_2)_\alpha$—S—R', or —$(CH_2)_\alpha$—$SO_2Cl$ ($0 \leq \alpha \leq 3$, —R'=—$CH_3$, or —$C_2H_5$)

r: r=0 to {number of benzene rings in $Z^1$}×2 x: x=0, 1

—$Z^2$—: (1+r') valent organic group having at least one benzene ring,

-$A^2$: —$(CH_2)_\beta$—$SO_3H$, —$(CH_2)_\beta$-Hal, —$(CH_2)_\beta$—SH, —$(CH_2)_\beta$—S—R', or —$(CH_2)_\beta$—$SO_2Cl$ ($0 \leq \beta \leq 3$, —R'=—$CH_3$, or —$C_2H_5$)

r': r'=0 to [number of benzene rings in $Z^2$]×2

—Y: —H, —OH, —$C_\gamma H_{2\gamma+1}$ ($1 \leq \gamma \leq 16$),

—$C_\delta H_{2\delta}$—W ($1 \leq \delta \leq 3$), or —$C_\epsilon F_{2\epsilon}$—W ($1 \leq \epsilon \leq 3$)

(W=Hal, OH, CN, $CO_2H$, $SO_3H$, SH, $SCH_3$, $SC_2H_5$, or $SO_2Cl$)

a, b, c: 1.0<2a+b+c<3.0, 0<a<1.0, 0<b<2.0, 0<c<2.0

ρ, ρ", ρ''': $0 \leq$(ρ, ρ", ρ''')<2

ρ': $0 \leq$ρ'$\leq 2$

In the formula (I), those compounds in which the organic diphosphonic acid ingredient contains 4,4''-bis(phosphonic acid) terphenyl or 4,4''-bis(methylene phosphonic acid) biphenyl, the organic monophosphonic acid ingredient contains those having a sulfophenyl group, and the third monophosphonic acid ingredient contains those having hydrogen group, hydroxyl group, or methyl group are preferred.

[2.2. Second Specific Example]

The second specific example of the crosslinked type layered metal phosphonate compound according to this embodiment includes those having the α-type layered structure and the composition represented by the following formula (2). The crosslinked type layered metal phosphonate compound represented by the formula (2) contains two ingredients of an organic diphosphonic acid ingredient and a monophosphonic acid ingredient having a small-size substituent (—Y) in which one of the two types of the phosphonic acid ingredients has a sulfonic group or a group that can be converted into the sulfonic group. In the formula (2), since details for —$Z^1$— and —$Z^2$— are as has been described above, descriptions therefor are to be omitted.

[Chemical formula 6]

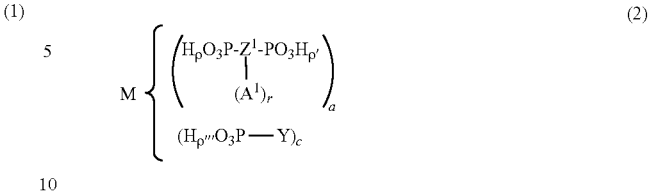
(2)

in which

M: hexacoordinate metal atom capable of taking a tetra atomic valence,

—$Z^1$—: (2+r) valent organic group having at least one benzene ring, alkylene chain, or oligo (oxyalkylene) chain, -$A^1$: —$(CH_2)_\alpha$—$SO_3H$, —$(CH_2)_\alpha$-Hal, —$(CH_2)_\alpha$—SH, —$(CH_2)_\alpha$—S—R', or —$(CH_2)_\alpha$—$SO_2Cl$ ($0 \leq \alpha \leq 3$, —R'=—$CH_3$, or —$C_2H_5$)

r: r=0 to [number of benzene rings in $Z^1$]×2

Y: —H, —OH, —$C_\gamma H_{2\gamma+1}$ ($1 \leq \gamma \leq 16$),

—$C_\delta H_{2\delta}$—W ($1 \leq \delta \leq 3$), or —$C_\epsilon F_{2\epsilon}$—W ($1 \leq \epsilon \leq 3$)

(W=Hal, OH, CN, $CO_2H$, $SO_3H$, SH, $SCH_3$, $SC_2H_5$, or $SO_2Cl$)

a, c: 1.0<2a+c<3.0, 0<a<1.0, 0<c<2.0

ρ, ρ''': $0 \leq$(ρ, ρ''')<2

ρ': $0 \leq$ρ'$\leq 2$

In the formula (2), those compounds in which the organic diphosphonic acid ingredient contains 4,4''-bis(phosphonic acid) terphenyl or 4,4'-bis(methylene phosphonic acid) biphenyl, or sulfonation products thereof, the monophosphonic acid ingredients contains those having hydrogen group, hydroxyl group, methyl group, or sulfodifluoromethylene group are preferred.

[2.3. Third Specific Example]

The third specific example of the crosslinked type layered metal phosphonate compound according to this embodiment includes those having the α-type layered structure and the composition represented by the following formula (3). The crosslinked type layered metal phosphonate compound represented by the formula (3) contains two ingredients of an organic diphosphonic acid ingredient and an organic monophosphonic acid ingredient having a benzene ring (containing phosphoric acid ingredient), and one of the two types of the phosphonic acid ingredients has a sulfonic group or a group that can be converted into the sulfonic group. In the formula (3), since the details for —$Z^1$— and —$Z^2$— are as has been described above, descriptions therefor are to be omitted.

[Chemical formula 7]

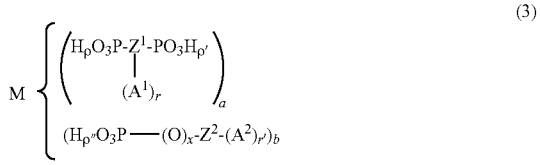
(3)

in which

M: hexacoordinate metal atom capable of taking a tetra atomic valence,

—$Z^1$—: (2+r) valent organic group having at least one benzene ring, alkylene chain, or oligo (oxyalkylene) chain, -$A^1$: —$(CH_2)_\alpha$—$SO_3H$, —$(CH_2)_\alpha$-Hal, —$(CH_2)_\alpha$—SH, —$(CH_2)_\alpha$—S—R', or —$(CH_2)_\alpha$—$SO_2Cl$ ($0 \leq \alpha \leq 3$, —R'=—$CH_3$, or —$C_2H_5$)

r: r=0 to {number of benzene rings in $Z^1$}×2 x: x=0, 1

—$Z^2$—: (1+r') valent organic group having at least one benzene ring,

-$A^2$: —$(CH_2)_\beta$—$SO_3H$, —$(CH_2)_\beta$-Hal, —$(CH_2)_\beta$—SH, —$(CH_2)_\beta$—S—R', or —$(CH_2)_\beta$—$SO_2Cl$ ($0 \leq \beta \leq 3$, —R'=—$CH_3$, or —$C_2H_5$)

r': r'=0 to {number of benzene rings in $Z^2$}×2 a, b: 1.0<2a+b<3.0, 0<a<1.0, 0<b<2.0

$\rho$, $\rho$": $0 \leq (\rho, \rho") < 2$ $\rho$': $0 \leq \rho' \leq 2$

In the formula (3), those compounds in which the organic diphosphonic acid ingredient contains α,ω-alkylene bis(phosphonic acid), and the organic monophosphonic acid ingredient contains those having the sulfophenyl group are preferred.

[II Crosslinked Type Layered Metal Phosphonate Compound (2)]

The crosslinked type layered metal phosphonate compound according the second embodiment of the invention contains two or more phosphonic acid ingredients (organic diphosphonic acid ingredient and monophosphonic acid ingredient) in which two or more of them have a sulfonic group or a group that can be converted into the sulfonic group and include specifically the following conditions (a) to (f).

[1. Constitution of Crosslinked Type Layered Metal Phosphonate Compound According to the Second Embodiment]

(a) The crosslinked type layered metal phosphonate compound has a two dimensional layered structure in which the metal oxide octahedron having a hexacoordinate metal atom as the central atom (M) and a phosphonic acid tetrahedron are connected by sharing oxygen atoms.

(b) The crosslinked type layered metal phosphonate compound contains at least one organic diphosphonic acid ingredient in which both ends of the compound are bonded with different hexacoordinate metal atoms in different layered structures each by way of at least one P—O-M bond, (c) The crosslinked type layered metal phosphonate compound has at least one monophosphonic acid ingredient that is bonded with different hexacoordinate metal atoms in the layered structure by way of at least one P—O-M bond.

(d) At least two or more of the organic diphosphonic acid ingredients and the monophosphonic acid ingredients have a sulfonic group or a group that can be converted into the sulfonic group and rest of them do not have such group.

(e) The average molecular cross sectional area for the substituent of the organic diphosphonic acid ingredient and the monophosphonic acid ingredient contained in the crosslinked type layered metal phosphonate compound is equal with or less than the free area of one surface phosphonic group of the two dimensional layered structure.

(f) the crosslinked type layered metal phosphonate compound does not contain a fluorine atom bonded with the central atom (M).

In the crosslinked type layered metal phosphonate compound according to this embodiment, at least two or more of organic diphosphonic acid ingredients and monophosphonic acid ingredients have a sulfonic group or a group that can be converted into the sulfonic group. This is different from the first embodiment. All the phosphonic acid ingredients may contain the sulfonic group or the group that can be converted into the sulfonic group so long as they satisfy the condition (e). Since the crosslinked type layered metal phosphonate compound of the invention is synthesized under the presence of the sulfuric acid catalyst, the starting composition can be reflected on the copolymerized composition and the degree of freedom for the structural designs high. Accordingly, there is no restriction for the portion of introducing the sulfonic group or the group that can be converted into the sulfonic group.

Since other matters regarding the conditions (a) to (f) are identical with those in the first embodiment, detailed descriptions therefor are to be omitted.

[2. Specific Example of the Crosslinked Type Layered Metal Phosphonate Compound According to the Second Embodiment]

[2.1. First Specific Example]

The first specific example of the crosslinked type layered metal phosphonate compound according to this invention includes those having the α-type layered structure and the composition represented by the following formula (4). The crosslinked type layered metal phosphonate compound represented by the formula (4) contains three ingredients of an organic diphosphonic acid ingredient, an organic monophosphonic acid ingredient having a benzene ring (containing phosphoric acid ingredient), and a third monophosphonic acid ingredient having a small-size substituent (—Y) in which two or more of the three types of the phosphonic acid-ingredients have a sulfonic group or a group that can be converted into the sulfonic group. In the formula (4), since details for —$Z^1$— and —$Z^2$— are as has been described above, descriptions therefor are to be omitted.

[Chemical formula 8]

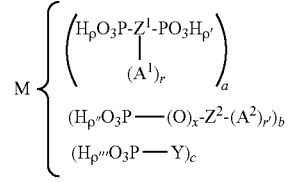

(4)

in which

M: hexacoordinate metal atom capable of taking a tetra atomic valence,

—$Z^1$—: (2+r) valent organic group having at least one benzene ring, alkylene chain, or oligo (oxyalkylene) chain, -$A^1$: —$(CH_2)_\alpha$—$SO_3H$, —$(CH_2)_\alpha$-Hal, —$(CH_2)_\alpha$—SH, —$(CH_2)_\alpha$—S—R', or —$(CH_2)_\alpha$—$SO_2Cl$ ($0 \leq \alpha \leq 3$, —R'=—$CH_3$, or —$C_2H_5$)

r: r=0 to {number of benzene rings in $Z^1$}×2 x: x=0.1

—$Z^2$—: (1+r') valent organic group having at least one benzene ring,

-$A^2$: —$(CH_2)_\beta$—$SO_3H$, —$(CH_2)_\beta$-Hal, —$(CH_2)_\beta$—SH, —$(CH_2)_\beta$—S—R', or —$(CH_2)_\beta$—$SO_2Cl$ ($0 \leq \beta \leq 3$, —R'=—$CH_3$, or —$C_2H_5$)

r': r'=0 to {number of benzene rings in $Z^2$}×2

—Y: —H, —OH, —$C_\gamma H_{2\gamma+1}$ ($1 \leq \gamma \leq 16$), —$C_\delta H_{2\delta}$—W ($0 \leq \delta \leq 3$), or —$C_\epsilon F_{2\epsilon}$—W ($0 \leq \epsilon \leq 3$)

(W=Hal, OH, CN, $CO_2H$, $SO_3H$, SH, $SCH_3$, $SC_2H_5$ or $SO_2Cl$)

a, b, c: 1.0<2a+b+c<3.0, 0<a<1.0, 0<b<2.0, 0<c<2.0

$\rho$, $\rho$", $\rho$''': $0 \leq (\rho, \rho", \rho''') < 2$ $\rho$': $0 \leq \rho' \leq 2$ In the formula (4), those compounds in which the organic diphosphonic acid ingredient contains 4,4"-bis(phosphonic acid) terphenyl or 4,4'-bis(methylene phosphonic acid) biphenyl, or sulfonation products thereof, the organic monophosphonic acid ingredient contains those having a sulfophenyl group, and the third monophosphonic acid ingredient contains those having hydrogen group, hydroxyl group, or methyl group, or sulfodifluoromethylene group are preferred.

[2.2. Second Specific Example]

The second specific example of the crosslinked type layered metal phosphonate compound according to this invention includes those having the α-type layered structure and the composition represented by the following formula (5). The crosslinked type layered metal phosphonate compound represented by the formula (5) contains two ingredients of an organic diphosphonic acid ingredient and a monophosphonic acid ingredient having a small-size substituent (—Y) in which both of the two types of the phosphonic acid ingredients have a sulfonic group or a group that can be converted into the sulfonic group. In the formula (5), —$Z^1$— includes a (2+r) valent organic group having at least one benzene ring. Since other matters regarding —$Z^1$— are as have been described above, descriptions therefor are to be omitted.

[Chemical formula 9]

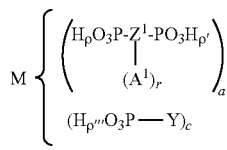

(5)

in which

M: hexacoordinate metal atom capable of taking a tetra atomic valence,

—$Z^1$—: (2+r) valent organic group having at least one benzene ring

-$A^1$: —$(CH_2)_\alpha$—$SO_3H$, —$(CH_2)_\alpha$-Hal, —$(CH_2)_\alpha$—SH, —$(CH_2)_\alpha$—S—R', or —$(CH_2)_\alpha$—$SO_2Cl$ ($0 \leq \alpha \leq 3$, —R'=—$CH_3$, or —$C_2H_5$)

r: r=1 to {number of benzene rings in $Z^1$}×2

—Y: —$C_\delta H_{2\delta}$—W ($1 \leq \delta \leq 3$), or —$C_\epsilon F_{2\epsilon}$—W ($1 \leq \epsilon \leq 3$) (W=Hal, $SO_3H$, SH, $SCH_3$, $SC_2H_5$ or $SO_2Cl$)

a, c: 1.0<2a+c<3.0, 0<a<1.0, 0<c<2.0

ρ, ρ''': 0≦(ρ, ρ''')<2

ρ': 0≦ρ'≦2

In the formula (5), those compounds in which the organic diphosphonic acid ingredient contains sulfonation products of 4,4''-bis(phosphonic acid) terphenyl or 4,4'-bis(methylene phosphonic acid) biphenyl, the monophosphonic acid ingredients contains those having sulfodifluoromethylene group are preferred.

[2.3. Third Specific Example]

The third specific example of the crosslinked type layered metal phosphonate compound according to this embodiment includes those having the α-type layered structure and the composition represented by the following formula (6). The crosslinked type layered metal phosphonate compound represented by the formula (6) contains two ingredients of an organic diphosphonic acid ingredient and an organic monophosphonic acid ingredient having a benzene ring (containing phosphoric acid ingredient), and both of the two types of the phosphonic acid ingredients have the sulfonic group or the group that can be converted into the sulfonic group. In the formula (6), —$Z^1$— includes a (2+r) valent organic group having at least one benzene ring. Since other matters regarding —$Z^1$— and details for —$Z^2$— are as has been described above, descriptions therefor are to be omitted.

[Chemical formula 10]

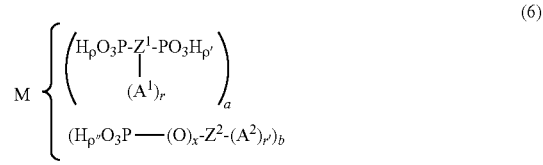

(6)

in which

M: hexacoordinate metal atom capable of taking a tetra atomic valence,

—$Z^1$—: (2+r) valent organic group having at least one benzene ring,

-$A^1$: —$(CH_2)_\alpha$—$SO_3H$, —$(CH_2)_\alpha$-Hal, —$(CH_2)_\alpha$—SH, —$(CH_2)_\alpha$—S—R', or —$(CH_2)_\alpha$—$SO_2Cl$ ($0 \leq \alpha \leq 3$, —R'=—$CH_3$, or —$C_2H_5$)

r: r=1 to {number of benzene rings in $Z^1$}×2 x: x=0, 1

—$Z^2$—: (1+r') valent organic group having at least one benzene ring,

-$A^2$: —$(CH_2)_\beta$—$SO_3H$, —$(CH_2)_\beta$-Hal, —$(CH_2)_\beta$—SH, —$(CH_2)_\beta$—S—R', or —$(CH_2)_\beta$—$SO_2Cl$ ($0 \leq \beta \leq 3$, —R'=—$CH_3$, or —$C_2H_5$)

r': r'=1 to {number of benzene rings in $Z^2$}×2 a, b: 1.0<2a+b<3.0, 0<a<1.0, 0<b<2.0

ρ, ρ'': 0≦(ρ, ρ'')<2

ρ': 0≦ρ'≦2

In the formula (6), those compounds in which the organic diphosphonic acid ingredient contains sulfonation products of 4,4''-bis(phosphonic acid) terphenyl or 4,4'-bis(methylene phosphonic acid) biphenyl, and the organic monophosphonic acid ingredients contains those having sulfophenyl group are preferred.

[III Production Process for Crosslinked Type Layered Metal Phosphonate Compound]

The production process for the crosslinked type layered metal phosphonate compound according to the invention includes a reaction step of reacting at least one organic diphosphonic acid or a derivative thereof, at least one monophosphonic acid or a derivative thereof, and a metal source under the presence of a sulfuric acid catalyst.

[1. Organic Diphosphonic Acid and Derivative Thereof]

"Organic diphosphonic acid" means those in which two phosphonic groups (—$PO(OH)_2$) are bonded to both ends of a bivalent organic group. "Derivative of organic diphosphonic acid" means those in which H atoms in the phosphonic groups are entirely or partially substituted by other substituents. The type of the substituent is not particularly restricted and can optionally be selected depending on the purpose.

As the organic diphosphonic acid or the derivative thereof, those represented by the following formula (a) are specifically preferred.

In the formula (a), two H atoms in the phosphonic group (—$PO(OH)_2$) may be substituted independently by Cat or —$X^1$ respectively. In the formula (a) since details for —$Z^1$— are as has been described above, descriptions therefor are to be omitted.

[Chemical formula 11]

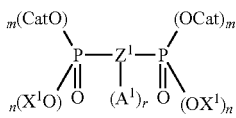

(a)

in which —Z$^1$—: (2+r) valent organic group having at least one benzene ring, alkylene chain, or oligo(oxyalkylene) chain, -A$^1$: —(CH$_2$)$_\alpha$—SO$_3$H, —(CH$_2$)$_\alpha$-Hal, —(CH$_2$)$_\alpha$—SH, —(CH$_2$)$_\alpha$—S—R', or —(CH$_2$)$_\alpha$—SO$_2$Cl (0≦α≦3, —R'=—CH$_3$, or —C$_2$H$_5$)

r: r=0 to [number of benzene rings in Z$^1$]×2

—X$^1$: —H, —C$_n$H$_{2n+1}$, or —Si(CH$_3$)$_3$ (n=1 to 3)

Cat: Li, Na or K m, n: m=0 to 2, n=0 to 2

For the starting material, one organic diphosphonic acid or the derivative thereof may be used or two or more of them may be used. However, in a case of using two or more organic diphosphonic acids or derivatives thereof, it is necessary that the lengths when the both ends are bonded with the adjacent layer (length as the organic diphosphonic acid ingredient) are substantially identical.

[2. Monophosphonic Acid and Derivative Thereof]

"Monophosphonic acid" means those having one phosphonic group (—PO(OH)$_2$). The monophosphonic acid may be those in which the P atom of the phosphonic group is bonded directly or by way of the O atom with an organic group (organic monophosphonic acid, organic phosphoric acid), or those in which the P atom is bonded with a group other than the organic group (for example, —H, —OH) (inorganic phosphonic acid, inorganic phosphoric acid). That is, the "monophosphonic acid" in the invention includes those having a phosphoric acid bond. "Derivative of monophosphonic acid" means those in which H atoms of the phosphonic group are entirely or partially substituted by other substituents. The type of the organic group and the substituent is not particularly restricted and can be selected optionally depending on the purpose.

As the monophosphonic acid or the derivatives thereof, those represented by the formula (b) or the formula (c) are specifically preferred.

In the formula (b) and the formula (c), two H atoms in the phosphonic group (—PO(OH)$_2$) may be substituted independently by Cat or —X$^1$ to —X$^2$ respectively. Since the details for —Z$^2$— in the formula (b) are as has been described above, descriptions therefor are to be omitted.

[Chemical formula 12]

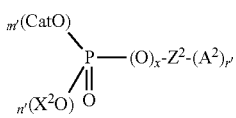

(b)

in which x: x=0, 1

—Z$^2$—: (1+r') valent organic group having at least one benzene ring,

-A$^2$: —(CH$_2$)$_\beta$—SO$_3$H, —(CH$_2$)$_\beta$-Hal, —(CH$_2$)$_\beta$—SH, —(CH$_2$)$_\beta$—S—R', or —(CH$_2$)$_\beta$—SO$_2$Cl (0≦β≦3, —R'=—CH$_3$, or —C$_2$H$_5$)

r': r'=0 to [number of benzene rings in Z$^2$]×2

—X$^2$: —H, —C$_n$H$_{2n+1}$, or —Si(CH$_3$)$_3$ (n=1 to 3)

Cat: Li, Na or K m', n': m'=0 to 2, n'=0 to 2.

[Chemical formula 13]

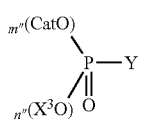

(c)

in which

—Y: —H, —OH, —C$_\gamma$H$_{2\gamma+1}$ (1≦γ≦16), —C$_\delta$H$_{2\delta}$—W (1≦δ≦3), or —C$_\epsilon$F$_{2\epsilon}$—W (1≦ε≦3)

(W=Hal, OH, CN, CO$_2$H, SO$_3$H, SH, SCH$_3$, SC$_2$H$_5$ or SO$_2$Cl)

—X$^3$: —H, —C$_n$H$_{2n+1}$, or —Si(CH$_3$)$_3$ (n=1 to 3)

Cat: Li, Na or K m", n": m"=0 to 2, n"=0 to 2

For the starting material, one monophosphonic acid or a derivative thereof may be used, or two or more of them may be used. In a case of using two or more monophosphonic acids or derivatives thereof, the lengths for the monophosphonic acid or the derivatives thereof may be identical or different with each other.

[3. Metal Source]

"Metal source" means a compound capable of forming an ion of a hexacoordinate metal atom as the central atom (M) of an octahedron of a metal oxide upon reaction.

The metal source includes, specifically, (1) oxy chlorides such as ZrOCl$_2$.8H$_2$O, TiOCl$_2$.nH$_2$O, HfOCl$_2$ (2) sulfates such as Zr(SO$_4$)$_2$, Ti(SO$_4$)$_2$ and Hf(SO$_4$)$_2$ (3) acetates such as Zr(OCOCH$_3$)$_4$, Cu(OCOCH$_3$)$_2$, and Pb(OCOCH$_3$)$_4$, (4) alkoxides such as Zr(OPr)$_4$, Ti(OPr)$_4$, (5) chlorides such as ZrCl$_4$, TiCl$_4$, HfCl$_4$, WCl$_4$, MoCl$_4$, CeCl$_4$, CuCl$_2$, AlCl$_3$, SnCl$_4$, and PbCl$_4$, (6) nitrates such as Zr(NO$_3$)$_4$, Ti(NO$_3$)$_4$, and Al(NO$_3$)$_3$, and (7) oxysulfates such as TiOSO$_4$.nH$_2$O.

They may be used each alone or may be used by two or more in combination.

The type of the metal source sometimes gives an effect on the crystallinity and the grain size of the layered compound. For example, in a case of Zr the crystallinity of the layered compound differs depending on the type of the metal source. The degree of the crystallinity of the layered compound is in the order of: Zr(OCOCH$_3$)$_4$>Zr(OPr)$_4$>Zr(SO$_4$)$_2$>ZrOCl$_2$.8H$_2$O.

[4. Condition for Starting Material]

As the starting material, those satisfying the following conditions are used.

[4.1 Condition (a)]

The blending ratio of the organic diphosphonic acid or the derivative thereof, the monophosphonic acid or the derivative thereof, and the metal source is such that the molar ratio (M/P ratio) of the central atom (M) to the amount of P contained in the phosphonic group or the derivative thereof is: 1/3<M/P<1.0.

The M/P ratio for the α-type or γ-type layered metal phosphonate compound is theoretically 1/2. However, there may be a case where a portion of the tetrahedron is depleted, or the organic diphosphonic acid or the derivative thereof is bonded by way of one of the phosphonic group or the derivative thereof with the hexacoordinate metal atom and the other of them is in a free state. Accordingly, the M/P ratio may be deviated somewhat from 1/2.

However, in a case where the M/P ratio deviates excessively; it is difficult to maintain a layered structure of high crystallinity. Accordingly, the M/P ratio is preferably $1/3 < M/P < 1.0$.

[4.2 Condition (b)]

The blending ratio of the organic diphosphonic acid or the derivatives thereof and the monophosphonic acid or the derivatives thereof is such that the average molecular cross sectional area for the substituent of the organic diphosphonic acid ingredient and the monophosphonic acid ingredient constituting the crosslinked type layered metal phosphonate compound is equal with or less than the free area of one surface phosphonic group of the two dimensional layered structure. The average molecular cross sectional area is preferably 70% or less of the free area.

"Organic diphosphonic acid ingredient constituting the crosslinked type layered metal phosphonate compound" represents the organic diphosphonic acid ingredient after the introduction of the sulfonic acid in a case, for example, of introducing the sulfonic group by post-sulfonation after synthesizing a layered compound not having the sulfonic group. This is also identical for the monophosphonic ingredient.

In this invention, since sulfuric acid is used as the catalyst, the starting composition is reflected as it is on the copolymerized composition. Accordingly, when the blending ratio of the starting materials is optimized in addition to the M/P ratio such that the average molecular cross sectional area of the starting material (or the phosphonic acid ingredient after a post treatment in a case of applying the post treatment after synthesis of the layered compound) is equal with or less than the free cross sectional area, preferably, of 70% or less of the free cross sectional area, since they are introduced uniformly between the layers, the layered structure is not destructed by steric hindrance.

As the starting materials, those further satisfying the following conditions are preferably used.

[4.3 Condition (c)]

At least one of the organic diphosphonic acid or the derivative thereof, and the monophosphonic acid or the derivative thereof has a sulfonic group or a group that can be converted into the sulfonic group A portion of the crosslinked type layered metal phosphonate compound according to the invention can be produced also by the post-sulfonation. However, by the post-sulfonation, instable groups may sometimes be lost upon sulfonation. On the contrary, when a phosphonic acid previously having a sulfonic group or a group that can be converted into the sulfonic group is used as the starting material, a crosslinked type layered metal phosphonate compound having a group instable to sulfonation can be synthesized.

So long as the conditions (a) and (b) described above are satisfied, the sulfonic group or the group that converted into the sulfonic group may be contained in two or more starting materials, or may be contained in all of the starting materials.

[5. Sulfuric Acid Catalyst]

In the invention, sulfuric acid is used as the catalyst. This is different from the existent method. Upon synthesis, sulfuric acid may be added to the isolated organic diphosphonic acid or the derivative thereof and the monophosphonic acid or the derivative thereof. Alternatively, sulfuric acid contained in a stock solution to be described later may be used as it is as the catalyst. Particularly, since the method of using the stock solution requires no isolation operation, there is no restriction on the type of the organic diphosphonic acid and the monophosphonic acid used for the synthesis and it is possible to synthesize crosslinked type layered metal phosphonate compounds of all types of compositions.

The concentration for the sulfuric acid in the reaction solution is selected optimally in accordance with the type of the central atom (M). For example, in a case where the central atom (M) is Zr, a layered compound of higher crystallinity is obtained as the concentration of sulfuric acid is higher. In this case, specifically, the concentration of sulfuric acid is preferably 5N or more and, more preferably, 9N or more.

On the other hand, in a case where the central atom (M) is Ti, a layered compound of high crystallinity is obtained even when the concentration of sulfuric acid is 5N or less.

The sulfuric acid functions not only as a synthesis catalyst for the layered compound but also as a catalyst for hydrolyzing a phosphonate ester into a phosphonic acid. Accordingly, when the sulfuric acid catalyst is used, it is possible to use a phosphonate ester as the starting material for synthesizing the layered compound. That is, since the phosphonic acid may not always be used as the starting material, a step of hydrolyzing the phosphonate ester is not required.

[6. Reaction Method]

When the organic diphosphonic acid or the derivative thereof, the monophosphonic acid or the derivatives thereof and the metal compound are blended at a predetermined ratio and reacted under the presence of a sulfuric acid catalyst, a crosslinked type layered metal phosphonate compound according to the invention is obtained. In this case, when reaction is carried out while stirring the starting solution under heating, a layered compound of high crystallinity is obtained.

The reaction time is selected optimally in accordance with the type and the composition of the starting material and the reaction temperature. In a case of using other methods, the reaction time is usually about 24 hours. On the contrary, when the sulfuric acid catalyst is used, the reaction time can be shortened to 5 to 1 hours. Accordingly, it is possible to synthesize a multi-ingredient crosslinked type layered metal phosphonate compound having high crystallinity of the layered structure although the particle size small and having a copolymerized composition that reflects the starting composition.

The reaction method for the starting materials include specifically the following methods.

[6.1 First Specific Example]

The first specific example of the reaction method is a method of reacting starting materials blended at a predetermined ratio simultaneously under the presence of a sulfuric acid catalyst. In this case, sulfuric acid may be added to a mixture of isolated starting materials.

Alternatively, a stock solution may be prepared previously, to which (1) the metal source, and
(2) the remaining ingredient of the organic diphosphonic acid or the derivative thereof or the monophosphonic acid or the derivative thereof, may be added.

"Stock solution" means those in which at least one of organic diphosphonic acids or derivatives thereof and monophosphonic acids or derivatives thereof for synthesizing the crosslinked type layered metal phosphonate compounds and having a sulfonic group or a group that can be converted into the sulfonic group is dissolved or dispersed in an aqueous solution of sulfuric acid or a mixed solution of the aqueous solution of sulfuric acid and an organic solvent.

The stock solution may contain one of phosphonic acids having a sulfonic group or a group that can be converted into the sulfonic group or derivative thereof or may contain two or more of them. Further, the stock solution may contain one or more of phosphonic acids or derivatives thereof having a sulfonic group or a group that can be converted into the sulfonic group and, in addition, one or more of phosphonic acids or derivatives thereof not having the sulfonic group or the group that can be converted into the sulfonic group.

Further, for the synthesis, one stock solution may be used, or two or more stock solutions different in the type of the dissolved phosphonic acid or derivative thereof may be used in combination.

In a case where the organic diphosphonic acid, the monophosphonic acid, or the derivative thereof used as the starting material has at least one benzene ring, a phosphonic acid or a derivative thereof not having a sulfonic group or a group that can be converted into the sulfonic group can be used as the starting material for synthesizing the layered compound. In this case, after synthesizing a layered compound not having a sulfonic group or a group that can be converted into the sulfonic group under the presence of the sulfuric acid catalyst, a sulfonic group or a group that can be converted into the sulfonic group is introduced to the benzene ring by post-sulfonation.

[6.2. Second Specific Example]

A second specific example of the reaction method is a method of carrying out the reaction with a metal source divisionally in two stages (2-step method) and includes a first reaction step and a second reaction step.

The first reaction step is a step of reacting an organic diphosphonic acid or a derivative thereof with a metal source.

The metal source is added by an entire amount required for synthesizing the layered compound. This is for reliably reacting the phosphonic group or the derivative thereof on both ends of the organic diphosphonic acid or the derivative thereof with the central atom (M) contained in the metal source.

The organic diphosphonic acid or the derivative thereof may or may not have a sulfonic group or a group that can be converted into the sulfonic group. Further, for the organic diphosphonic acid or the derivative thereof, an isolated material may be used or a stock solution may also be used.

A method of adding and reacting the metal source to a stock solution in which an organic diphosphonic acid or a derivative thereof having a sulfonic group or a group that can be converted into the sulfonic group is dissolved or dispersed in an aqueous solution of sulfuric acid or a mixed solution of the aqueous solution of sulfuric acid and an organic solvent is particularly preferred since this does not require isolation operation and can introduce the sulfonic group or the group that can be converted into the sulfonic group to an optional position between the layers.

In the first reaction step, while sulfuric acid may be used as the catalyst, the sulfuric acid catalyst is not always necessary.

The second reaction step is a step of adding a monophosphonic acid or a derivative thereof to a reaction solution obtained in the first reaction step and reacting the same under the presence of a sulfuric acid catalyst.

The monophosphonic acid or the derivative thereof may or may not have a sulfonic group or a group that can be converted into the sulfonic group. Further, for the monophosphonic acid or the derivative thereof, an isolated material may be used, or a stock solution may also be used.

Particularly, a method of adding and reacting a stock solution in which the monophosphonic acid or the derivative thereof having the sulfonic group or a group that can be converted into the sulfonic group is dissolved or dispersed in an aqueous solution of sulfuric acid or a mixed solution of the aqueous solution of sulfuric acid and an organic solvent to the reaction solution is particularly preferred since this does not require isolation operation and the sulfonic group or the group that can be converted into the sulfonic group can be introduced at an optimal position between the layers.

Also in the 2-step method, in a case where the organic diphosphonic acid, monophosphonic acid, or the derivative thereof used as the starting material has at least one benzene ring, a phosphonic acid or a derivative thereof not having a sulfonic group or a group that can be converted into the sulfonic group can be used as the starting material for synthesizing the layered compound. In this case, after synthesizing the layered compound not having the sulfonic group or the group that can be converted into the sulfonic group under the presence of the sulfuric catalyst, the sulfonic group or the group that can be converted into the sulfonic group is introduced to the benzene ring by post-sulfonation.

IV Stock Solution (1)

The stock solution according to the invention includes one or more member selected from organic diphosphonic acids having a sulfonic group or a group that can be converted into the sulfonic group and derivatives thereof, and monophosphonic acids having the sulfonic group or the group that can be converted into the sulfonic group and derivatives thereof dissolved or dispersed in an aqueous solution of sulfuric acid or a mixed solution of the aqueous solution of sulfuric acid and an organic solvent.

The stock solution may contain a phosphonic acid having a sulfonic group or a group that can be converted into the sulfonic group or the derivatives thereof, or may contain two or more of them. Further, the stock solution may also contain, in addition to one or more of phosphonic acids having the sulfonic group or the group that can be converted into the sulfonic group or derivatives thereof, one or more of phosphonic acids not having the sulfonic group or the group that can be converted into the sulfonic group or derivatives thereof.

Further, the stock solution may also contain, in addition to the aqueous solution of sulfuric acid, an organic solvent such as DMSO, sulfolane, and diglime. Some organic solvents have a function of promoting reaction between the metal source and the organic diphosphonic acid or monophosphonic acid, or derivatives thereof.

The concentration of sulfuric acid, the concentration of the organic solvent, the concentration of the phosphonic acid or derivatives thereof contained in the stock solution is not particularly restricted and can be selected optionally in accordance with the purpose.

Since details for the group that can be converted into the sulfonic group, the organic diphosphonic acids or the derivatives thereof, the monophosphonic acids or the derivatives thereof are as have been described above, descriptions therefor are to be omitted.

V. Production Process for Stock Solution (1)

The production process for the stock solution according to the invention includes a sulfonation step and a dilution step.

The sulfonation step is a step of adding for sulfonation a sulfonating agent to one or more member selected from organic diphosphonic acids and derivatives thereof, and monophosphonic acids and derivatives thereof. It is necessary that the sulfonation step is conducted under a non-aqueous condition such as under a nitrogen stream.

As the sulfonating agent, concentrated sulfuric acid, fuming sulfuric acid ($H_2SO_4 \cdot nSO_3$), anhydrous sulfuric acid ($SO_3$), chlorosulfonic acid ($ClSO_3H$), etc. can be used.

The phosphonic acid or the derivatives thereof to be reacted with the sulfonating agent may also be organic diphosphonic acids or derivatives thereof, organic monophosphonic acids or derivatives thereof, or aliphatic phosphonic acids or derivatives thereof. Particularly, when a phosphonic acid having at least one benzene ring in the molecule and a sulfonating agent are reacted, a sulfonic group or a group that can be converted into the sulfonic group can be introduced easily to the benzene ring. Further, when the reaction condition is optimized, the number of sulfonic groups, or the groups that can be converted into the sulfonic groups which are introduced into the benzene ring can be controlled.

The dilution step is a step of adding water for dilution to the reaction solution obtained in the sulfonation step.

When water is added to the reaction solution, an excess sulfonating agent is converted into sulfuric acid. In this case, when the dilution amount of water is controlled, the concentration of sulfuric acid and the concentration of the phosphonic acid or the derivative thereof in the stock solution can be controlled. Further, after dilution with water, an organic solvent such as DMSO, sulfolane, or diglime may also be added optionally.

A crosslinked type layered metal phosphonate compound according to the invention is obtained by portioning the stock solution into a required amount, optionally diluting the portion by further adding water, then adding a metal source and other phosphonic acid or a derivative thereof (including those prepared in the form of the stock solution) optionally and reacting them simultaneously or successively in two steps.

VI The Effect of Crosslinked Type Layered Metal Phosphonate Compound and Production Process Therefor, as Well as Stock Solution and the Production Process Thereof In a case of synthesizing a crosslinked type layered metal phosphonate compound, when HF is used as a catalyst, a layered compound of high crystallinity is obtained. It is considered that a soluble intermediate reaction product $ZrF_6$ is formed and reaction with a phosphonic acid proceeds moderately when HF is used as the catalyst. However, the method involves a drawback that a plurality types of phosphonic acids cannot be introduced uniformly in the layered structure. It is considered that the reactivity between the intermediate reaction product $ZrF_6$ and the phosphonic acids is different depending on the type of the phosphonic acids. Further, use of HF as the catalyst involves a problem that F atoms intrude in the synthesized compound.

On the other hand, a method of hydrothermic reaction or a method of using HCl or HBr as a catalyst has an advantage capable of obtaining a layered compound in which a plurality types of phosphonic acids are introduced uniformly. Further, F atoms do not intrude into the synthesized compound. However, it has a drawback that the crystallinity of the layered compound obtained by the method is lower compared with the case of using HF as the catalyst.

On the contrary, when sulfuric acid is used as the catalyst, not only the F atoms do not intrude but also the crystallinity is extremely high, and a copolymerized composition reflecting the starting composition can be obtained. Although the reaction mechanism has not yet been apparent, it is considered to be attributable to that:

(1) the ion of the central metal (M) forms a water soluble complex salt together with $SO_4^{2-}$ and this reacts moderately with the phosphonic acid, and
(2) no remarkable difference is caused for the reactivity between the ion of the central metal (M) and the phosphonic acid even when different types of phosphonic acids are present during reaction since $SO_4^{-2}$ is an anion of a larger size compared with $F^-$.

Particularly, when a metal source and a diphosphonic acid are at first reacted and then they are reacted with a monophosphonic acid, the crystallinity of the layered structure is further improved compared with a case of charging them together. Further, also a plurality types of phosphonic acids can be introduced uniformly between the layers.

This is considered that (1) when an organic diphosphonic acid having phosphonic groups on both terminal ends and, accordingly, disadvantageous for the homogeneous reaction is previously reacted with an excess amount of a metal source, a reactive complex of phosphonic groups on both terminal ends and the ion of the central atom (M) can be formed reliably, and
(2) uniform reaction between a plurality types of phosphonic acids and the ion of the central atom (M) is promoted by forming a reactive complex of the organic diphosphonic acid of the ion of the control metal (M) and then conducting reaction with the monophosphonic acid as a second step.

Further, in a case of synthesizing the crosslinked type layered metal phosphonate compound, when the stock solution is used;

(1) isolation of a sulfonated organic phosphonic acid is no more required,
(2) the sulfonic group can be introduced easily not only to the organic diphosphonic acid ingredient as the crosslinking ingredient but also to the phosphonic acid ingredient other than the crosslinking ingredient between the layers, and
(3) the stock solution contains sulfuric acid as a byproduct upon sulfonation of the phosphonic acid, the sulfuric acid is utilized as a reaction catalyst for the metal source. Accordingly, not only the sulfonation product of the phosphonic acid ingredient for which no isolation method has yet been established but also the sulfonation product and the non-sulfonation product of the phosphonic acid ingredient can be introduced at an optional ratio. Further, even a phosphonic acid ingredient having a substituent instable to the post-sulfonation can be also introduced.
(4) Since sulfonation products of various phosphonic acids of different sulfonation degree (for example, phosphonic acids having a monosulfonated diphenyl ether group or a disulfonated diphenyl ether group) can be obtained by controlling the synthesis condition for the stock solution, the sulfonation degree of the layered compound can be controlled freely by using them as the starting material.

Further, since various types of phosphonic acid ingredients can be uniformly introduced easily, the degree of freedom for the material design is higher compared with the existent method.

For example, when organic diphosphonic acids of different molecular sizes are used as the starting material, various crosslinked type layered metal phosphonate compounds of different interlayer distance (that is, interlayer space size) can be synthesized.

Further, when a sulfonated monophosphonic acid is used as the starting material in addition to the organic diphosphonic acid, a crosslinked type layered metal phosphonate compound in which the sulfonic group ingredient is distributed being fixed at the layer surface can be synthesized.

Further, when a plurality of phosphonic acids of different structures are used as the starting material, arrangement of the sulfonic groups in the layered compound and circumstance surrounding them can be controlled. For example, since the sulfophenyl group is a large-size substituent, when all the phosphonic acid tetrahedrons in the layered structure are substituted by the phosphonic acid ingredients having sulfophenyl groups, the crystallinity of the layered compound is lowered remarkably. However, when a phosphonic acid having a large-size substituent such as a sulfophenyl group and a monophosphonic acid having a small-size substituent (—Y) are used in combination, since the steric hindrance of the large-size substituent can be moderated, an introducing position of the sulfonic group can be controlled relatively freely without lowering the crystallinity of the layered compound.

Since the thus obtained crosslinked type layered metal phosphonate compound is crosslinked by the organic diphosphonic acid ingredient between the layers, it is not dissolved in water (that is, does not undergo dispersion by layer separative). Further, since it has a two dimensional layered structure of inorganic materials as the main chain, it has higher durability to hydrogen peroxide compared with existent polymeric electrolytes. Further, since the crystallinity is made higher compared with that obtained by hydrothermic reaction or HCl catalytic reaction, durability to hydrolysis is also high. Further, since HF is not used as the catalyst, there is no possibility of intrusion of the F atoms which may possibly result in environmental problems.

VII Non-Crosslinked Type Layered Metal Phosphonate Compound (1)

The non-crosslinked type layered metal phosphonate compound according to the first embodiment of the invention contains two or more phosphonic acid ingredients and only one of them has a sulfonic group or a group that can be converted into the sulfonic group and, specifically, it has the following conditions (a) to (d).

[1. Constitution of Non-Crosslinked Type Layered Metal Phosphonate Compound According to the First Embodiment]
[1.1. Condition (a)]

The non-crosslinked type layered metal phosphonate compound according to the invention has a two dimensional layered structure in which a metal oxide octahedron having a hexacoordinate metal atom as the central atom (M) and a phosphonic acid tetrahedron are connected by sharing oxygen atoms.

Generally, "organic phosphonic acid" means an organic acid compound having three O atoms bonded to a pentavalent P atom, and "organic phosphoric acid" means an organic acid compound in which four O atom are connected to a pentavalent P atom. In the invention, "non-crosslinked type layered metal phosphonate compound" includes those in which a portion of the monophosphonic acid ingredient to be described later is an ingredient derived from inorganic phosphoric acid.

The non-crosslinked type layered metal phosphonate compound according to the invention is a compound in which tetrahedrons contained in the layered structure formed by bonding of octahedrons and tetrahedrons are entirely or partially substituted by the monophosphonic acid ingredient to be described later.

The hexacoordinate metal atom as the central atom (M) for the octahedron includes, specifically, Zr(IVa), Ti(IVa), Hf(IVa), Th(IVa), Si(IVb), Ge(IVb), Sn(IVb), Pb (IVb), Cu(Ib), Zn(Ib), Al(IIIb), Ga (IIIb), Nb(Va), Fe(VIII), Co(VIII), La(La), Ce(La), Mo(VIa), W(VIa), Mn(VIIa), etc. The octahedron contained in the layered structure may contain one of such hexacoordinate metal atoms, or may contain two or more of hexacoordinate metal atoms. Further, in a case of containing two or more of the hexacoordinate metal atoms, two or more hexacoordinate metal atoms may be contained within one identical layer, or different hexacoordinate metal atoms may be contained in octahedrons in different layers respectively.

Further, in a case where the central atom (M) of the octahedron is a hexacoordinate metal atom capable of taking a tetra atomic valence, the non-crosslinked type layered metal phosphonate compound can take an α-type or γ-type layered structure.

The hexacoordinate metal atom capable of taking the tetra atomic valence, Zr(IVa), Ti(IVa), Hf(IVa), Th(IVa), Si(IVb), Ge(IVb), Sn(IVb), Pb(IVb), Ce(La), Mo(VIa), W(VIa), and Mn(VIIa).

As to be described later, in a case of using sulfuric acid as the catalyst, a non-crosslinked type layered metal phosphonate compound of high crystallinity is obtained. The degree of the crystallinity is in proportion with the size of the layered structure and it is shown by a Scherrer's formula that this is in inverse proportion with the half-width value (°) for a d(001) peak obtained by measurement of an X-ray powder refraction pattern using $CuK_\alpha$ as an X-ray source.

For improving the durability to hydrolysis, the crystallinity is preferably 7° or less and, more preferably, 3° or less as the half-width value of the d(001) peak.

[1.2. Condition (b)]

The non-crosslinked type layered metal phosphonate compound contains two or more monophosphonic acid ingredients.

"Monophosphonic acid ingredient" means those having one $—PO_3$ group. The monophosphonic acid ingredient may be those in which the P atom in the $—PO_3$ group is bonded directly or by way of an O atom to an organic group (organic monophosphonic acid ingredient, organic phosphoric acid ingredient), or the P atom is bonded with a group other than the organic group (for example, $—H$, $—OH$) (inorganic phosphonic acid ingredient, inorganic phosphoric acid ingredient). That is, "monophosphonic acid ingredient" in the invention means those containing a phosphoric acid bond.

A first specific example of the monophosphonic acid ingredient is represented by following formula (A2):

$$(—O)_3P—(O)_x—Z^1—(A^1)_r \qquad (A2)$$

In the formula (A2), $Z^1$ represents a (1+r) valent organic group having at least one benzene ring, or an alkylene chain.

$A^1$ represents a sulfonic group or a group that can be converted into the sulfonic group, or an aliphatic group having a sulfonic group or a group that can be converted into the sulfonic group.

"Group that can be converted into the sulfonic group" means a group that can be converted into a sulfonic group by such a moderate reaction as not breaking the layered structure of the layered compound (for example, by hydrolysis). The group that can be converted into the sulfonic group includes, specifically, -Hal (Hal; halogen), $—SH$, $—S—R'$, ($—R'$: $—CH_3$, or $—C_2H_5$), $—SO_2Cl$, etc.

x is 0 or 1, r represents an integer from "0" to "number of benzene rings in $Z^1$)×2" when $Z^1$ is a (1+r) valent organic group. On the other hand, r represents an integer from 1 to m (m is the number of carbon atoms in the alkylene chain) when $Z^1$ is an alkylene chain.

The (1+r') valent organic group and the alkylene chain constituting $Z^1$ are preferably those represented respectively by the following equation (A2.1) and the (A2.2) equation.

[Chemical formula 14]

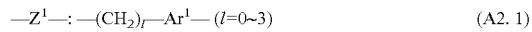

$$—Z^1—: —(CH_2)_l—Ar^1— \; (l=0\sim3) \qquad (A2.1)$$

$$—(CH_2)_m— \; (m=1\sim24) \qquad (A2.2)$$

In the formula (A2.1), $Ar^1$ represents a monocyclic or polycyclic aromatic group. The polycyclic aromatic group includes those in which (1) a plurality of benzene rings are connected by a single bond,
(2) a plurality of benzene rings are connected by way of a bivalent group, (3) condensed ring (acenes), and
(4) combination of (1) to (3).

Ar¹ is particularly preferably those represented by the following formulae (A2.1.1) to (A2.1.3).

[Chemical formula 15]

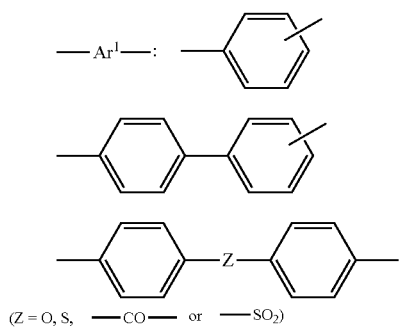

(Z = O, S, —CO— or —SO₂)

A second specific example of the monophosphonic acid ingredient includes those represented by the following equation (B2).

The monophosphonic acid ingredient represented by the formula (B2) has a compositional formula identical with that of the monophosphonic acid ingredient represented by the formula (A2). However, in the compositional formula of the non-crosslinked type layered metal phosphonate compound to be described later, when contains both the monophosphonic acid ingredient represented by the formula (A2) and the monophosphonic acid ingredient represented by the formula (B2), the monophosphonic acid ingredient represented by the formula (A2) and the monophosphonic acid ingredient represented by the formula (B2) represent monophosphonic acid ingredients of different compositions.

Since $Z^2$, $A^2$, r' and x' in the formula (B2) represent the contents identical with $Z^1$, $A^1$, r, and x in the formula (A2), explanations therefor are to be omitted.

A third specific example of the monophosphonic acid ingredient includes those represented by the following formula (C2).

In the formula (C2), —Y¹ includes those in which a substituent is bonded to the fluoroalkylene chain.

—Y¹ is particularly preferably those represented by the following formula (C2.1).

—W preferably represents specifically —SO₃H, -Hal, —SH, —S—R' (R': —CH₃, or —C₂H₅), —SO₂Cl, —OH, —CN, —CO₂H, etc.

A fourth specific example of the monophosphonic acid ingredient includes those represented by the following formula (D2):

In the formula (D2), —Y represents a substituent not having a sulfonic group or a group that can be converted into the sulfonic group. —Y² may be an organic group or may be a group other than the organic group.

The small-size substituent constituting —Y includes —H, —OH, —C$_\gamma$H$_{2\gamma+1}$ ($1 \leq \gamma \leq 16$), etc.

The monophosphonic acid ingredient is bonded by way of a P—O-M bond to the hexacoordinate metal atom. In the layered metal phosphonate compound, the phosphonic acid tetrahedron is bonded by way of the P—O-M bond with the hexacoordinate metal atom such that the apex of the tetrahedron is directed to the outside of the layer plane. While the layered structure is formed so long as the central atom M for the metal oxide is a hexacoordinate metal atom, and it has been known that the structure takes α-type or γ-type structure particularly in a case of the hexacoordinate metal atom capable of taking a tetra atomic valent.

This is also identical with the non-crosslinked type layered metal phosphonate compound according to the invention and the bottom of the tetrahedron at the end of the monophosphonic acid ingredient is directed to the plane where octahedrons are arranged. That is, oxygen atoms by the number of three in total are present respectively at the terminal end of the monophosphonic acid ingredient.

In the non-crosslinked type layered metal phosphonate compound having the α-type layered structure, the monophosphonic acid ingredient may be in a state of bonding by way of three P—O-M bonds with the hexacoordinate metal atom (that is, all of three oxygen atoms are shared with different octahedrons) or may be in a state of bonding by way of one or two P—O-M bonds with the hexacoordinate metal atom (that is, a state in which one or two oxygen atoms are shared with different octahedrons). Oxygen atoms not concerned with the P—O-M bond may be bonded with other substituent such as H or may be bonded by way of a double bond with a P atom.

Also for the non-crosslinked type layered metal phosphonate compound having the γ-type layered structure, the way of bonding the monophosphonic acid ingredient and the octahedron is in an identical state but the number of P—O-M bonds is decreased each by the number of one compared with the α-type.

The α-type and the γ-type can be prepared selectively depending on the type of the starting material, starting composition thereof, and control for the reaction condition.

The non-crosslinked type layered metal phosphonate compound according to the invention may contain two types of monophosphonic acid ingredients, or may contain three or more of them. Further, the lengths for the monophosphonic acid ingredients may be identical or may be different with each other.

[1.3. Condition (c)]

In the non-crosslinked type layered metal phosphonate compound according to this embodiment, one of the monophosphonic acid ingredients has a sulfonic group or a group that can be converted into the sulfonic group. Remaining monophosphonic acid ingredient has no sulfonic group or a group that can be converted into the sulfonic group.

In a case where the monophosphonic acid ingredient has a benzene ring, each of them can have a sulfonic group or a group that can be converted into the sulfonic group by the number corresponding to "number of benzene rings×2" at the maximum per one molecule respectively by controlling the reaction conditions.

[1.4. Condition (d)]

The non-crosslinked type layered metal phosphonate compound does not contain fluorine atoms bonded to the central atom (M).

In a case of synthesizing the layered metal phosphonate compound, when HF is used as the catalyst, a portion of F atoms is bonded with the central atom (M) of the metal oxide octahedron. On the contrary, since the non-crosslinked type layered metal phosphonate compound of the invention is synthesized under the presence of the sulfuric catalyst as to be described later, it does not substantially contain F atoms bonded with the central atom (M).

The non-crosslinked type layered metal phosphonate compound of the invention is preferably those further having the following conditions.

[1.5. Condition (e)]

The average molecular cross sectional area for the substituent of the monophosphonic acid ingredient contained in the non-crosslinked type layered metal phosphonate compound is 70% or less of the free cross sectional area of one surface phosphonic group in the two dimensional layered structure.

While the free area is determined depending on the type of the hexacoordinate metal atom and the crystal structure, it can be determined experimentally from the lattice constant. The free area is determined for several hexacoordinate metal atom on the α-type and the γ-type layered structures ("Intercalation Chemistry" Ed. by M. Stanley, Wittingam, Allan, J. Jacobson, Academic Press 1982, p. 152; G. Alberti, et al., Adb. Mater., 1996, 8, 291). It is reported as α-type: Zr(24 Å$^2$(24×10$^{-2}$ nm$^2$)), Ti(21.6 Å$^2$ (21.6×10$^{-2}$ nm$^2$)), Sn(21.4 Å$^2$ (21.4×10$^{-2}$ nm$^2$)), Hf(23.7 Å$^2$ (23.7×10$^{-2}$ nm$^2$)), Pb(21.5 Å$^2$ (21.5×10$^{-2}$ nm$^2$)), and γ-type: Zr(35.7 Å$^2$ (35.7×10$^{-2}$ Å$^2$)), Ti(33.0 Å$^2$ (33.0×10$^{-2}$ nm$^2$)).

"Substituent" means herein a group connected to the apex of the tetrahedron having P as the central atom.

"Molecular cross sectional area" means a cross sectional area for the largest portion of the substituent as viewed from the direction perpendicular to the bottom of the tetrahedron. "Average molecular cross sectional area" means the total ($\Sigma S_i \times N_i$) for the product of each of the molecular cross sectional areas ($S_i$) of monophosphonic acid ingredient connected to the layers and the mole fraction ($N_i$) thereof.

When the average molecular cross sectional area exceeds 70% of the free area, the steric hindrance of the substituent increases and it becomes difficult to maintain the two dimensional layered structure of high crystallinity.

The molecular cross sectional area can be calculated from a CPK model drawn by a commercial software (for example, "Chem3D (registered trade mark"). For example, in the monophosphonic acid ingredient, the molecular cross sectional area is 14.6 Å$^2$ (14.6×10$^{-2}$ nm$^2$) for the phenyl group, 17.2 Å$^2$ (17.2×10$^{-2}$ nm$^2$) for the sulfophenyl group and 4.1 Å$^2$ (4.1×10$^{-2}$ nm$^2$) for the hydrogen group. On the other hand, the free area of α-type crosslinked type zirconium phosphonate is 24 Å$^2$ (24×10$^{-2}$ nm$^2$).

It has been known as the experimental fact that only the α-type layered compound of low crystallinity can be synthesized for Zr(O$_3$P-Ph-SO$_3$H)$_2$ as the homopolymer of sulfophenyl phosphonic acid even when any type of catalyst is used. The compound has a layered structure of low stability. In this case, it can be estimated that since the molecular cross sectional area of the sulfophenyl group as the substituent for the monophosphonic acid ingredient exceeds 70% size of the free area, the effect of the steric hindrance appears.

On the other hand, the α-type layered zirconium compound having two monophosphonic acid ingredients having the sulfophenyl group and the phenyl group at 1:1 molar ratio has the average molecular cross sectional area (15.9 Å$^2$ (15.9×10$^{-2}$ nm$^2$))≦70% of free area (=16.8 Å$^2$ (16.8×10$^{-2}$ nm$^2$)). Accordingly, the layered structure is stabilized to obtain a layered zirconium phosphonate compound of high crystallinity.

[2. Specific Example of Non-Crosslinked Type Layered Metal Phosphonate Compound According to the First Embodiment]

[2.1. First Embodiment]

A first specific example of the non-crosslinked type layered metal phosphonate compound according to this embodiment includes those having the α-type layered structure and the composition represented by the following formula (21). The non-crosslinked type layered metal phosphonate compound represented by the formula (21) contains a first monophosphonic acid ingredient (O$_3$P—(O)$_x$—Z$^1$-(A$^1$)$_r$) having an aromatic substituent having a sulfonic group or a group that can be converted into the sulfonic group (large-size substituent) as the essential ingredient (a>0, r≧1). Further, it contains one or more second monophosphonic acid ingredients having a small-size substituent (O$_3$P—(O)$_{x'}$—Z$^2$-(A$^2$)$_{r'}$), a third monophosphonic acid ingredient (O$_3$P—Y$^2$), and a fourth monophosphonic acid ingredient (O$_3$P—Y$^2$) as the essential ingredient (0<b+c+d).

In the formula (21), —Z$^2$— may be any of (1+r') valent organic group, or an alkylene chain. Further, since details for —Z$^1$— and —Z$^2$— in the formula (21) are as has been described above, descriptions therefor are to be omitted.

[Chemical formula 16]

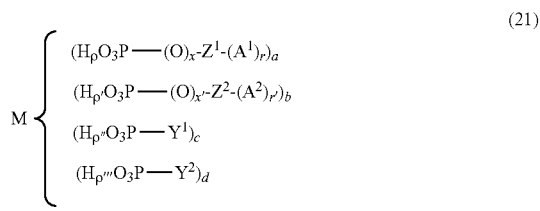

(21)

in which

M: hexacoordinate metal atom capable of taking a tetra atomic valence,

—Z$^1$—: (1+r) valent organic group having at least one benzene ring,

-A$^1$=—(CH$_2$)$_\alpha$—W (0≦α≦3)

(—W=—SO$_3$H, -Hal, —SH, —SCH$_3$, —SC$_2$H$_5$, or —SO$_2$Cl)

r=1 to [number of benzene rings in Z$^1$]×2 x=0, 1

(1) —Z$^2$—: (1+r') valent organic group having at least one benzene ring,

-A$^2$=—(CH$_2$)$_{\alpha'}$—W (0≦α'≦3)

(—W=—OH, —CN, or —CO$_2$H)

r'=0 to [number of benzene rings in Z$^2$]×2 x'=0, 1

(2) —Z$^2$—: —(CH$_2$)$_m$— (m=1 to 24)

-A$^2$=—W(—W=—OH, —CN, or —CO$_2$H)

r'=1 x'=0, 1

—Y$^1$: —(CF$_2$)$_q$—W (1≦q≦3)

(—W=—OH, —CN, or —CO$_2$H)

—Y$^2$: —H, —OH, —C$_\gamma$H$_{2\gamma+1}$ (1≦γ≦16)

a, b, c, d: 1.0<a+b+c+d<3.0, 0<a<3.0, 0≦b<3.0, 0≦c<3.0, 0≦d<3.0, 0<b+c+d

ρ, ρ', ρ", ρ"': 0≦(ρ, ρ', ρ", ρ"')≦2

In the formula (21), those compounds in which the first monophosphonic acid ingredient contains sulfophenyl phosphonic acid or sulfonated diphenyl ether (mono)phosphonic acid, the second monophosphonic acid ingredient contains phenyl phosphonic acid, and the fourth monophosphonic acid ingredient contains inorganic phosphonic acid, phosphoric acid, or methyl phosphonic acid (third monophosphonic acid ingredient: none) are preferred.

[2.2. Second Specific Example]

A second specific example of the non-crosslinked type layered metal phosphonate compound according to this embodiment includes those having the α-type layered structure and the composition represented by the following formula (22). The non-crosslinked type layered metal phosphonate compound represented by the formula (22) has the first monophosphonic acid ingredient ($O_3P-(O)_x-Z^1-(A^1)_r$) having an aliphatic substituent (small-size substituent) having a sulfonic group or a group that can be converted into the sulfonic group as the essential ingredient ($a>0, r \geq 1$). Further, it includes one or more of second monophosphonic acid ingredients having the small-size substituent ($O_3P-(O)_{x'}-Z^2-(A^2)_{r'}$), a third monophosphonic acid ingredient ($O_3P-Y^1$), and a fourth monophosphonic acid ingredient ($O_3P-Y^2$) as the essential ingredient ($0<b+c+d$).

In the formula (22), $-Z^2-$ may be any of the $(1+r')$ valent organic group or the alkylene chain. Further, since the details for $-Z^2-$ in the formula (22) are as has been described above, descriptions therefor are to be omitted.

[Chemical formula 17]

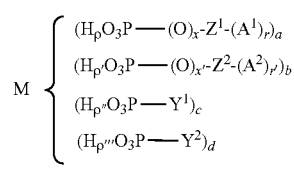

(22)

in which

M: hexacoordinate metal atom capable of taking a tetra atomic valence, $-Z^1-$: $-(CH_2)_m-$ (m=1 to 24)

-$A^1$=$-W(-W$=$-SO_3H$, -Hal, $-SH$, $-SCH_3$, $-SC_2H_5$, or $-SO_2Cl$)

r=1 x'=0, 1

(1) $-Z^2-$: $(1+r')$ valent organic group having at least one benzene ring,

-$A^2$=$-(CH_2)_{\alpha'}-W$ ($0 \leq \alpha' \leq 3$)

($-W$=$-OH$, $-CN$, or $-CO_2H$)

r'=0 to [number of benzene rings in $Z^2$]×2 x'=0, 1

(2) $-Z^2-$: $-(CH_2)_m-$ (m=1 to 24)

-$A^2$: $-W(-W$=$-OH$, $-CN$, or $-CO_2H$)

r'=1 x'=0, 1

$-Y^1$: $-(CF_2)_q-W$ ($1 \leq q \leq 3$) ($-W$=$-OH$, $-CN$, or $-CO_2H$)

$-Y^2$: $-H$, $-OH$, $-C_\gamma H_{2\gamma+1}$ ($1 \leq \gamma \leq 16$)

a, b, c, d: $1.0<a+b+c+d<3.0, 0<a<3.0, 0 \leq b<3.0, 0 \leq c<3.0, 0 \leq d<3.0, 0<b+c+d$ ρ, ρ', ρ", ρ'": $0 \leq (\rho, \rho', \rho", \rho''') \leq 2$ In the formula (22), those compounds in which the first monophosphonic acid ingredient contains 3-sulfopropylene phosphonic acid, the second monophosphonic acid ingredient contains phenyl phosphonic acid, and the fourth monophosphonic acid ingredient contains inorganic phosphonic acid, phosphoric acid, or methyl phosphonic acid (third monophosphonic acid ingredient: none) are preferred.

[2.3 Third Specific Example]

A third specific example of the non-crosslinked type layered metal phosphonate compound according to this embodiment includes those having the α-type layered structure and the composition represented by the following formula (23). The non-crosslinked type layered metal phosphonate compound represented by the formula (23) contains a third monophosphonic acid ingredient having a fluorocarbon type substituent (small-size substituent) having a sulfonic group or a group that can be converted into the sulfonic group as the essential ingredient ($c>0$). Further, it contains one or more of the first monophosphonic acid ingredients having the small-size substituent ($O_3P-(O)_x-Z^1-(A^1)_r$), the second monophosphonic acid ingredient ($O_3P-(O)_{x'}-Z^2-(A^2)_{r'}$), and the forth monophosphonic acid ingredient ($O_3P-Y^2$) ($0<a+b+d$) as the essential ingredient.

In the formula (23), $-Z^1-$ and $-Z^2-$ may be, independently, $(1+r)$ valent or $(1+r')$ valent organic group or alkylene chain but the first monophosphonic acid ingredient and the second monophosphonic acid ingredient are different from each other ($-(O)_x-Z^1-(A^1)_r \neq -(O)_{x'}-Z^2-(A^2)_{r'}$). Further, since details for $-Z^1-$ and $-Z^2-$ in the formula (23) are has been described above, descriptions therefor are to be omitted.

[Chemical formula 18]

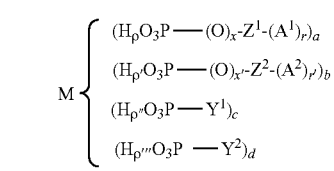

(23)

in which

M: hexacoordinate metal atom capable of taking a tetra atomic valence, (1) $-Z^1-$, $-Z^2-$: $(1+r)$ valent or $(1+r')$ valent organic group having at least one benzene ring, -$A^1$-, -$A^2$=$-(CH_2)_{\alpha,\alpha'}-W$ ($0 \leq \alpha, \alpha' \leq 3$)

($-W$=$-OH$, $-CN$, or $-CO_2H$)

r, r'=0 to [number of benzene rings in $Z^1, Z^2$]×2 x, x'=0, 1

(2) $-Z^1-$, $-Z^2-$: $-(CH_2)_m-$ (m=1 to 24)

-$A^1$, -$A^2$: $-W(-W$=$-OH$, $-CN$, or $-CO_2H$)

r, r'=1 x, x'=0, 1

$-(O)_x-Z^1-(A^1)_r \neq -(O)_{x'}-Z^2-(A^2)_{r'}$ $-Y^1$: $-(CF_2)_q-W$ ($1 \leq q \leq 3$)

($-W$=$-SO_3H$, -Hal, $-SH$, $-SCH_3$, $-SC_2H_5$, or $-SO_2Cl$)

$-Y^2$: $-H$, $-OH$, $-C_\gamma H_{2\gamma+1}$ ($1 \leq \gamma \leq 16$)

a, b, c, d: $1.0<a+b+c+d<3.0, 0 \leq a<3.0, 0 \leq b<3.0, 0<c<3.0, 0 \leq d<3.0, 0<a+b+d$ ρ, ρ', ρ", ρ'": $0 \leq (\rho, \rho', \rho", \rho''') \leq 2$ In the formula (23), those compounds in which the first monophosphonic acid ingredient contains sulfodifluoromethylene phosphonic acid, the second monophosphonic acid ingredient contains phenyl phosphonic acid, and the fourth monophosphonic acid ingredient contains inorganic phosphonic acid, phosphoric acid, or methyl phosphonic acid (third monophosphonic acid ingredient: none) are preferred.

[VIII Non-crosslinked Type Layered Metal Phosphonate Compound (2)]

The non-crosslinked type layered metal phosphonate compound according to the second embodiment of the invention contains two or more phosphonic acid ingredients in which two or more of them have a sulfonic group or a group that can be converted into the sulfonic group and, specifically, have the following conditions (a) to (d).

[1. Constitution of Non-crosslinked Type Layered Metal Phosphonate Compound According to the Second Embodiment (a) The non-crosslinked type layered metal phosphonate compound has a two dimensional layered structure in which the metal oxide octahedrons having a hexacoordinate metal atom as a central atom (M) and phosphonic acid tetrahedrons are connected by sharing oxygen atoms.
(b) The non-crosslinked type layered metal phosphonate compound contains two or more monophosphonic acid ingredients bonded by way of at least one P—O-M bond with different hexacoordinate metal atoms in the layered structure.
(c) At least two or more of the monophosphonic acid ingredients have a sulfonic group or a group that can be converted into the sulfonic group and others have no such group.
(d) The non-crosslinked type layered metal phosphonate compound does not contain a fluorine atom bonded with the central atom (M).

The non-crosslinked type layered metal phosphonate compound according to this embodiment preferably satisfies the following condition further.

(e) The average molecular cross sectional area for the substituent of the monophosphonic acid ingredient contained in the non-crosslinked type layered metal phosphonate compound is 70% or less of the free area of one surface phosphonic group in the two dimensional layered structure.

In the non-crosslinked type layered metal phosphonate compound according to this embodiment, two or more of the monophosphonic acid ingredients have the sulfonic group or the group that can be converted into the sulfonic groups. This is different from the first embodiment. The sulfonic group or the group that can be converted into the sulfonic group may be contained in all of the phosphonic acid ingredients. In this case, when the condition (e) is further satisfied, the layered structure is stabilized and a non-crosslinked type layered metal phosphonate compound of high crystallinity can be obtained.

Since the non-crosslinked type layered metal phosphonate compound according to the invention is synthesized under the presence of the sulfuric acid, the starting composition can be reflected on the copolymerized composition and the degree of freedom for the structural design is high. Accordingly, there is no restriction for the portion of introducing the sulfonic group or the group that can be converted into the sulfonic group.

Since other matters regarding the conditions (a) to (e) are identical with those in the first embodiment, detailed descriptions are to be omitted.

[2. Specific Example of Non-crosslinked Type Layered Metal Phosphonate Compound According to Second Embodiment]
[2.1. First Specific Example]

A first specific example of the non-crosslinked type layered metal phosphonate compound according to this embodiment includes those having the α-type layered structure and the composition represented by the following formula (24). The non-crosslinked type layered metal phosphonate compound represented by the formula (24) contains a first monophosphonic acid ingredient $(O_3P—(O)_x—Z^1-(A^1)_r)$ as an essential ingredient (a>0). Further, it contains one or more of a second monophosphonic acid ingredient $(O_3P—(O)_{x'}—Z^2-(A^2)_{r'})$ a third monophosphonic acid ingredient $(O_3P—Y^1)$, and a fourth monophosphonic acid ingredient $(O_3P—Y^2)$ as an essential ingredient (0<b+c+d).

In the formula (24), $—Z^1—$ and $—Z^2—$ may independently contain any of (1+r) valent or (1+r') valent organic group or alkylene group but the first monophosphonic acid ingredient and the second monophosphonic acid ingredient are different from each other $(—(O)_x—Z^1-(A^1)_r \neq —(O)_{x'}—Z^2-(A^2)_{r'})$. In the formula (24) since the details for $—Z^1—$ and $—Z^2—$ are as has been described above, descriptions therefor are to be omitted.

[Chemical formula 19]

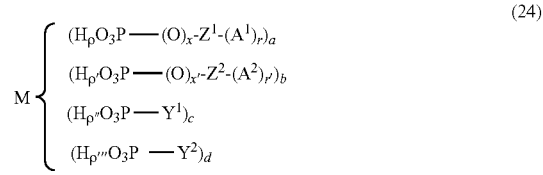

in which
M: hexacoordinate metal atom capable of taking a tetra atomic valence,
(1) $—Z^1, —Z^2—$: (1+r) valent or (1+r') valent organic group having at least one benzene ring,
  -$A^1$, -$A^2=—(CH_2)_{\alpha,\alpha}$—W (0≦α, α≦3)
  (—W=—$SO_3H$, -Hal, —SH, —$SCH_3$, —$SC_2H_5$, —$SO_2Cl$, —OH, —CN or —$CO_2H$)
  r', r'=0 to {number of benzene rings in $Z^1$, $Z^2$}×2
  x, x'=0, 1
(2) $—Z^1, —Z^2—$: —$(CH_2)_m$— (m=1 to 24)
  -$A^1$, -$A^2=—W$
  (—W=—$SO_3H$, -Hal, —SH, —$SCH_3$, —$SC_2H_5$, —$SO_2Cl$, —OH, —CN or —$CO_2H$)
  r, r'=1
  x, x'=0, 1
  $-(O)_x-Z^1-(A^1)_r \neq -(O)_{x'}-Z^2-(A^2)_{r'}$
  $Y^1$: $(CF_2)_q$—W (1≦q≦3)
  (—W=—$SO_3H$, -Hal, —SH, —$SCH_3$, —$SC_2H_5$, —$SO_2Cl$, —OH, —CN or —$CO_2H$)
  —$Y^2$: —H, —OH, —$C_yH_{2y+1}$ (1≦y≦16)
a, b, c, d: 1.0<a+b+c+d<3.0, 0<a<3.0, 0≦b<3.0, 0≦c<3.0, 0≦d<3.0, 0<b+c+d
ρ, ρ', ρ", ρ''': 0≦(ρ, ρ', ρ", ρ''')≦2

In the formula (24), layered compounds in which two or more of the first monophosphonic acid ingredient, the second monophosphonic acid ingredient, and the third monophosphonic acid ingredient contain those having:
(1) sulfonated aromatic group such as sulfophenyl group, sulfonated biphenyl group, and sulfonated diphenyl ether group,
(2) sulfonated aliphatic group such as sulfopropyl group,
(3) sulfonated (fluorinated) aliphatic group such as sulfodifluoromethyl group, or
(4) sulfonated aromatic-aliphatic group such as sulfophenylethyl group, and the remaining monophosphonic acid ingredients have a sterically compact group (for example, hydrogen group, methyl group, and phenyl group) are preferred.

[2.2. Second Specific Example]

A second specific example of the non-crosslinked type layered metal phosphonate compound according to this embodiment include those having the α-type layered structure and the composition represented by the following formula (24.1). The non-crosslinked type layered metal phosphonate compound represented by the formula (24.1) contains a first monophosphonic acid ingredient ($O_3P$—$(O)_x$-$Z^1$-$(A^1)_r$) and a second monophosphonic acid ingredient ($O_3P$—$(O)_{x'}$-$Z^2$-$(A^2)_{r'}$) each having an aromatic substituent (large-size substituent) having a sulfonic group or a group that can be converted into the sulfonic group as an essential ingredients (a>0, r≧1, b>0, r'≧1).

Further, for moderating the steric hindrance of the first monophosphonic acid ingredient and the second monophosphonic acid ingredient, the compound contains one or more of a third monophosphonic acid ingredients ($O_3P$—$Y^1$) and a fourth monophosphonic acid ingredient ($O_3P$—$Y^2$) each having a small-size substituent as essential ingredients (0<c+d).

In the formula (24.1), the first monophosphonic acid ingredient and the second monophosphonic acid ingredient are different from each other (—$(O)_x$—$Z^1$-$(A^1)_r$≠—$(O)_{x'}$—$Z^2$-$(A^2)_{r'}$). Further, since details for —$Z^1$— and —$Z^2$— in the formula (24.1) are as has been described above, descriptions therefor are to be omitted.

[Chemical formula 20]

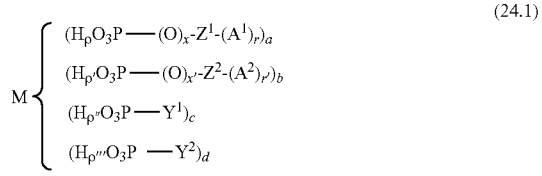

(24.1)

in which

M: hexacoordinate metal atom capable of taking a tetra atomic valence,

—$Z^1$—: (1+r) valent organic group having at least one benzene ring,

-$A^1$=—$(CH_2)_\alpha$—W (0≦α≦3)

(—W=—$SO_3H$, -Hal, —SH, —$SCH_3$, —$SC_2H_5$ or —$SO_2Cl$)

r=1 to [number of benzene rings in $Z^1$]×2 x=0, 1

—$Z^2$—: (1+r') valent organic group having at least one benzene ring,

-$A^2$=—$(CH_2)_{\alpha'}$—W (0≦α'≦3)

(—W=—$SO_3H$, -Hal, —SH, —$SCH_3$, —$SC_2H_5$ or —$SO_2Cl$)

r'=1 to {number of benzene rings in $Z^2$}×2 x'=0, 1

-$(O)_x$-$Z^1$-$(A^1)_r$≠-$(O)_{x'}$-$Z^2$-$(A^2)_{r'}$

—$Y^1$: —$(CF_2)_q$—W (1≦q≦3)

(—W=—$SO_3H$, -Hal, —SH, —$SCH_3$, —$SC_2H_5$, —$SO_2Cl$, —OH, —CN or —$CO_2H$)

—$Y^2$: —H, —OH, —$C_\gamma H_{2\gamma+1}$ (1≦γ≦16)

a, b, c, d: 1.0<a+b+c+d<3.0, 0<a<3.0, 0<b<3.0, 0≦c<3.0, 0≦d<3.0, 0<c+d

ρ, ρ', ρ", ρ''': 0≦(ρ, ρ', ρ", ρ''')≦2

In the formula (24.1), the compounds in which the first monophosphonic acid ingredient contains sulfophenyl phosphonic acid, the second monophosphonic acid ingredient contains sulfonated diphenyl ether (mono)phosphonic acid, and the fourth monophosphonic acid ingredient contains inorganic phosphonic acid, phosphoric acid, or methyl phosphonic acid (third monophosphonic acid ingredient: none) are preferred.

[2.3. Third Specific Example]

A third specific example of the non-crosslinked type layered metal phosphonate compound according to this embodiment includes those having the α-type layered structure and the composition represented by the following formula (24.2). The non-crosslinked type layered metal phosphonate compound represented by the formula (24.2) contains a first monophosphonic acid ingredient having an aromatic substituent (large-size substituent) having a sulfonic group or a group that can be converted into the sulfonic group ($O_3P$—$(O)_x$—$Z^1$-$(A^1)_r$) as an essential ingredient (a>0, r≦1). Further, it contains at least one of a second monophosphonic acid ingredient capable of having a small-size substituent having a sulfonic group or a group that can be converted into the sulfonic group ($O_3P$—$(O)_{x'}$—$Z^2$-$(A^2)_{r'}$) and a third monophosphonic acid ingredient ($O_3P$—$Y^1$) as an essential ingredient (0<b+c). A fourth monophosphonic acid ingredient ($O_3P$—$Y^2$) is an optional ingredient.

—$Z^2$— in the formula (24.2) means that it may be any of a (1+r') valent organic group or an alkylene chain. Further, since details for —$Z^1$— and —$Z^2$— in the formula (24.2) are as has been described above, descriptions therefor are to be omitted.

[Chemical formula 21]

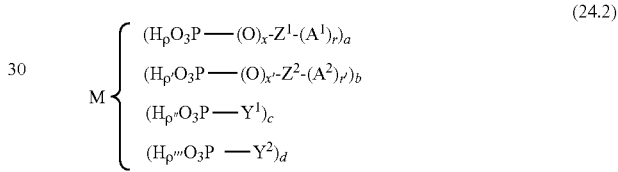

(24.2)

in which

M: hexacoordinate metal atom capable of taking a tetra atomic valence,

—$Z^1$—: (1+r) valent organic group having at least one benzene ring,

-$A^1$=—$(CH_2)_\alpha$—W (0≦α≦3)

(—W=—$SO_3H$, -Hal, —SH, —$SCH_3$, —$SC_2H_5$ or —$SO_2Cl$)

r=1 to [number of benzene rings in $Z^1$]×2 x=0, 1

(1) —$Z^2$—: (1+r') valent organic group having at least one benzene ring,

-$A^2$=—$(CH_2)_{\alpha'}$—W (0≦α'≦3)

(—W=—OH, —CN or —$CO_2H$)

r'=0 to {number of benzene rings in $Z^2$}×2 x'=0, 1

(2) —$Z^2$—: —$(CH_2)_m$— (m=1 to 24)

-$A^2$=—W (—W=—$SO_3H$, -Hal, —SH, —$SCH_3$, —$SC_2H_5$, —$SO_2Cl$, —OH, —CN or —$CO_2H$)

r'=1 x'=0, 1

—$Y^1$: —$(CF_2)_q$—W (1≦q≦3)

(—W=—$SO_3H$, -Hal, —SH, —$SCH_3$, —$SC_2H_5$, —$SO_2Cl$, —OH, —CN or —$CO_2H$)

—$Y^2$: —H, —OH, —$C_\gamma H_{2\gamma+1}$ (1≦γ≦16)

a, b, c, d: 1.0<a+b+c+d<3.0, 0<a<3.0, 0≦b<3.0, 0≦c<3.0, 0≦d<3.0, 0<b+c

ρ, ρ', ρ", ρ''': 0≦(ρ, ρ', ρ", ρ''')≦2

In the formula (24.2), those compounds in which the first monophosphonic acid ingredient contains sulfophenyl phosphonic acid or sulfonated diphenyl ether (mono)phosphonic acid, the third monophosphonic acid ingredient contains sulfodifluoromethylene phosphonic acid, and the fourth monophosphonic acid ingredient contains inorganic phosphonic acid, phosphoric acid, or methyl phosphonic acid (with no second monophosphonic acid ingredient) are preferred.

[2.4. Fourth Specific Example]

A fourth specific example of the non-crosslinked type layered metal phosphonate compound according to this embodiment includes those having the α-type layered structure and a composition represented by the following formula (24.3). The non-crosslinked type layered metal phosphonate compound represented by the formula (24.3) contains a first monophosphonic acid ingredient having an aliphatic substituent (small-size substituent) having a sulfonic group or a group that can be converted into the sulfonic group $(O_3P—(O)_x—Z^1-(A^1)_r)$ as an essential ingredient (a>0, r≧1). Further, the compound contains one or more of second monophosphonic acid ingredients $(O_3P—(O)_{x'}—Z^2-(A^2)_{r'})$ and a third monophosphonic acid ingredient $(O_3P—Y^1)$ capable of having a small-size substituent having a sulfonic group or a group that can be converted into the sulfonic group as an essential ingredient (0<b+c). A fourth monophosphonic acid ingredient $(O_3P—Y^2)$ is an optional ingredient.

In the formula (24.3), $—Z^2—$ may be any of a (1+r') valent organic group or an alkylene chain but the first monophosphonic acid ingredient and the second monophosphonic acid ingredient are different from each other $(—(O)_x—Z^1-(A^1)_r \neq —(O)_{x'}—Z^2-(A^2)_{r'})$. Further, since the details for $—Z^2—$ in the formula (24.3) are as has been described above, explanations therefor are to be omitted.

[Chemical formula 22]

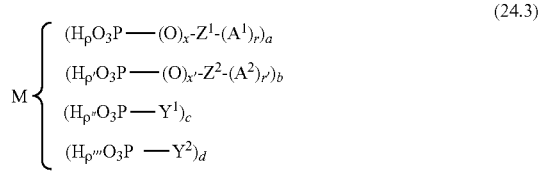

(24.3)

in which

M: hexacoordinate metal atom capable of taking a tetra atomic valence, $—Z^1—$: $—(CH_2)_m—$ (m=1 to 24)

$-A^1=$—W(—W=—SO$_3$H, -Hal, —SH, —SCH$_3$, —SC$_2$H$_5$ or —SO$_2$Cl)

r=1 x'=0, 1

(1) $—Z^2—$: (1+r') valent organic group having at least one benzene ring, $-A^2=$—(CH$_2$)$_{\alpha'}$—W (0≦α'≦3)

(—W=—OH, —CN or —CO$_2$H)

r'=0 to {number of benzene rings in $Z^2$}×2 x'=0, 1

(2) $—Z^2—$: —(CH$_2$)$_m$— (m=1 to 24)

$-A^2=$—W (—W=—SO$_3$H, -Hal, —SH, —SCH$_3$, —SC$_2$H$_5$, —SO$_2$Cl, —OH, —CN or —CO$_2$H)

r'=1 x'=0, 1

$-(O)_x-Z^1-(A^1)_r \neq -(O)_{x'}-Z^2-(A^2)_{r'}$ $—Y^1$: —(CF$_2$)$_q$—W (1≦q≦3)

(—W=—SO$_3$H, -Hal, —SH, —SCH$_3$, —SC$_2$H$_5$, —SO$_2$Cl, —OH, —CN or —CO$_2$H)

$—Y^2$: —H, —OH, —C$_\gamma$H$_{2\gamma+1}$ (1≦γ≦16)

a, b, c, d: 1.0<a+b+c+d<3.0, 0<a<3.0, 0≦b<3.0, 0≦c<3.0, 0≦c<3.0, 0<b+c

ρ, ρ', ρ", ρ''': 0≦(ρ, ρ', ρ", ρ''')≦2

In the formula (24.3), those compounds in which the first monophosphonic acid ingredient includes 3-sulfopropylene phosphonic acid, the second monophosphonic acid ingredient includes sulfophenyl phosphonic acid or sulfonated diphenyl ether (mono)phosphonic acid, the third monophosphonic acid ingredient is not contained or includes sulfodifluoromethylene phosphonic acid, and the fourth monophosphonic acid ingredient includes inorganic phosphonic acid, phosphoric acid, or methyl phosphonic acid are preferred.

[IX Production Process for Non-crosslinked Type Layered Metal Phosphonate Compound]

A production process for the non-crosslinked type layered metal phosphonate compound according to the invention includes a reaction step of reacting two or more monophosphonic acids or derivatives thereof and a metal source under the presence of a sulfuric catalyst.

[1. Monophosphonic Acid and Derivative Thereof]

"Monophosphonic acid" means those having a phosphonic group (—PO(OH)$_2$). The monophosphonic acid may be those in which a P atom in the phosphonic group is bonded directly or by way of an O atom with an organic group (organic monophosphonic acid, organic phosphoric acid) or those in which the P atom is bonded with a group other than the organic group (for example, —H, —OH) (inorganic phosphonic acid, inorganic phosphoric acid). That is, "monophosphonic acid" referred to in the invention also includes those having a phosphoric acid bond. "Derivative of monophosphonic acid" means those in which H atoms in the phosphonic group are entirely or partially substituted by other substituents. The type of the organic group and the substituent is not particularly restricted but can be selected optionally in accordance with the purpose.

As the monophosphonic acid or the derivatives thereof, those represented by the following formula (a2) to formula (d2) are preferred specifically.

In the formula (a2) to (d2), two H atoms in the phosphonic group (—PO(OH)$_2$) may be independently substituted by Cat or —X$^1$ to —X$^4$ respectively. Further, the monophosphonic acid represented by the formula (a2) and the monophosphonic acid represented by the formula (b2) are represented by an identical compositional formula but they represent monophosphonic acids different from each other when both of them are used for the starting material. Since details for each of the symbols in the formula (a2) to formula (d2) are as has been described above, descriptions therefor are to be omitted.

[Chemical formula 23]

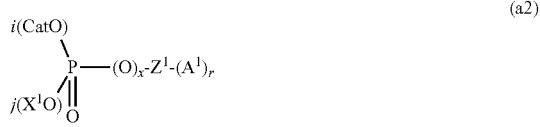

(a2)

in which x: x=0, 1

(1) $—Z^1—$: (1+r) valent organic group having at least one benzene ring, $-A^1=$—(CH$_2$)$_\alpha$—W (0≦α≦3)

(—W=—SO$_3$H, -Hal, —SH, —SCH$_3$, —SC$_2$H$_5$, —SO$_2$Cl, —OH, —CN or —CO$_2$H)

r=0 to [number of benzene rings in $Z^1$]×2

(2) —$Z^1$—: —$(CH_2)_m$— (m=1 to 24)
-$A^1$=—W
(—W=—$SO_3H$, -Hal, —SH, —$SCH_3$, —$SC_2H_5$, —$SO_2Cl$, —OH, —CN or —$CO_2H$)
r=1
—$X^1$—: —H, —$C_nH_{2n+1}$, or —$Si(CH_3)_3$ (n=1 to 3)
Cat: Li, Na, or K
i, j: $0 \leq i \leq 2$, $0 \leq j \leq 2$

[Chemical formula 24]

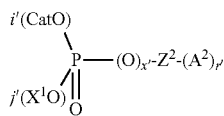

(b2)

in which
x': x'=0, 1
(1) —$Z^2$—: (1+r) valent organic group having at least one benzene ring,
-$A^2$=—$(CH_2)_{\alpha'}$—W ($0 \leq \alpha' \leq 3$)
(—W=—$SO_3H$, -Hal, —SH, —$SCH_3$, —$SC_2H_5$, —$SO_2Cl$, —OH, —CN or —$CO_2H$)
r'=0 to [number of benzene rings in $Z^2$]×2
(2) —$Z^2$—: —$(CH_2)_{m'}$— (m'=1 to 24)
-$A^1$=—W
(—W=—$SO_3H$, -Hal, —SH, —$SCH_3$, —$SC_2H_5$, —$SO_2Cl$, —OH, —CN or —$CO_2H$)
r'=1
—$X^2$: —H, —$C_nH_{2n+1}$, or —$Si(CH_3)_3$ (n=1 to 3)
Cat: Li, Na, or K
i', j' $0 \leq i' \leq 2$, $0 \leq j' \leq 2$

[Chemical formula 25]

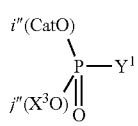

(c2)

in which —$Y^1$: —$(CF_2)_q$—W ($1 \leq q \leq 3$)
(—W=—$SO_3H$, -Hal, —SH, —$SCH_3$, —$SC_2H_5$, —$SO_2Cl$, —OH, —CN or —$CO_2H$)
—$X^3$: —H, —$C_nH_{2n+1}$, or —$Si(CH_3)_3$ (n=1 to 3)
Cat: Li, Na, or K
j'', j'': $0 \leq i'' \leq 2$, $0 \leq j'' \leq 2$

[Chemical formula 26]

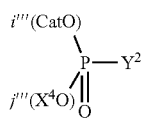

(d2)

in which
—$Y^2$: —H, —OH, —$C_\gamma H_{2\gamma+1}$ ($1 \leq \gamma \leq 16$)
—$X^4$: —H, —$C_nH_{2n+1}$, or —$Si(CH_3)_3$ (n=1 to 3)
Cat: Li, Na, or K
i''', j''': $0 \leq i''' \leq 2$, $0 \leq j''' \leq 2$ For the starting materials, two types of monophosphonic acids or derivatives thereof may be used or three or more of them may also be used. Further, the lengths for the monophosphonic acids or the derivatives thereof may be identical with or may be different from each other.

[2. Metal Source]

"Metal source" means a compound capable of forming an ion of a hexacoordinate metal atom as the central atom (M) of a metal oxide octahedron upon reaction.

The metal source includes, specifically,
(1) oxychlorides such as $ZrOCl_2 \cdot 8H_2O$, $TiOCl_2 \cdot nH_2O$, $HfOCl_2$,
(2) sulfates such as $Zr(SO_4)_2$, $Ti(SO_4)_2$ and $Hf(SO_4)_2$,
(3) acetates such as $Zr(OCOCH_3)_4$, $Cu(OCOCH_3)_2$, and $Pb(OCOCH_3)_4$,
(4) alkoxides such as $Zr(OPr)_4$ and $Ti(OPr)_4$,
(5) chlorides such as $ZrCl_4$, $TiCl_4$, $HfCl_4$, $WCl_4$, $MoCl_4$, $CeCl_4$, $CuCl_2$, $AlCl_3$, $SnCl_4$, and $PbCl_4$,
(6) nitrates such as $Zr(NO_3)_4$, $Ti(NO_3)_4$, and $Al(NO_3)_3$, and
(7) oxysulfates such as $TiOSO_4 \cdot nH_2O$.

They may be used each alone or may be used by two or more in combination.

The type of the metal source sometimes gives an effect on the crystallinity and the grain size of the layered compound. For example, in case of Zr the crystallinity of the layered compound differs in accordance with the type of the metal source. The degree of the crystallinity of the layered compound is in the order of: $Zr(OCOCH_3)_4 > Zr(OPr)_4 > Zr(SO_4)_2 > ZrOCl_2 \cdot 8H_2O$.

[3. Condition for Starting Material]

As the starting material, those satisfying the following conditions are used.

[3.1 Condition (a)]

The blending ratio of monophosphonic acid or the derivative thereof and the metal source is such that the molar ratio (M/P ratio) of the central atom (M) to the amount of P contained in the monophosphonic group or the derivative thereof is: $1/3 < M/P < 1.0$.

The M/P ratio for the layered metal phosphonate compound is theoretically 1/2. However, depending on the synthesis conditions, a portion of the tetrahedron is depleted or a portion of the octahedron of the metal oxide is depleted sometimes. Accordingly, the M/P ratio may be deviated somewhat from 1/2.

However, in a case where the deviation of the M/P ratio is excessive, it become difficult to maintain the highly crystalline layered structure. Accordingly, M/P ratio is preferably: $1/3 < M/P < 1.0$.

For the starting material, it is preferred to use those further satisfying the following conditions (b) and/or (c).

[3.2 Condition (b)]

The blending ratio of the monophosphonic acid or the derivatives thereof is such that the average molecular cross sectional area for the substituent of the monophosphonic acid ingredient constituting the non-crosslinked type layered metal phosphonate compound is 70% or less of the free area of one surface phosphonic group of the two dimensional layered structure.

"The monophosphonic acid ingredient constituting the non-crosslinked type layered metal phosphonate compound" represents the monophosphonic acid ingredient after the introduction of the sulfonic group in a case for example, of introducing the sulfonic group by the post-sulfonation after the synthesis of the layered compound not having the sulfonic group.

In the invention, since the sulfuric acid is used as the catalyst, the starting composition is reflected as it is on the copolymerized composition. Accordingly, when optimizing the blending ratio of the starting materials such that the average molecular cross sectional area of the starting material (or monophosphonic acid ingredient after post treatment in a case of applying the post treatment after the synthesis of the layered compound) to 70% or less of the free area in addition to the M/P ratio, since they are introduced uniformly to the layer surface, there is less possibility that the crystallinity is lowered by the steric hindrance.

[3.3 Condition (c)]

At least one of the monophosphonic acids or the derivatives thereof has a sulfonic group or a group that can be converted into the sulfonic group.

A portion of the non-crosslinked type layered metal phosphonate compound according to the invention can be produced also by the post-sulfonation. However, instable groups may sometimes be lost upon sulfonation in the post-sulfonation. On the contrary, in a case of previously using a monophosphonic acid having a sulfonic group or a group that can be converted into the sulfonic group for the starting material, non-crosslinked type layered metal phosphonate compound having a group instable to sulfonation can be synthesized.

So long as the condition (a) described above is satisfied, the sulfonic group or the group that can be converted into the sulfonic group may be contained in two or more starting materials, or may be contained in all starting materials. Further, for obtaining a layered compound of higher crystallinity, it is preferred to further satisfy the condition (b).

[4. Sulfuric Acid Catalyst]

In the invention, sulfuric acid is used as the catalyst. This is different from the existent method. Upon synthesis, sulfuric acid may be added to isolated monophosphonic acid or the derivative thereof. Alternatively, sulfuric acid contained in a stock solution to be described later may be used as it is as the catalyst. Particularly, since the method of using the stock solution requires no isolation operation, there is no restriction on the type of the monophosphonic acid used for the synthesis and it is possible to synthesize non-crosslinked type layered metal phosphonate compounds of all types of compositions.

The concentration for the sulfuric acid in the reaction solution is selected optimally in accordance with the type of the central atom (M). For example, in the case where the central atom (M) is Zr, a layered compound of higher crystallinity is obtained as the concentration of sulfuric acid is higher. In this case, specifically, the concentration of sulfuric acid is preferably 5N or more and, more preferably, 9N or more.

On the other hand, in a case where the central atom (M) is Ti, a layered compound of high crystallinity is obtained even when the concentration of sulfuric acid is 5N or less.

The sulfuric acid functions not only as the synthesis catalyst for the layered compound but also as a catalyst for hydrolyzing the phosphonate ester into phosphonic acid. Accordingly, when the sulfuric acid catalyst is used, it is possible to use a phosphonate ester as the starting material for synthesizing the layered compound. That is, since the phosphonic acid may not always be used as the starting material, a step of hydrolyzing the phosphonate ester is not required.

[6. Reaction Method]

When the monophosphonic acid or the derivatives thereof and the metal compound are blended at a predetermined ratio and reacted under the presence of a sulfuric acid catalyst, a non-crosslinked type layered metal phosphonate compound according to the invention is obtained. In this case, when reaction is carried out while stirring the starting solution under heating, a layered compound of high crystallinity is obtained.

The reaction time is selected optimally in accordance with the type and the composition of the starting material and the reaction temperature. In a case of using other methods, the reaction time is usually about 24 hours. On the contrary, when the sulfuric acid catalyst is used, the reaction time can be shortened to 5 to 1 hours. Accordingly, it is possible to synthesize a multi-ingredient non-crosslinked type layered metal phosphonate compound having high crystallinity for the layered structure although the particle size is small and having copolymerized composition reflecting the starting composition.

The reaction is carried out by reacting the starting materials blended at a predetermined ratio simultaneously under the presence of the sulfuric catalyst. In this case, sulfuric acid may also be added to a mixture of isolated starting materials.

Alternatively, a stock solution may be prepared previously, to which (1) a metal source, and
(2) remaining ingredients of the monophosphonic acid or the derivative thereof, may be added.

"Stock solution" means those in which at least one of the monophosphonic acid or the derivative thereof for synthesizing the non-crosslinked type layered metal phosphonate compound and having a sulfonic group or a group that can be converted into the sulfonic group is dissolved or dispersed in an aqueous solution of sulfuric acid or a mixed solution of the aqueous solution of sulfuric acid and an organic solvent.

The stock solution may contain one type of phosphonic acid having a sulfonic group or a group that can be converted into the sulfonic group or a derivative thereof or may contain two or more of them. Further, the stock solution may contain one or more phosphonic acid or derivatives thereof having a sulfonic group or a group that can be converted into sulfonic group and, in addition, one or more phosphonic acids or derivatives thereof not having the sulfonic group or the group that can be converted into the sulfonic group.

Further, for the synthesis, one stock solution may be used, or two or more stock solutions different in the type of the dissolved phosphonic acid or the derivative thereof may be used in combination.

In a case where one of the monophosphonic acid or the derivatives thereof used as the starting material has at least one benzene ring, a phosphonic acid or a derivative thereof not having a sulfonic group or a group that can be converted into the sulfonic group can be used as the starting material for synthesizing the layered compound. In this case, after synthesizing a layered compound not having a sulfonic group or a group that can be converted into the sulfonic group under the presence of the sulfuric acid catalyst, a sulfonic group or a group that can be converted into the sulfonic group is introduced to the benzene ring by post-sulfonation.

[X Stock Solution (2)]

The stock solution according to the invention includes one or more member selected from monophosphonic acids having a sulfonic group or a group that can be converted into the sulfonic group and derivatives thereof dissolved or dispersed in an aqueous solution of sulfuric acid or a mixed solution of the aqueous solution of sulfuric acid and an organic solvent.

The stock solution may contain a phosphonic acid having a sulfonic group or a group that can be converted into the sulfonic group or the derivatives thereof, or may contain two or more of them. Further, the stock solution may also contain, in addition to one or more phosphonic acids having a sulfonic group or a group that can be converted into the sulfonic group or derivatives thereof, one or more phosphonic acids not having a sulfonic group or a group that can be converted into the sulfonic group or derivatives thereof.

Further, the stock solution may also contain, in addition to the aqueous solution of sulfuric acid, organic solvents such as DMSO, sulfolane, and diglime. Some organic solvents have a function of promoting reaction between a metal source and monophosphonic acid, or derivatives thereof.

The concentration of sulfuric acid, the concentration of the organic solvent, the concentration of the phosphonic acid or derivatives thereof contained in the stock solution are not particularly restricted and can be selected optionally in accordance with the purpose.

Since details for the group that can be converted into the sulfonic group, the monophosphonic acids and derivatives thereof are as have been described above, descriptions therefor are to be omitted.

[XI. Production Process for Stock Solution (2)]

The production process for the stock solution according to the invention includes a sulfonation step and a dilution step.

The sulfonation step is a step of adding for sulfonation a sulfonating agent to at least one monophosphonic acid and derivative thereof. It is necessary that the sulfonation step is conducted under a non-aqueous condition such as under a nitrogen gas stream.

As the sulfonating agent, concentrated sulfuric acid, fuming sulfuric acid ($H_2SO_4 \cdot nSO_3$), sulfuric trioxide ($SO_3$), chlorosulfonic acid ($ClSO_3H$), etc. can be used.

The phosphonic acid or the derivative thereof to be reacted with the sulfonating agent may be an aliphatic compound but those having at least one benzene ring in the molecule are preferred. When such phosphonic acid or the derivative thereof and the sulfonating agent are reacted, the sulfonic group or the group that can be converted into the sulfonic group can be introduced easily to the benzene ring. Further, when the reaction condition is optimized, the number of sulfonic groups, or the groups that can be converted into the sulfonic groups to be introduced into the benzene ring can be controlled.

The dilution step is a step of adding water for dilution to the reaction solution obtained in the sulfonation step.

When water is added to the reaction solution, an excess sulfonating agent is converted into sulfuric acid. In this case, when the dilution amount of water is controlled, the concentration of sulfuric acid and the concentration of the phosphonic acid or the derivative thereof in the stock solution can be controlled. Further, after dilution with water, an organic solvent such as DMSO, sulfolane, or diglime may also be added optionally.

A non-crosslinked type layered metal phosphonate compound according to the invention is obtained by portioning the stock solution into a required amount, further adding water optionally thereto for dilution, then adding a metal source and other phosphonic acid or a derivative thereof (including those in the form of a stock solution) optionally and by reacting them.

[XII Effect of Non-crosslinked Type Layered Metal Phosphonate Compound and Production Process Therefor]

In a case of synthesizing a non-crosslinked type layered metal phosphonate compound, when HF is used as a catalyst, a layered compound of high crystallinity is obtained. It is considered that a soluble intermediate reaction product $ZrF_6$ is formed and reaction with phosphonic acid proceeds moderately when HF is used as the catalyst. However, the method involves a drawback that a plurality types of phosphonic acids cannot be introduced uniformly in the layered structure. This is considered that the reactivity between the intermediate reaction product $ZrF_6$ and the phosphonic acid is different depending on the type of the phosphonic acid. Further, use of HF as the catalyst involves a problem that F atoms intrude into the synthesized compound.

On the other hand, a method of hydrothermic reaction or a method of using HCl or HBr as a catalyst has an advantage capable of obtaining a layered compound in which a plurality types of phosphonic acids are introduced uniformly. Further, F atoms do not intrude into the synthesized compound. However, it has a drawback that the crystallinity of the layered compound obtained by the method is lower compared with the case of using HF as the catalyst.

On the contrary, when sulfuric acid is used as the catalyst, not only the F atoms do not intrude but also the crystallinity is extremely high, and a copolymerized composition reflecting the starting composition can be obtained. Although the reaction mechanism has not yet been apparent, it is considered to be attributable to that:

(1) the ion of the central metal (M) forms a water soluble complex salt together with $SO_4^{2-}$ and this reacts moderately with the phosphonic acid, and (2) no remarkable difference appears for the reactivity between the ion of the central metal (M) and the phosphonic acid even when different types of phosphonic acids are present during reaction since $SO_4^{-2}$ is an anion of a larger-size compared with F.

Further, in a case of synthesizing the non-crosslinked type layered metal phosphonate compound, when the stock solution is used.

(1) isolation of a sulfonated organic phosphonic acid is no more required, (2) the site for introducing the sulfonic group can be selected freely and sulfonic groups can be introduced easily also for two or more monophosphonic acid ingredients, and (3) the stock solution contains sulfuric acid as a byproduct upon sulfonation of the phosphonic acid, and the sulfuric acid can be utilized as a reaction catalyst for the metal source. Accordingly, not only the sulfonation product of the phosphonic acid ingredient for which no isolation method has yet been established can be introduced easily but also the sulfonation product and the non-sulfonation product of the phosphonic acid ingredient can be introduced at an optional ratio. Further, even a phosphonic acid ingredient having a substituent instable to the post-sulfonation can be introduced.

(4) Since sulfonation products of various monophosphonic acids of different sulfonation degrees (for example, monophosphonic acids having a monosulfonated diphenyl ether group or a disulfonated diphenyl ether group) can be obtained by controlling the synthesis condition for the stock solution, the sulfonation degree of the layered compound can be controlled freely by using them as the starting material.

Further, since various types of phosphonic acid ingredients can be uniformly introduced easily, the degree of freedom for the material design is higher compared with the existent method.

For example, when a plurality of phosphonic acids of different structures are used for the starting material, arrangement of the sulfonic groups in the layered compound and circumstance around them can be controlled. For example, since the sulfophenyl group is a large-size substituent, when all the phosphonic acid tetrahedrons in the layered structure are substituted by the phosphonic ingredients having the sulfophenyl group, the crystallinity of the layered compound is lowered. However, in a case of using a phosphonic acid having a large-size substituent such as the sulfophenyl group and a phosphonic acid having a small-size substituent (—Y) in combination, the steric hindrance of the large-size substituent can be moderated, so that the introduction position of the sulfonic group can be freely controlled relatively without lowering the crystallinity of the layered compound.

Since the non-crosslinked type layered metal phosphonate compound obtained as described above has an inorganic two dimensional layered structure as the main chain, it is more durable to hydrogen peroxide compared with existent polymeric electrolytes. Further, since the crystallinity is increased more compared with those obtained by hydrothermic reaction or HCl catalytic reaction, durability to hydrolysis is also high. Further, since HF is not used as the catalyst, there is no possibility of introducing F atoms that may possibly result in environmental problems.

EXAMPLE

[Instrumental Analysis]

X-ray powder diffractometry (XRD) was carried out by Rigaku RINT-2200 diffractometer using Cu—Kα as a source. $^{13}$C NMR measurement and $^{31}$P NMR measurement were carried out by Advance 400 manufactured by Bruker Co. using tetramethyl silane and 85% phosphoric acid respectively as an external standard. For IR measurement, a sample powder was directly measured by an attenuated total reflection method (ATR) using Avantar 360FT-IR manufactured by Nicolet Co. For the solution NMR, a sample dissolved in DMSO-$d_6$ was measured by JNM Lambda 500 manufactured by JEOL Co.

[Adsorption Measurement]

For $N_2$ adsorptiometry, Autosorb-1 manufactured by Quantachrome Co. was used. A sample of about 30 mg was weighed in a sample tube and, after evacuation at 120° C. for 8 hours, nitrogen adsorptiometry was carried out while immersing the sample tube in liquid nitrogen, to obtain a nitrogen adsorption isothermal curve. Steam adsorptiometry was carried out by using an automatic steam adsorption measuring apparatus: BELSORP 18 manufactured by Bell Japan Inc.

[Neutralization Titration]

A sample in an amount of sulfonic acid of about 250 μeq was taken in a 100 mL beaker, 25 mL of 2M NaCl aqueous solution was added and they were sealed and stirred for one night. Then, after dilution with 200 mL of water, it was titrated with 0.05M NaOH by using an automatic titrator "Tinet" manufactured by Metrohm Co. to obtain a titration curve.

Example 1

[Synthesis Of Biphenyl Bismethylene Crosslinked Type 2-ingredient Zirconium Phosphonate Copolymer Having Substituent R and Sulfonation Product Thereof (1): Synthesis of Copolymer by 12N Sulfuric Acid-catalytic Reaction and Post-sulfonation]

Biphenyl bismethylene crosslinked type zirconium phosphonate copolymers having a hydrogen group or a methyl group as the substituent R (ZP1362, ZP1350) were synthesized by reaction using 12N sulfuric acid as a catalyst. Then, they were sulfonated in fuming sulfuric acid to synthesize sulfonation products of biphenyl bismethylene crosslinked type zirconium phosphonates (ZP1385, ZP1386). For the starting composition, the molar ratio of biphenyl bismethylene phosphonic acid and phosphonic acid having the substituent R was 0.33:1.34.

For comparison, a biphenyl bismethylene crosslinked type zirconium phosphonate (ZP1365) not having the substituent R was synthesized by 12N sulfuric acid-catalytic reaction in the same manner. Specific operation methods for the synthesis of ZP1362 and ZP1385 are to be described below.

[1. Synthesis of Sample]

Biphenyl-4,4'-bis(diethyl methylene phosphonate ester) (1.02 g, 2.2 mmol) and a 50 wt % aqueous solution of phosphonic acid (1.11 g, 8.8 mmol) were taken in a 100 mL round-bottom flask and dispersed with addition of 20 mL of 12N sulfuric acid and 20 mL of dimethylsulfoxide (DMSO). The mixture was heated to 100° C. and stirred for 2 hours. $ZrOCl_2 \cdot 8H_2O$ (2.17 g, 6.72 mmol) dissolved in 3 mL of water was added dropwise for 20 min to the clear solution. White precipitation was resulted instantly to form a clouded liquid dispersion and stirring was continued at that temperature for 24 hours to conduct reaction. After pouring the reaction mixture into 200 mL of water, and stirring for one hour, it was centrifuged to take out a solid content. The crude product was dispersed in 400 mL of water and stirred under heating at a refluxing temperature for one hour, and then solids were recovered by filtration. They were dried in vacuum to obtain a product ZP1362 (2.1 g; yield 97%).

Then, ZP1362 (0.97 g) was taken in a 50 mL round-bottom flask and dissolved with addition of a concentrated sulfuric acid (18 g) slowly. 60% fuming sulfuric acid (12 g) was added carefully into the solution and sealed, and stirring was continued at a room temperature for one day. The $SO_3$ concentration in this case corresponded to 24%. After the completion of the reaction, the reaction mixture was added carefully onto ice obtained from 50 g of distilled water in a 200 mL beaker (exothermic), and stirred for one hour. Solids taken out by centrifugation were dispersed in 300 mL of water and stirred under heating at a refluxing temperature for one hour and then the solids was recovered by filtration. They were dried in vacuum to obtain a product ZP1385 (1.1 g; yield 81%).

[2. Evaluation for Sample]

Figure 2:
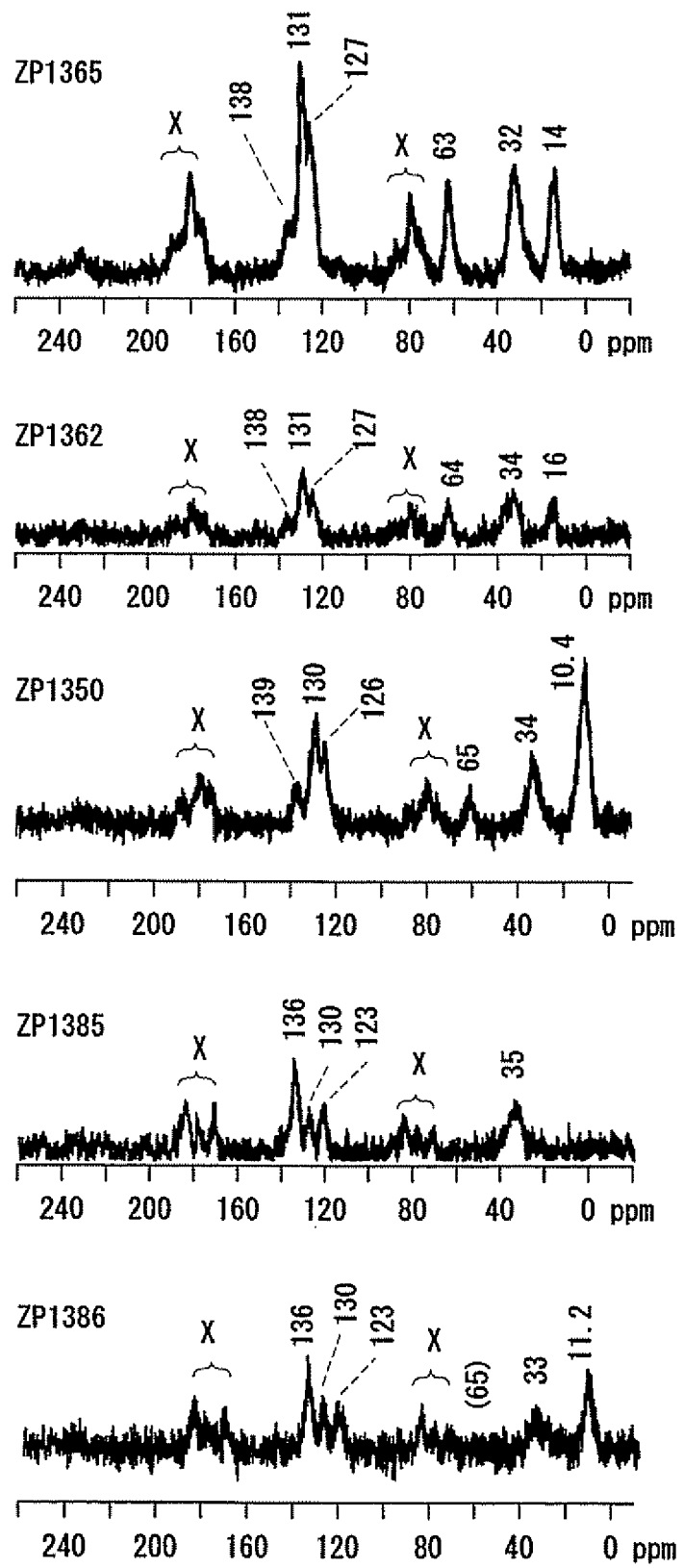
FIG. 2 is $^{13}$C MAS-NMR spectra (X: spinning side band) for non-sulfonation products and sulfonation products (post-sulfonation) of a copolymers of biphenyl bismethylene crosslinked type 2-ingredient zirconium phosphonates.
Figure 3:
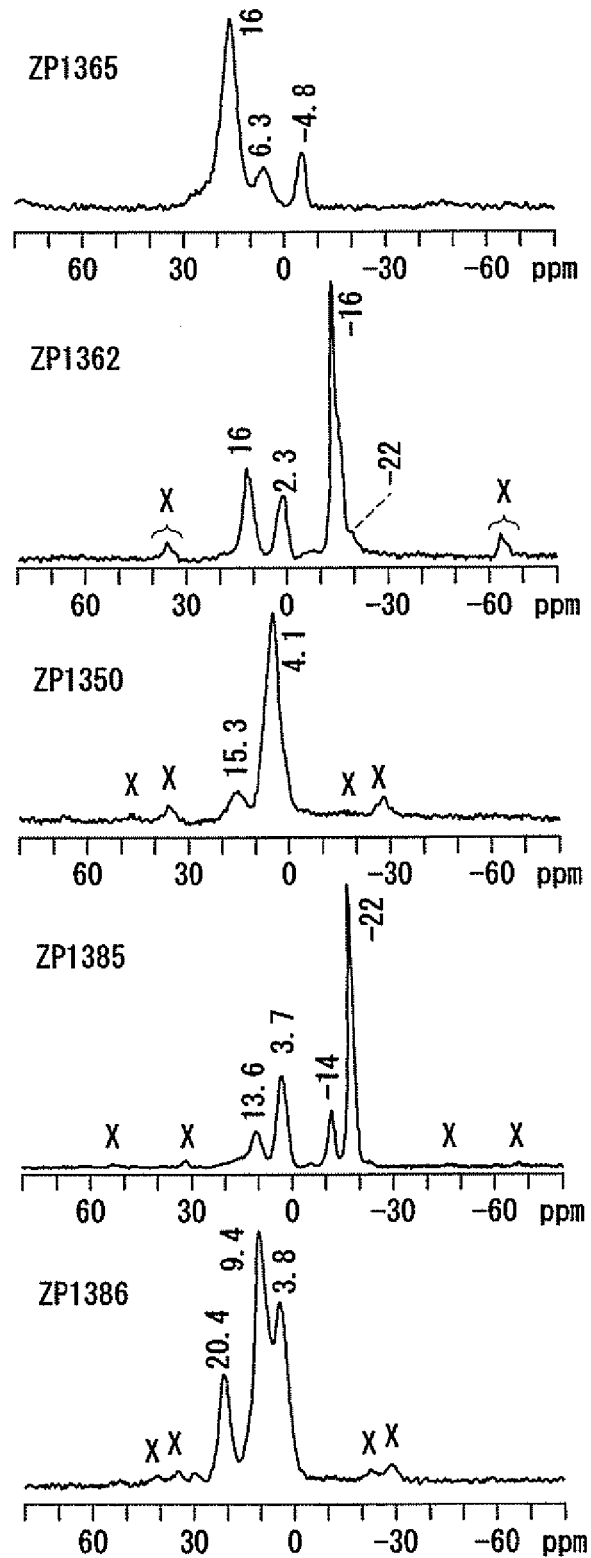
FIG. 3 is $^{31}$P MAS-NMR spectra (X: spinning side band) for non-sulfonation products and sulfonation products (post-sulfonation) of copolymers of biphenyl bismethylene crosslinked type 2-ingredient zirconium phosphonates.
Figure 4:
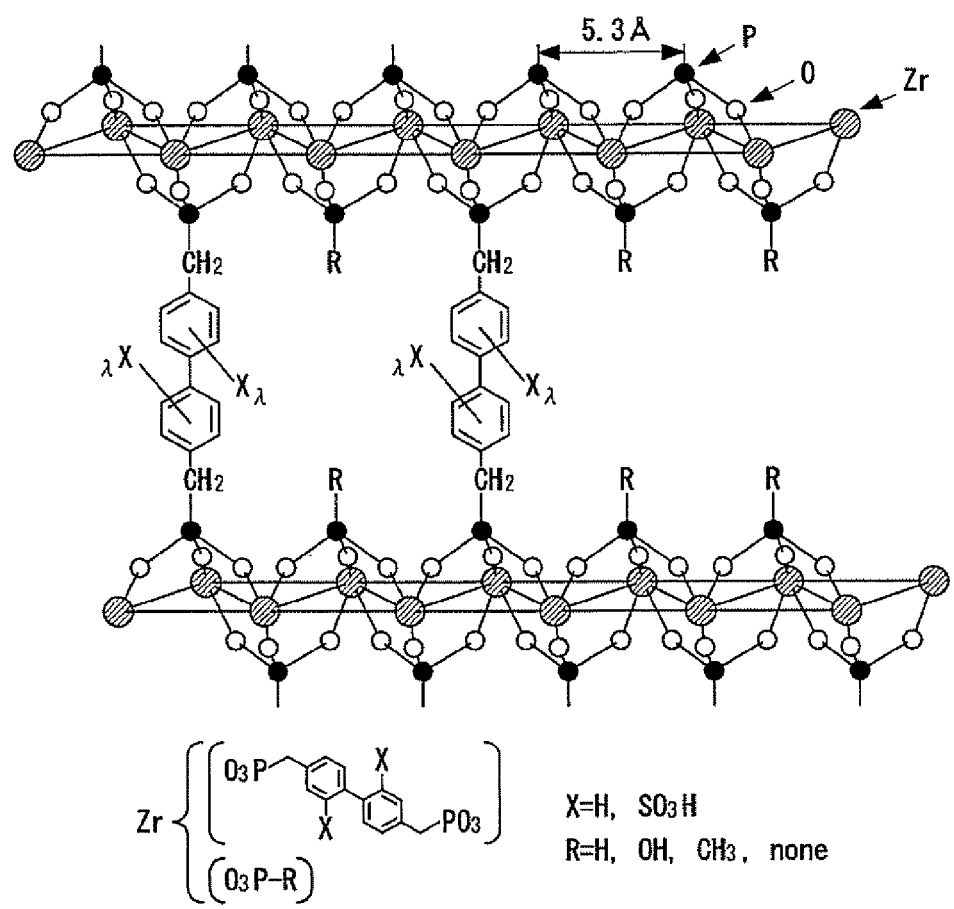
FIG. 4 is a structural model of a non-sulfonation product and a sulfonation product of a copolymer of biphenyl bismethylene crosslinked type 2-ingredient zirconium phosphonates.

For all the products described above, XRD patterns are shown in FIG. 1, $^{13}$C MAS-NMR spectra are shown in FIG. 2, and $^{31}$P MAS-NMR spectra are shown in FIG. 3, collectively. In the XRD patterns for all products, since the presence of d(001) series and/or the presence of asymmetric (hk) peaks are observed, presence of an α-type lameller (layered) structure is suggested. Then, the d(020) peak observed near 2.65 Å (0.265 nm) suggests the α-type layered structure derived from zirconium phosphonate. d(001) peaks corresponding to the inter-layer distance were observed in common near 14 Å. Expected structure and structural formula of the products are shown in FIG. 4.

ZP1362 and ZP1350 of non-sulfonated biphenyl bismethylene crosslinked type 2-ingredient copolymers are compared with the biphenylbismethylene phosphonate homopolymer ZP1365. At first, for the comparative sample ZP1365, it is suggested that the crystallinity of the layered structure is not so high since the (hk) reflection is indistinct in the XRD pattern (FIG. 1). This is considered that bonding between phosphonic acid and $Zr^{4+}$ is more incomplete since an ethyl phosphonate portion remains as shown by peaks at 14 ppm and 63 ppm in $^{13}$C MAS-NMR spectra (FIG. 2) and that the relative intensity of a peak (about 15 ppm) attributable to the P atom bonded by way of one Zr atom and O atom is higher compared with peaks (about −5 ppm and 2-6 ppm) attributable to the P atom bonded by way of three and two Zr atoms and O atoms by in $^{13}$P MAS-NMR spectra (FIG. 3). That is, it is considered that the diphosphonic acid ingredient is not reacted completely on both ends due to the steric hindrance.

On the other hand, in the biphenyl bismethylene crosslinked type zirconium phosphonate copolymers introduced with the phosphonic acid ingredient having a hydrogen group or methyl group (ZP1362, ZP1350), the (hk) reflection is more distinct in the XRD pattern (FIG. 1), and the relative intensity of the peak (about 15 ppm) attributable to the P atom bonded by way of one Zr atom and O atom is lower in $^{31}$P MSA-NMR spectra (FIG. 3). This suggests that steric hindrance is moderated by the introduction of a compact substituent to improve the reactivity between $Zr^{4+}$ and both ends of the diphosphonic acid.

Introduction of the hydrogen group was confirmed at −16 ppm peak in $^{31}$P MAS-NMR spectra (FIG. 3) and 2456 cm$^{-1}$ absorption in IR. Further, introduction of the methyl group was confirmed at 4.1 ppm peak in $^{31}$P MAS-NMR spectra (FIG. 3), 10.4 ppm peak in $^{13}$C MAS-NMR spectra (FIG. 2), and 785 cm$^{-1}$ adsorption in IR.

The non-sulfonated biphenyl bismethylene crosslinked type 2-ingredient copolymers (ZP1362, ZP1350) are investigated in comparison with the sulfonated biphenyl bismethylene phosphonic acid copolymers (ZP1385, ZP1386) treated by post-sulfonation.

It can be confirmed that the layered structure is kept from the XRD-patterns (FIG. 1). For ZP1386, a 8.9 Å peak was observed along with a d(001) peak near 14 Å and this is considered that the phosphonic acid ingredient is re-arranged in the course of the post sulfonation to by-produce a homopolymer Zr (O$_3$P—CH$_3$)$_2$. In the $^{13}$C MAS-NMR spectra (FIG. 2) for the (ZP1385, ZP1386), change was observed for the relative intensity of the peak attributable to the aromatic carbon. That is, the relative intensity of peaks at 130 ppm, 123 ppm to the 136 ppm peak was reversed and lowered after post-sulfonation. The reversion of the intensity suggests sulfonation on the aromatic ring.

Further, in the post sulfonated copolymers (ZP1385, ZP1386), peaks near 65 ppm, 15 ppm attributable to the unreacted ester portion of the diphosphonic acid observed for the non-sulfonated copolymer disappeared. Further, in the $^{31}$P MAS-NMR spectra (FIG. 3) thereof, the relative intensity of the peak (2-6 ppm) attributable to the P atom bonded by way of two Zr atoms and O atoms was increased compared with the peak (about 15-20 ppm) attributable to the P atom bonded by way of one Zr atom and O atom. The results suggest that reaction of the phosphonic acid ingredient proceeded in the course of the post sulfonation proceeds.

It is suggested that most of hydrogen groups were oxidized to P—OH in ZP1385 by the appearance of peak at −22 ppm in the $^{31}$P MAS-NMR spectra (FIG. 3) and disappearance of 2456 cm$^{-1}$ absorption in IR. Further, it was confirmed that the methyl group in ZP1386 was kept by a peak at 9.4 ppm, in $^{31}$P MAS-NMR spectra (FIG. 3), a peak at 11.2 ppm in $^{13}$C MAS-NMR spectra (FIG. 2), and absorption at 783 cm$^{-1}$ in IR.

The result for the measurement of the BET specific surface area by nitrogen adsorption and measurement for the EW value by neutralization titration for the copolymers before and after post sulfonation are collectively shown in Table 1.

The BET specific surface area of 305 m$^2$/g (ZP1362) and 467 m$^2$/g (ZP1350) of non-sulfonated copolymers were lowered to small values both to less than the measuring limit in the sulfonated copolymers (ZP1385, ZP1386). EW value of the sulfonated copolymers was 330 (theoretical value 581) for ZP1385 and 320 (theoretical value 577) for ZP1386. However, it is apparent that the sulfonated polymers are not dissolved in water in view of the post treatment operation in the term of experiment.

TABLE 1

| | R | X | d(001) Å | d(020) Å | IR cm$^{-1}$ | BET m$^2$/g | EW (Theoretical value) g/mol |
|---|---|---|---|---|---|---|---|
| ZP1365 | none | H | 14.0 | 2.61 | — | 309 | — |
| ZP1362 | H | H | 14.2 | 2.69 | 2456 | 305 | — |
| ZP1350 | CH$_3$ | H | 14.8 | 2.63 | 786 | 467 | — |
| ZP1385 | OH | SO$_3$H | 14.0 | 2.64 | — | over | 330(581) |
| ZP1386 | CH$_3$ | SO$_3$H | 14.0 | 2.66 | 783 | over | 320(577) |

For the biphenyl bismethylene crosslinked type zirconium phosphonate copolymers introduced with the phosphonic acid ingredient having a hydrogen group, the copolymerized composition was investigated by the comparison of the peak areas in $^{31}$P MAS-NMR spectra (FIG. 3). Since the area ratio of the P—H peak to the peak area derived from the biphenyl bismethylene diphosphonic acid is 1:1.4 in the non-sulfonation product ZP1362, and the ratio of the total area for both peaks of P—OH and P—H to the peak area derived from the diphosphonic acid in the sulfonation product ZP1385 is 1:1.5, it can be considered that the starting composition per one P atom (0.33×2:1.33 ≈1:2) is reflected on the copolymerized composition in both cases.

Example 2

[Synthesis of Biphenyl Bismethylene Crosslinked Type 2-ingredient Zirconium Phosphonate Copolymer Having Substituent R (2): Synthesis of Copolymer by 12N Sulfuric Acid-catalytic Reaction and Stock Solution Method]

A biphenyl bismethylene diphosphonic acid ester was at first sulfonated to form a stock solution of 12N sulfuric acid, and sulfonated biphenyl bismethylene crosslinked type zirconium phosphonate copolymers having a substituent R of hydrogen group, methyl group, and hydroxyl group (ZP1400, ZP1414, ZP1422) were synthesized directly using the stock solution by 12N sulfuric acid-catalytic reaction. In this case, the starting composition was defined such that the molar ratio of the sulfonated biphenyl bismethylene phosphoric acid in the stock solution and the phosphonic acid having the substituent R was 0.33:1.34. Specific operation methods are to be described below for the synthesis of ZP1400.

[1. Preparation of Sample]

Biphenyl-4,4'-bis(diethyl ester methylene phosphonate) (10.2 g, 22 mmol) was taken in a 500 mL round-bottom flask, and stirred under heating at 80° C. for one day with addition of a 25% fuming sulfuric acid (73.8 g, 229 mmol) under a nitrogen gas stream. Then, after cooling the reaction mixture in an ice bath, water (97.6 g) was added to form a 12N sulfuric acid solution of a disulfonation product of biphenyl-4,4'-bis (methylene phosphonic acid). This stock solution was portioned into a predetermined small amount and used for the synthesis of a crosslinked zirconium phosphonate copolymer.

The stock solution containing 2.2 mmol of a sulfonation product of biphenyl-4,4'-bis(methylene phosphonic acid) and a 50 wt % aqueous solution of phosphonic acid (1.47 g, 9.0 mmol) were taken in a 100 mL round-bottom flask and 20 mL of DMSO was added. ZrOCl$_2$.8H$_2$O (2.2 g, 6.7 mmol) dissolved in 3 mL of water was added dropwise for 15 min into the mixture which was heated at 100° C. and stirred. Precipitation occurs instantly to form a clouded liquid dispersion and reaction was conducted while continuing stirring at that temperature for 24 hours. After pouring the reaction mixture into 200 mL of water and then stirring for one hour, they were centrifugated to take out solids by decantation. The solids were dispersed in 400 mL of water and stirred under heating at a refluxing temperature for one hour. Solids obtained by filtration were vacuum-dried at 80° C. to obtain a product ZP1400 (2.3 g; yield 95%).

[2. Evaluation for Sample]

Figure 5:
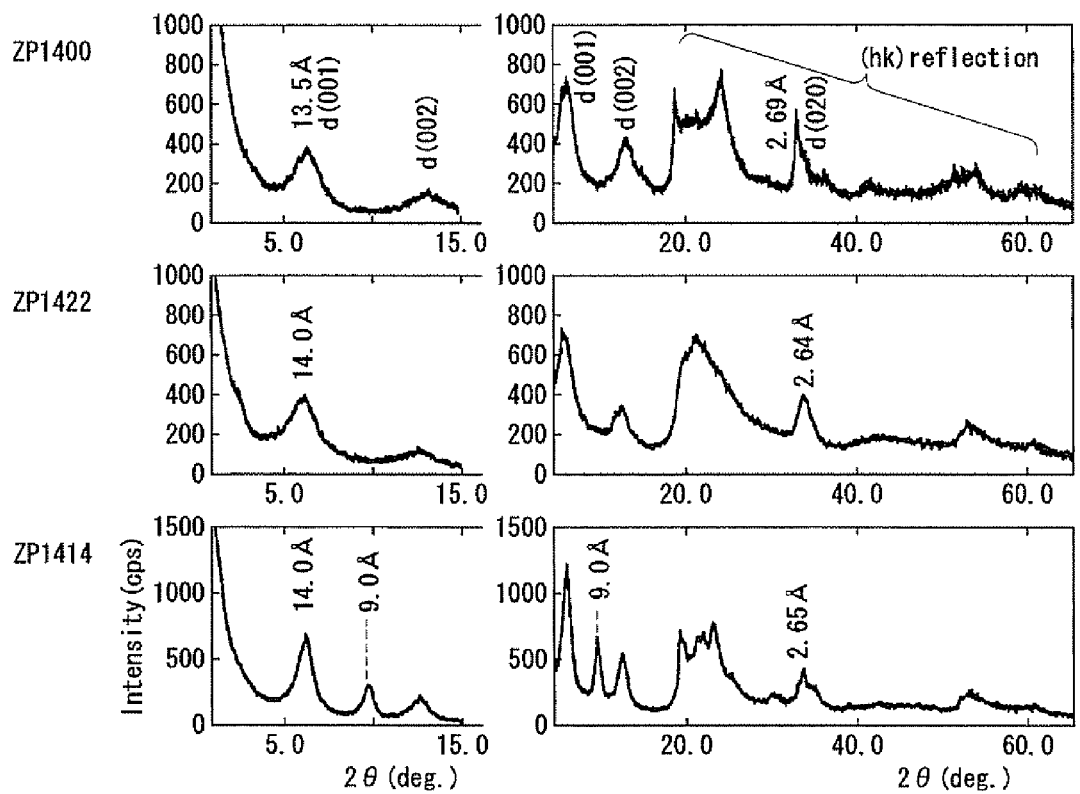
FIG. 5 is XRD patterns of copolymers of sulfonated biphenyl bismethylene crosslinked type 2-ingredient zirconium phosphonates synthesized by a stock solution method.
Figure 6:
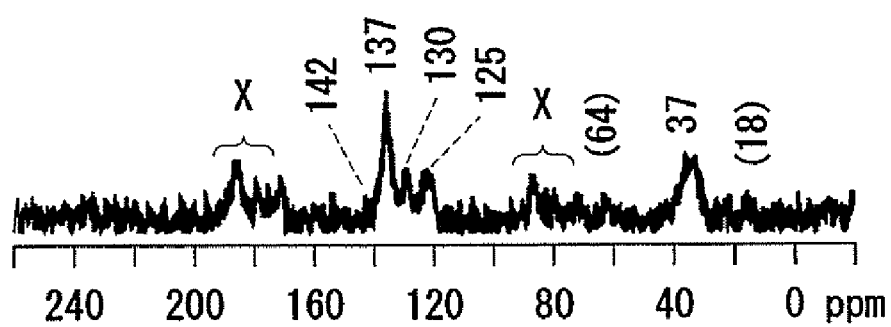
FIG. 6 is a $^{13}$C MAS-NMR spectrum (X: spinning side band) of a copolymer (ZP 1400) of a sulfonated biphenyl bismethylene crosslinked type 2-ingredient zirconium phosphonates synthesized by a stock solution method.
Figure 7:
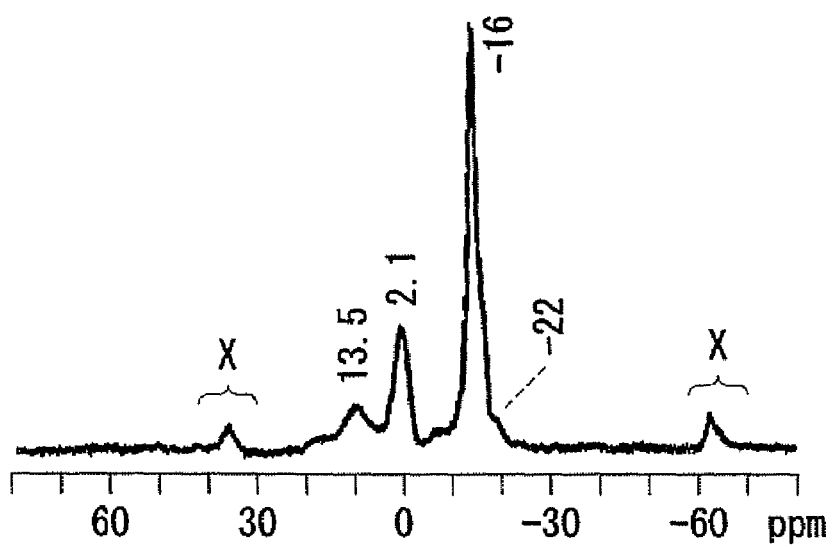
FIG. 7 is a $^{31}$P MAS-NMR spectrum (X: spinning side band) of a copolymer (ZP 1400) of a sulfonated biphenyl bismethylene crosslinked type 2-ingredient zirconium phosphonates synthesized by a stock solution method.

Since a d(001) peak at about 14 Å and distinct (hk) reflection are present in XRD pattern (FIG. 5) for the product ZP1400, formation of a α-type lamellar (layered) structure is suggested. Further, in $^{13}$C MAS-NMR spectra (FIG. 6), since the relative intensity of a peak at 137 ppm to peaks at 130 ppm, 125 ppm attributable to the aromatic carbon is increased and a relation identical with that for ZP1385 synthesized by the post-sulfonation is observed, sulfonation on the aromatic ring can be confirmed. Further, in view of the absence of peaks near 65 ppm, 15 ppm, it has been confirmed that no unreacted ester portions remain in the diphosphonic acid ingredient. Further, since the relative intensity of a peak (2 ppm) attributable to the P atom bonded by way of two Zr atoms and O atoms in the $^{13}$P MAS-NMR spectra (FIG. 7) compared with a peak (about 14 ppm) attributable to the P atom bonded by way of one Zr atom and O atom is at an intensity about identical with that of ZP1385, it can be seen that the reaction of the diphosphonic acid ingredient is promoted.

On other hand, a peak at −16 ppm and 2458 cm$^{-1}$ absorption of IR suggest that the hydrogen group was kept. Then, since the ratio of the P—H peak area to the peak area derived from the diphosphonic acid is 1:1.4 in the copolymerized composition of ZP1400, it can be regarded that the starting composition per one P atom (1:2) is reflected also in this synthesis method. However, the BET specific surface area is 411 m$^2$/g and the EW value is 1120 (theoretical value 549) (Table 2).

The results are different from those for ZP1385 synthesized by the post-sulfonation. In the synthesis of ZP1400, it is estimated that desulfonation occurred partially from the diphosphonic acid ingredient upon forming the crosslinked copolymer from the sulfonated biphenyl bismethylene diphosphonic acid.

Figure 8:
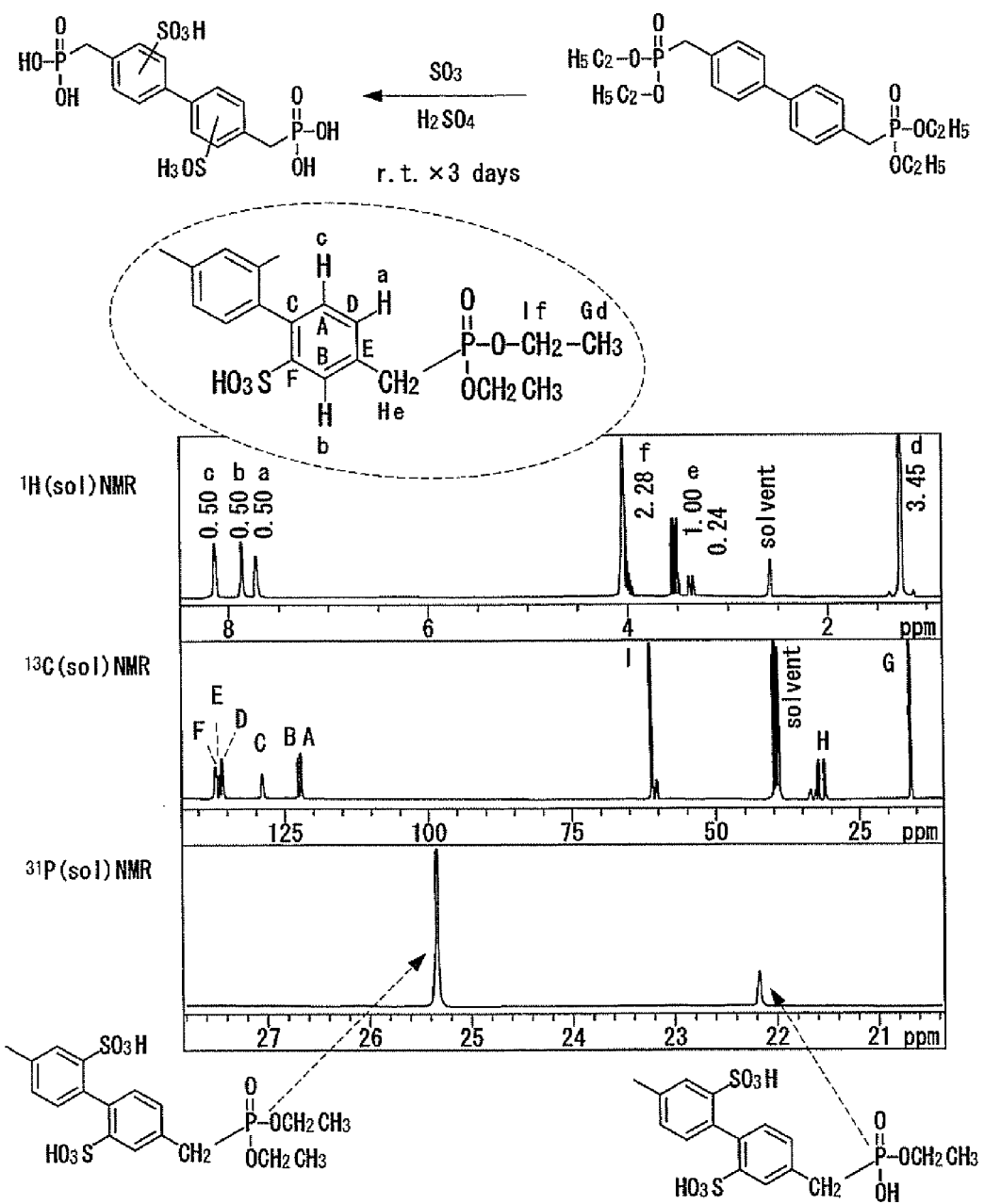
FIG. 8 is a solution NMR spectra of a sulfonation product of ethyl biphenyl bismethylene phosphonate ester obtained from a stock solution.

It has been confirmed that two positions (2,2'-) on the aromatic ring of the biphenyl bismethylene diphosphonic acid in the stock solution of the sulfonated diphosphonic acid is sulfonated as described below. That is, when biphenyl-4, 4'-bis(diethyl ester methylene diphosphonate) was stirred in a 25% fuming sulfuric acid under a nitrogen gas stream at a room temperature for three days, since colorless transparent plate crystals were precipitated, various NMR measurements were carried out by using the solutions of the crystallization products. As a result, it can be confirmed from (FIG. 8) for disulfonation on 2,2'-position in the compound and, at the same time, it is suggested that crystals were precipitated in view of a structure where a portion of the ethyl phosphonate ester is hydrolyzed.

By the method of using the stock solution, sulfonated biphenyl bismethylene crosslinked type zirconium phosphonate copolymers (ZP1414, ZP1422) having a methyl group and a hydroxyl group as the substituent R were synthesized in the same manner by 12N sulfuric acid-catalytic reaction. Also in the XRD patterns (FIG. 5), formation of the α-type lamellar (layered) structure is suggested due to the presence of a d(001) peak of 14 Å and distinct (hk) reflection. However, in ZP1414, since a d(001) peak of 9 Å attributable to the hompolymer Zr(O$_3$P—CH$_3$)$_2$ is observed simultaneously, it suggests that the degree of copolymerization is low. Table 2 collectively shows the characteristics also in conjunction with the result of ZP1400.

TABLE 2

| R | | d(001) Å | d(020) Å | IR cm$^{-1}$ | BET m$^2$/g | EW(theoretical value) g/mol |
|---|---|---|---|---|---|---|
| ZP1400 | H | 13.5 | 2.69 | 2458 | 411 | 1120(549) |
| ZP1414 | CH$_3$ | 14.0 | 2.64 | 785 | 416 | 1400(577) |
| ZP1422 | OH | 14.0 | 2.65 | — | 248 | 620(636) |

From the results described above, it can be seen that the sulfonated biphenyl bismethylene crosslinked type zirconium phosphonate copolymers having the hydrogen group and the hydroxyl group (or methyl group) as the substituent R can be synthesized by 12N sulfuric acid-catalytic reaction by the method of using the stock solution of sulfonation products of biphenyl bismethylene diphosphonic acid.

By using a xylyrene diphosphonate ester instead of biphenyl bismethylene diphosphonate ester, xylyrene crosslinked type zirconium phosphonate copolymers having the substituent R (═H, OH, CH$_3$, etc.) can be synthesized in the same manner by 12N sulfuric acid—catalytic reaction. Further, a crosslinked type copolymer in which the diphosphonic acid ingredient is sulfonated could be synthesized in the same manner by the stock solution method or the post-sulfonation.

Comparative Example 1

[Synthesis of Biphenyl Bismethylene Crosslinked Type Zirconium Phosphonate Copolymer Having Hydrogen Group (3): Effect of Addition of HF Catalyst]

Effect of the addition of an HF catalyst at a ratio: F/Zr=18 (molar ratio) was investigated in a case of synthesizing the biphenyl bismethylene crosslinked type zirconium phosphonate copolymer (starting composition a:c=0.33:1.34) having the hydrogen group by the 12N sulfuric acid-catalytic reaction described in Example 1.

[1. Preparation of Sample]

In the same manner as in Example 1, biphenyl-4,4'-bis (diethyl ester methylene diphosphonate) (1.02 g, 2.2 mmol) and a 50 wt % aqueous solution of phosphonic acid (1.1 g, 8.8 mmol) were dispersed in 20 mL of 12N sulfuric acid and 20 mL of DMSO. The mixture was heated at 100° C. and stirred for 2 hours. The clear solution was transferred to an inner cylinder type autoclave made of polytetrafluoroethylene, ZrOCl$_2$.8H$_2$O (2.2 g, 6.7 mmol) dissolved in 3 mL of water with addition of an aqueous 48% HF solution (5.0 g, 119 mmol) was added there, sealed and reacted while standing still at 80° C. for 24 hours. The post treatment was carried out in the same manner as in Example 1 to obtain the product ZP1352.

[2. Evaluation of Sample]

Figure 9:
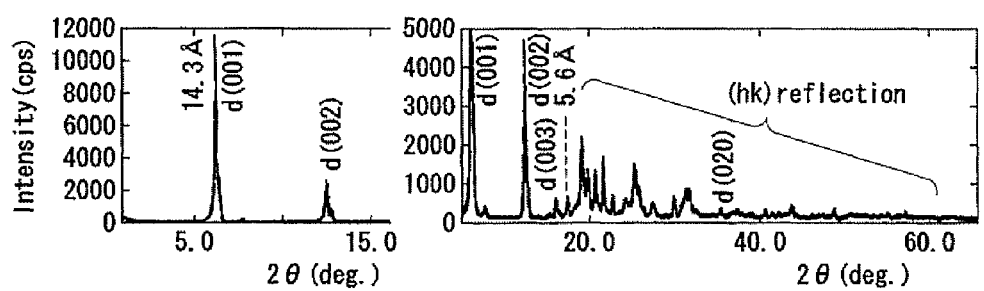
FIG. 9 is XRD patterns of a product (ZP1352)
Figure 10:
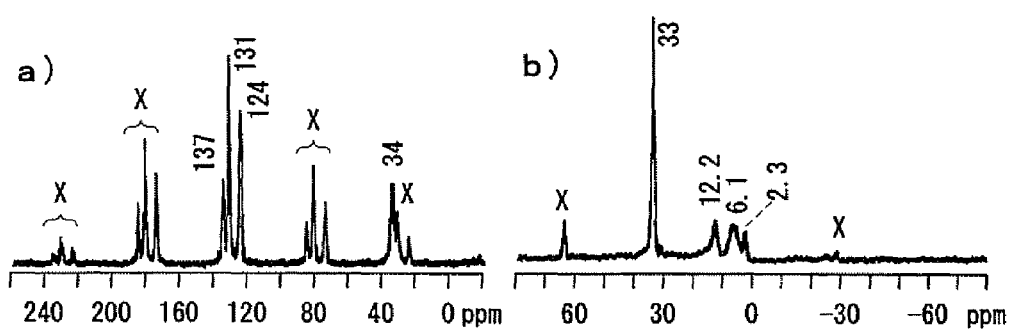
FIG. 10 shows (a) $^{13}$C MAS-NMR spectra and (b) $^{31}$P MAS-NMR spectra (X: spinning side band) of a product (ZP1352)

In the XRD pattern for the product ZP1352 (FIG. 9), while a d(001) peak of 14.3 Å and a distinct (hk) reflection peak are observed at an extremely high intensity, the presence of the d(001) peak of 5.6 Å attributable to the homopolymer Zr(O$_3$P—H)$_2$ is also observed. Further, in the $^{31}$P MAS-NMR spectra for ZP1352 (FIG. 10), while several peaks attributable to diphosphonic acid are observed (Zr-bonded: 2 ppm, 6 ppm, 12 ppm, free acid: 33 ppm), a P—H peak (−16 ppm) is not observed at all. Also in IR, 2456 cm$^{-1}$ absorption derived from P—H was not observed. The results suggest that reaction of the diphosphonic acid and Zr$^{4+}$ proceeds selectively by the addition of HF to hinder the copolymerizing reaction.

Example 3

[Synthesis of Sulfonated Biphenyl Bismethylene Crosslinked Type 3-ingredient Zirconium Phosphonate Copolymer Having Sulfophenyl Group and Hydrogen Group (1): Charged Molar Ratio For Aromatic Phosphonic Acid Ingredient and (Hydrogen Group) Phosphonic Acid Ingredient is Set to 0.33:1.34]

Figure 11:
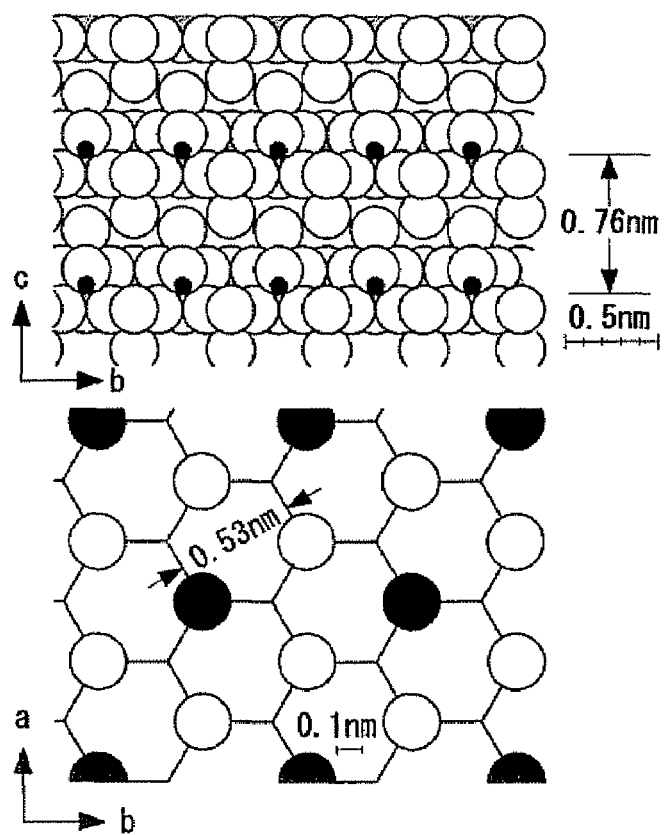
FIG. 11 shows a structural model of α-Zr (O$_3$P—OH)$_2$, and an ideal arrangement model of a 2-ingredient copolymer having R group (white circle) and a biphenyl bismethylene crosslinking ingredient (black circle) at 1.34:0.33 molar ratio overwritten on the ab plane thereof.

In the crosslinked type 2-ingredient zirconium phosphonate copolymer in which the aromatic diphosphonic acid crosslinking ingredient is sulfonated, since the steric hindrance of the crosslinking ingredient (compositional ratio a) is large, it is suggested from the structural chart for the a-b plane of α-zirconium phosphate (FIG. 11) that it is difficult to increase the starting composition for copolymerization with the monophosphonic acid ingredient having a compact substituent R (composition ratio c) to more than a:c=0.33:1.34. Then, it was considered to moderate the steric hindrance by substituting a portion of the aromatic diphosphonic acid ingredient with an aromatic monophosphonic acid ingredient.

For ZP1400 synthesized from phosphonic acid with R=H and sulfonated biphenyl hismethylene diposphonic acid at a starting composition of a:c=0.33:1.34, sulfonated biphenyl bismethylene crosslinked type 3-ingredient zirconium phosphonate copolymers (ZP1430, ZP1429, ZP1428) were synthesized by replacing a portion of the diphosphonic acid with a twice amount of sulfophenyl phosphonic acid (→compositional ratio: b=β), that is, at a starting composition of a:b:c= (0.33-0.5β):β:1.34 and changing as: β=0.47, 0.54, and 0.60. For the synthesis of ZP1429, specific operation method is to be described below.

[1. Preparation of Sample]

Phenyl phosphonic acid (40.0 g, 0.25 mol) was taken in a 200 mL round-bottom flask, a 60% of fuming sulfuric acid (77.3 g, 0.58 mol) was added and stirred under heating at 80° C. for one day under a nitrogen gas stream. Then, after cooling the reaction mixture in an iced bath, water (86.0 g) was added to form a 12N sulfuric acid solution (32 wt %) of 3-sulfophenyl phosphonic acid. This stock solution was portioned into a predetermined small amount and used for the synthesis of the zirconium phosphonate copolymer.

A stock solution containing 0.74 mmol of the sulfonation product of biphenyl-4,4'-bis(methylene phosphonic acid) (prepared in Example 2), the stock solution containing 5.92 mmol of 3-sulfophenyl phosphonic acid, and a 50 wt % aqueous solution of phosphonic acid (2.4 g, 14.8 mmol) were taken in a 100 mL round-bottom flask and 0.4 mL of DMSO was added. $ZrOCl_2 \cdot 8H_2O$ (3.6 g, 11.1 mmol) dissolved in 2 mL of water was added dropwise for 15 min into the mixture heated and stirred at 100° C. Reaction was carried out while continuing stirring for 24 hours at that temperature. After pouring the reaction mixture into 200 mL of water and stirring for one hour, it was centrifugated to take out solids (gel). The crude product was dispersed in 300 mL of 6N HCl and stirred under heating at a refluxing temperature for one hour, and then solids (gel) were recovered by centrifugation. The solids were dispersed in 400 mL of water and stirred under heating at a refluxing temperature for one hour, and then solids (gel) were recovered by centrifugation to obtain a product ZP1429 (3.7 g; yield 97%) by freeze drying.

[2. Evaluation of Sample]

Figure 12:
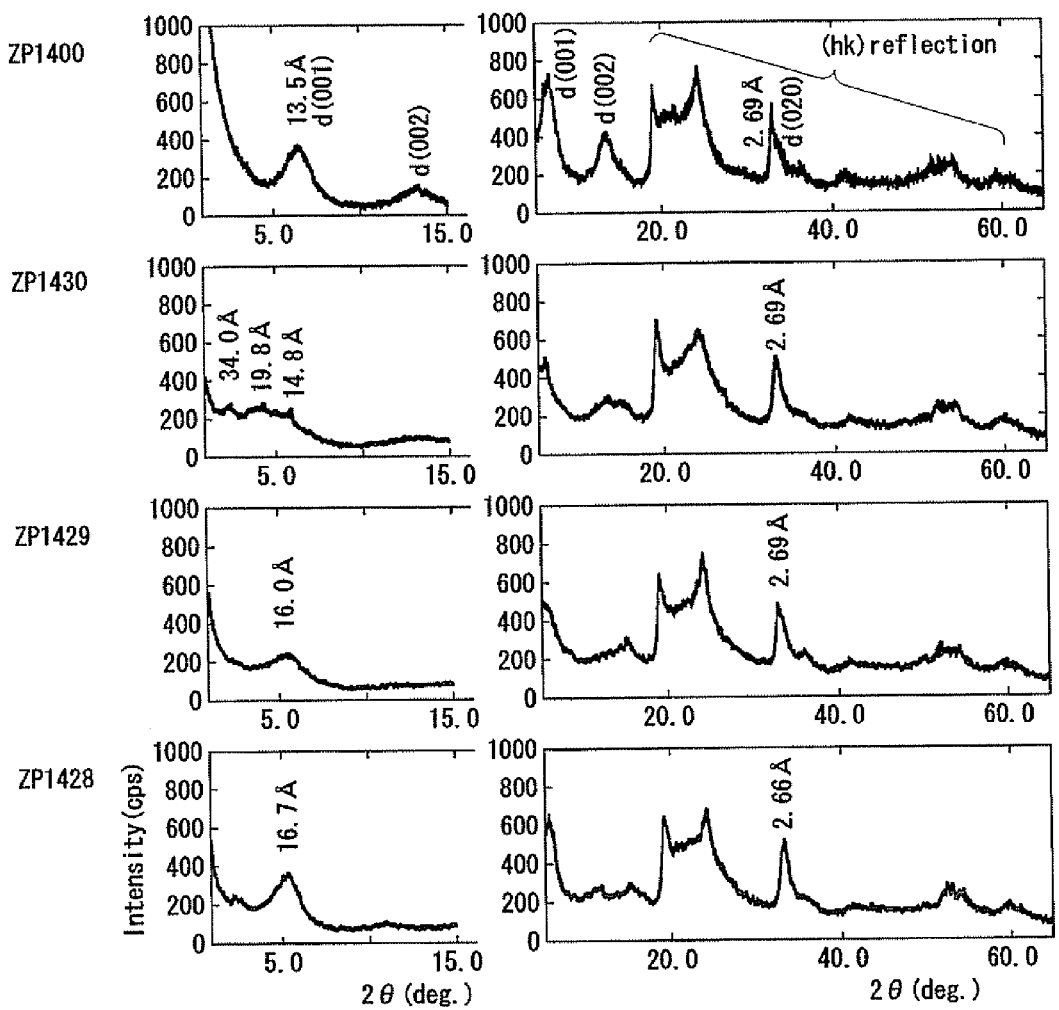
FIG. 12 is XRD patterns of crosslinked type 3-ingredient copolymers of a starting composition (a:b:c) in which the hydrogen group ingredient is charged at c=1.34 and a portion of the amount of crosslinking ingredient of diphosphonic acid (a=0.33) is substituted by a sulfophenyl group ingredient (b=0.47 to 0.60)
Figure 13:
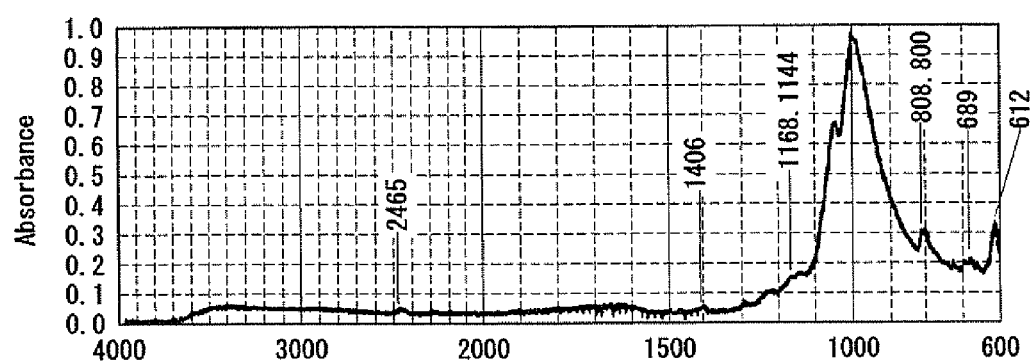
FIG. 13 is an IR spectrum of a sulfonated biphenyl bismethylene crosslinked type 3-Ingredient copolymer (ZP 1429, starting composition a:b:c=0.77:0.33:1.34)

XRD patterns for the sulfonated biphenyl bismethylene crosslinked type 3-ingredient zirconium phosphonate copolymers (ZP1430, ZP1429, ZP1428) are shown together with that for ZP1400 in FIG. 12. For the composition, in which the amount of substituting the diphosphonic acid by sulfophenyl phosphonic acid exceeds a certain amount relative to the starting composition a:c=0.33:1.34 for the ZP1400, the obtained crosslinked type 3-ingredient copolymer has an uniform α-type lamellar (layered) structure. The d(001) corresponding to the interlayer distance increases to a value exceeding 16 Å. In IR spectra for ZP1429 (FIG. 13), absorption attributable to the sulfophenyl group was observed at 808 to 800 cm$^{-1}$, 689 cm$^{-1}$ and 612 cm$^{-1}$, and absorption attributable to the hydrogen group is observed at 2465 cm$^{-1}$. When considering that the yield of ZP1429 is 97% in conjunction with the result described above, it is considered that homogeneously copolymerized crosslinked type 3-ingredient zirconium phosphonate copolymers are obtained. It is apparent that the sulfonated copolymers are not soluble to water from the post treatment procedure in the term of the experiment.

Figure 14:
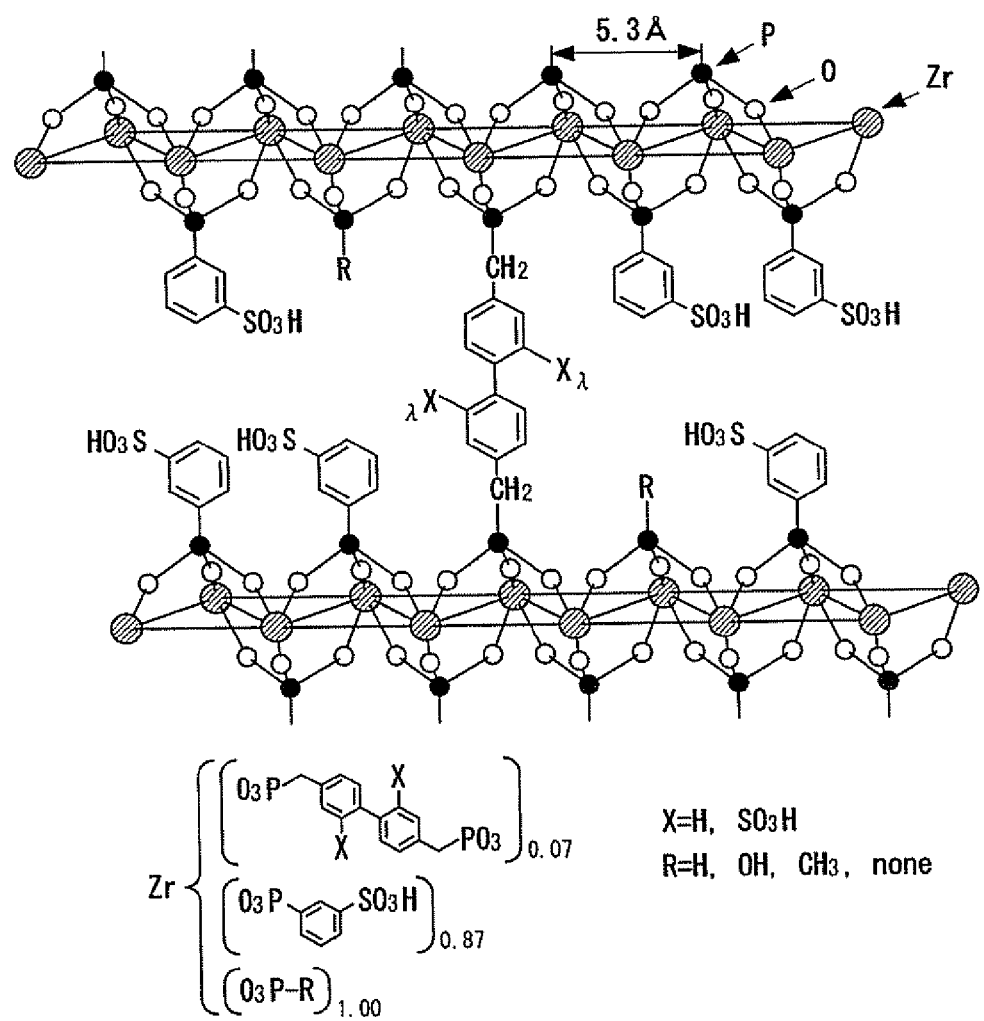
FIG. 14 shows a structural model and a structural formula of (sulfonated) biphenyl bismethylene crosslinked type 3-ingredient copolymer (starting composition a:b:c=0.07:0.33: 1.34) having a hydrogen group ingredient and a sulfophenyl group ingredient.

FIG. 14 shows an expected structure and a structural formula of the products. The characteristics are shown collectively in Table 3. A BET specific surface area is lowered greatly compared with ZP1400. On the other hand, EW value is decreased more to approach a theoretical value. It is estimated from the result that while desulfonation occurred partially when the crosslinked type copolymer is formed from the sulfonated biphenyl bismethylene diphosphonic acid in the synthesis of ZP1400, the steric hindrance is moderated in the synthesis of the crosslinked 3-ingredient copolymers by substituting a portion of the diphosphonic acids with sulfophenyl phosphonic acid, and the aromatic phosphonic acid ingredient can maintain the sulfonic group as it is.

TABLE 3

| a:b:c molar ratio | Yield % | d(001) Å | d(020) Å | BET m$^2$/g | EW (theoretical value) g/mol |
|---|---|---|---|---|---|
| ZP1400 0.33:0:1.34 | 100 | 13.5 | 2.69 | 411 | 1120(549) |
| ZP1430 0.10:0.47:1.34 | 97 | ~14.8 | 2.69 | 1 | 750(617) |
| ZP1429 0.07:0.54:1.34 | 97 | 16.0 | 2.69 | 4 | 740(586) |
| ZP1428 0.03:0.60:1.34 | 88 | 16.7 | 2.66 | 6 | 630(558) |

Example 4

[Synthesis of Sulfonated Biphenyl Bismethylene Crosslinked Type 3-ingredient Zirconium Phosphonate Copolymer Having Sulfophenyl Group and Hydrogen Group (2): Starting Molar Ratio of Aromatic Phosphonic Acid Ingredient and (Hydrogen Group) Phosphonic Acid Ingredient, Changed from 0.33:134]

The starting composition of the sulfonated biphenyl bismethylene crosslinked type 3-ingredient zirconium phosphate copolymer having a sulfophenyl group (ZP1429) was a:b:c=0.07:0.54:1.34 by molar ratio, in which the ratio of the aromatic phosphonic acid ingredient and the phosphonic acid ingredient having the hydrogen group was kept at 0.33:1.34. In a previous case of synthesizing a non-crosslinked type zirconium phosphonate copolymers from the sulfophenyl phosphonic acid and the phosphonic acid having the hydrogen group, it has been experienced that they could be copolymerized uniformly to the ratio of 1.3:0.7.

Then, based on the starting composition of ZP1429 (a:b:c=0.07:0.54:1.34), synthesis of the crosslinked type 3-ingredient copolymer increased for the acid group density was tried in the same manner as in Example 3 by changing the starting composition as a:b:c=0.07:(0.54+γ):(1.34-γ) by further replacing a portion of the hydrogen group ingredient with the sulfophenyl group ingredient. Specifically, the compositional ratio c (=1.34-γ) of the hydrogen group ingredient was decreased to 1.0, 0.94, 0.70, and 0.56 in the starting composition.

Figure 15:
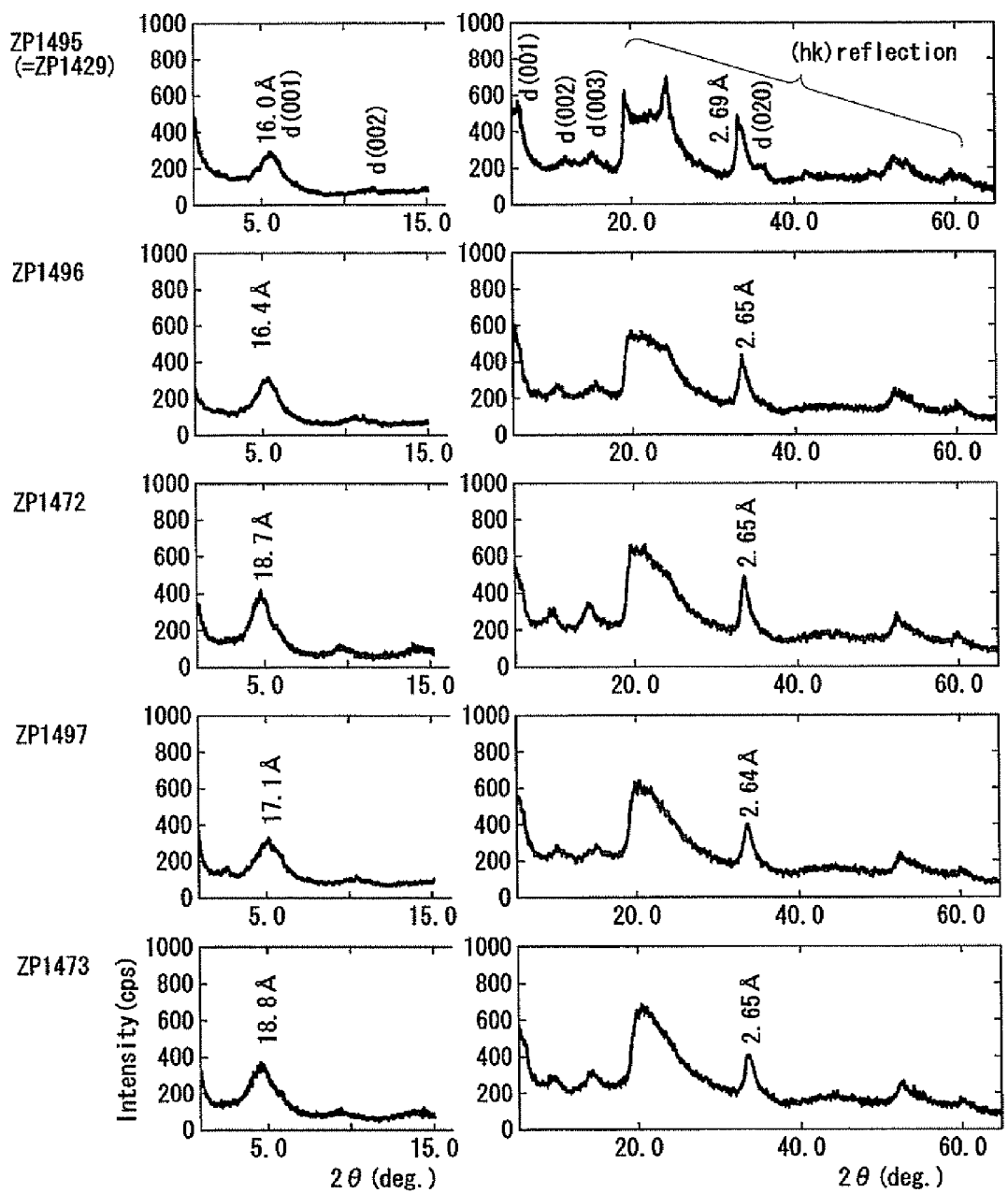
FIG. 15 is an XRD patterns of copolymers of sulfonated biphenyl bismethylene crosslinked type 3-ingredient zirconium phosphonates (a=0.07:b:c) in which the starting composition is: hydrogen group ingredient c=1.0 to 0.56 and the sulfophenyl group ingredient b=0.87 to 1.31.
Figure 16:
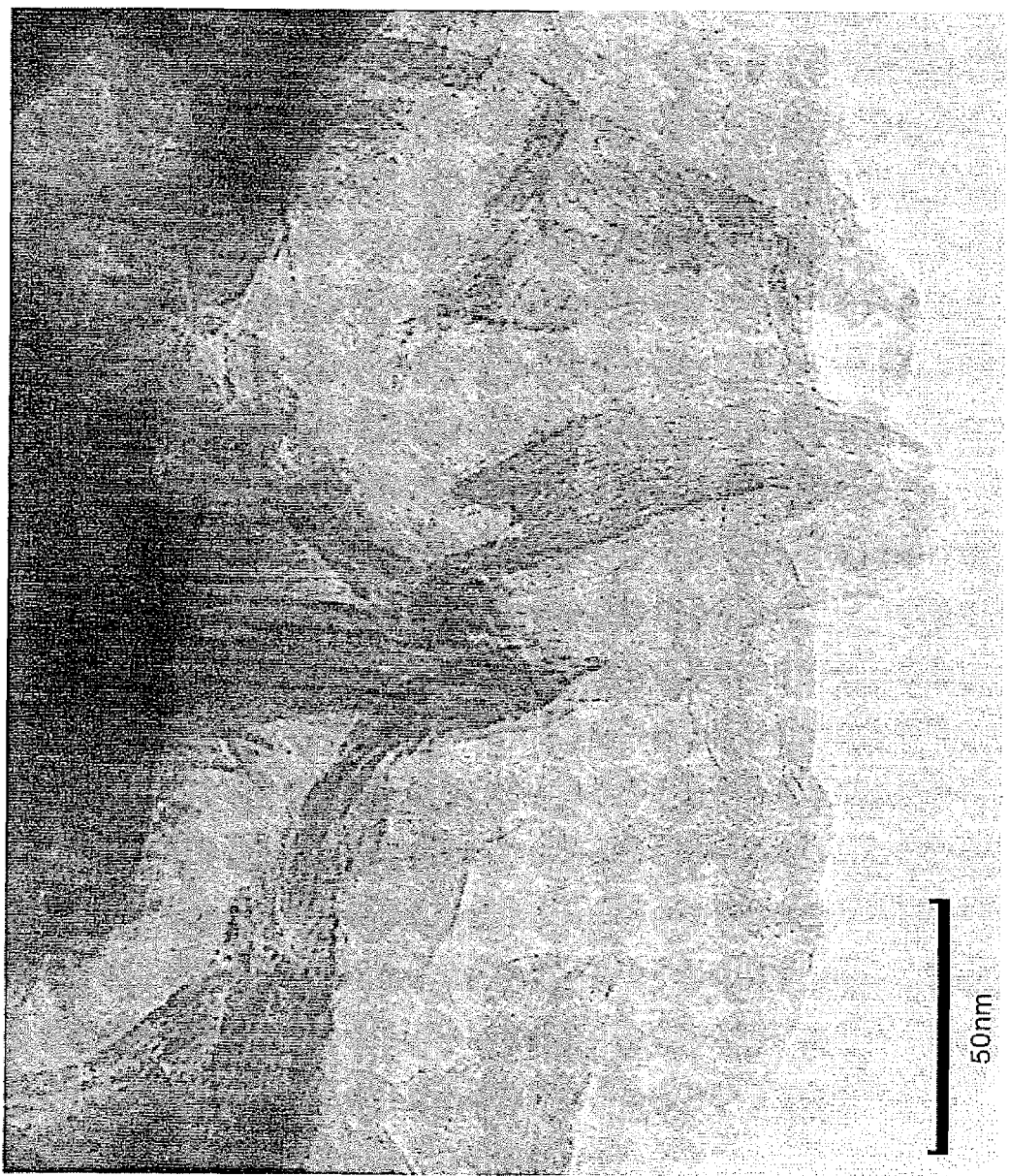
FIG. 16 is a TEM photograph for ZP1495.

FIG. 15 shows XRD patterns for the products (ZP1496, ZP1472, ZP1497, and ZP1473), and ZP1495 re-synthesized from ZP1429, and physical properties are collectively shown in Table 4. All of them are water insoluble products and since they show XRD patterns in which d(001) peaks and distinct (hk) reflection are present, this suggests that the products have a uniform α-type lamellar (layered) structure. In view of the result of TEM photographic observation for ZP1495 (FIG. 16), it can be seen that this is a granule structure of a high aspect ratio in which sub-micron size sheets (layers) are laminated by about 10 sheets each at about 1 nm distance. Accordingly, it is considered that copolymerization proceeds uniformly also in this case.

As the hydrogen group ingredient is decreased in the starting composition, while d(001) corresponding to the interlayer distance increases to about 19 Å, the BET specific surface area shows a value below a measuring limit on the way even when the amount of sample is increased to 100 mg or more. However, the EW value shows a value close to the theoretical value and decreases gradually in accordance with the compositional change. The results suggests that in the synthesis of the crosslinked type 3-ingredient zirconium phosphonate copolymer, a copolymer with increased density for acid groups is formed by increasing the starting composition (molar ratio) of the sulfonated aromatic phosphonic acid ingredient and the phosphonic acid ingredient having the hydrogen group to more than 0.33:1.34.

TABLE 4

| | a:b:c molar ratio | Yield % | d(001) Å | d(020) Å | BET m²/g | EW (throretical value) g/mol |
|---|---|---|---|---|---|---|
| ZP1495 | 0.07:0.54:1.34 | 100 | 16.0 | 2.69 | 19 | 540(586) |
| ZP1496 | 0.07:0.87:1.00 | 98 | 16.4 | 2.65 | 5 | 460(432) |
| ZP1472 | 0.07:0.94:0.94 | 99 | 18.7 | 2.65 | over | 460(414) |
| ZP1497 | 0.07:1.17:0.70 | 79 | 17.1 | 2.64 | over | 420(365) |
| ZP1473 | 0.07:1.31:0.56 | 86 | 18.8 | 2.65 | over | 400(344) |

(note)
ZP1495 is a re-synthesized product from ZP1429. "Over" for BET means that the value exceeds measuring limit for the amount sample of 100 mg or more.

Example 5

[Synthesis of (Sulfonated) Biphenyl Bismethylene Crosslinked Type 3-ingredient Zirconium Phosphonate Copolymer (3) Having Sulfophenyl Group and Hydrogen Group: Introduction of Various Substituents R (=H, OH, $CH_3$) and Absence or Presence of Sulfonation for the Diphosphonic Acid Ingredient]

For biphenyl bismethylene crosslinked 3-ingredient zirconium phosphonate copolymer having the substituent R (=H, OH, $CH_3$) and the sulfophenyl group, those where the diphosphonic acid ingredient was sulfonated (ZP1561, ZP1562) and not sulfonated (ZP1498, ZP1507, ZP1563) were synthesized. They were synthesized at the identical molar ratio with that for the starting composition of ZP1496 (a:b:c=0.07:0.87: 1.00) and in the same manner as in Example 3. In the synthesis for the latter, diphosphonic acid ester was used as it was instead of the stock solution of the sulfonated diphosphonic acid, and 12N sulfuric acid was added by a predetermined amount.

Figure 17:
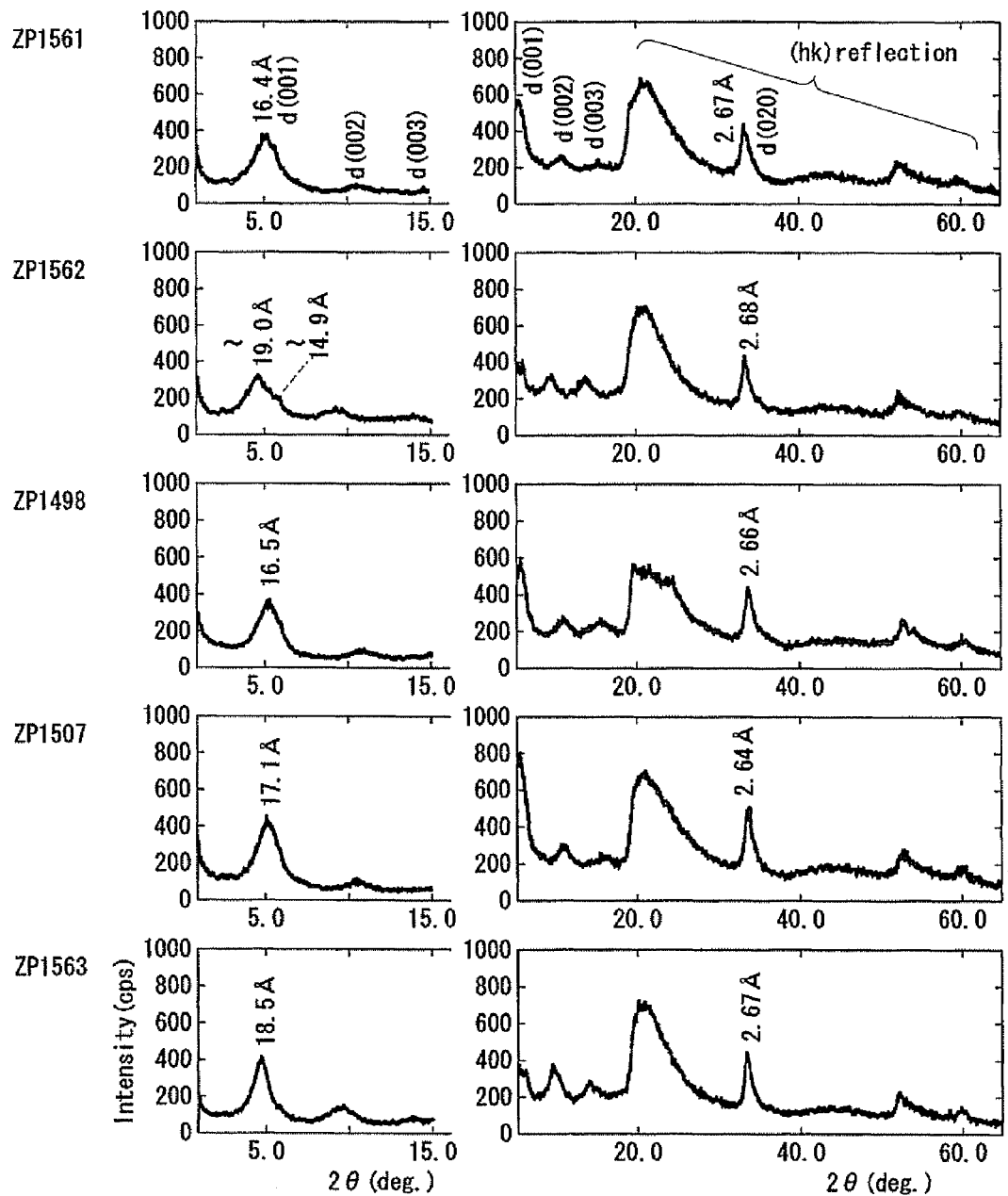
FIG. 17 is XRD patterns of (sulfonated)biphenyl bismethylene crosslinked type 3-ingredient copolymers (starting composition a:b:c=0.07:0.87:1.00) having a substituent ingredients of R=H, OH, CH$_3$ and a sulfophenyl group ingredient.

Their XRD patterns are shown in FIG. 17 and physical properties are shown collectively in Table 5. The results suggest that also the crosslinked type 3-ingredient zirconium phosphonate copolymers have the α-type lamellar (layered) structure and are increased for the density of the acid groups.

TABLE 5

| | —R | —X | Yield % | d(001) Å | d(020) Å | BET m²/g | EW (throretical value) g/mol |
|---|---|---|---|---|---|---|---|
| ZP1496 | H | $SO_3H$ | 98 | 16.4 | 2.65 | 5 | 460(432) |
| ZP1561 | OH | $SO_3H$ | 96 | 16.4 | 2.67 | over | 410(450) |
| ZP1562 | $CH_3$ | $SO_3H$ | — | 19.0~ | 2.68 | 5 | 350(448) |
| ZP1498 | H | H | 98 | 16.5 | 2.66 | 2 | 470(460) |
| ZP1507 | OH | H | 100 | 17.1 | 2.64 | over | 440(478) |
| ZP1563 | $CH_3$ | H | 98 | 18.5 | 2.65 | 10 | 380(476) |

(note)
starting composition a:b:c = 0.07:087:1.00 (molar ratio) "Over" for BET means that the value exceeds measuring limit for the amount sample of 100 mg or more.

Figure 18:
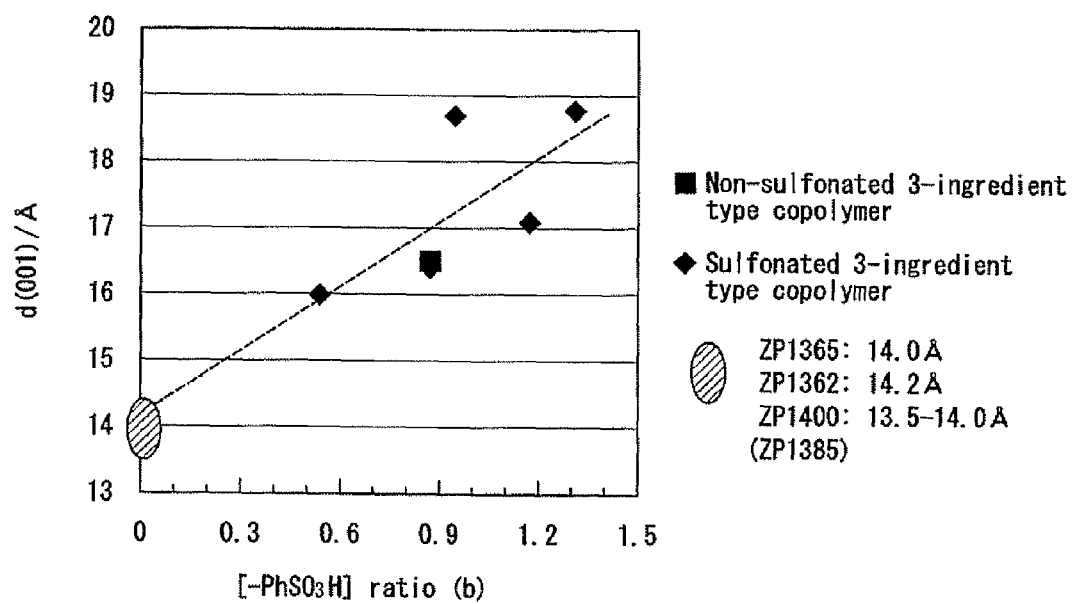
FIG. 18 shows d(001)/Å of (sulfonated) biphenyl bismethylene crosslinked type copolymer with the copolymerization starting composition of 0.07:b:1.86−b (b=0 to 3)

Then, for the d(001) values corresponding to interlayer distance of biphenyl bismethylene crosslinked type polymers, the result obtained so far are compared collectively. For the homopolymer ZP1365 only consisting of the biphenyl bismethylene diphosphonic acid ingredient, crosslinked type 2-ingredient copolymer ZP1362 with the ingredient having the hydroxyl group, sulfonated crosslinked type 2-ingredient copolymer ZP1400 (ZP1385) thereof, and crosslinked type 3-ingredient copolymer ZP1498 having the hydrogen group and the sulfophenyl group, and sulfonated crosslinked type 3-ingredient copolymers ZP1472 to 1473, and ZP1495 to 1497 thereof, FIG. 18 shows plotting d(001) value relative to the content of the sulfophenyl groups of them.

In the homopolymer and the crosslinked type 2-ingredient copolymer not having the sulfophenyl group, the value for d(001) is about 14 Å irrespective of the presence or absence of sulfonation for the diphosphonic acid ingredient. On the other hand, in the crosslinked type 3-ingredient copolymer having the sulfophenyl group, while the value of d(001) increases to about 19 Å as the sulfophenyl group content increases up to 1.3, this does not depend at all on the presence or absence of sulfonation for the diphosphonic acid ingredient also in this case. When the plotted values are connected, a linear relation is found between the values of d(001) and the content of the sulfophenyl group.

Figure 19:
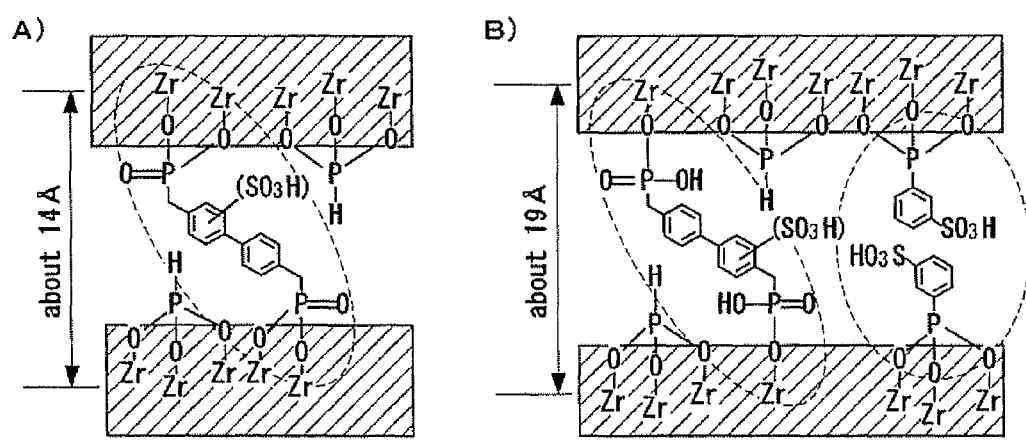
FIG. 19 shows estimated crosslinked structures for 2-ingredient system and 3-ingredient system biphenyl bismethylene crosslinked type copolymers.

For explaining the same, two structural models drawn in FIG. 19 are considered. FIG. 19A is a structural model for the biphenyl bismethylene crosslinked type 2-ingredient copolymer with reference to the result of $^{31}P$ MAS-NMR spectra, and it is considered that this mainly includes a crosslinked structure in which the P atoms of the diphosphonic acid crosslinking ingredient are bonded by way of two Zr atoms and O atoms. On the other hand, FIG. 19B is a structural model of the biphenyl bismethylene crosslinked type 3-ingredient copolymer, and the interlayer distance larger than that of the former is determined by the ratio of the opposing sulfophenyl groups, and it is considered that the larger interlayer distance corresponds to constituting the crosslinked structure in which the P atom of the diphosphonic acid crosslinking ingredient are bonded by way of one Zr atom and O atom.

Example 6

[Measurement of Proton Conductivity of Biphenyl Bismethylene Crosslinked Type Zirconium Phosphonate Copolymer: in Water and Under Humidified Atmosphere]

A composite product of a crosslinked type copolymer and PTFE (=polytetrafluoroethylene) (disk or film) was prepared and the proton conductivity was measured in water, or while changing the relative humidity (R. H.) to about 20 to 95%.

[1. Preparation of Sample]

A sample preparation is to be described at first. While a liquid dispersion manufactured by Dupont Co. was mainly used for PTFE, a powder sample manufactured by Daikin Co. was also used for comparison. After mixing a crosslinked type copolymer and a liquid dispersion containing PTFE in a 20 wt % amount thereof, it was heated at 135° C. and removed with a solvent, and the obtained solids were pulverized and mixed with agate to obtain a film-like composite product. The composite product was cut into small pieces to obtain a disk of φ=10 mm, 15 mm by press molding. A disk at φ=15 mm was put between aluminum sheets and stretched under a slight pressure to obtain a uniform film. On the other hand, a disk at φ=10 mm was used as it was, or a Pt electrode at φ=7 mm was coated on both surfaces thereof by a sputtering method, to which a fine gold wire was connected by a silver paste to form a sample for measurement.

[2. Test Method]

Figure 20:
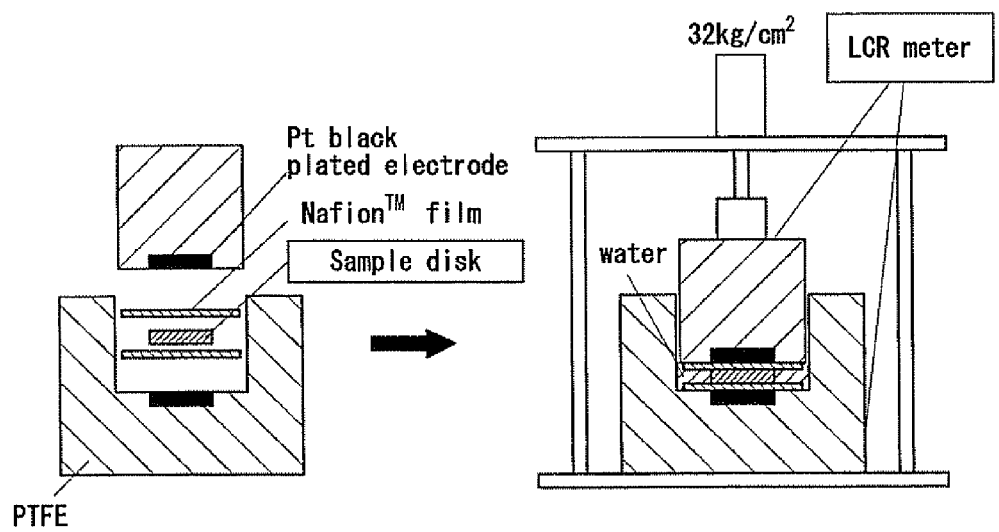
FIG. 20 is a view showing a measuring method ((at 25° C.) in water) for the conductivity in the direction of the film thickness σ(⊥)
Figure 21:
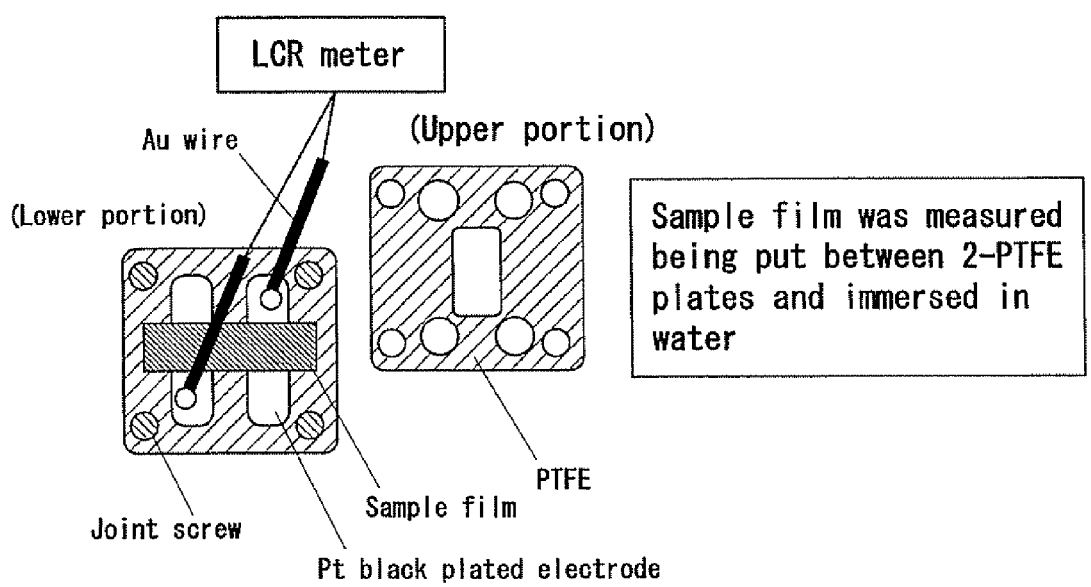
FIG. 21 is a view showing a measuring method ((at 25° C.) in water) for conductivity in the direction within the film surface σ(//)

The measurement in water was carried out for the evaluation of conductivity σ(⊥) in the direction of film thickness by using a composite disk of: φ=10 mm in the apparatus shown in FIG. 20, and the evaluation for the conductivity σ (//) in the direction within the film plane was conducted by using a composite film (1×3.5 cm$^2$) in the apparatus shown in FIG. 21.

On the other hand, in the measurement of changing the relative humidity (R.H.), the conductivity was determined by using a composite disk coated with a Pt electrode at 65° C. by an AC impedance method within a range from 5 MHz to 50 Hz. In this case, the relative humidity was changed by repeating the procedures of keeping the RH at about 20% for 1.5 hours and then successively increasing the humidity each by R.H.=10 to 15%, and keeping for one hour till it reached about 95%. Measurement was carried out by the AC impedance method at each R.H.

[3. Result]

The sulfonation products of the biphenyl bismethylene crosslinked type (2-ingredient) zirconium phosphonate polymers synthesized in Examples 1 and 2 were measured for the conductivity σ (⊥) in the direction of the film thickness as the PTFE 20 wt % composite product but current could not be detected within a range capable of measurement. Further, it was quite identical also for the sulfonated xylyrene crosslinked type (2-ingredient) zirconium phosphonate polymer mentioned in Example 2.

On the other hand since current could be detected in water at 25° C. for the (sulfonated) biphenyl bismethylene crosslinked 3-ingredient zirconium phosphonate copolymer synthesized in Examples 4 and 5 as the PTFE 20 wt % composite product, the results are collectively shown for σ (⊥) and σ(//) collectively in Table 6.

TABLE 6

PTFE: aqueous dispersion $$Zr \left\{ \begin{array}{c} \left( \begin{array}{c} O_3P\text{-}CH_2\text{-}C_6H_3(X)\text{-}C_6H_3(X)\text{-}CH_2\text{-}PO_3 \end{array} \right)_{0.07} \\ \left( \begin{array}{c} O_3P\text{-}C_6H_4\text{-}SO_3H \end{array} \right)_{0.87} \\ (O_3P\text{—}R)_{1.00} \end{array} \right\}$$

X = H  : ZP1498, ZP1507, ZP1563
X = SO$_3$H : ZP1496, ZP1561, ZP1562

| [X = H] | σ(⊥) | σ(//) |
|---|---|---|
| ZP1498 R = H | σ(⊥) = 0.04 S/cm | σ(") = 0.03 S/cm |
| ZP1507 R = OH | σ(⊥) = 0.04 S/cm | σ(") = 0.03 S/cm |
| ZP1563 R = CH$_3$ | σ(⊥) = 0.04 S/cm | σ(") = 0.02 S/cm |

| [X = SO$_3$H] | σ(⊥) |
|---|---|
| ZP1496 R = H | σ(⊥) = 0.04 S/cm |
| ZP1561 R = OH | σ(⊥) = 0.05 mS/cm |
| ZP1562 R = CH$_3$ | σ(⊥) = 0.05 S/cm |

It can be seen that current flows both in the direction of the film thickness and in the direction within the film plane in water. The conductivity differs slightly depending on the presence or absence of sulfonation for the biphenyl dismethylene crosslinking ingredient of the crosslinked three ingredient copolymer. This suggests that the sulfophenyl group is concerned more for the development of the proton conductivity. In a case of compositing ZP1496 and 20 wt % of PTFE powder, a conductivity of: σ (⊥)=0.02 S/cm in water was obtained.

Figure 22:
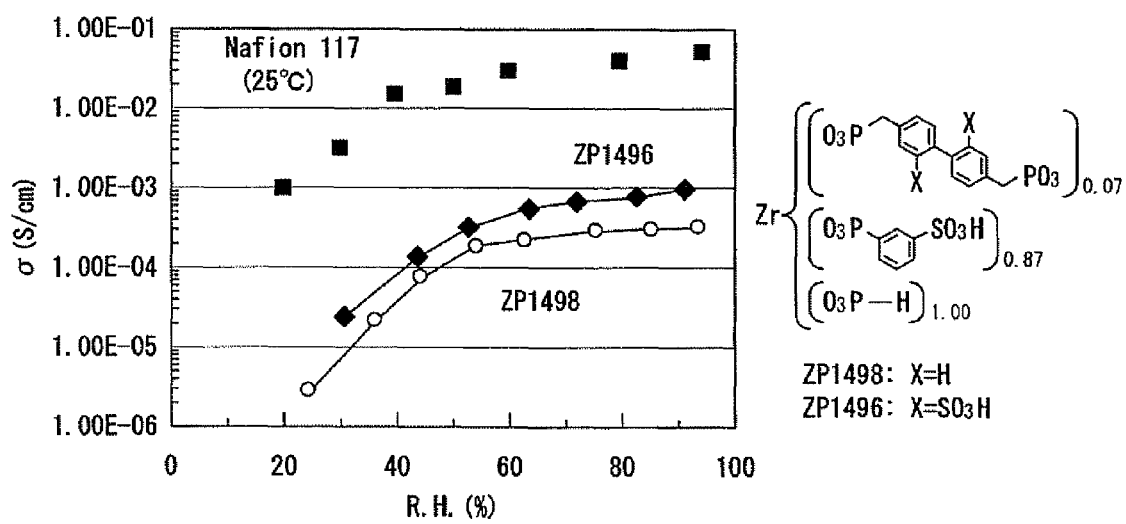
FIG. 22 shows the proton conductivity (measured at 20 to 95% R.H., 65° C.) of (sulfonated) biphenyl bismethylene crosslinked type 3-ingredient copolymers having substituent R and sulfophenyl group as the PTFE 20 wt % composite product.

For biphenyl bismethylene crosslinked type 3-ingredient zirconium phosphonate copolymers ZP1496 and ZP1498 having sulfophenyl group and hydrogen group and having the difference in the presence or absence of the sulfonation for the crosslinking ingredient, FIG. 22 shows the result of measurement for the conductivity of the PTFE 20 wt % composite products by changing the relative humidity. While both of them show conductivity even not in water, a somewhat difference is observed depending on the presence or absence of sulfonation for crosslinking ingredient.

Example 7

[Synthesis of Biphenyl Bismethylene Crosslinked Type 3-ingredient Zirconium Phosphonate Copolymer Having Sulfophenyl Group and Hydrogen Group (4): Synthesis by 2-step Method and Effect of Zr Source]

The method of synthesizing a crosslinked type multi-ingredient copolymer described so far is a method of charging the diphosphonic acid ingredient and a plurality types of monophosphonic acids collectively and reacting them with a Zr source (1-step method). For further improving the crystallinity of the layered structure of the product, it was considered to promote the reaction between the entire phosphonic groups and the Zr source by a 2-step method of previously reacting a diphosphonic acid crosslinking ingredient having phosphonic groups on both terminal end with a necessary entirely amount of the Zr source and then adding a plurality types of monophosphonic acid ingredients. The necessary entirely amount of the Zr source is an amount based on the one-half amount of the entire phosphonic groups.

Then, in the synthesis of the biphenyl bismethylene crosslinked type 3-ingredient zirconium phosphonate copolymer having hydrogen group and sulfophenyl group, the charging method of the phosphonic acid ingredient, the effect by the type of the Zr source, and the polymerization time were investigated. Reaction conditions of them are shown collectively in Table 7. For the synthesis of ZP1580 by the 2-step method, specific operation method is to be described below.

[1. Preparation of Sample]

0.20 g (0.58 mmol) of biphenyl-4,4'-bis(methylene phosphonic acid) was taken in a 100 mL of an round-bottom flask and dissolved with addition of 10 mL of DMSO. $ZrOCl_2·8H_2O$ (2.8 g, 8.8 mmol) dissolved in 3 mL of water was added to the flask and stirred under heating at 100° C. for one hour. A mixture of a stock solution containing 8.8 mL of 12N sulfuric acid and 7.6 mmol of 3-sulfophenyl phosphonic acid (prepared in Example 3) and an aqueous 50 wt % solution of phosphonic acid (1.4 g, 8.8 mmol) was added dropwise for several minutes, and reaction was carried out by continuing stirring under heating at 100° C. for 24 hours.

After pouring the reaction mixture into 200 mL of water and stirring for one hour, it was centrifugally separated to take out solids (gel). The crude product was dispersed in 300 mL of 6N HCl and stirred under heating at a reflux temperature for one hour, and then solids (gel) were recovered by centrifugation. The solids were dispersed in 400 mL of water and, after stirring under heating at a refluxing temperature for one hour, the solids (gel) were recovered by centrifugation and freeze-dried to obtain a product ZP1580 (3.3 g; yield 95%).

[2. Evaluation for Sample]

Figure 23:
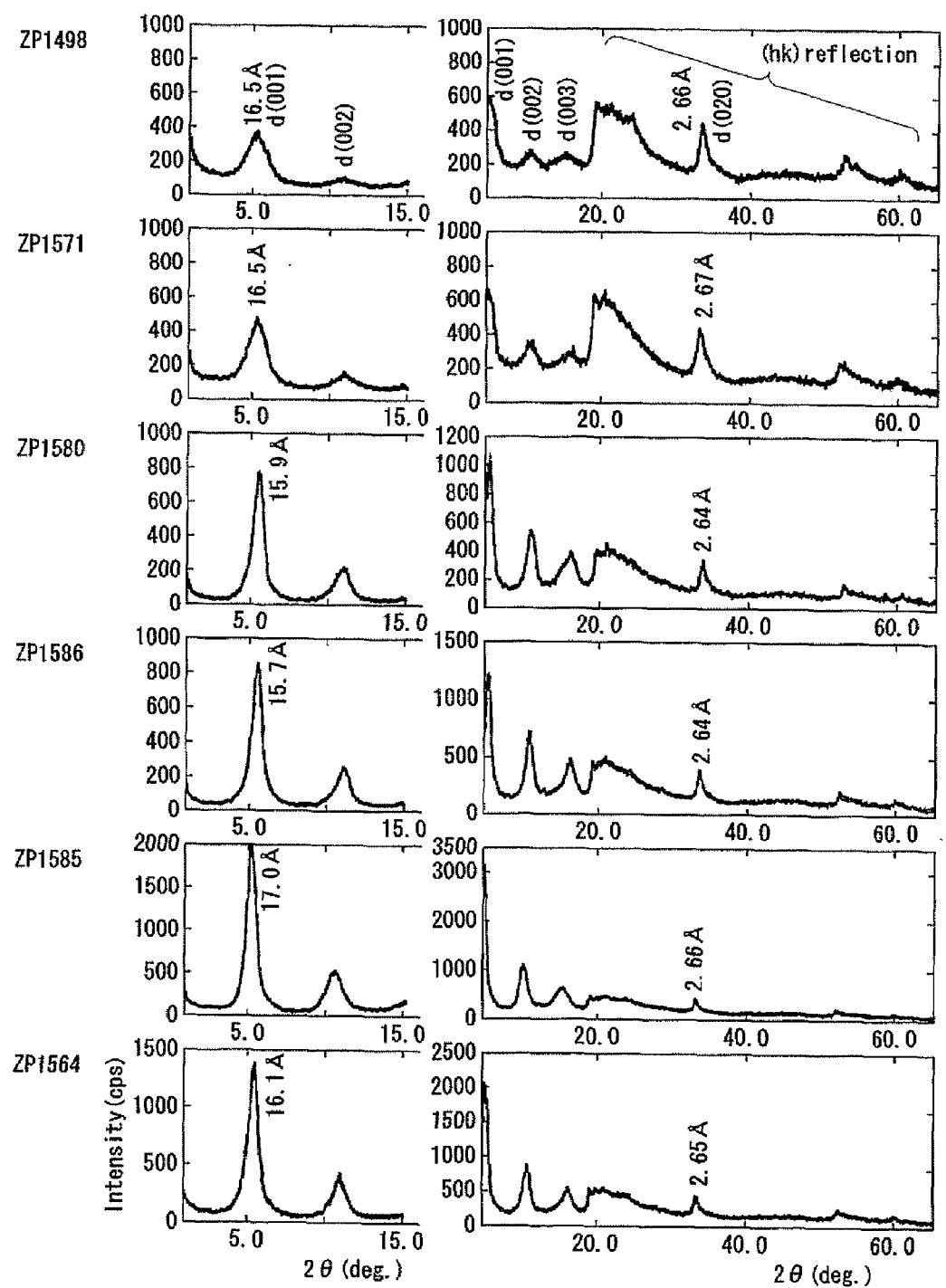
FIG. 23 is XRD patterns of biphenyl bismethylene crosslinked type 3-ingredient copolymers having sulfophenyl groups and hydrogen groups.
Figure 24:
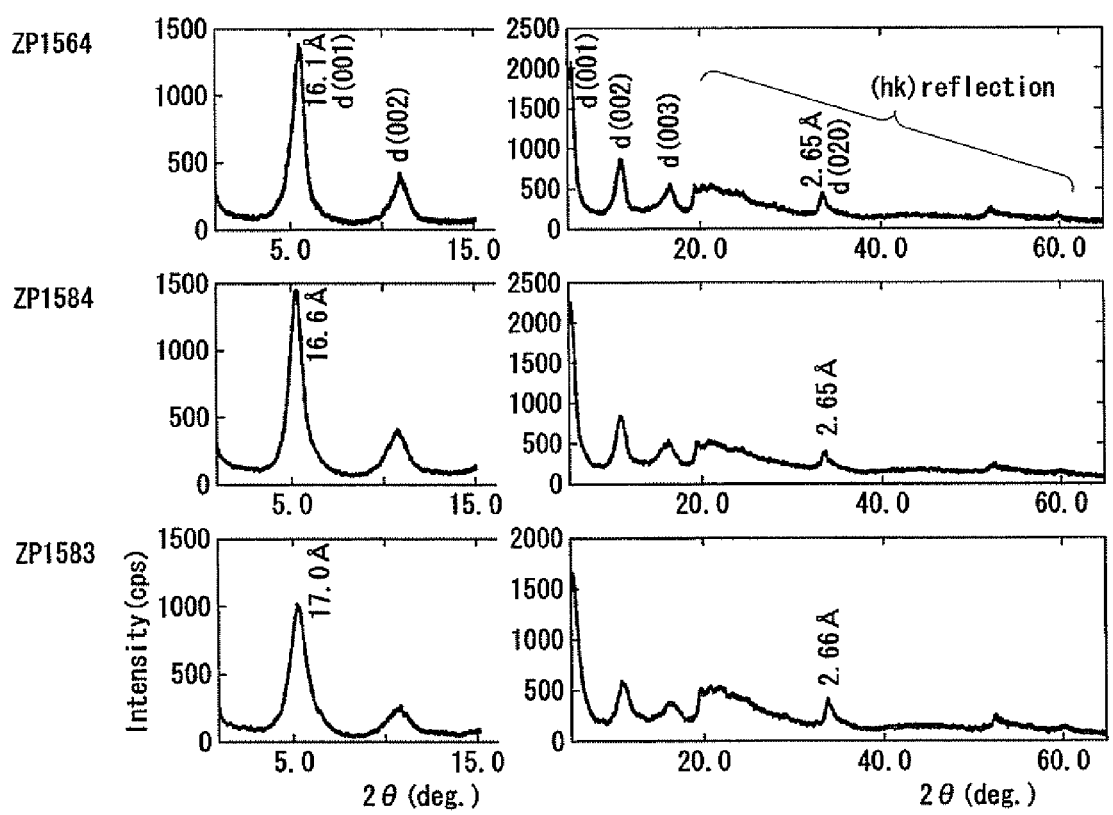
FIG. 24 is XRD patterns of biphenyl bismethylene crosslinked type 3-ingredient copolymers having sulfophenyl groups and hydrogen groups.

Table 7 also collectively shows physical properties of all products. Further, XRD patterns for the products are shown in FIG. 23 and FIG. 24.

For ZP1498, ZP1571, ZP1580, investigation was conducted by using biphenyl bismethylene diphosphonic acid ester (1a) or biphenyl bismethylene diphosphonic acid (1b) for the diphosphonic acid ingredient, and using $ZrOCl_2·8H_2O$ for the Zr source.

When comparing ZP1498 and ZP1571, increase in the d(001) peak intensity was observed slightly by changing the way of charging of the phosphonic acid ingredient from collective charging to 2-step method in two stages. When comparing ZP1571 and ZP1580, it can be seen that the d(001) peak intensity increases further by using the diphosphonic acid (1b) for the 2-step method. They suggest improvement in the crystallinity of the layered structure. Scarce change was observed for the EW value and the BET specific surface area.

In the 2-step method of using the diphosphonic acid (1b), when synthesis was carried out while changing the type of the Zr source to $Zr(SO_4)_2$, $Zr(OCOCH_3)_4$, and $Zr(OPr)_4$, the products ZP1586, ZP1585, and ZP1564 showed d(001) peaks at further higher intensity. The d(001) peak intensity of ZP1585 using $Zr(OCOCH_3)_4$ is twice or more the value for ZP1580.

Further, the effect of the polymerization time was investigated for the synthesis by the 2-step method using $Zr(OPr)_4$. While the polymerization time in the second-step was shortened from 24 hr to 1 hr, no remarkable lowering in the d(001) peak intensity was observed for the products ZP1564, ZP1584, and ZP1583 (FIG. 24: XRD pattern). The d(001) peak intensity for ZP1583 by reaction only for one hour is still larger than the value for ZP1580 by reaction for 24 hours using $ZrOC_2·8H_2O$ (Table 7). This suggests that the effect of the type of the Zr source on the reaction is remarkable.

TABLE 7

| | | Reaction condition[a] | | | | | | | |
|---|---|---|---|---|---|---|---|---|---|
| | | 1st step (100° C. × 1 h) | 2nd step (100° C.) | | | | | | |
| Product | Zr source | 1st phosphonic acid[b] | 2nd phosphonic acid[c] | Reaction time | Yield/% | d(001)/cps | d(020) | EW/g/mol | BET/m$_2$/g |
| ZP1498 | $ZrOCl_2$ | [1a +2 +3] | — | 24 h | 98 | 0.35k (16.5 A) | (2.66 A) | 470 | 2 |
| ZP1571 | $ZrOCl_2$ | 1a | 2 + 3 | 24 h | 96 | 0.45k (16.5 A) | (2.67 A) | 452 | 1 |
| ZP1580 | $ZrOCl_2$ | 1b | 2 + 3 | 24 h | 95 | 0.80k (15.9 A) | (2.64 A) | 444 | 7 |
| ZP1586 | $Zr(SO_4)_2$ | 1b | 2 + 3 | 24 h | 99 | 0.85k (15.7 A) | (2.64 A) | 422 | 1 |
| ZP1585 | $Zr(OAc)_4$ | 1b | 2 + 3 | 24 h | 101 | 2.00k (17.0 A) | (2.64 A) | 502 | 3 |
| ZP1564 | $Zr(OPr)_4$ | 1b | 2 + 3 | 24 h | 89 | 1.35k (16.1 A) | (2.65 A) | 497 | 36 |
| ZP1584 | $Zr(OPr)_4$ | 1b | 2 + 3 | 5 h | 82 | 1.45k (16.6 A) | (2.65 A) | — | 21 |
| ZP1583 | $Zr(OPr)_4$ | 1b | 2 + 3 | 1 h | 75 | 1.00k (17.0 A) | (2.66 A) | — | 22 |

(note)
[a]reaction condition (solvent) 12N sulfuric acid + DMSO, P/Zr = 2 (atomic ratio),
[b,c]phosphonic acid:
1a = biphenyl-4,4'-bis(methylenediethylphosphonate)
1b = biphenyl-4,4'-bis(methylenephosphonic acid)
2 = 3-sulfophenylphosphonic acid
3 = $H_3PO_3$ phosphonic acid charged molar ratio a:b:c = 0.07:0.87:1.00

Example 8

[Synthesis and Properties of (Sulfonated) Terphenyl Crosslinked 3-ingredient Zirconium Phosphonate Copolymer Having Substituent R (=H, CH$_3$) and Sulfophenyl Group: Starting Composition (Molar Ratio) a:b:c=0.07:0.87: 1.00]

Biphenyl bismethylene crosslinked type 3-ingredient zirconium phosphonate polymer has a BET specific surface area of less than 10 m$^2$/g in most cases. Then, for providing a larger BET specific surface area, it was considered to use terphenyl diphosphonic acid as the crosslinking ingredient diphosphonic acid having a larger molecular size. Specific operation method for synthesizing the terphenyl crosslinked type 3-ingredient copolymer having the sulfophenyl group is to be described below.

[1. Preparation of Sample]
[1.1 Synthesis of Terphenyl Diphosphonic Acid]

Terphenyl phosphonic acid was synthesized with reference to a literature (A. Clearfield, et al., J. Am. Chem. Soc., 2003, 125, 103754). Terphenyl (10.0 g, 43 mmol) was taken in a 200 mL of s three-necked flask having a cooling tube and a dropping funnel and bromobenzene (70 mL) was added and dissolved by stirring under heating at 130° C. in a nitrogen gas stream. After adding a small piece of iodine in the solution, bromine (4.7 mL, 86 mmol) was added dropwise for 6 hours and stirring was continued for one night at that temperature. Addition of the small iodine piece and dropping of bromine (1.5 mL) (3 hours) were carried out again and they were reacted in the same manner for one night. After cooling, the reaction mixture was separated by filtration to obtain white powdery solids. The solids were dispersed in a 10% aqueous solution of sodium thiosulfate and washed. The solids were separated by filtration, dispersed in 100 mL of water and further washed by boiling and stirring for one hour. The solids recovered by filtration were dried under a reduced pressure at 80° C. to obtain 11.6 g (70%) of products of 4,4,1-dibromoterphenyl 4,4"-dibromoterphenyl (10.0 g, 26 mmol) was taken in a 300 mL three-necked flask having a cooling tube and a dropping funnel, and diisopropyl benzene (166 mL) and nickel bromide (0.65 g, 3 mmol) were added and stirred under heating at 180° C. in a nitrogen gas stream. Triethyl phosphite (12.9 mL, 75 mmol) was dropped for 6 hours and stirring was continued at that temperature for one night. Addition of nickel bromide (0.43 g) and dropping of triethyl phosphite (8.6 mL) (3 hours) were conducted again and reacted in the same manner for one night. The reaction mixture was separated by filtration after cooling to remove solids and the filtrate was heated to 65° C. under a reduced pressure by a vacuum pump to remove unreacted triethyl phosphite and then a pale yellow powder, precipitated by leaving the mother liquid as it was, was separated by filtration. The powder was dried by heating to 150° C. under a reduced pressure by vacuum pump to obtain 8.3 g (64%) of terphenyl-4,4"-bis(diethyl phosphonate ester) product.

Figure 25:
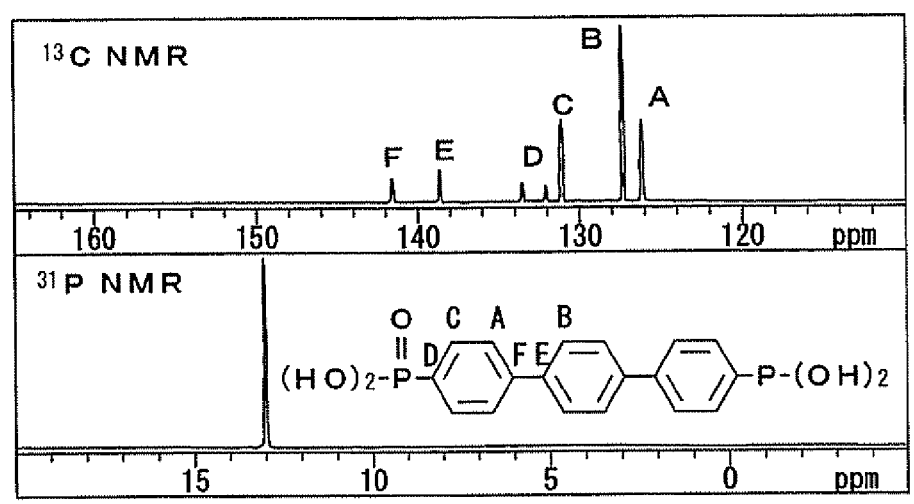
FIG. 25 is a solution NMR spectra of 4,4'-bisphosphonic acid terphenyl.

The terphenyl-4,4"-bis(diethyl phosphonate ester) (8.3 g) described above was taken in a 300 mL round-bottom flask having a cooling tube, 120 mL of 48 wt % hydrobromic acid was added, and the mixture was heated and stirred at 110° C. for one day. The solids obtained by filtrating the reaction mixture after cooling were dispersed in 0.5 L of water and stirred under heating at a refluxing temperature for one hour. The solids recovered by filtration were dried in vacuum to obtain (6.0 g: yield 93%) of terphenyl-4,4"-bis phosphonic acid product. Various NMR measurements were carried out for the DMSO-d$_6$ solution (FIG. 25) to confirm the structure.

[1.2 Synthesis of Sulfonated Terphenyl Crosslinked Type 3-Ingredient Copolymer]

Synthesis of sulfonated terphenyl crosslinked type 3-ingredient copolymer ZP1633 having the sulfophenyl group by using terphenyl diphosphonic acid by the 2-step method is to be described.

Terphenyl-4,4"-bisphosphonic acid (0.20 g, 0.51 mmol) was taken in a 100 mL round-bottom flask and 25% fuming sulfuric acid (9.7 g) was added and they were heated and stirred at 80° C. for 20 hours in a nitrogen gas stream. After cooling the reaction mixture, the stock solution was prepared by adding 7.6 mL of 12N sulfuric acid and 1.9 mL of water, and the entire amount thereof was used for the following reaction.

Then, 10 mL of DMSO and acetic acid solution of zirconium acetate (Zr % 15 to 16; 4.7 g, 7.7 mmol) were added in a flask containing the stock solution and heated and stirred at 100° C. for one hour. A mixture of dimethyl methyl phosphonate (0.95 g; 7.7 mmol) and a stock solution containing 6.7 mmol of 3-sulfonyl phosphonic acid (prepared in Example 3) was added dropwise for several minutes and reaction was carried out by continuing heating and stirring at 100° C. for 24 hours. After the completion of the reaction and after pouring the reaction mixture into 200 mL of water, they were stirred for one hour and then centrifugated to recover solids (gel). The crude product was dispersed in 300 mL of 6N HCl and heated and stirred at a refluxing temperature for one hour to recover solids (gel) by centrifugation. After dispersing the solids in 400 mL of water and heating and stirring them at a refluxing temperature for one hour, the solids (gel) were recovered by centrifugation and freeze dried to obtain ZP1633 product (3.1 g; yield 93%).

[2. Evaluation for Sample]

Figure 26:
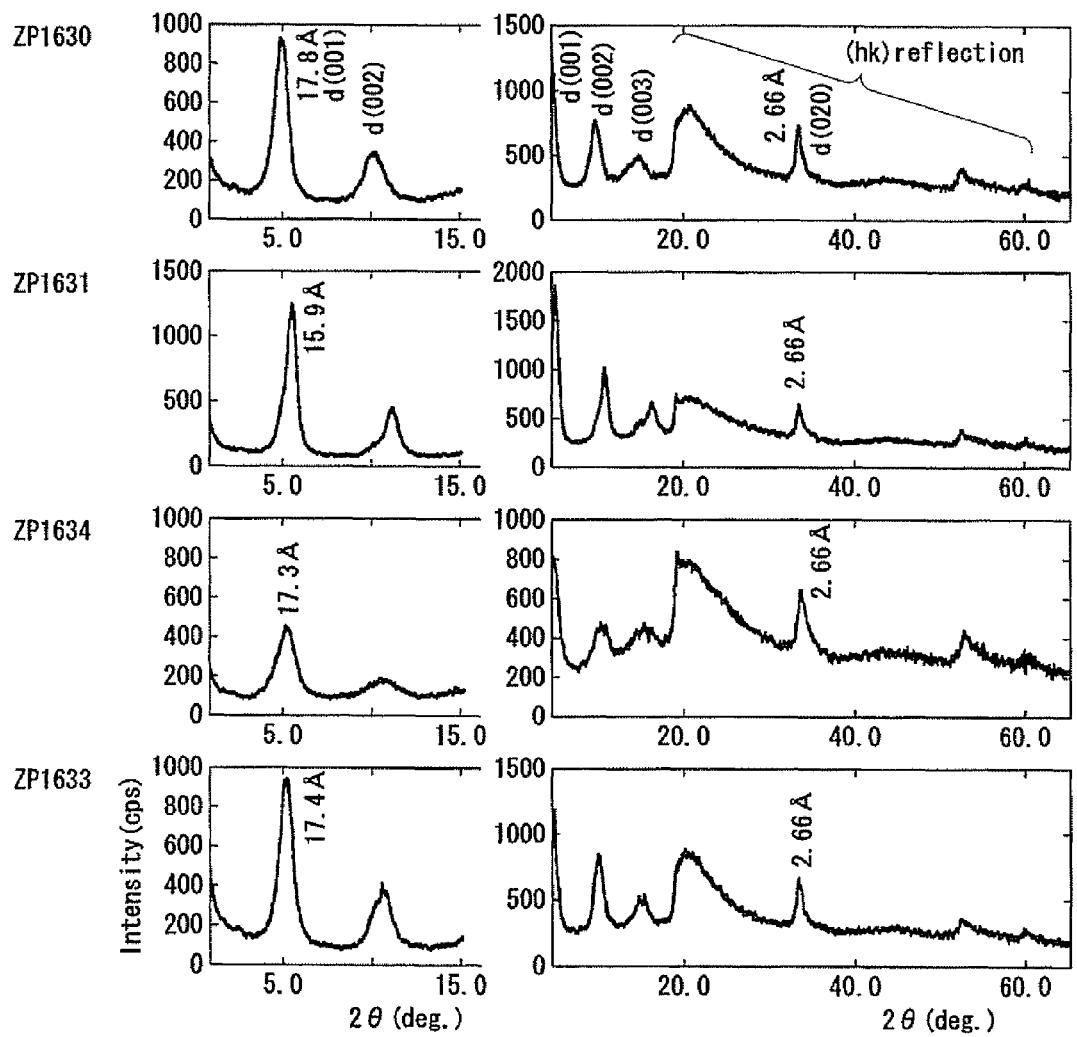
FIG. 26 is XRD patterns of various types of terphenyl crosslinked type 3-ingredient copolymers.
Figure 27:
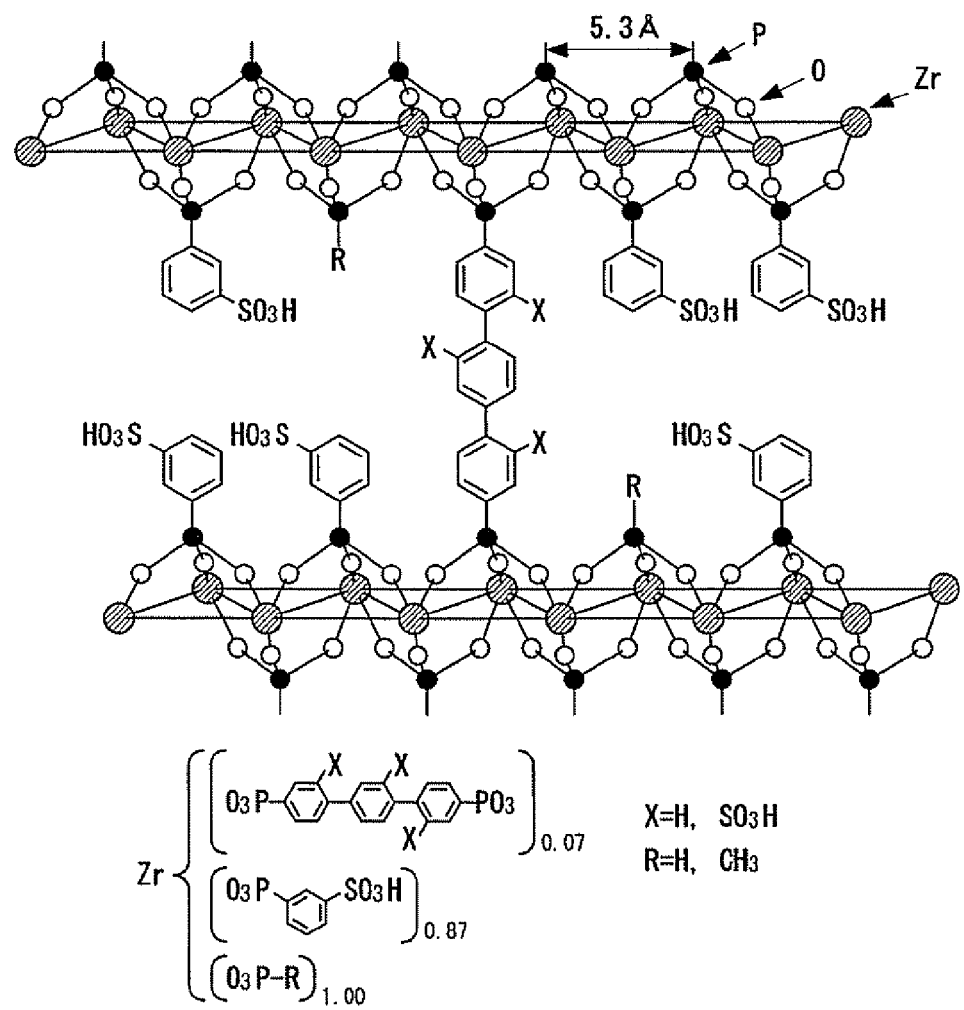
FIG. 27 shows a structural model and a structural formula of the (sulfonated) terphenyl crosslinked type 3-ingredient copolymer (starting composition a:b:c=0.07:0.87:1.00) having a substituent R and a sulfophenyl group ingredient.

FIG. 26 shows XRD patterns for various kinds of sulfonated terphenyl crosslinked type 3-ingredient copolymers synthesized in the same manner. The synthesizing conditions and properties of them are collectively shown in Table 8. FIG. 27 shows an expected structure and a structural formula of the product.

Any of the terphenyl crosslinked type 3-ingredient copolymers (ZP1630, ZP1631, and ZP1633) having the sulfophenyl group synthesized by the 2-step method shows XRD patterns suggesting that each of them has high crystallinity for the layered structure, and has a BET specific surface area of about 50 m$^2$/g and has an EW value close to the theoretical value. However, ZP1634 synthesized by the 1-step method of charging all the phosphonic acids simultaneously shows an XRD pattern suggesting that the crystallinity of the layered structure is not so high and the BET specific surface area is as small as 1 m$^2$/g.

TABLE 8

| Starting phosphonic[a] Acid composition (molar ratio = 0.07:0.87:1.00) | ZrP-reaction[b] | Yield % | d(001) Å(cps) | d(020) Å | BET m²/g | EW Obs.[cal.] |
|---|---|---|---|---|---|---|
| ZP1630 HTP:SPh:H | 2-Step | 81 | 17.8(0.9k) | 2.66 | 50 | 431[463] |
| ZP1631 STP:SPh:H | 2-Step | 91 | 15.9(1.2k) | 2.66 | 49 | 395[463] |
| ZP1634 STP:SPh:H | 1-Step | 86 | 17.3(0.5k) | 2.66 | 1 | not measured[463] |
| ZP1633 STP:SPh:CH₃ | 2-Step | 93 | 17.4(0.9k) | 2.66 | 49 | 363[409] |

[a]Phosphonic acid: HTP = terphenyl, STP = sulfonated terphenyl, HPh = phenyl, SPh = sulfophenyl
[b]Zr source: Zr(OAc)₄ in AcOH, P/Zr = 2 (atomic ratio)

Figure 28:
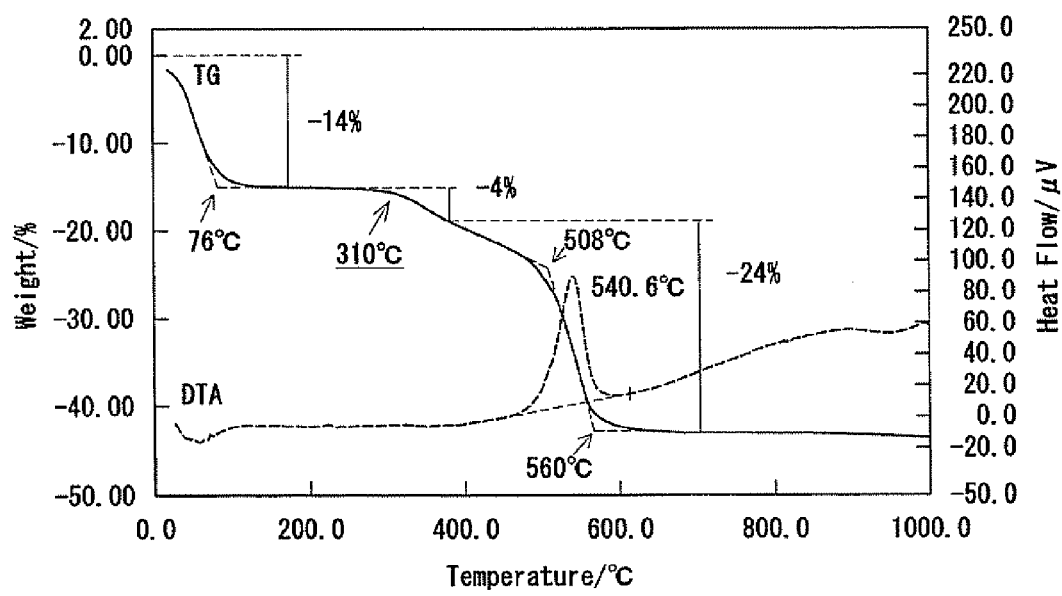
FIG. 28 shows the result of thermogravimetry (in air, 10° C./min) of a sulfonated terphenyl crosslinked type 3-ingredient copolymer (ZP1633) having a methyl group and a sulfophenyl group.

The FIG. 28 shows the result of thermogravimetric measurement of the terphenyl crosslinked type 3-ingredient copolymer ZP1633 in air. Since a heat decomposition starting temperature considered to be due to removal of sulfonic acid from the sulfophenyl group or the sulfonated terphenyl crosslinking ingredient is observed near 310° C., it is suggested that the heat stability is high.

Figure 29:
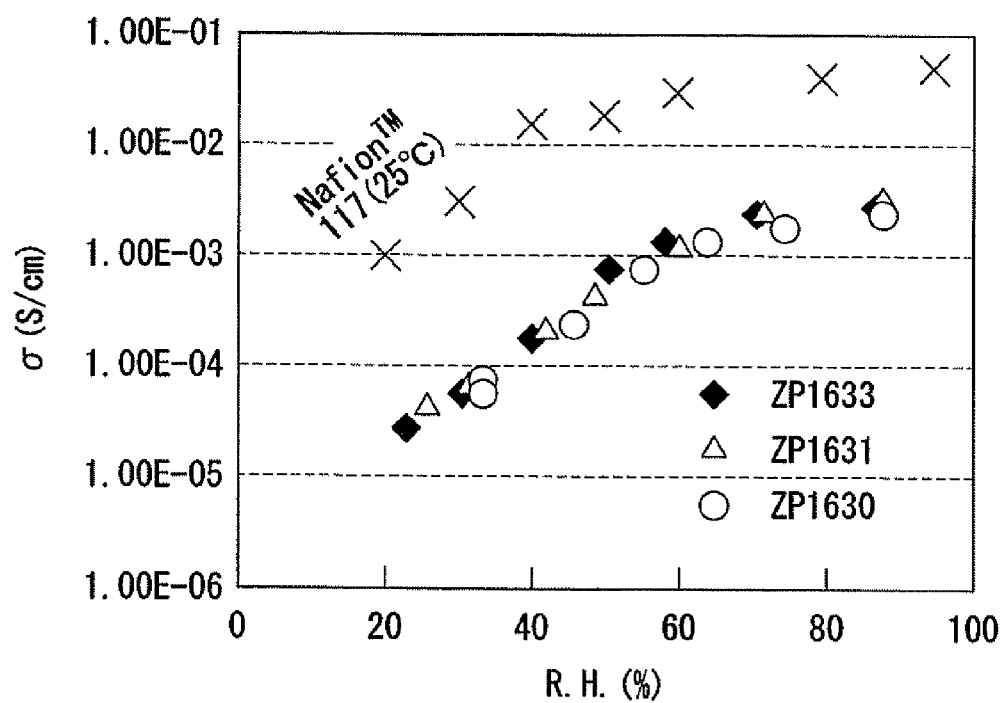
FIG. 29 shows a proton conductivity (measured at 20 to 95% R.H., 65° C.) of (sulfonated) terphenyl crosslinked type 3-ingredient copolymer having a substituent R and a sulfophenyl group as the PTFE 20 wt % composite product.

For the terphenyl crosslinked type 3-ingredient copolymers having sulfophenyl groups (ZP1630, ZP1631, ZP1633), PTFE 20 wt % composite products thereof were prepared and the conductivity was measured at 65° C. by an AC impedance method while changing the relative humidity for about 20 to 90% in accordance with Example 6 and the result is shown in FIG. 29. It can be confirmed that there is no significant difference for the level of the conductivity of the three products but any of them develops the conductivity to some extent.

Example 21

[Investigation on the Synthesis Condition for Zirconium Phenyl Phosphonate and Zirconium Methyl Phosphonate: Catalytic Reaction in Concentrated Aqueous Sulfuric Acid Solution]

[1. Synthesis of Sample]

Reaction for phenyl phosphonic acid (PPA) and zirconyl chloride octahydrate (ZrOCl₂.8H₂O) was carried out by three methods (Table 9: (1) to (3)), and crude products were separated by filtration and then washed with water and dried to obtain products quantitatively. In the synthesis method (1), gels obtained by mixing PPA and ZrOCl₂.8H₂O in water were separated by filtration and washed with water and then charged in a polytetrafluoroethylene (PTFE) inner cylinder type autoclave, dispersed in water and reacted by heating while standing still. In the synthesis method (2) both reactants were charged in a 200 mL round-bottom flask having a cooling tube, dispersed in 12N HCl and reacted by heating and stirring at 100° C. In the synthesis method (3), reaction was carried out by using 12N H₂SO₄ as the dispersant.

TABLE 9

| Sample No. | Synthesis method | PPA (mol) | MPM (mol) | ZrOCl₂ (mol) | Solvent (mL) | Reaction condition | d(001) Peak (cps)/(Å) | d(020) (Å) |
|---|---|---|---|---|---|---|---|---|
| ZP818 | (1) | 0.040 | | 0.020 | water (150) | 200° C. × 10 d | 1.6k/15.5 | 2.67 |
| ZP839 | (2) | 0.030 | | 0.015 | 12N HCl (130) | reflux × 24 h | 2.4k/15.1 | 2.65 |
| ZP840 | (2) | 0.030 | | 0.015 | 12N HCl (130) | reflux × 112 h | 3.4k/15.0 | 2.65 |
| ZP841 | (3) | 0.030 | | 0.015 | 12N H₂SO₄ (120) | reflux × 24 h | 4.9k/15.0 | 2.64 |
| ZP838 | (2) | | 0.030 | 0.015 | 9N HCl (130) | reflux × 24 h | 1.8k/9.0 | 2.66 |
| ZP854 | (3) | | 0.030 | 0.015 | 12N H₂SO₄ (75) | reflux × 24 h | 3.9k/8.7 | 2.66 |

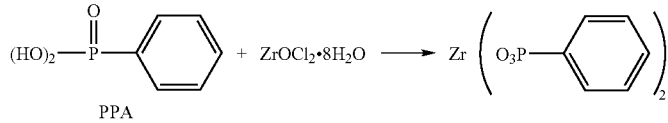

PPA
(1) Hydrothermic synthesis method
(2) Heating method in concentrated aqueous hydrochloric acid solution
(3) Heating method in concentrated aqueous sulfuric acid solution

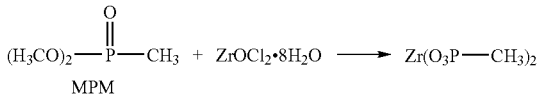

MPM
(2) Heating method in concentrated aqueous hydrochloric acid solution
(3) Heating method in concentrated aqueous sulfuric acid solution

[2. Evaluation for Sample]

Figure 30:
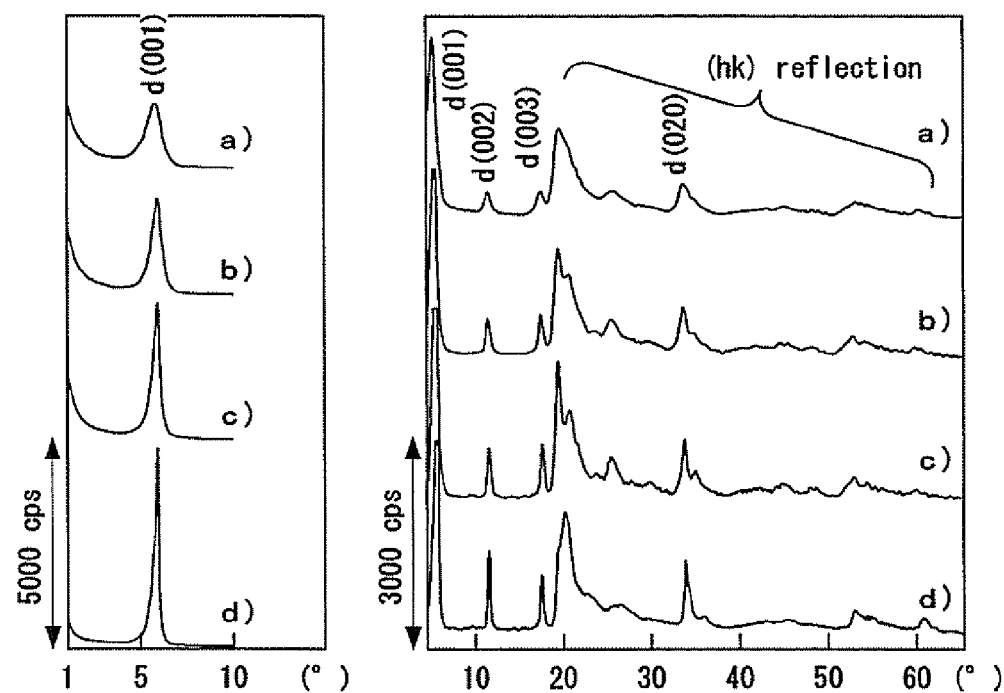
FIG. 30 is XRD patterns of zirconium phenyl phosphonate: (A) for ZP-818, (B) for ZP-839, (C) for ZP-840, and (D) for ZP-841.
Figure 31:
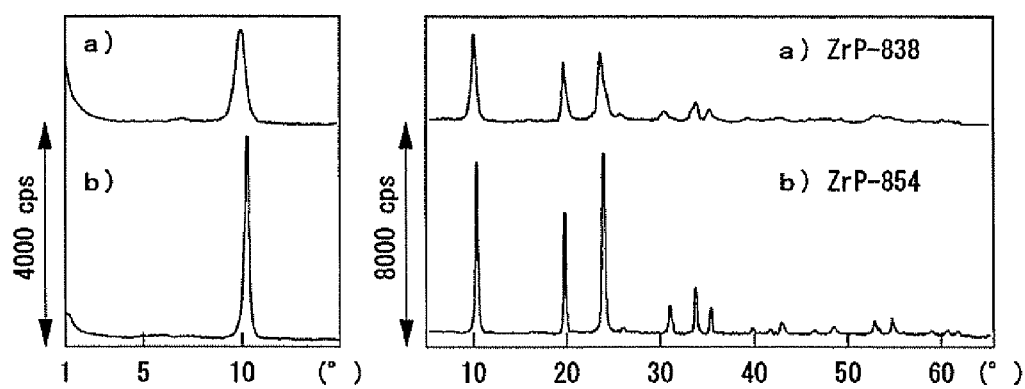
FIG. 31 is XRD patterns of zirconium methyl phosphonate: (A) for ZP-838 and (B) for ZP-854.

FIG. 30 shows XRD patterns for the products. Distinct (001) reflection and prism type (hk) reflection and d(020) peak near 2.65 Å were observed in each of them suggesting that the products were zirconium phosphonate having the α-type lamella (layered) structure. The intensity of the d(001) peak observed near 15 Å was lowest for the product (1) ZP818 and, the intensity increased as the reaction time was longer (24 hr→112 h) for the product (2) ZP839 and ZP840. It showed, however the maximum intensity even when the reaction time was not long (24 hr) for the product ZP841 (3). Since the half-value width for the intensity of the d(001) peak is in inverse proportion with the expansion size of the layered structure, the result suggests that the crystallinity of the layered structure of the product increased. That is, it has been found that when phosphonic acid (PPA) and zirconyl chloride octahydrate (ZrOCl₂. 8H₂O) were reacted in 12N H₂SO₄, a product of a layered structure having high crystallinity was obtained by the catalytic effect thereof.

It has known that not only the phosphonic acid but also the phosphonate ester can be used as the starting material in the method (2). Reaction between dimethyl methyl phosphonate ester (MPM) and zirconyl chloride octahydrate ($ZrOCl_2.8H_2O$) was carried out by the method (2) and (3) at 100° C. for 24 hours in the same manner and XRD patterns for the obtained products (ZP838, ZP854) were compared. Due to the difference for the intensity of d(001) peaks, it has been found that products of a layered structure of higher crystallinity were obtained by the reaction with zirconyl chloride octahydrate ($ZrOCl_2.8H_2O$) even by using the phosphonic acid ester (MPM) in 12N $H_2SO_4$.

From the foregoing results, it has been found that products of a layered structure of high crystallinity not having fluorine atom bonded to the metal atom can be obtained by conducting reaction with the metal (salt) compound using phosphonic acid or phosphonic acid ester as the starting material in an aqueous concentrated sulfuric acid solution.

Example 22

Figure 32:
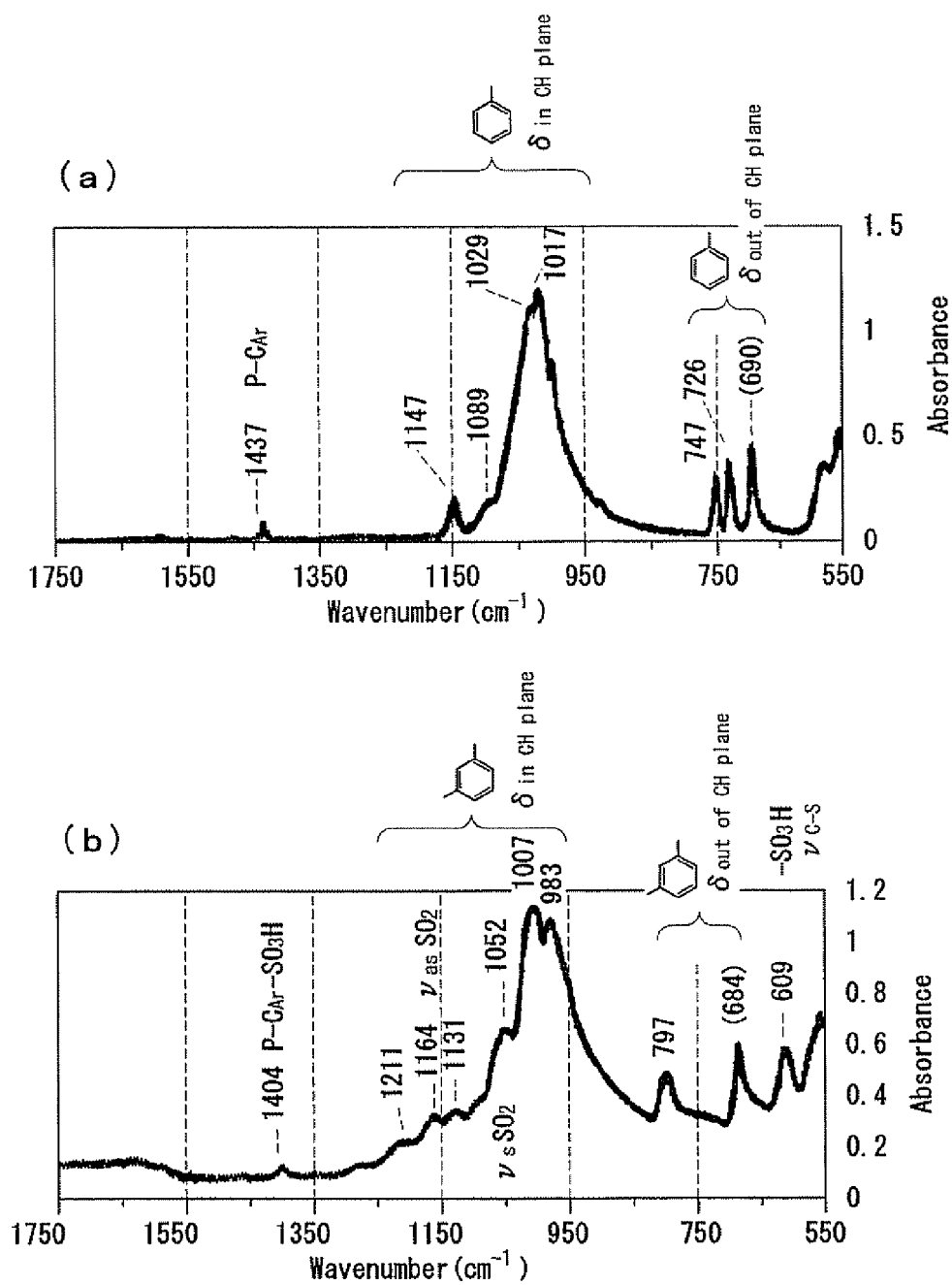
FIG. 32 shows IR spectra change before and after the sulfonation treatment for zirconium phenyl phosphonate.
Figure 33:
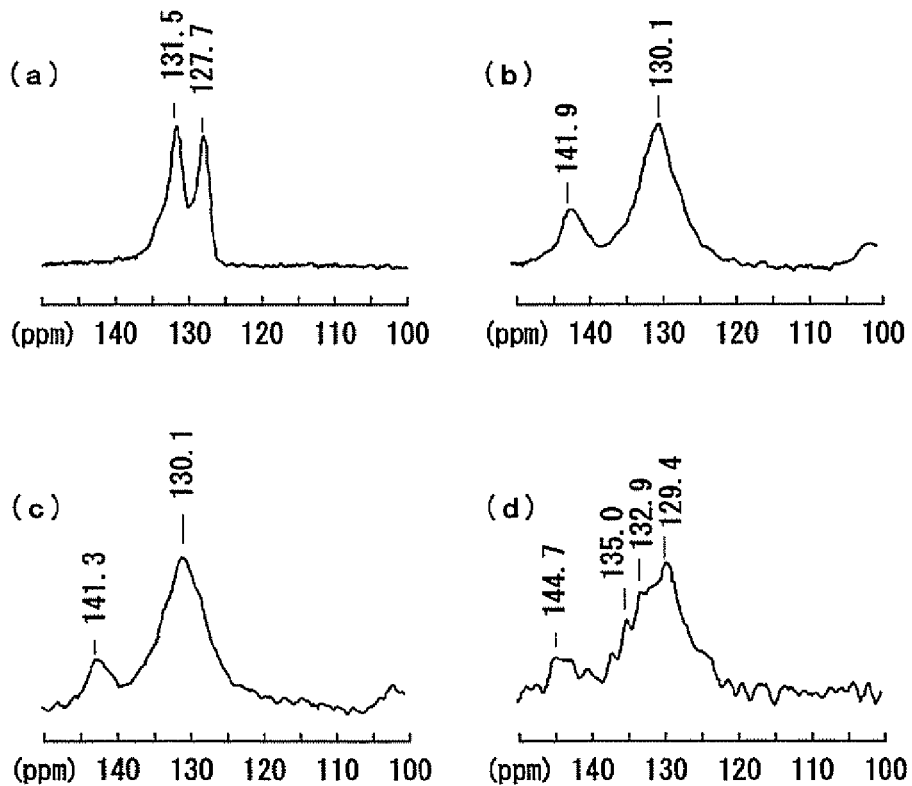
FIG. 33 is $^{13}$C-NMR spectra of phenyl group homopolymers/copolymers {Zr(O$_3$P—C$_6$H$_4$—SO$_3$H)$_{2x}$(O$_3$P-Ph)$_{2-2x}$}: in which (A) for ZP 855 (comparative specimen: x=0%); (B) for ZP 823 (PS-method: x=100%); (C) for ZP 863 (2M-method and x=100%); (D) for ZP 869 (2M-method: x=50%)

[Synthesis of Zirconium Sulfophenyl Phosphonate and Zirconium Sulfophenyl Phosphonate Copolymer Having Phenyl Group: Instabilization of the Layered Structure Due to Steric Hindrance of Sulfophenyl Group and Moderation by Introduction of Phenyl Group]
[1. Synthesis of Sample]
Zirconium sulfophenyl phosphonates were synthesized by two methods. One is a method of sulfonating a previously synthesized layered compound of zirconium phenyl phosphonate by post reaction and another is a method of sulfonating phenyl phosphonic acid which is then formed into a solution of 12N sulfuric acid ("stock solution"), and conducting reaction with $ZrOCl_2.8H_2O$ in 12N sulfuric acid by using the stock solution, thereby synthesizing a sulfonation product of a layered compound. Then, zirconium sulfophenyl phosphonate copolymer having the phenyl group was synthesized by utilizing the second method.
(1) 5 g of zirconium phenyl phosphonate (ZP855) synthesized in the same manner as in the synthesis method (3) of Example 21 was charged in a 100 mL round-bottom flask having a cooling tube, 25 mL of a 25% fuming sulfuric aced was added and reacted by stirring at a room temperature for three days under a nitrogen gas stream. The reaction mixture was poured into a beaker containing ice from 100 mL of distilled water to hydrolyze unreacted $SO_3$, to obtain semi-transparent liquid dispersion. The liquid dispersion was dialyzed by using 40 L of water to remove sulfuric acid contained therein. Concentrated hydrochloric acid was added to the obtained liquid dispersion in such an amount to provide about 6N concentration to precipitate the products, and the liquid dispersion was stirred at 100° C. for one hour to remove residual sulfuric acid. Solids were recovered by centrifugation and the aqueous dispersion was dialyzed using 20 L of water and the product ZP823 was obtained by freeze drying.
(2-1) 40 g of phenyl phosphonic acid was charged in a 100 mL round-bottom flask having a cooling tube, 77.3 g of a 60% fuming sulfuric acid was added and they were reacted by stirring at 80° C. for 1 day in a nitrogen gas stream. The reaction mixture was poured into a beaker containing ice formed by freezing 60 g of distilled water and, further, the reaction mixture in the round-bottom flask was washed out thoroughly with 16 g of water. An aqueous solution of 12N sulfuric acid of a 32 wt % sulfophenyl phosphonic acid was obtained by making the entire amount of finally added water to 86.0 g, to form a stock solution (SPPA-1600). 14.9 g of the stock solution was charged in a 100 mL round-bottom flask, and $ZrOCl_2.8H_2O$ (4.83 g) and 17.5 mL of an aqueous solution of a 12N sulfuric acid were added and reacted by stirring under heating at 100° C. for 24 hours. The reaction mixture was poured into a beaker containing 200 mL of water to obtain a semi-transparent liquid dispersion. The subsequent treatment was conducted in the same manner as in (1) above and the product ZP863 was obtained by freeze drying.
(2-2) 7.43 g (15 mmol) of the stock solution (SPPA-1600), 2.37 g (15 mmol) of phenyl phosphonic acid, and 21.2 mL of an aqueous solution of a 12N sulfuric acid were charged in a 100 mL round-bottom flask having a cooling tube and heated and stirred at 100° C. An aqueous solution of $ZrOCl_2.8H_2O$ (4.83 g, 15 mmol) dissolved in 4 mL of water was added dropwise and reacted by stirring at that temperature for 24 hours. The reaction mixture was poured into a beaker containing 200 mL of water to obtain a clouded liquid dispersion. After recovering solids by centrifugation, heat treatment in hydrochloric acid at about 6N and dialysis were conducted in the same manner as in (1) above to obtain ZP869 product by freeze drying.
[2. Evaluation of Sample]
Sulfonation of the products was confirmed in the measurement of IR spectra by the presence of $v_{C-S}$ absorption attributable to aromatic sulfonic acid observed near 610 $cm^{-1}$ in the IR spectra measurement (FIG. 32). Further, in the $^{13}C$ MAS-NMR measurement (FIG. 33), sulfonation could be confirmed by the phenyl group peaks at about 132, 128 ppm and sulfophenyl group peaks at about 142, 130 ppm and, at the same time, it was confirmed that the product ZP869 had both the sulfophenyl group and the phenyl group.

The sulfonic group was determined by neutralization titration. A sample in an amount of 50 µeq having a sulfonic group was taken in a sealed vessel and stirred with addition of 25 mL of an aqueous solution of 2M NaCl at a room temperature for one night. The solution was diluted with 20 mL of water, and an aqueous solution of 0.05M KOH was dropped at a constant speed by an automatic titrator "Tinet" manufactured by Metrohm Co. to obtain a titration curve. A neutralization equivalent amount was determined from the value showing a maximum value near pH≈4 in the differentiation curve thereof. Both the values for ZP823 and ZP863 were 3.5 meq/g, which agreed with the starting composition. The value of 1.2 meg/g for the ZP869 corresponds to the amount of sulfonic acid of about 60% for the starting composition.

Figure 34:
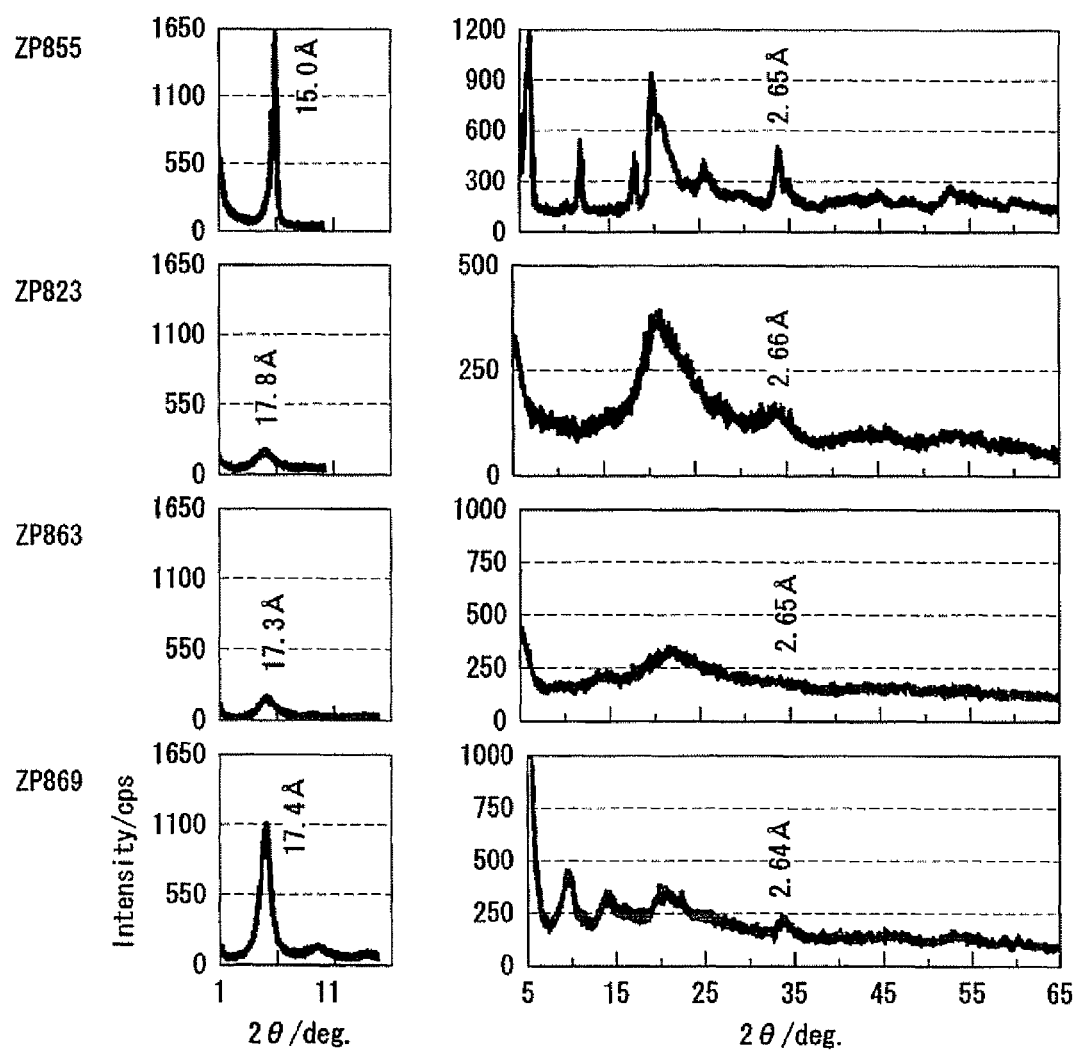
FIG. 34 is XRD patterns for zirconium phenyl phosphonates and sulfonation products thereof.

When comparing XRD patterns (FIG. 34), the d(001) peak intensity was remarkably lowered in zirconium sulfophenyl phosphonate ZP823 (17.8 Å) and ZP863 (17.3 Å) obtained by the two synthesis methods, compared with zirconium phenyl phosphonate ZP855 (15.0 Å). However, zirconium sulfophenyl phosphonate copolymer ZP869 introduced with the phenyl group showed a d(001) peak at a high intensity at 17.4 Å. The result of such XRD suggests that since the zirconium phosphonate containing 100% sulfophenyl groups having a bulky sulfonic group is instable in the structure, it is difficult to obtain a product of a layered structure of high crystallinity by any one of the synthesis methods.

On the other hand, in the 2-ingredient Compound ZP869 introduced with the phenyl phosphonic acid, it is suggested that the steric hindrance of the sulfophenyl group was moderated to obtain a layered structure of high crystallinity. Further, presence of d(001) peak only by the number of one at 17.4 Å shows that the 2-ingredient phosphonic acid was reacted uniformly to provide a uniform interlayer distance.

That is, by the method of using the stock solution, it has been found that a layered zirconium phosphonate in which the phenyl phosphonic acid having a substituent instable to the post-sulfonation is uniformly copolymerized with sulfophenyl phosphonic acid can be synthesized by the method of using the stock solution.

Figure 35:
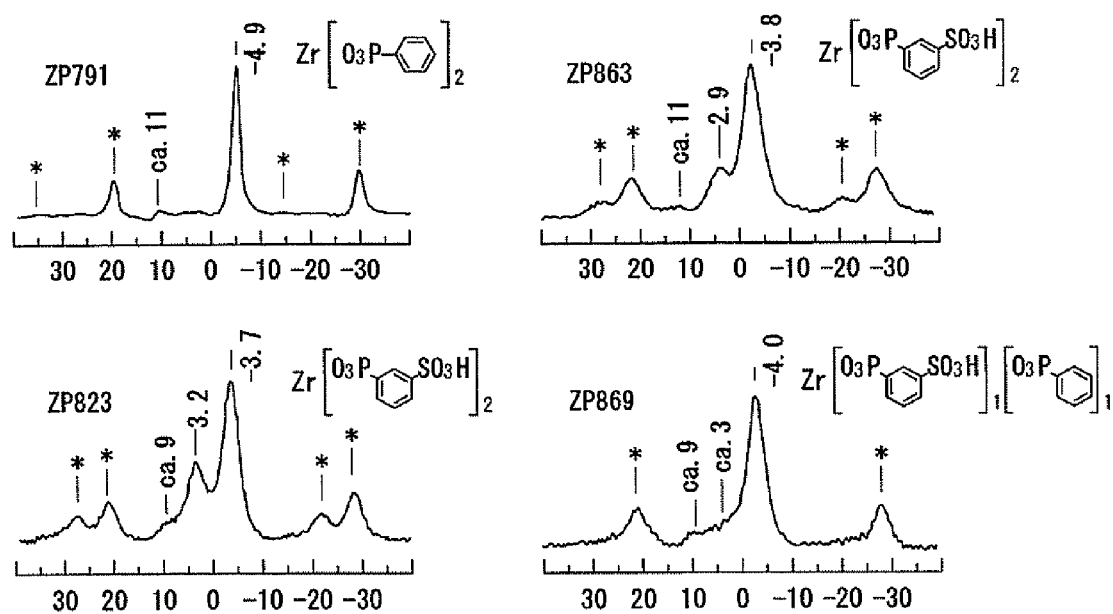
FIG. 35 is $^{31}$P MAS-NMR spectra of layered zirconium phosphonates having phenyl group and/or sulfophenyl group.

The state of moderating the steric hindrance of the bulky sulfophenyl group by the introduction of the phenyl group is observed in details from $^{31}$P MAS-NMR spectra (FIG. 35). The zirconium phenyl phosphonate ZP791 with no steric hindrance shows only the peak at about −5 ppm attributable to the P atom bonded by way of three Zr atoms and O atoms. Zirconium sulfophenyl phosphonate ZP823, ZP863 introduced with sulfonic groups by 100% show the peak (about −4 ppm) together with peak at about +3 ppm attributable to the P atom bonded by way of two Zr atoms and O atoms.

On the other hand, in the 2-ingredient compound ZP869 introduced with the phenyl phosphonic acid, since the peak at about +3 ppm is weakened to a small shoulder and the peak at −4 ppm is predominant, it can be confirmed that the steric hindrance of the sulfophenyl group can be moderated by the introduction of the phenyl group.

Figure 36:
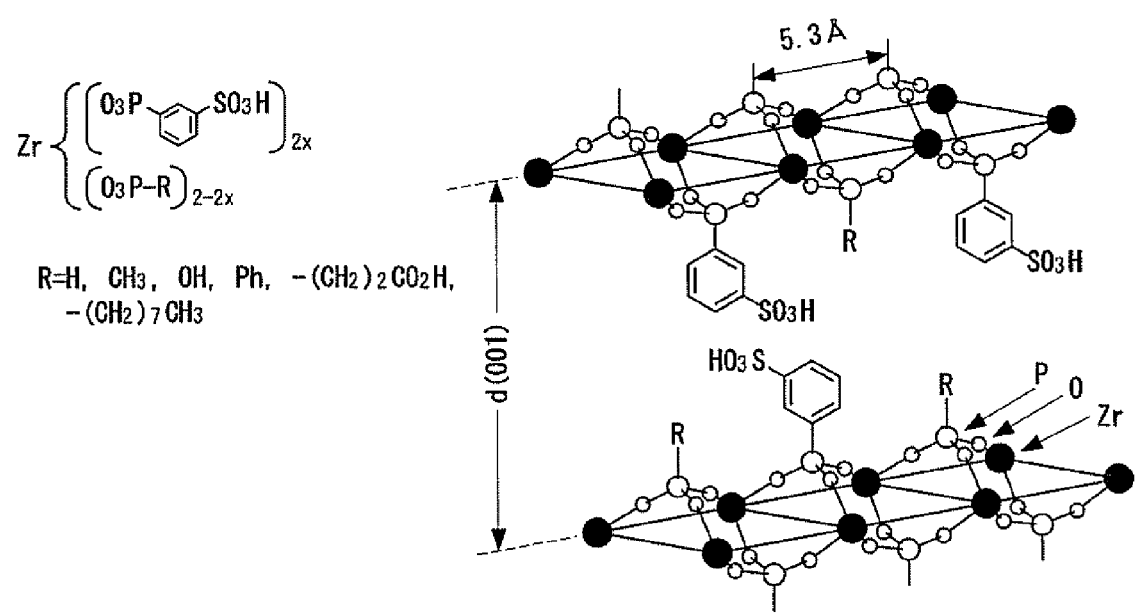
FIG. 36 shows a structural model and a structural formula of a zirconium sulfophenyl phosphonate 2-ingredient copolymer having a substituent R.

From the results described above, it can be seen that while zirconium sulfophenyl phosphonate not having fluorine atoms bonded with metal atoms (homopolymer) can be synthesized by carrying out the reaction in an aqueous solution of a concentrated sulfuric acid, it is difficult to obtain a product of a layered structure of high crystallinity. In this case, as an advantage of conducting reaction in the aqueous solution of the concentrated sulfuric acid, no complicate isolation operation is necessary since the sulfophenyl phosphonic acid after sulfonation of phenyl phosphonic acid can be used as a stock solution. Further, the method of using the stock solution can also include an advantage capable of synthesizing a copolymer of zirconium sulfophenyl phosphonate introduced with the phenyl group as a substituent instable to the post-sulfonation and a product of a layered structure of high crystallinity can be synthesized. FIG. 36 shows a structural model and a structural formula together for the 2-ingredient zirconium sulfophenyl phosphonate copolymer having various substituents R synthesized in Examples 22 to 26.

Example 23

[Synthesis of Zirconium Sulfophenyl Phosphonate Copolymer Having Methyl Group: Copolymer Introduced with Hydrophobic and Small Molecular Size Methyl Group]
[1. Synthesis of Sample]
Zirconium sulfophenyl phosphonate copolymers having methyl group were synthesized in accordance with two methods described above.
(1) In the method of post-sulfonation, in accordance with the reaction operation of Example 21, a predetermined amount of phenyl phosphonic acid and that of dimethyl methyl phosphonate were reacted in a 12N sulfuric acid with ZrOCl$_2$.8H$_2$O at 100° C. for 24 hours to synthesize zirconium phenyl-/methyl-phosphonate copolymers. Then, in accordance with the reaction operations in Example 22 (1), the zirconium phenyl-/methyl-phosphonate copolymer was sulfonated. Upon pouring the reaction mixture to ice, since crude products were precipitated, they were separated by filtration and applied with the treatment in about 6N hydrochloric acid in the same manner and dried under a reduced pressure at 80° C. to obtain a product.
(2) In the method by the stock solution of sulfonated phosphonic acid, the 12N sulfuric acid solution of sulfophenyl phosphonic acid prepared in Example 22 (2-1) was used as the stock solution, a predetermined amount of dimethyl methyl phosphonate was added and reacted with ZrOCl$_2$.8H$_2$O in the 12N sulfuric acid at 100° C. for 24 hours to directly synthesize a zirconium sulfophenyl-/methyl-phosphonate copolymer. The reaction operation was in accordance with the method of Example 22(2-2) and the product was obtained by drying under a reduced pressure at 80° C. after removing water after dialysis.

Figure 37:
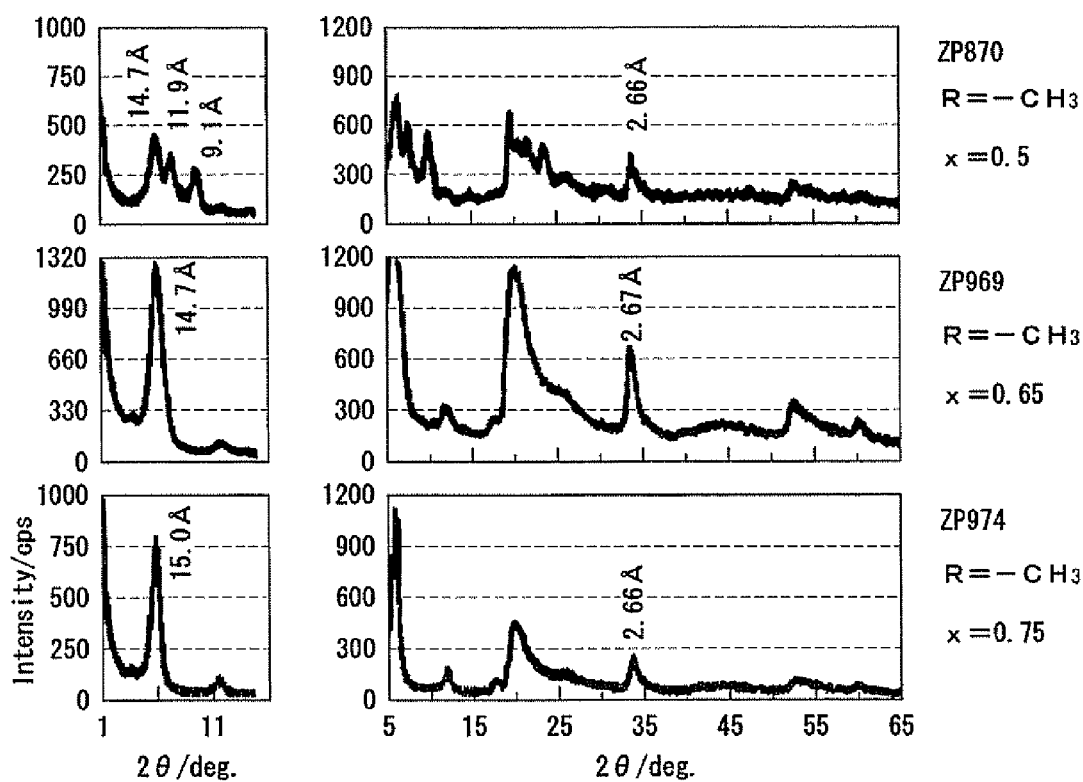
FIG. 37 is XRD patterns of (non-sulfonated) zirconium phenyl-/methyl-phosphonate copolymers.
Figure 38:
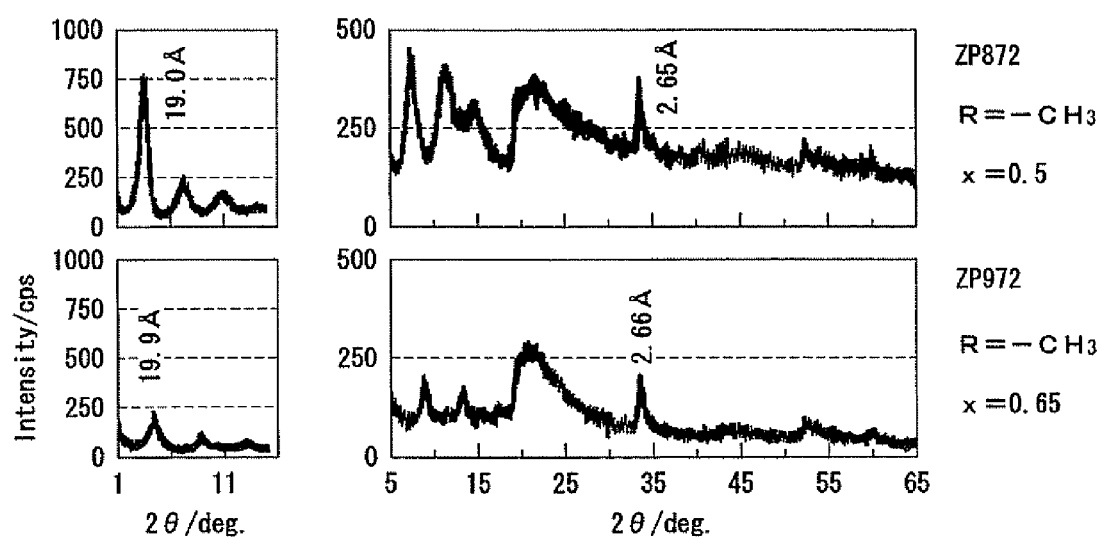
FIG. 38 is XRD patterns of sulfonated zirconium phenyl-/methyl-phosphonate copolymers synthesized by post-sulfonation.
Figure 39:
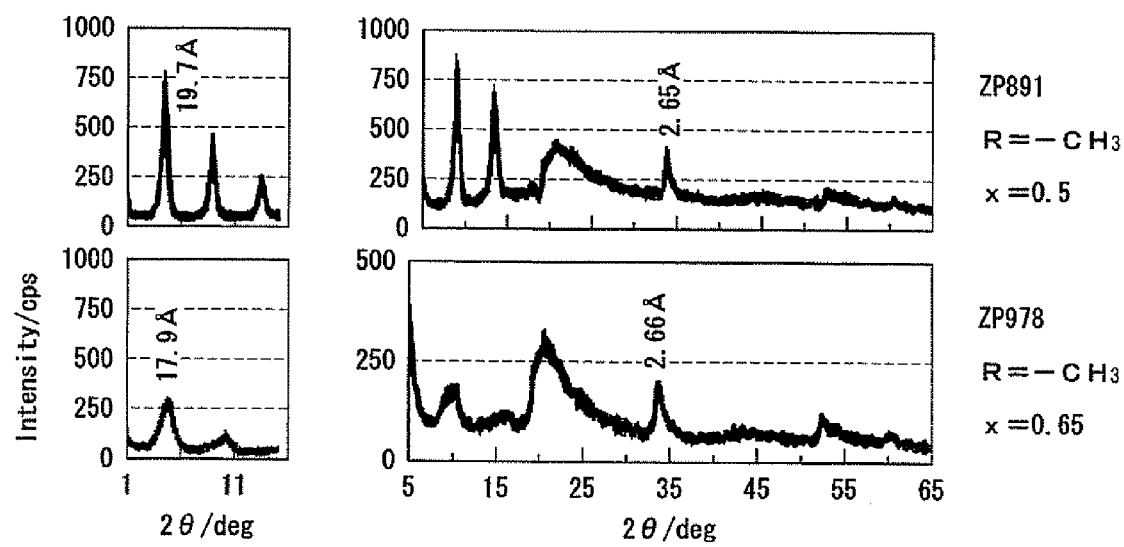
FIG. 39 is XRD patterns of a sulfonated zirconium phenyl-/methyl-phosphonates synthesized by a sulfonated stock solution.

[2. Evaluation for Sample]
Synthesis was carried out at a starting composition of Zr:P=1:2 (atomic ratio) while changing the molar ratio (x) of phenyl phosphonic acid or sulfophenyl phosphonic acid (hereinafter both of them are referred to as phenyl type phosphonic acid) to the entire phosphonic acid as: x=0.50, 0.65, and 0.75. That is, the starting compositional molar ratio of phenyl type phosphonic acid:dimethyl methyl phosphonate (2x:2-2x) was changed as 1.0:1.0, 1.3:0.7, and 1.5:0.5. FIG. 37 to FIG. 39 show XRD patterns for the obtained zirconium phenyl-/methyl-phosphonate copolymers and sulfonation products thereof.

Figure 40:
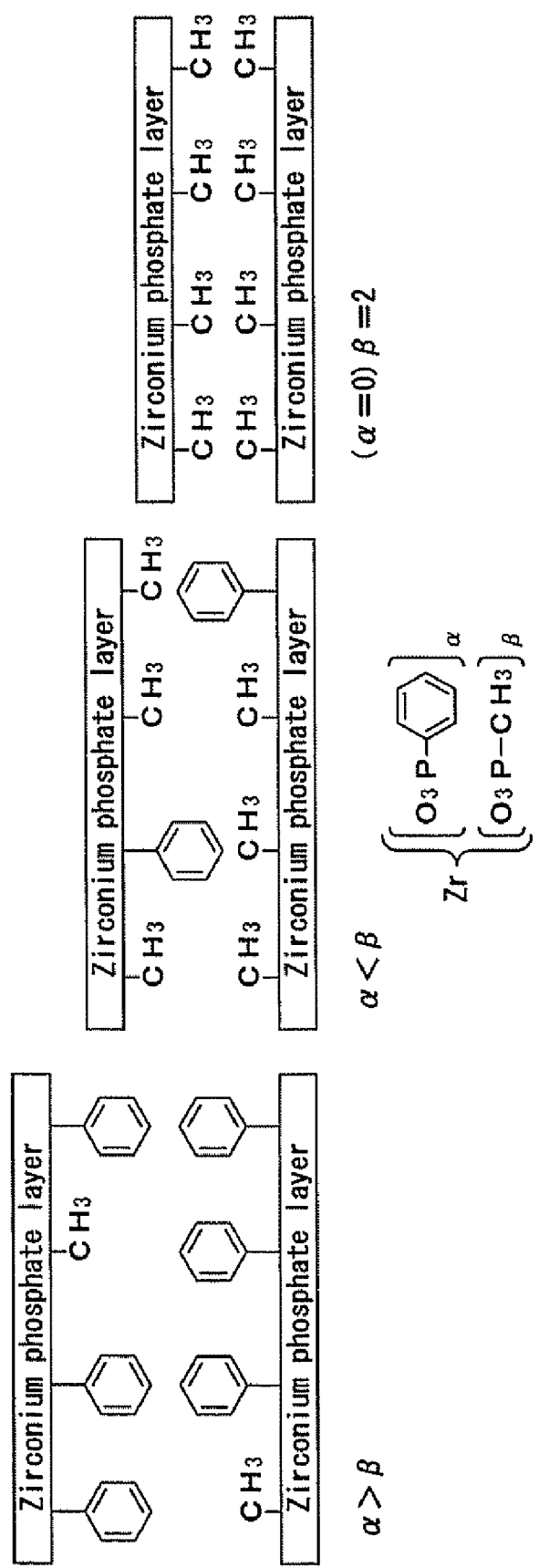
FIG. 40 is structural models of zirconium phenyl-/methyl-phosphonates.

In the not sulfonated zirconium phenyl-/methyl-phosphonate copolymers in FIG. 37, since three peaks of 14.7 Å, 11.9 Å, and 9.1 Å are observed in a case where x=0.50 (ZP870), it is considered that two types of phosphonic acids are not uniformly copolymerized but products of three structures represented by the structural formula Zr(O$_3$P-Ph)$_\alpha$(O$_3$P—CH$_3$)$_\beta$ ($\alpha$>$\beta$, $\alpha$<$\beta$, ($\alpha$=0) $\beta$=2) shown in FIG. 40 are present together. However, when the ratio of phenyl phosphonic acid is increased as: x≧0.65 (ZP969, ZP974), since only the peak of about 15 Å is present, it is considered that only the structure: $\alpha$≧$\beta$ is present. As shown in FIG. 38, when they are post-sulfonated, the product at x=0.50 (ZP872) shows only a sharp 19 Å peak, it is considered that re-reaction occurred (to form only the structure $\alpha$>$\beta$ and, at the same time) the crystallinity of the layered structure is improved. The product at x=0.65 (ZP972) shows only the 19 Å peak and, since the intensity is lowered, it is considered that the steric hindrance of the sulfophenyl group is large. Also for the products synthesized by the method of using the stock solution, similar trend is observed for the crystallinity of the layered structure in a case: x=0.50 (ZP891) and x=0.65 (ZP978) (FIG. 39).

Figure 41:
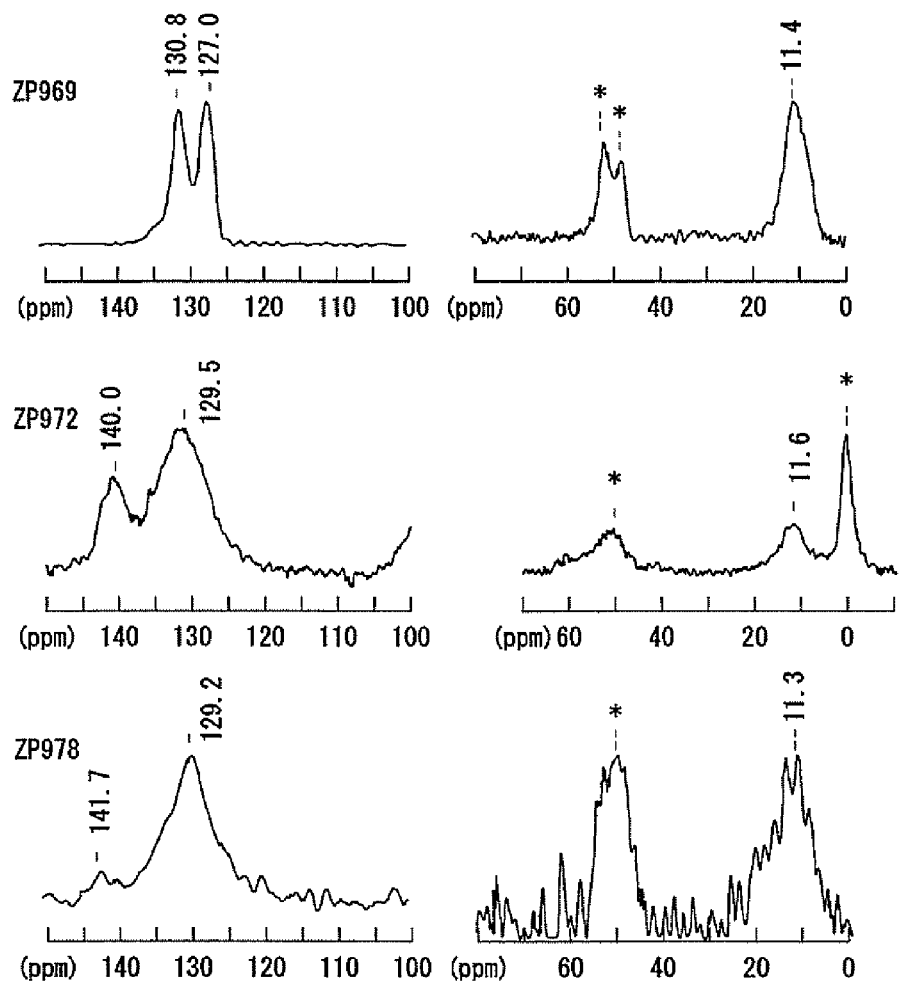
FIG. 41 is $^{13}$CMAS-NMR spectra (*=spinning side band) of zirconium phenyl phosphonate copolymers having a methyl group and sulfonation products thereof where ZP969: Zr{(O$_3$P—C$_6$H$_5$)$_{1.3}$(O$_3$P—CH$_3$)$_{0.7}$}, ZP972: Zr{O$_3$P—C$_6$H$_4$—SO$_3$H)$_{1.3}$(O$_3$P—CH$_3$)$_{0.7}$} (synthesized by post-sulfonation), ZP978:Zr{O$_3$P—C$_6$H$_4$—SO$_3$H)$_{1.0}$(O$_3$P—CH$_3$)$_{1.0}$} (synthesized by sulfonated stock solution)

FIG. 41 shows $^{13}$C MAS-NMR spectra of the copolymers. Peaks for the phenyl group can be observed at 127 and 131 ppm, the peaks for the sulfophenyl group can be observed at about 130 ppm and about 140 ppm, and the peak for the methyl group can be observed at about 11 ppm, and the structure can be confirmed.

Figure 42:
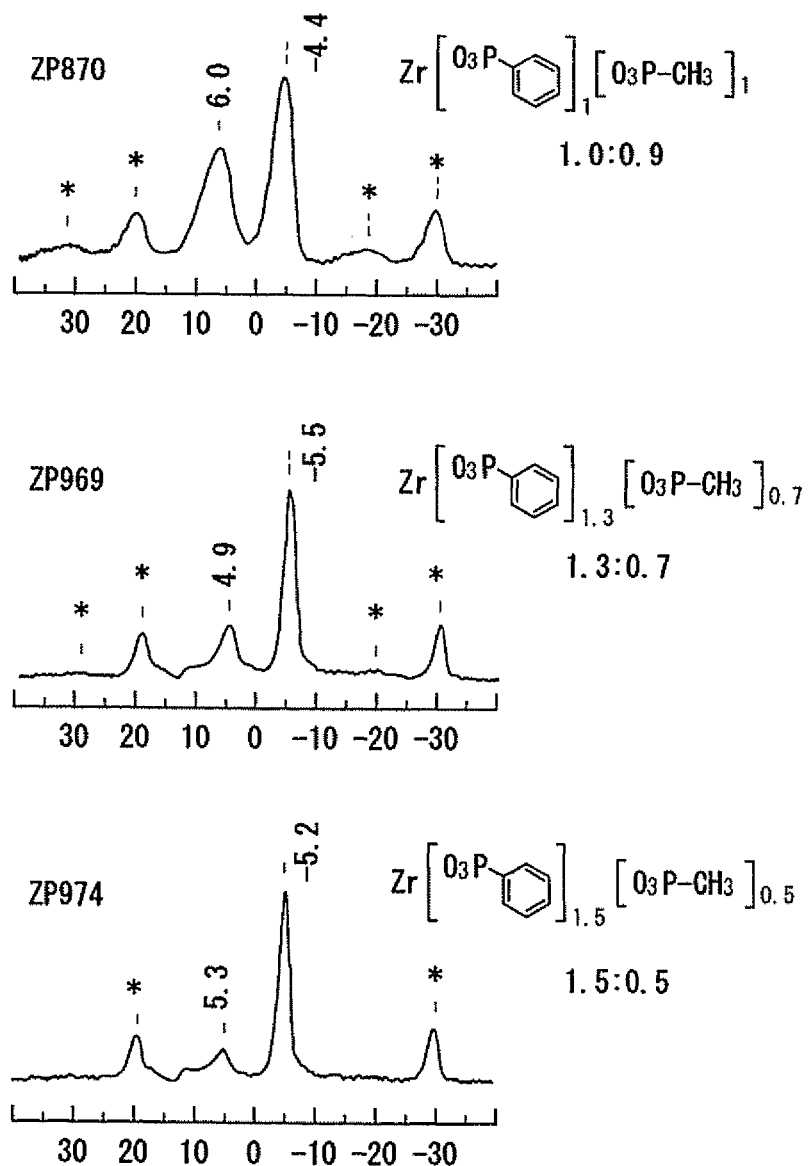
FIG. 42 is $^{31}$P MAS-NMR spectra (*=spinning side band) of non-sulfonated zirconium phenyl phosphonate copolymer.
Figure 43:
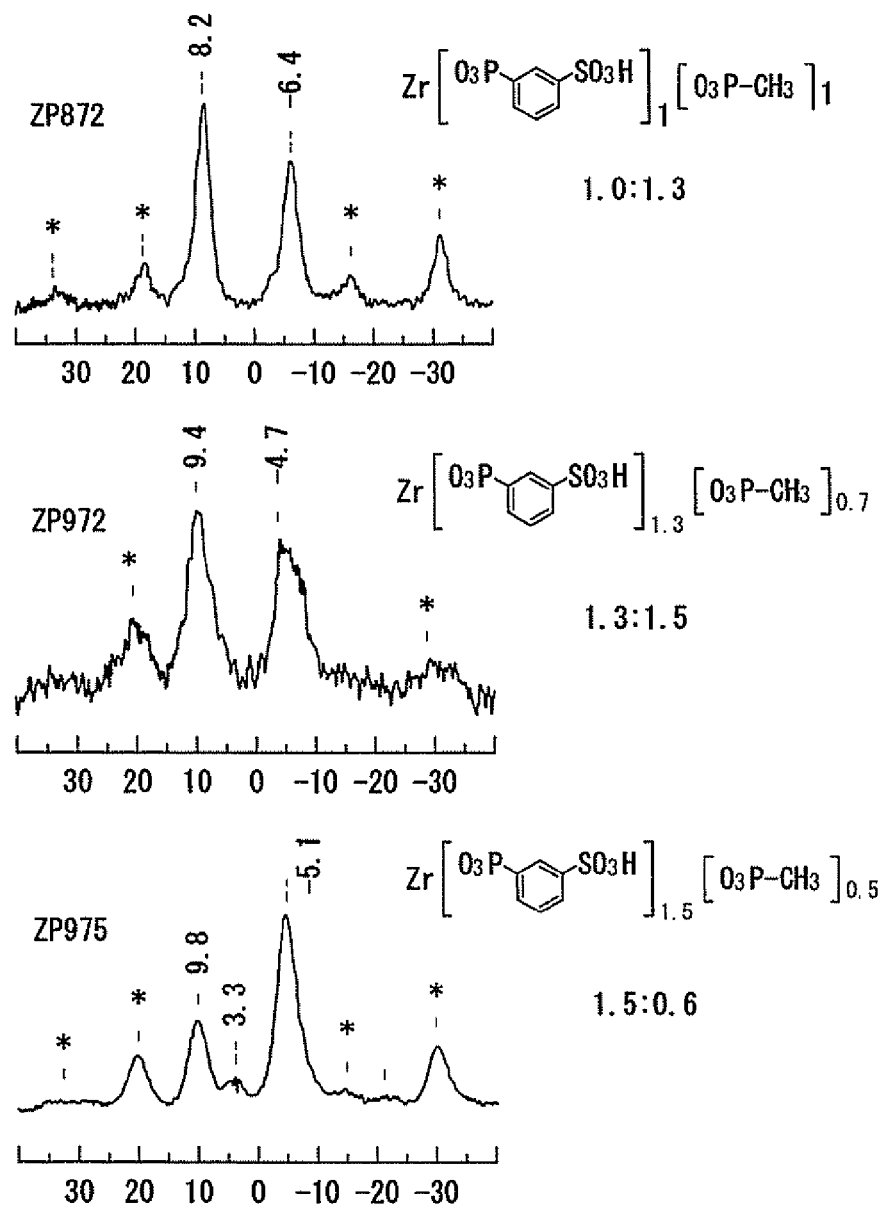
FIG. 43 is $^{31}$P MAS-NMR spectra of zirconium sulfophenyl phosphonate copolymers synthesized by post-sulfonation.
Figure 44:
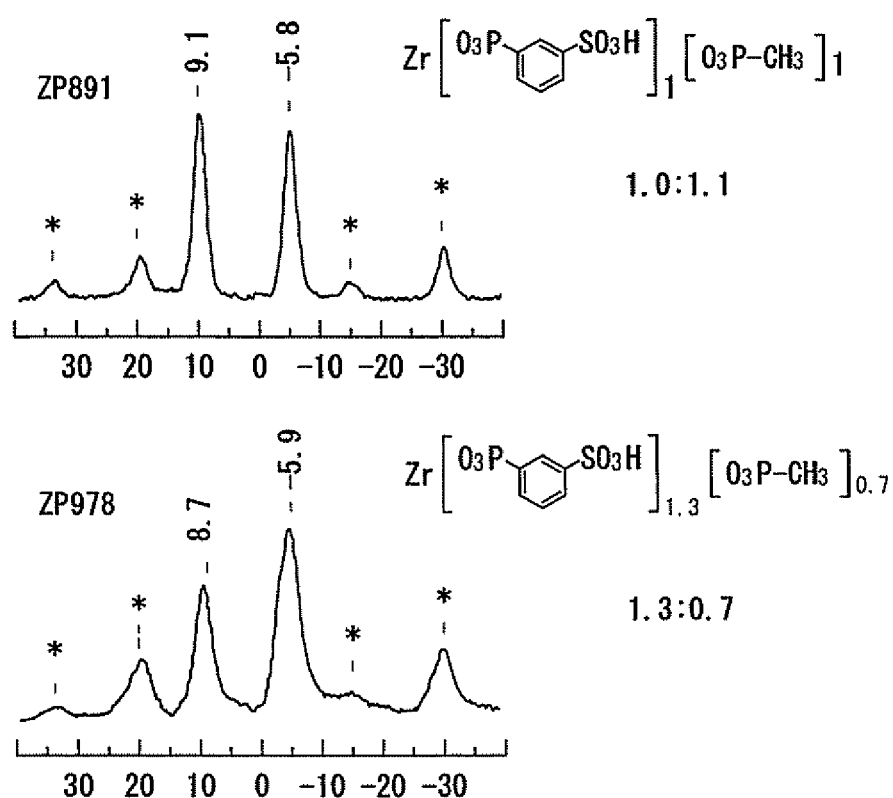
FIG. 44 is $^{31}$P MAS-NMR spectra of zirconium sulfophenyl phosphonate copolymers synthesized by a sulfonated stock solution.

FIG. 42 to FIG. 44 show $^{31}$P MAS-NMR spectra of the copolymers. In the zirconium phenyl-/methyl-phosphonate copolymer, about −4 to −5 ppm peak attributable to the phenyl group and about 5 to 6 ppm peaks attributable to the methyl group are observed. In the zirconium sulfophenyl-/methyl-phosphonate copolymers, since about −5 to −6 ppm peaks attributable to the sulfophenyl group and about 8 to 10 ppm peaks attributable to the methyl group are observed, the structure can be confirmed again.

Further, the composition of the product copolymers was investigated by determining the area ratio of the peaks. In the zirconium phenyl-/methyl-phosphonate copolymer, the peak area ratio is 1.0:0.9 (ZP870), 1.3:0.7 (ZP969), and 1.5:0.5 (ZP974), and the product compositional ratio and the starting compositional ratio show good correspondence. On other hand, when they are treated by post-sulfonation, the peak area ratio was changed to 1.0:1.3 (ZP872), 1.3:1.5 (ZP972), and 1.5:0.6 (ZP975), and the content of the methyl group was increased in each of the product compositional ratio. It is estimated that upon occurrence of re-reaction in the reaction process of the post-sulfonation (the crystallinity of the layered structure was increased, but at the same time) water soluble sulfophenyl phosphonic acid leached to some extent. On the other hand, in the zirconium sulfophenyl-/methyl-phosphonate copolymers synthesized by using the stock solution, the peak area ratios were: 1.0:1.1 (ZP891), 1.3:0.7 (ZP978) and a copolymerized compositional ratio showing good correspondence to the starting compositional ratio was obtained.

In the same manner as in Example 22, a titration curve by neutralization was determined, and a neutralization equivalent amount was determined based on the value showing a maximum near pH≈4 on the differentiation curve thereof. The values for ZP872, ZP972, and ZP975 are 2.1, 2.5, and 4.0 meq/g respectively which correspond to the amount of sulfonic acid of 0.9 times, 0.9 times, and 1.3 times the starting composition. The values for ZP891 and ZP978 are 2.8 and 2.2 meq/g, which correspond to the amount of sulfonic acid of 1.2 times and 0.8 times the starting composition.

From the result described above, it can be seen that by carrying out the reaction in an aqueous solution of a concentrated sulfuric acid in a case where the substituent of the second ingredient phosphonic acid is a methyl group which is hydrophobic and small in the molecule size, a copolymer of zirconium phenyl phosphonate having a copolymerized composition reflecting the starting composition not having the fluorine atom bonded to the metal atom can be synthesized. Further, for synthesizing the copolymer of the zirconium sulfophenyl phosphonate having the methyl group, not having the fluorine atom bonded to the metal atom and having a copolymerized composition reflecting the starting composition, a method of using the stock solution of the sulfonated phosphonic acid is excellent over the method of post-sulfonation. It has been found that with the starting composition at X=0.50, a product having a layered structure of high crystallinity can be synthesized by any of the methods.

Example 24

[Synthesis of Zirconium Sulfophenyl Phosphonate Copolymer Having a Hydroxyl Group or a Carboxyethyl Group: Copolymer Introduced with Oh Group of Small Molecule Size or $C_2H_5CO_2H$ Group of Large Molecule Size as Hydrophilic Substituent]
[1. Synthesis of Sample]

Synthesis of Zirconium Sulfophenyl Phosphonate copolymer (x=0.50) having a hydroxyl group or a carboxyethyl group as the substituent other than the methyl group was carried out by the identical two methods with those in the previous example using phosphoric acid and carboxyethyl phosphonic acid as the second ingredient phosphonic acid at a starting composition of Zr:P=1:2.
[2. Evaluation for Sample]

Figure 45:
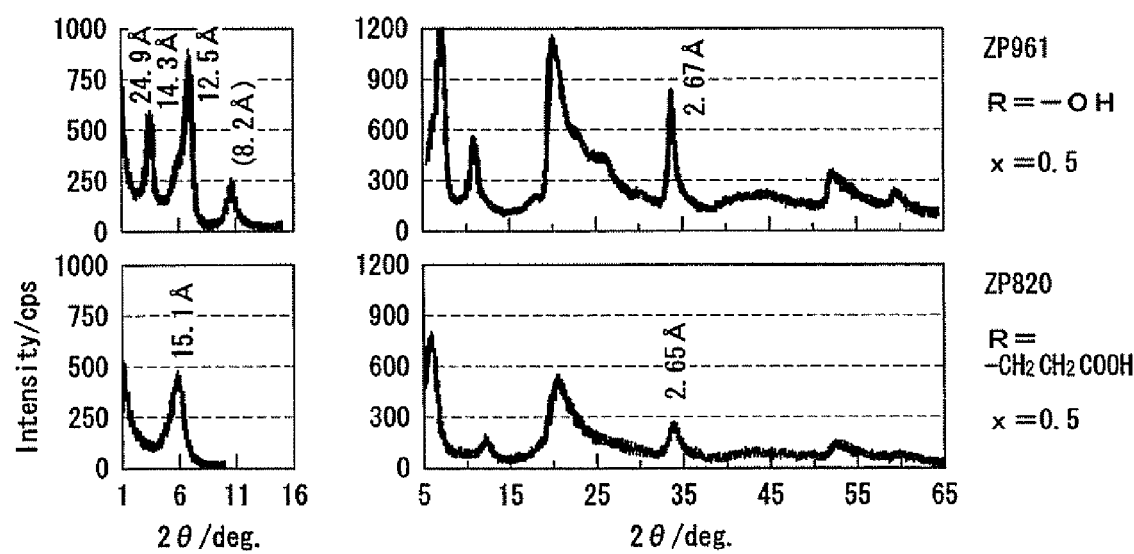
FIG. 45 is XRD patterns of non-sulfonated phenyl phosphonate copolymers.
Figure 46:
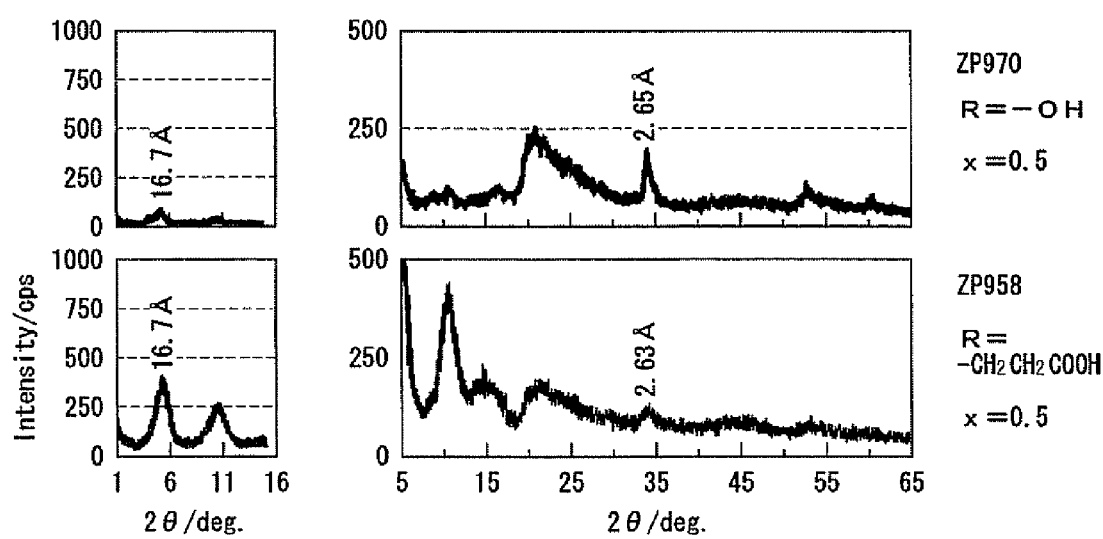
FIG. 46 is XRD patterns of sulfonated phenyl phosphonate copolymer synthesized by a post-sulfonation.
Figure 47:
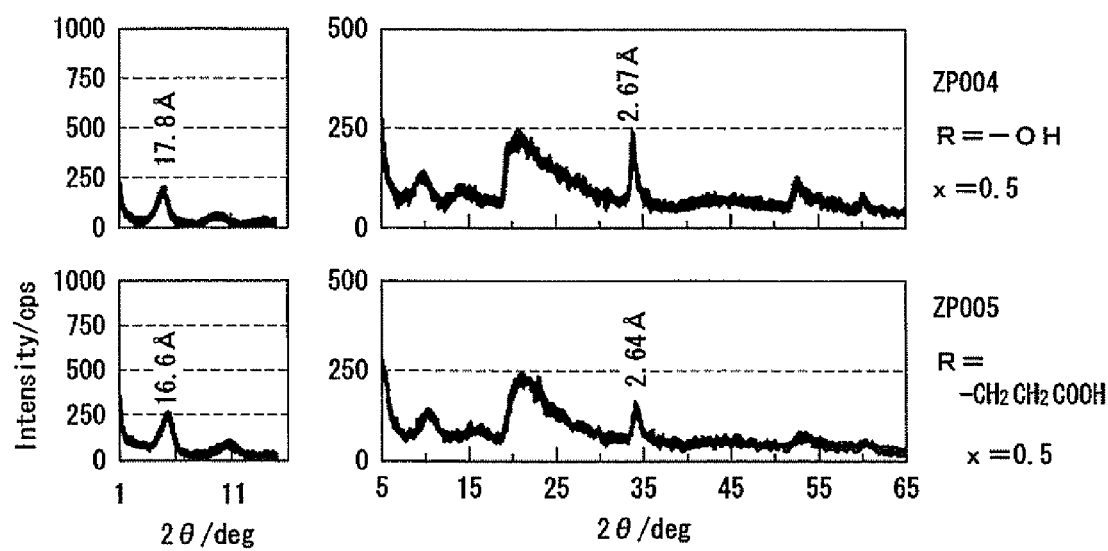
FIG. 47 is XRD patterns of sulfonated phenyl phosphonate copolymers synthesized by a sulfonated stock solution.
Figure 48:
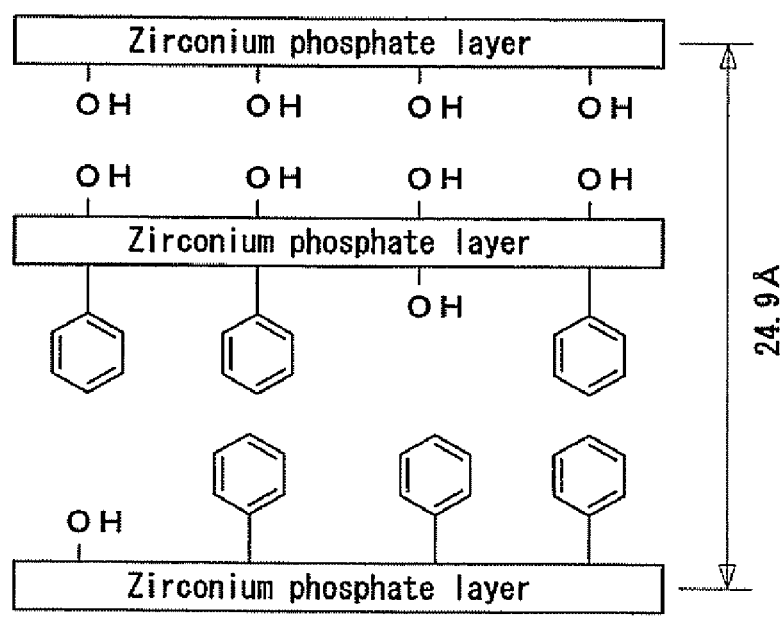
FIG. 48 shows a structural model of a stage compound of a zirconium phenyl phosphonate having a hydroxyl group.

FIG. 45 to FIG. 47 show XRD patterns for obtained zirconium phenyl phosphonate copolymers and sulfonation products thereof. In the not sulfonated zirconium phenyl phosphonate copolymer in FIG. 45, since three peaks of 24.9 Å, 14.3 Å (shoulder), and 12.5 Å are observed in a case of R=OH (ZP961), it is considered that the two types of phosphonic acids are not uniformly copolymerized. Specifically, it is considered that the two peaks for 14.3 Å (shoulder) and 12.5 Å are attributable to products of $ZR(O_3P-Ph)_\alpha(O_3P-OH)_\beta$, corresponding to the two structures at α>β, and α<β. It is considered that the peak of 24.9 Å is attributable to "staged compound" of $Zr(O_3P-Ph)_\alpha(O_3P-OH)_\beta$ at α>β and (α=0), β=2 with reference to a literature (W. R. Leenstra, Inorg. Chem., 1998, 37, 5317) (refer to FIG. 48).

In a case of R=$C_2H_4CO_2H$ (ZP820), only the peak of about 15 Å is obtained and it is considered that the two types of the phosphonic acids were uniformly copolymerized. Each of the sulfophenyl phosphonic acid copolymers obtained by treating the copolymers by post-sulfonation (ZP970, ZP958; FIG. 46) and sulfophenyl phosphonic acid copolymers synthesized by using the stock solution of sulfophenyl phosphonic acid (ZP004, ZP005; FIG. 47) was product showing uniform interlayer distance (about 17 Å) like in Example 23.

Figure 49:
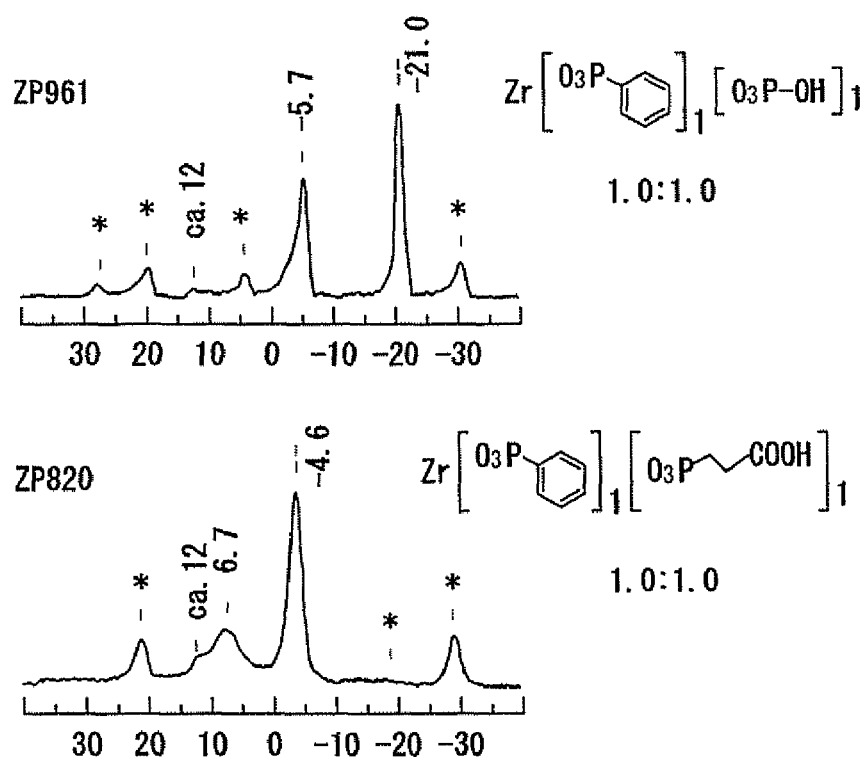
FIG. 49 is $^{31}$P MAS-NMR spectra (*=spinning side band) of non-sulfonated zirconium phenyl phosphonate copolymers.
Figure 50:
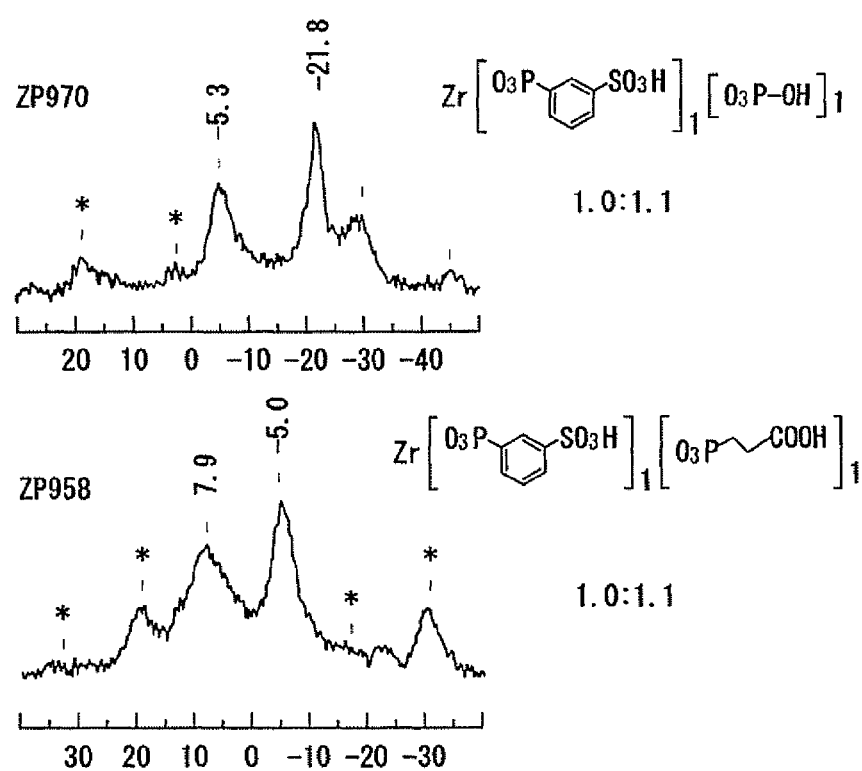
FIG. 50 is $^{31}$P MAS-NMR spectra of zirconium sulfophenyl phosphonate copolymers synthesized by post-sulfonation.
Figure 51:
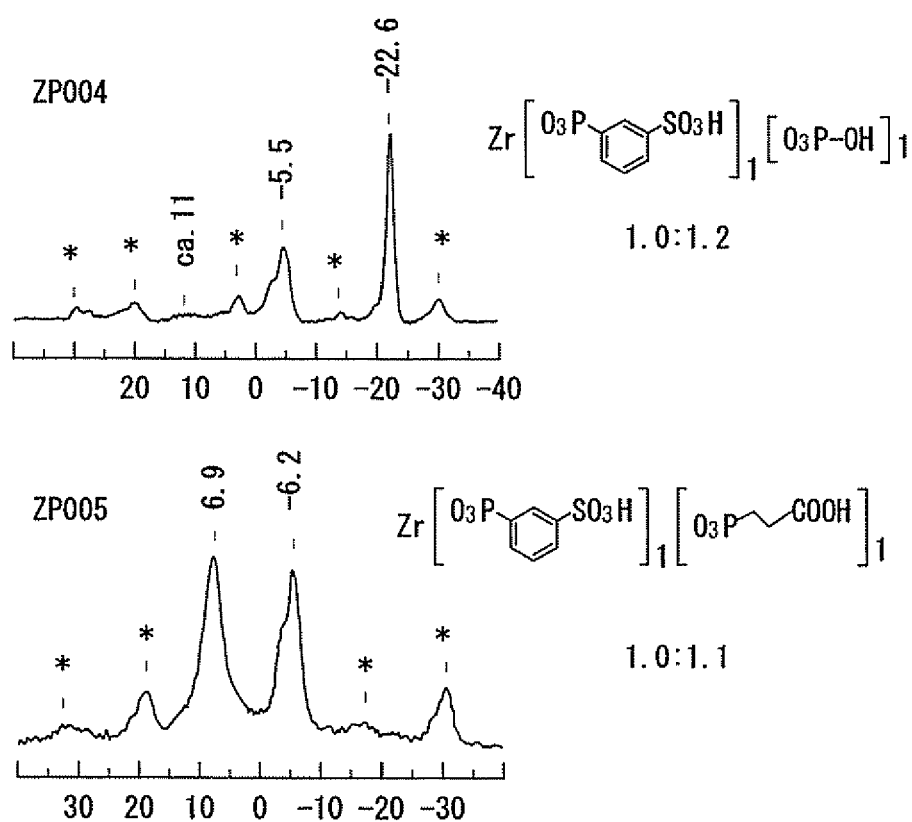
FIG. 51 is $^{31}$P MAS-NMR spectra of zirconium sulfophenyl phosphonate copolymers synthesized by a sulfonated stock solution.

FIG. 49 to FIG. 51 show $^{31}P$ MAS-NMR spectra for the copolymers. The copolymerized compositional ratio determined from each of the peak area ratios (described in each of the drawings) is a value close to the starting compositional ratio 1:1.

A titration curve by neutralization was determined in the same manner as in Example 22 and a neutralization equivalent amount determined from the values showing the maximum near pH≈4 in the differentiation curve thereof were 2.6, and 1.3 meq/g for ZP970 and ZP958, and 2.1 and 1.3 meq/g for ZP004 and ZP005. For the differentiation curve a maximum was observed also near pH≈8. The second neutralization equivalent amounts determined from the values were 4.7 and 3.5 meq/g for ZP970 and ZP958 and 4.0 and 3.5 meq/g for ZP004 and ZP005. It is considered that the neutralization equivalent amount determined near pH≈4 is due to the sulfonic acid, and the neutralization equivalent amount determined near pH≈8 is due to the total for the acid amount of the hydroxyl group or the carboxylic group as a weaker acid and the amount of the sulfonic acid. Accordingly, the amount of sulfonic acid in ZP970, ZP958, ZP004, and ZP005 to the starting composition is 1.1 times, 0.6 times, 0.9 times, and 0.6 times, and the total amount of acid was 1.0 time and 0.85 times, 0.85 times, 0.85 times to the starting composition.

The results described above show that zirconium sulfophenyl phosphonate copolymers not having fluorine atom bonded to the metal atom and having copolymerized composition reflecting the starting composition can be synthesized also in a case where the substituent of the second ingredient phosphonic acid is R=OH or R=$C_2H_4CO_2H$ which is highly polar and hydrophilic by carrying out the reaction in an aqueous solution of a concentrated sulfuric acid.

Example 25

[Synthesis of Zirconium Sulfophenyl Phosphonate Copolymer Having Octyl Group: Copolymer Having $C_8H_{17}$ which is Hydrophobic and Large in Molecule Size]
[1. Synthesis of Sample]

Synthesis of Zirconium Sulfophenyl Phosphonate copolymer (x=0.50) having an octyl group as the substituent other than the methyl group was carried out by the method of using the stock solution of sulfophenyl phosphonic acid using octyl phosphonic acid as the second ingredient phosphonic acid.

The octyl phosphonic acid was synthesized with reference to the method of a literature (G. M. Kosolapoff, "Organic Reactions". Vol. 6, p. 286, John Wiley (1951)).

66.5 g (0.4 mol) of triethyl phosphite and 77.3 g (0.4 mol) of 1-bromooctane were charged in a 300 mL round-bottom flask having a cooling tube, and reacted by stirring and heating at 100° C. for 8 hours under a nitrogen gas stream. After allowing them to cool, and re-assembling the apparatus for distillation, temperature was elevated and heating was conducted moderately to 120° C. under a reduced pressure of 10 Torr ($1.33 \times 10^3$ Pa) and unreacted starting material and reaction by-products are removed to obtain 83.7 g (84%) of colorless transparent diethyl octyl phosphonate. 5.0 g of diethyl octyl phosphonate and 22 mL of 48% bromic acid were charged in a 100 mL of round-bottom flask having a Dean-Stark trap and a cooling tube, they were gradually heated to 160° C. and stirred at that temperature for 2.5 hours. Since colorless transparent plate crystals were precipitated when the reaction mixture was cooled, they were filtered and dried to obtain 2.7 g (70%) of products.

By using a stock solution of sulfophenyl phosphonic acid (SPPA-1600) and octyl phosphonic acid, zirconium sulfophenyl phosphonate copolymer (x=0.50: ZP977) having an octyl group was synthesized in accordance with Example 2(2) under the condition to provide a starting composition of $ZrOCl_2 \cdot 8H_2O$ at Zr:P=1:2.

[2. Evaluation for Sample]

Figure 52:
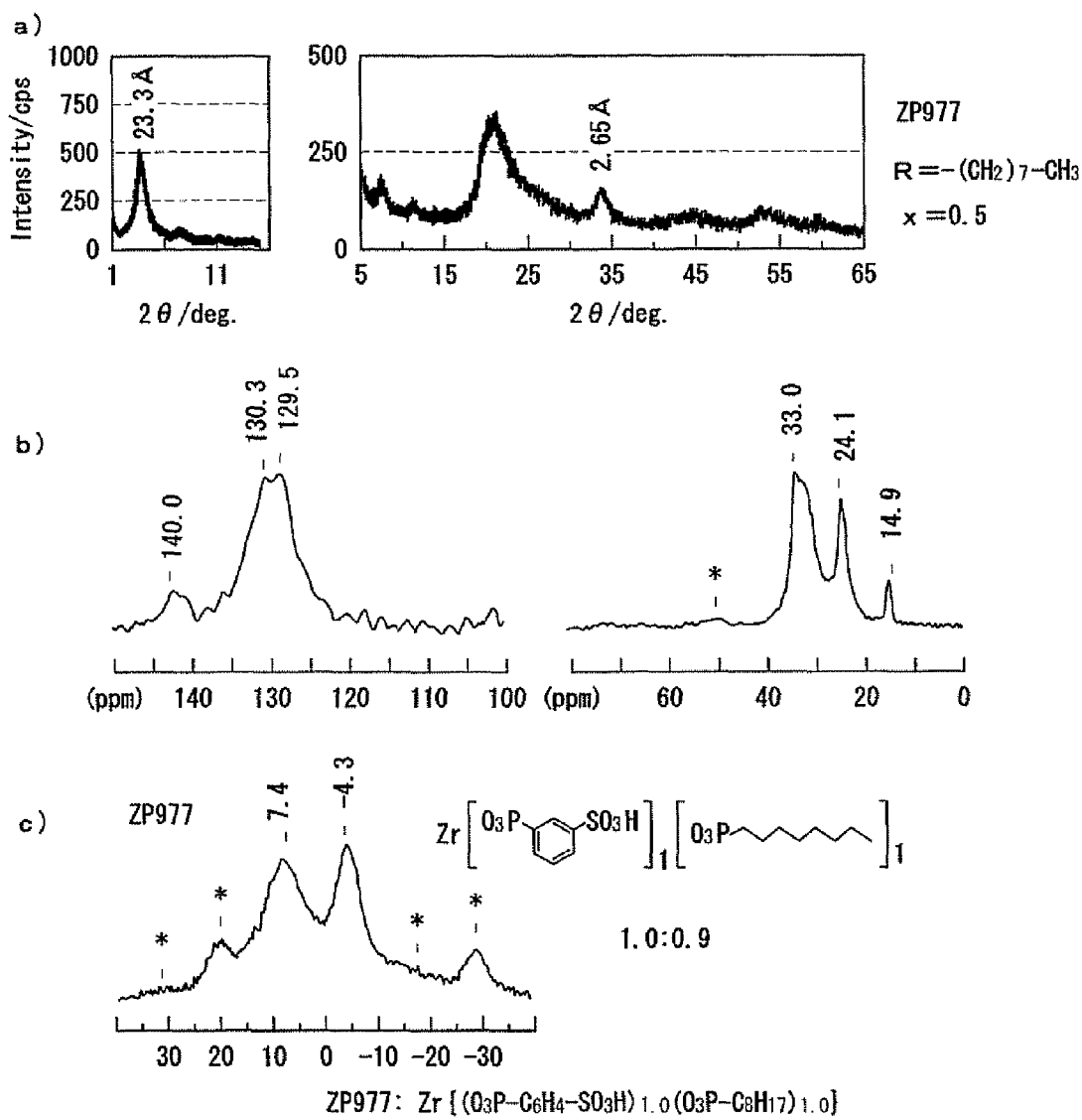
FIG. 52 shows XRD pattern in (A), $^{13}$CMAS-NMR spectra in (B) and $^{31}$PMAS-NMR spectra (*=spinning side band) in (C) of zirconium sulfophenyl phosphonate copolymer having an octyl group synthesized by a stock solution; (ZP977: Zr{$(O_3P-C_6H_4-SO_3H)$ $1.0(O_3P-C_8H_{19})_{1.0}$)}.

A titration curve was determined by neutralization for the products in the same manner as in Example 22, and a neutralization equivalent amount of 1.2 meq/g was determined from the value showing a maximum near pH≈4 at the differentiation curve. The value corresponds to 0.6 times of amount of sulfonic acid relative to the starting composition. The result of the XRD pattern, $^{13}C$ MAS-NMR spectra, and $^{31}P$ MAS-NMR spectra shown in FIG. 52 suggest that zirconium sulfophenyl-/octyl-phosphonate copolymers not having fluorine atom bonded to the metal atom and having a polymerized composition reflecting the starting composition can be synthesized by the method of using the stock solution of sulfophenylene phosphonic acid even when octyl phosphonic acid having an octyl group of high hydrophobic property and large molecular size is used as the second ingredient.

Example 26

[Evaluation for Proton Conductivity of Composite Disk Including Zirconium Sulfophenyl Phosphonate Copolymers Having Various Substituents and Polytetrafluoroethylene (PTFE)]

[1. Synthesis of Sample]

As the zirconium sulfophenyl phosphonate copolymers introduced with various substituents, the copolymer ZP891 having the methyl group, the copolymer ZP004 having the hydroxyl group, the copolymer ZP005 having the carboxyethyl group, and the copolymer ZP977 having the octyl group synthesized at a 1:1 starting composition reported in the previous examples were used. Further, a copolymer ZP1423 having a hydrogen group was newly synthesized by carrying out the reaction with the inorganic phosphonic acid ($H_3PO_3$) by the method of using the stock solution of sulfophenyl phosphonic acid at a starting composition of 0.7:1.3 (molar ratio of sulfophenyl group: x=0.35) and used for the evaluation. Presence of hydrogen groups in the copolymer was confirmed by IR absorption at 2469 cm$^{-1}$ based on $v_{P-H}$ and by $^{31}P$ MAS-NMR peaks at −16 ppm attributable to P—H.

[2. Test Method]

About 0.2 g of each zirconium sulfophenyl phosphonate copolymer was charged in a 20 mL sample bottle and, after weighing precisely, 5.6 wt % of an aqueous dispersion of polytetrafluoroethylene (PTFE) was added to prepare a liquid dispersion at copolymer:PTFT=80:20 (wt/wt). After thoroughly stirring the liquid dispersion, it was stood still in a drying furnace kept at 130° C. to evaporate water content. By pulverizing the obtained powder in agate, a paste-like solid mixture was obtained. The paste-like solid mixture was pulverized by an electric mill into a small piece, and a disk of 10 mm diameter and about 0.4 mm thickness was prepared by press molding. A circular Pt-electrode of 6 mm diameter was coated by a sputtering method to the center on both surfaces of the disk, and the conductivity was measured by an AC impedance method while changing the relative humidity from about 20% to about 90% at about 65° C.

[3. Result]

Figure 53:
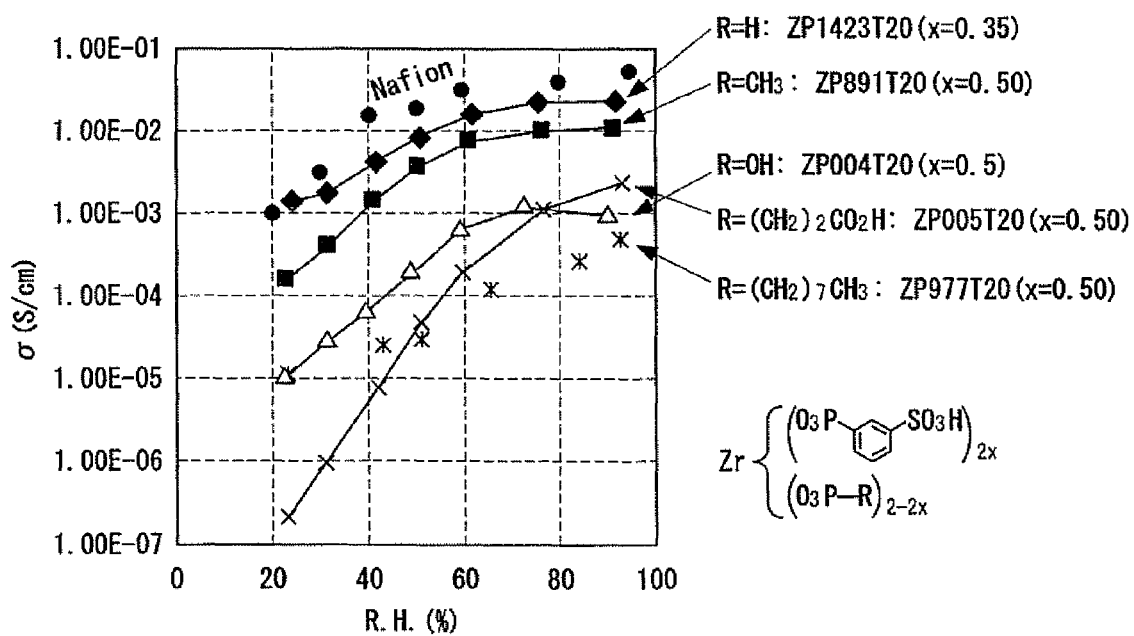
FIG. 53 is a graph showing relative humidity dependence of the proton conductivity (65° C.) of composite products of zirconium sulfophenyl phosphonates copolymers having various substituents and PTFE (20 wt %)

It was found that the conductivity of the composite disk measured upon changing the relative humidity exhibited different behaviors depending on the types of the substituent of the zirconium sulfophenyl phosphate copolymers (FIG. 53). The result shows that the zirconium sulfophenyl phosphonate copolymer can operate as an electrolyte and also suggests that the conductivity behavior can be controlled by changing the type of the substituent of the second ingredient and copolymerized composition thereof with sulfophenyl group.

In a case of utilizing as electrolyte material, the copolymer of zirconium sulfophenyl phosphonate having various substituents, not having fluorine atom bonded to the metal atom, and having a copolymerized composition reflecting the starting composition, it has a merit with no possibility of by-producing noxious fluoro compounds such as dioxin in the process of discarding the material. In this example, while the polytetrafluoroethylene (PTFE) was used and composited with the electrolyte material for film formation, since there is no technical problem of substituting PTFE with other hydrocarbon type organic polymers, the electrolyte composites obtained as described above also has no possibility of by-producing noxious fluorine compounds in the process of discarding them.

Example 27

[Synthesis of Zirconium Sulfodiphenyl Ether Phosphonate Copolymer Having Hydrogen Group: Copolymer Having Different Type of Sulfonated Aromatic Group]

[1. Synthesis of Sample]

Two types of stock solutions of sulfodiphenyl ether (mono) phosphonic acid of different sulfonation degree were prepared by synthesizing diphenyl ether (mono) phosphonic acid as the phosphonic acid having other aromatic group than the phenyl group and using two types of sulfonating agents (fuming sulfunic acid or concentrated sulfuric acid). Zirconium sulfodiphenyl ether phosphonate copolymers (starting composition: x=0.33) having a hydrogen group were synthesized respectively by using an inorganic phosphonic acid ($H_3PO_4$) for the second ingredient phosphonic acid together with the stock solutions described above.

Figure 54:
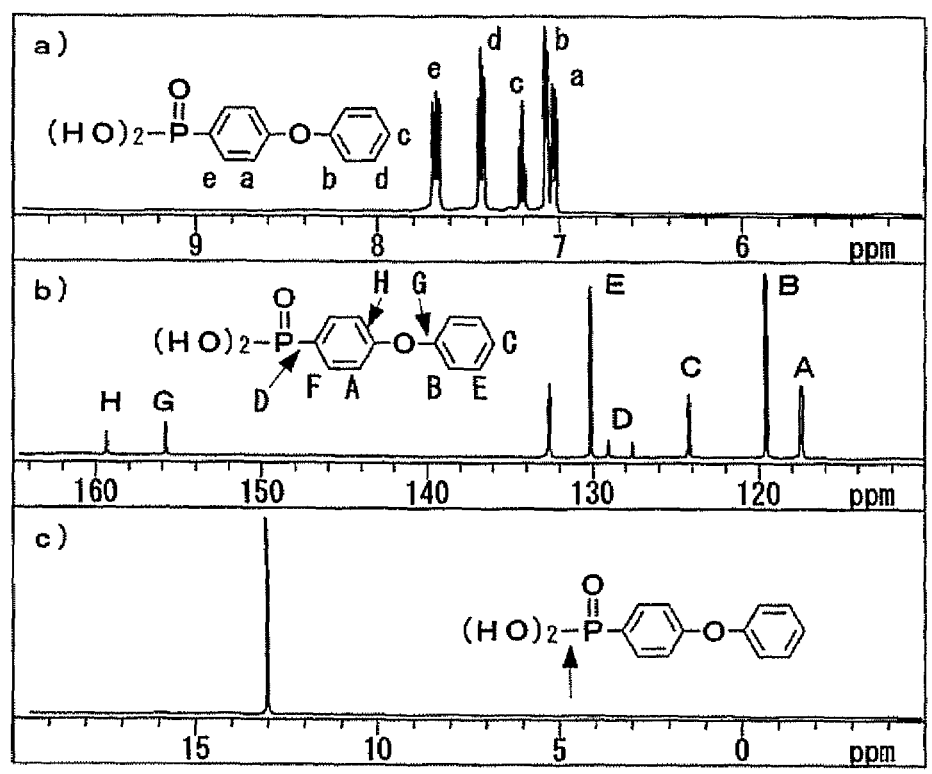
FIG. 54 is various solution NMR spectra of 4-diphenyl phosphonic acid ether ($^1$H NMR in (A), $^{13}$C NMR in (B), $^{31}$P NMR in (C))

The diphenyl ether phosphonic acid was synthesized with reference to the method of a literature (A. Clearfield, et al., J. Am. Chem. Soc. 2003, 125, 103754). 9.96 g (0.04 mol) of 4-bromodiphenyl ether and 50 mL of 1,3-diisopropyl benzene were charged in a 200 mL three-necked flask having a cooling tube and heated and stirred at 180° C. under a nitrogen gas stream, 0.50 g of nickel bromide was charged therein and then 10 mL of triethyl phosphite was dropped and mixed for 6 hours and heating and stirring were continued at that temperature for 18 hours. After charging 0.25 g of nickel bromide again, 5 mL of triethyl phosphite was dropped and mixed for 3 hours and heating and stirring were continued at 180° C. for 21 hours to conduct reaction. After allowing to cool, the reaction mixture was passed through celite on a funnel to remove a black powder catalyst, and the filtrate was distilled at a reduced pressure under heating to remove excess triethyl phosphite and obtain diethyl diphenyl ether-4-phosphonate ester. The ester was heated and stirred with 10.0 g of 48% hydrobromic acid for 10 hours at 108° C. in a 200 mL flask having a cooling tube to conduct hydrolysis. By recrystallization from acetone and n-hexane, 7.1 g (71%) of diphenyl ether-4-phosphonic acid product of white powder was obtained. The result of various solution NMR measurements for the products suggests formation of the aimed compound as shown in FIG. 54.

The zirconium phosphonate copolymer was synthesized in the case of using fuming sulfuric acid as the sulfonating agent according to the method of using the stock solution of sulfophenyl phosphonic acid described in Example 22(2). Since the synthesized amount in a case of 4-phosphonic acid diphenyl ether is small, a method of conducting sulfonation in situ on every time was adopted. 0.65 g (2.60 mmol) of 4-phosphonic acid diphenyl ether was charged in a 100 mL round-bottom flask having a cooling tube, 5.0 g of a 25% fuming sulfuric acid and 2.55 g of concentrated sulfuric acid were added and reacted by stirring at 100° C. under a nitrogen gas stream for one day. After cooling the reaction mixture by immersing the round-bottom flask in an ice bath, 9.18 g of distilled water was added to prepare an aqueous solution of a 12N sulfuric acid of sulfonated diphenyl ether-4-phosphonic acid (corresponding to the stock solution). 8 mL of dimethyl sulfoxide (DMSO) and 0.85 g (5.19 mmol) of an aqueous 50 wt % solution of phosphonic acid were added to the solution and violently stirred under heating to 100° C., into which a mixed solution of 2.37 g (3.9 mmol) of zirconium tetraacetate in acetic acid solution (Zr: 15 to 16%) and 0.5 g of water was dropped and mixed for about 10 min. They were stirred and reacted at that temperature for 24 hours. The reaction mixture was poured into a beaker containing 200 mL of water to obtain a clouded liquid dispersion. After recovering solids by a centrifugator, a heating and stirring treatment in about 6N hydrochloric acid and water was conducted, and ZP1685 product (1.3 g) was obtained by freeze drying.

On the other hand, for the synthesis of the zirconium phosphonate copolymer in a case of using a concentrated sulfuric acid as the sulfonating agent, the reaction was conducted in the same manner using only 9.08 g of a concentrated sulfuric acid instead of 5.0 g of the 25% fuming sulfuric acid and 2.55 g of the concentrated sulfuric acid in the synthesis described above. ZP1687 product (1.7 g) was obtained by freeze drying.

[2. Evaluation for Sample]

Figure 55:
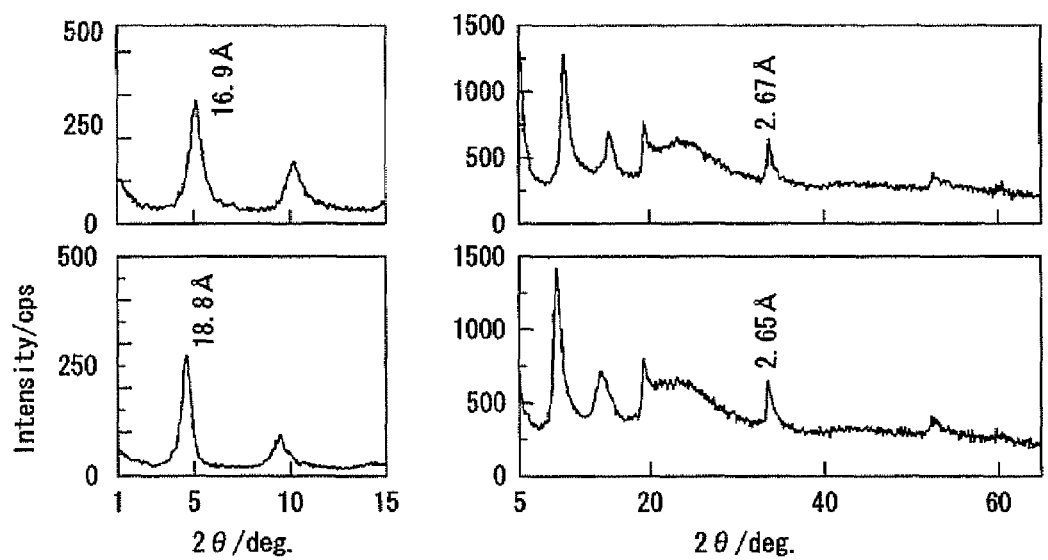
FIG. 55 is XRD patterns of zirconium diphenyl ether phosphonate copolymers having hydrogen groups (ZP1685 in (A), ZP1687 in (B))
Figure 56:
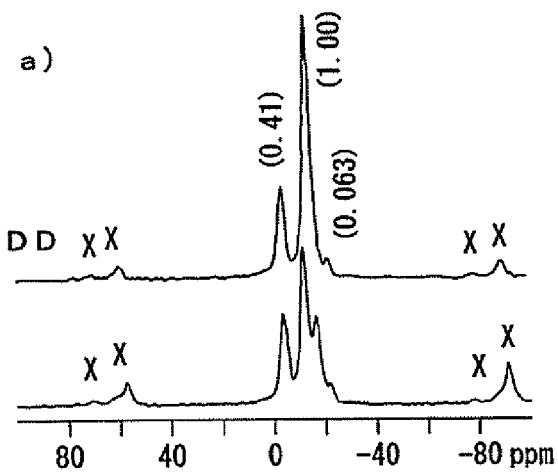
FIG. 56 is $^{31}$P MAS-NMR spectra of zirconium diphenyl ether phosphonate copolymers having hydrogen groups (DD=decoupling, numeral value=peak area ratio), and structural formulas (ZP1685 in (A), ZP1687 in (B)) (X=spinning side band)
Figure 56:
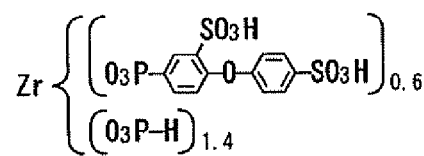
Figure 56:
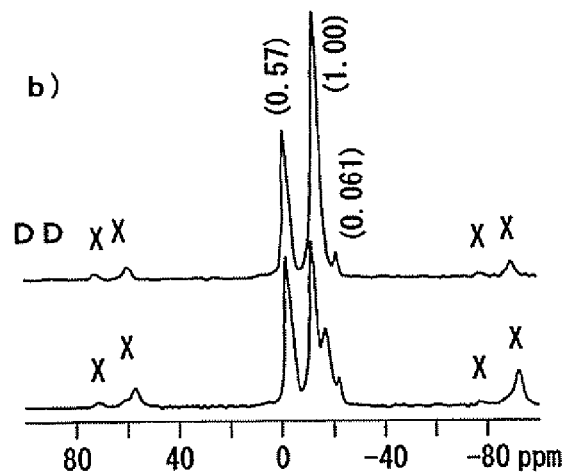
Figure 56:
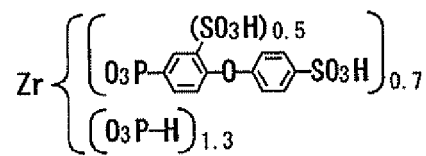
Figure 57:
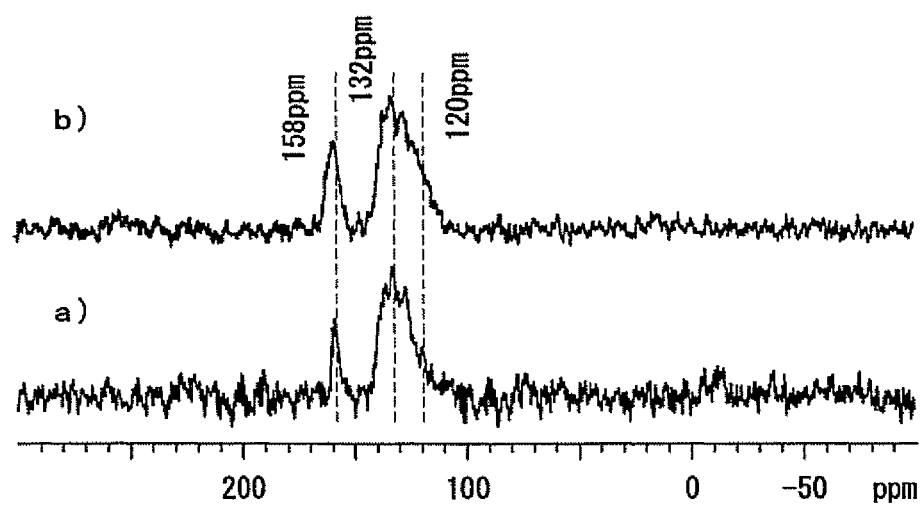
FIG. 57 is $^{13}$C MAS-NMR spectra of zirconium diphenyl ether phosphonate copolymers having a hydrogen groups (ZP1685 in (A), ZP1687 in (B))

For the products, a titration curve was determined by neutralization in the same manner as in Example 22 and a neutralization equivalent amount each of 2.6 meq/g and 2.4 meq/g was determined from the value showing a maximum near pH 4 at the differentiation curve thereof. For the product, XRD patters are shown in FIG. 55, $^{31}$P MAS-NMR spectra are shown in FIG. 56, and $^{13}$C MAS-NMR spectra are shown in FIG. 57.

The XRD patterns suggest the formation of uniform zirconium phosphonate copolymers having the α-type lamellar (layered) structure. The copolymerized compositions determined from the peak area ratio in the $^{31}$P MAS-NMR spectra were 0.6:1.4 and 0.7:1.3 both of which are close to the starting composition ((x=0.33→) 0.66:1.33). When the sulfonation degree for the diphenyl ether groups is calculated from the neutralization equivalent amount for the structural formulas using the copolymerized compositions, it was determined as 2.0 for ZP1685 and 1.5 for ZP1687. Since it is estimated that sulfonation occurs at first at 4'-position and then at 3-position relative to the O₃P— group on the diphenyl ether group, each of the estimated structural formulas is described in FIG. 56. It is estimated that the difference of the sulfonation degree on the 3-position of both products is reflected on the difference of the peak intensity at 120 ppm in the $^{13}$C MAS-NMR spectra (FIG. 57).

Also for other aromatic phosphonic acids than the phenyl phosphonic acid, copolymerization with the second ingredient phosphonic acid can be carried out by the method of using the stock solution of the sulfonation product, and it suggests that two types of sulfonated zirconium diphenyl-ether/hydroxyl phosphonate copolymers not having fluorine atom bonded to the metal atom and having a copolymerized composition reflecting the starting composition and of different sulfonation degree can be synthesized. The hydrogen group is a substituent instable, like the phenyl group, to the post sulfonation reaction.

Example 28

Synthesis of Zirconium Sulfophenyl-/Sulfodifluoromethyl-Phosphonate Copolymer: Copolymer Having Two Types of Sulfonic Groups

[1. Synthesis of Sample]
[1.1 Synthesis of Sulfodifluoro Methyl Phosphonic Acid]

Zirconium phosphonate copolymers having a sulfophenyl group and a sulfodifluoromethyl group (starting composition: x=0.50) was synthesized by a method of using a stock solution of sulfophenyl phosphonic acid.

Figure 58:
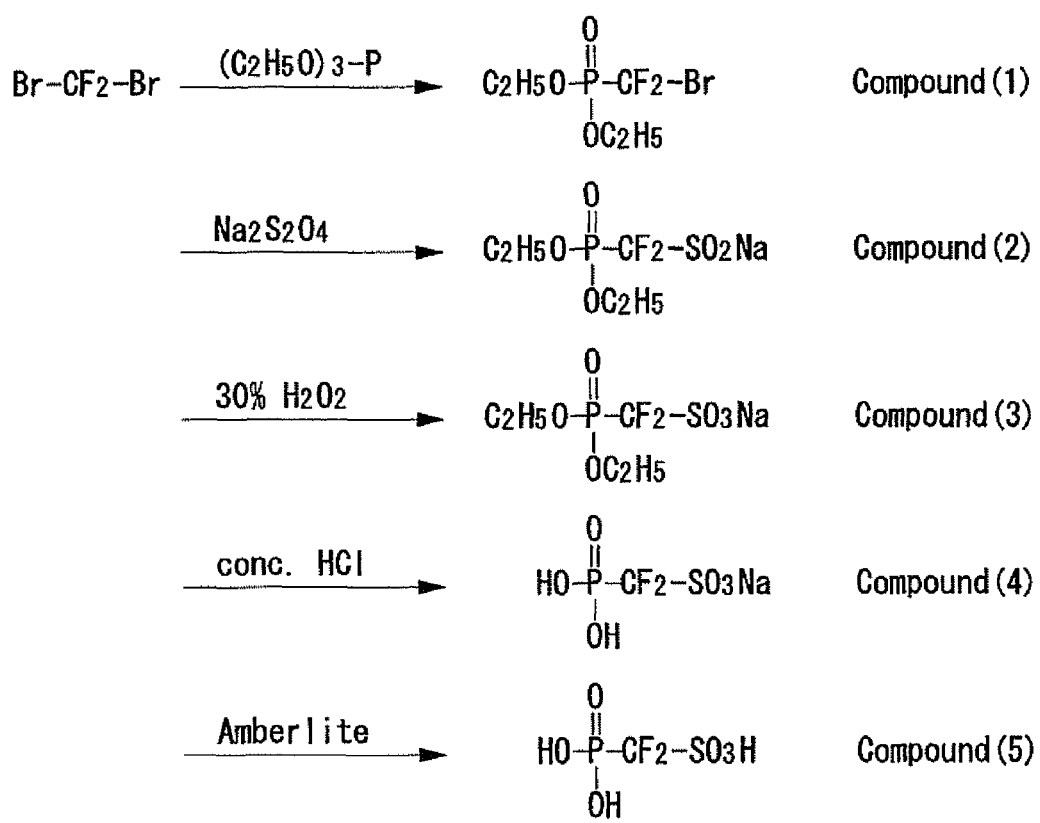
FIG. 58 shows synthetic reaction schemes of sulfodifluoromethyl phosphonic acids.

Sulfodifluoromethyl phosphonic acid was synthesized (FIG. 58) with reference to the method of a literature (J. Am. Chem. Soc., 1989, 111, 1773).

(1) Synthesis of Compound (1):

A mixture of 88.5 g (0.532 mol) of triethyl phosphite and 120 g (0.572 mol) of dibromodifluoro methane was charged in a 0.5 L autoclave and reacted at a room temperature for 23 hours. The reaction mixture was concentrated under a reduced pressure and the obtained residue was distilled under a reduced pressure to obtain 124.2 g (yield 87.4%) of a colorless oily compound (1). bp 75° C./1 mmHg.

(2) Synthesis of Compound (2):

63 g (0.749 mol) of sodium hydrogen carbonate, 130 g (0.749 mol) of sodium hydrogen sulfite ($Na_2S_2O_4$), and 200 mL of distilled water were weighed to a reaction vessel and stirred violently at a room temperature for 5 min. After 23 hours, the reaction mixture was concentrated at a reduced pressure, a mixture of the compound (2) and an inorganic salt was suspended in acetone and filtered to remove the inorganic salt. The filtrate was concentrated under a reduced pressure and precipitated solids were again suspended in ethyl acetate ester and filtered to remove the inorganic salt. The filtrate was concentrated at a reduced pressure to obtain 141 g (>100%) of the compound (2).

(3) Synthesis of Compound (3):

141 g (0.515 mol) of the compound (2) was weighed to a reaction vessel and dissolved in 350 mL of distilled water. It was cooled to 0° C., 120 mL (1.16 mol) of a 30% aqueous hydrogen peroxide was added and gradually heated to a room temperature and stirred for 5 hours. The reaction mixture was washed with toluene (300 mL×2). The aqueous layer was cooled to 0° C. and the mixture of the compound (3) and an inorganic salt was suspended in acetone and filtered to remove the inorganic salt. The procedures were repeated for three times to obtain 60 g (55% (two steps)) of the compound (3).

(4) Synthesis of Compound (4):

60 g (0.21 mol) of the compound (3) was weighed to a reaction vessel and 100 mL of a concentrated hydrochloric acid was added. It was heated to 120° C. and stirred for 17 hours. The reaction mixture was allowed to cool and concentrated at a reduced pressure to obtain 58 g (66% (three steps)) of the compound (4).

Figure 59:
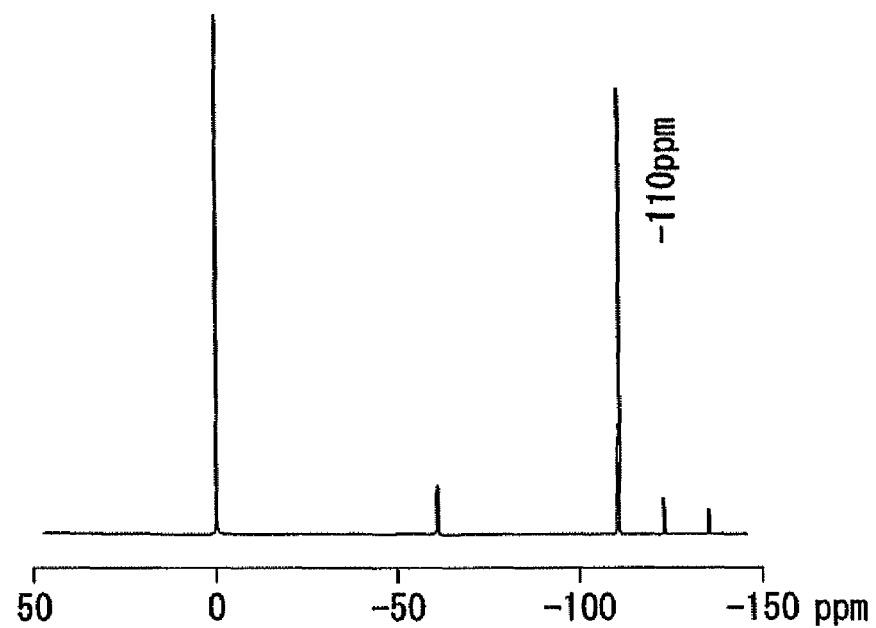
FIG. 59 is a $^{19}$F NMR spectrum of sulfodifluoromethylene phosphonic acid (5) (0 ppm=external standard)

(5) Synthesis of Compound (5):

The compound (4) (58 g) was treated with 600 g of an ion exchange resin to obtain 38 g (48% (4 steps)) of the compound (5). Solids of the obtained product were 90.5 wt %. The structure of the product was confirmed by $^{19}$F NMR (FIG. 59) in that a peak attributable to the starting material disappeared and a 110 ppm peak attributable to the product appeared.

[1.2 Synthesis of Copolymer]

According to the method of using the stock solution of the sulfophenyl phosphoric acid as explained in Example 22(2), a copolymer was synthesized by using the sulfodifluoromethyl phosphonic acid as it was. The (32 wt %) solution of the sulfophenyl phosphonic acid in the 12N sulfuric acid prepared in Example 22 (2-1) was used as the stock solution (5.52 g, 7.4 mmol), and sulfodifluoromethyl phosphonic acid (1.73 g, 7.4 mmol) and DMSO (10 mL) were added, and reacted with an acetic acid solution of $Zr(O_2CCH_3)_4$ (containing 15 to 16 wt % Zr: 4.50 g, 7.4 mmol) in the 12N sulfuric acid—DMSO at 100° C. for 24 hours. The synthesis procedures were according to the method of Example 22(2-2) and ZP1683 product (3.3 g) was obtained by freeze drying.

[2. Evaluation for Sample]

A titration curve by neutralization was determined for the product in the same manner as in Example 22, and a neutralization equivalent amount of 2.6 meq/g was determined from the value showing a maximum near pH≈4 at the differentiation curve.

Figure 60:
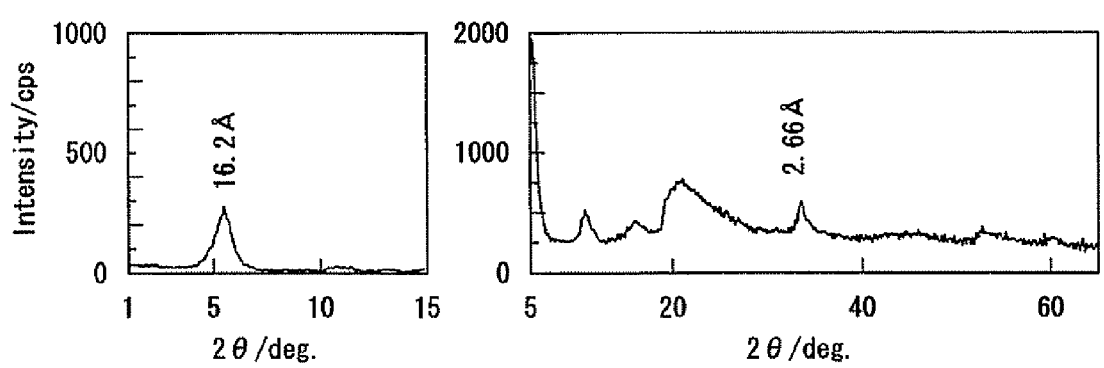
FIG. 60 is an XRD pattern of a zirconium sulfophenyl-/sulfodifluoromethyl-phosphonate copolymer (ZP1683)
Figure 61:
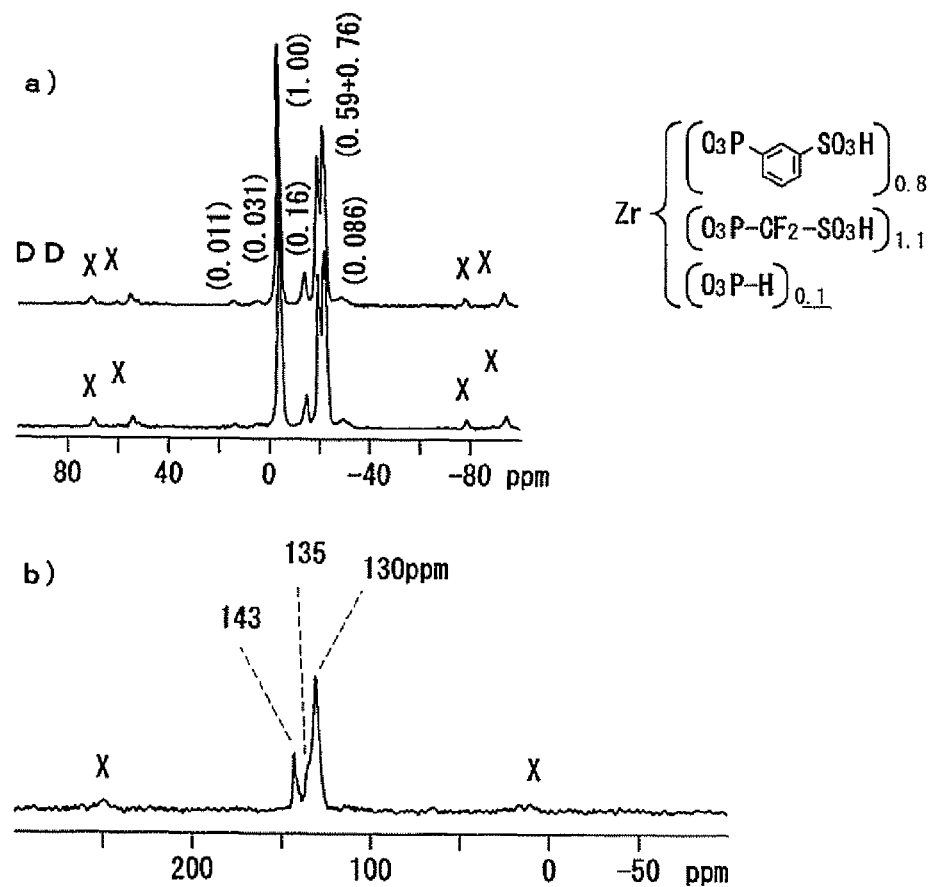
FIG. 61 shows $^{31}$P MAS-NMR spectra (DD=decoupling, numerical value=peak area ratio) in (A) and $^{13}$C MAS-NMR spectra (X=spinning side band) in (B) of a zirconium sulfophenyl-/sulfodifluoromethyl-phosphonate copolymer having hydrogen groups.

For the product, XRD patterns were shown in FIG. 60, and $^{31}$P MAS-NMR spectra and $^{13}$C MAS-NMR spectra are shown in FIG. 61. The XRD patterns suggest the formation of a uniform zirconium phosphonate copolymer having an α-type lamellar (layered) structure. In the $^{31}$P MAS-NMR spectra, an innegligible peak at −16 ppm was observed in addition to large peaks attributable to the sulfophenyl phosphonic acid and the sulfodifluoromethyl phosphonic acid. The copolymerized composition determined from the peak area ratio thereof was 0.8:1.1:0.1. The ratio for the two main ingredients of the copolymerized composition is a value close to the starting composition ((x=0.50→) 1.0:1.0) and it is estimated that a small amount of inorganic phosphonic acid ($H_3PO_3$) contained in the starting sulfodifluoromethyl phosphonic acid intruded to form a three-ingredient copolymer. The structural formula using the copolymerized composition is described in FIG. 61. Since the amount of the sulfonic acid according to the formula is 3.6 meq/g, the acid amount in the neutralization equivalent amount is 70% or more for the theoretical amount thereof.

Copolymerization with the second ingredient sulfonated phosphonic acid can be carried out by the method of using the stock solution of the sulfonation product and this suggests that zirconium sulfophenyl-/sulfodifluoromethyl-phosphonate copolymers having two types of sulfonic groups (not having fluorine atom bonded with the metal atom) and at a copolymerized composition reflecting the starting composition can be synthesized. In a case of using 3-sulfopropyl phosphonic acid or the like instead of the sulfodifluoromethyl phosphonic acid, a zirconium phosphonate copolymer having two types of sulfonic groups not containing fluorine atoms at all can be synthesized.

Example 29

Synthesis of Zirconium Sulfophenyl-/Sulfodifluoromethyl-Phosphonate Copolymer Having Hydrogen Group: 3-Ingredient Copolymer Having Two Types of Sulfonic Group

[1. Synthesis of Sample]

A three ingredient copolymer was synthesized according to the method of using the stock solution of the sulfodifluoromethyl phosphonic acid and the sulfophenyl phosphonic acid described in Example 28 by newly adding inorganic phosphonic acid ($H_3PO_3$). The (32 wt %) solution of the sulfophenyl phosphonic acid in the 12N sulfuric acid prepared in Example 22(2-1) was used as a stock solution (3.36 g, 4.5 mmol), and sulfodifluoromethyl phosphonic acid (1.06 g, 4.5 mmol) and 50 wt % aqueous solution of the inorganic phosphonic acid (1.48 g, 9.0 mmol) were weighed and dissolved with addition of DMSO (5 mL). Further after adding 10 mL of a 12N sulfuric acid, an acetic acid solution of $Zr(O_2CCH_3)_4$ (containing 15 to 16 wt % Zr: 5.47 g, 9.0 mmol) was added and reacted at 100° C. for 24 hours. The synthesis procedures were according to the method of Example 22 (2-2) and the ZP1717 product (3.3 g) was obtained by freeze drying.

[2. Evaluation of Sample]

A titration curve was determined by neutralization for the product in the same manner as in Example 22 and a neutralization equivalent amount of 1.9 meq/g was determined from the value showing a maximum near pH≈4 at the differentiation curve thereof.

Figure 62:
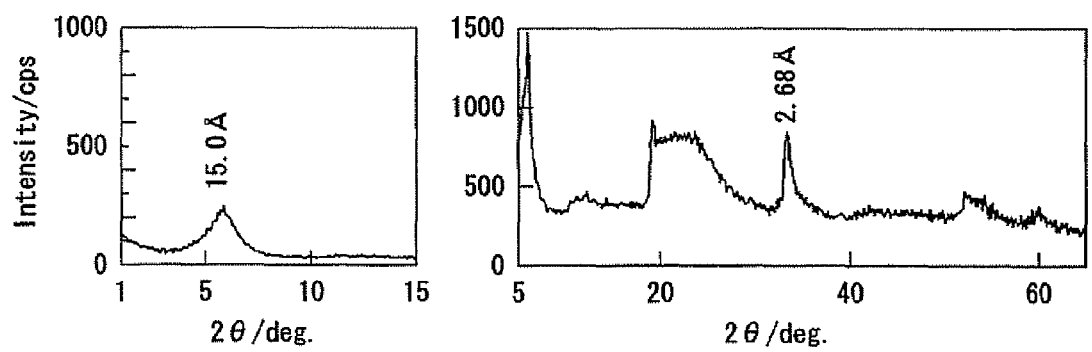
FIG. 62 is an XRD pattern of a zirconium sulfophenyl-/sulfodifluoromethyl-phosphonate copolymer having a hydrogen groups (ZP1717)
Figure 63:
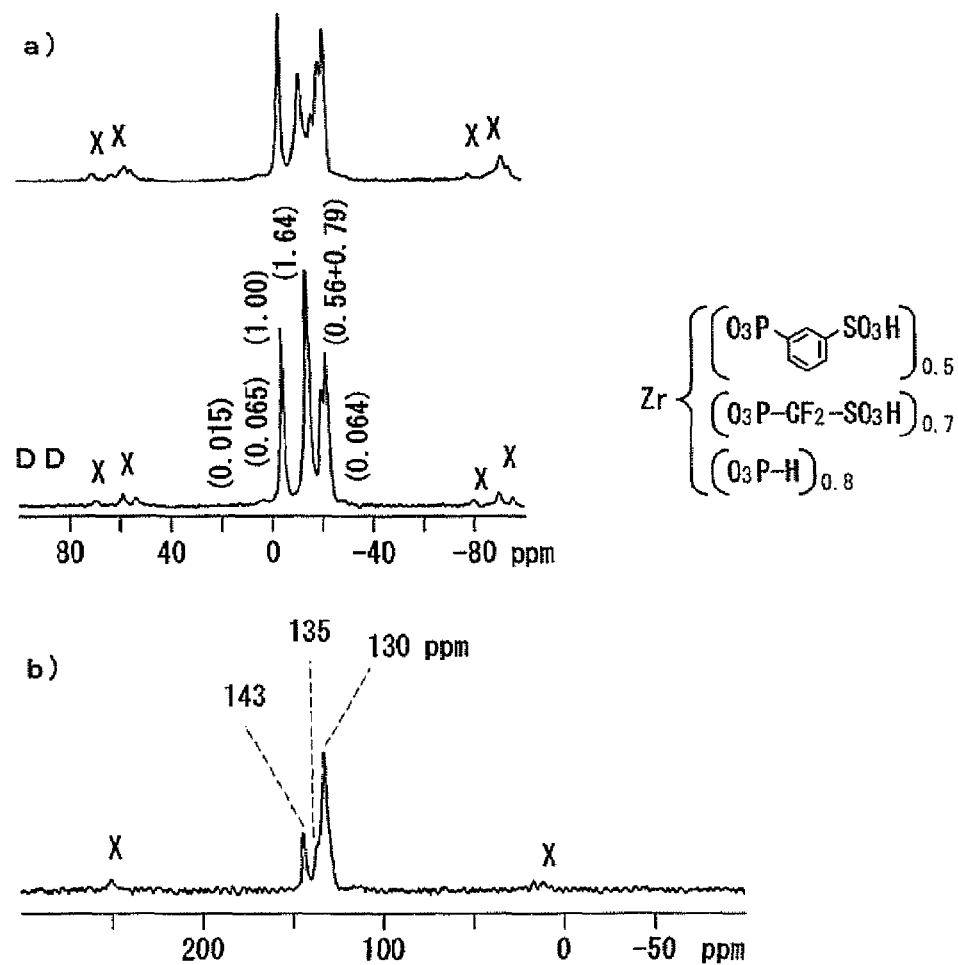
FIG. 63 shows $^{31}$P MAS-NMR spectra (DD=decoupling, numeral value=peak area ratio) in (A) and $^{13}$C MAS-NMR spectra (X=spinning side band) in (B) of a zirconium sulfophenyl-/sulfodifluoromethyl-phosphonate having a hydrogen groups.

For the product, XRD patterns are shown in FIG. 62, $^{31}$P MAS-NMR spectra and $^{13}$C MAS-NMR spectra are shown in FIG. 63. The XRD patterns suggest the formation of a uniform zirconium phosphonate copolymer having the α-type lamellar (layered) structure. The copolymerized composition determined from the peak area ratio of $^{31}$P MAS-NMR spectra was 0.5:0.7:0.8. The copolymerized composition is a value close to the starting composition (0.5:0.5:1.0). The structural formula using the copolymerized composition is described in FIG. 63. Since the amount of sulfonic acid according to the formula is 2.8 meq/g, the amount of acid in the neutralization equivalent amount is 70% or less for the theoretical amount.

Copolymerization with the second ingredient sulfonated phosphonic acid and the third ingredient phosphonic acid can be carried out by the method of using the stock solution of the sulfonation product and this suggests that the zirconium sulfophenyl-/sulfodifluoromethyl-/hydro-phosphonate copolymer having a hydrogen group and two types of sulfonic groups (not having fluorine atom bonded with metal atoms) and at a copolymerized composition reflecting the starting composition can be synthesized. Further, by using 3-sulfopropyl phosphonic acid or the like instead of the sulfodifluoromethyl phosphonic acid, 3-ingredient zirconium phosphonate copolymer having two types of sulfonic groups not containing fluorine atoms at all can be synthesized.

Example 30

Investigation on Synthesis Condition for Titanium Sulfophenyl Phosphonate Having Phenyl Group: Effect of Ti-Source and Solvent Species on Reaction

[1. Synthesis of Sample]

Titanium sulfophenyl phosphonate copolymers having a phenyl group (x=0.50) were synthesized by a method of using a stock solution of sulfophenyl phosphonic acid. Under the synthesis conditions shown in Table 10, effects of Ti-source such as titanyl sulfate, titanium tetrachloride, titanium tetrapropoxide, and titanium sulfate, and the effect of solvents such as 12N sulfuric acid, 9N hydrochloric acid and water were investigated (Table 10).

TABLE 10

| Abbreviation | Ti-source mmol | Solvent mL | Yield % | d(001) cps/Å | d (020) Å |
|---|---|---|---|---|---|
| TiP1217 | $TiOSO_4 \cdot 1.5H_2O$ | $12N\ H_2SO_4$ | 56 | 0.7k/15.6 | 2.56 |
| TiP1221 | $TiCl_4$ | 9N HCl | 88 | 0.5k/15.6 | 2.58 |
| TiP1222 | $Ti(OPr)_4$ | $12N\ H_2SO_4$ | 82 | 0.6k/15.2 | 2.53 |
| TiP1232 | $Ti(SO_4)_2$ | $H_2O$ | 81 | 0.7k/15.3 | 2.54 |
| TiP1234 | $TiOSO_4 \cdot 1.5H_2O$ | $H_2O$ | 81 | 0.7k/15.3 | 2.53 |

Reaction condition: [sPPA] = [PPA] = [Ti-source] = 14 mmol, 100° C. × 24 hr

[2. Evaluation for Sample]

Figure 64:
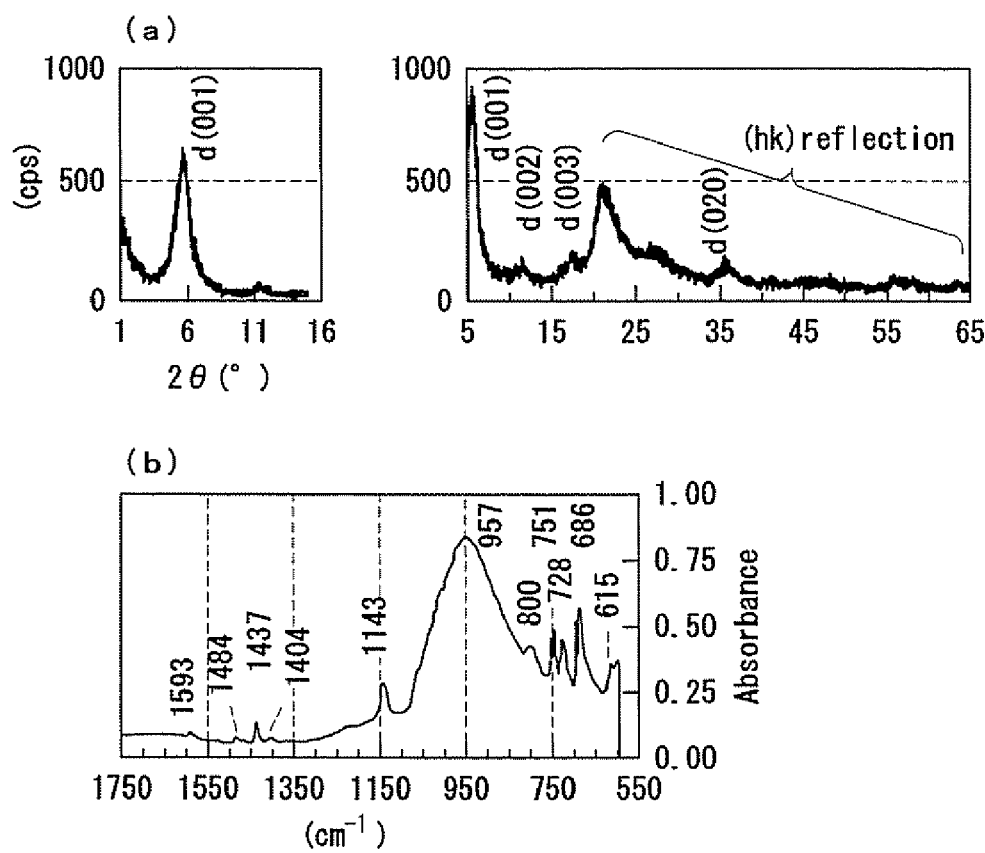
FIG. 64 shows an XRD pattern in (A) and an IR spectrum in (B) of TiP1217.

In each of the XRD patterns for the obtained products (for example, FIG. 64A; Table 10), distinct (001) reflection, prism type (hk) reflection and d(020) peak near 2.55 Å were recognized and this suggests that the product has the α-type lamellar (layered) structure of titanium phosphonate. In the intensity of the d(001) peak observed near 15 Å, since the half-value width is in inverse proportion with the expansion size of the layered structure, it shows high crystallinity in the layered structure of the product. In view of comparison, it can be seen that a layered structure of high crystallinity can be obtained when titanium sulfophenyl phosphonate copolymer having phenyl group is synthesized in $12N\ H_2SO_4$. It was confirmed that the product had both the sulfophenyl group and the phenyl group by the observation of absorption attributable to the sulfophenyl group (800 cm$^{-1}$, 686 cm$^{-1}$, 615 cm$^{-1}$) and absorption attributable to the phenyl group (near 751 cm$^{-1}$, 728 cm$^{-1}$) in IR spectra measurement (FIG. 64B). Accordingly, also in a case where the metal atom is titanium, copolymerization can be carried out with phenyl phosphonic acid by the method of using the stock solution of the sulfophenyl phosphonic acid and it can be seen that a 2-ingredient titanium sulfophenyl-/phenyl-phosphonate copolymer having a sulfonic group (not having fluorine atom bonded with metal atom) can be synthesized.

While the present invention has been described in details with reference to preferred embodiments, the invention is not restricted to such embodiments but various modifications are possible within a range not departing the scope of the invention.

What is claimed is:

1. A crosslinked type layered metal phosphonate compound in which
   (a) the crosslinked type layered metal phosphonate compound has a two dimensional layered structure in which metal oxide octahedrons having a hexacoordinate metal atom as a central atom (M) and phosphonic acid tetrahedrons are connected by sharing oxygen atoms,
   (b) the crosslinked type layered metal phosphonate compound contains at least one organic diphosphonic acid ingredient in which both ends thereof are connected respectively with different hexacoordinate metal atoms in different layered structures by way of at least one P—O-M bond,
   (c) the crosslinked type layered metal phosphonate compound contains at least one monophosphonic acid ingredient that is bonded with a different hexacoordinate metal atom in the layered structure by way of at least one P—O-M bond,
   (d) one of the organic diphosphonic acid ingredient and the monophosphonic acid ingredient has a sulfonic group or a group that can be converted into the sulfonic group and the rest of them has no such group,
   (e) the average molecular cross sectional area for the substituent of the organic diphosphonic acid ingredient and the monophosphonic acid ingredient contained in the crosslinked type layered metal phosphonate compound is equal with or less than the free area of one surface phosphonic acid of the two dimensional layered structure, and
   (f) the crosslinked type layered metal phosphonate compound does not contain a fluorine atom bonded with the central atom (M).

2. The crosslinked type layered metal phosphonate compound according to claim 1, wherein the central atom (M) is a hexacoordinate metal atom capable of taking a tetra atomic valence.

3. The crosslinked type layered metal phosphonate compound according to claim 2, having an α-type layered structure and a composition represented by the following formula (1):

[Chemical formula 1]

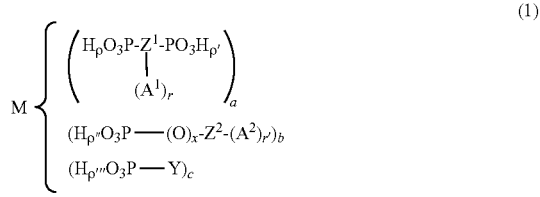

(1)

in which
   M: hexacoordinate metal atom capable of taking a tetra atomic valence,
   —$Z^1$—: (2+r) valent organic group having at least one benzene ring, alkylene chain, or oligo (oxyalkylene) chain,
   -$A^1$: —$(CH_2)_\alpha$—$SO_3H$, —$(CH_2)_\alpha$-Hal, —$(CH_2)_\alpha$—SH, —$(CH_2)_\alpha$—S—R', or —$(CH_2)_\alpha$—$SO_2Cl$ ($0 \leq \alpha \leq 3$, —R'=—$CH_3$, or —$C_2H_5$),
   r: r=0 to {number of benzene rings in $Z^1$} ×2,
   x: x=0, 1,
   —$Z^2$—: (1+r') valent organic group having at least one benzene ring,
   -$A^2$: —$(CH_2)_\beta$—$SO_3H$, —$(CH_2)_\beta$-Hal, —$(CH_2)_\beta$—SH, —$(CH_2)_\beta$—S—R', or —$(CH_2)_\beta$—$SO_2Cl$ ($0 \leq \beta \leq 3$, —R'=—$CH_3$, or —$C_2H_5$),
   r': r'=0 to [number of benzene rings in $Z^2$] ×2,
   —Y: —H, —OH, —$C_\gamma H_{2\gamma+\prime}$($1 \leq \gamma \leq 16$), —$C_\delta H_{2\delta}$—W ($1 \leq \delta \leq 3$), or —$C_\epsilon F_{2\epsilon}$—W($1 \leq \epsilon \leq 3$)(W=Hal, OH, CN, $CO_2H$, $SO_3H$, SH, $SCH_3$, $SC_2H_5$, or $SO_2Cl$),
   a, b, c: $1.0 < 2a+b+c < 3.0$, $0 < a < 1.0$, $0 < b < 2.0$, $0 < c < 2.0$,
   ρ, ρ", ρ''': $0 \leq (ρ, ρ", ρ''') < 2$, and
   ρ': $0 \leq ρ' \leq 2$.

4. The crosslinked type layered metal phosphonate compound according to claim 2, having an α-type layered structure and a composition represented by the following formula (2):

[Chemical formula 2]

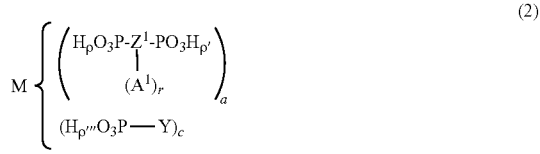

(2)

in which
- M: hexacoordinate metal atom capable of taking a tetra atomic valence,
- $-Z^1-$: (2+r) valent organic group having at least one benzene ring, alkylene chain, or oligo (oxyalkylene) chain,
- $-A^1$: $-(CH_2)_\alpha-SO_3H$, $-(CH_2)_\alpha$-Hal, $-(CH_2)_\alpha-SH$, $-(CH_2)_\alpha-S-R'$, or $-(CH_2)_\alpha-SO_2Cl$ ($0\leq\alpha\leq3$, $-R'=-CH_3$, or $-C_2H_5$),
- r: r=0 to [number of benzene rings in $Z^1$] ×2,
- $-Y$: $-H$, $-OH$, $-C_\gamma H_{2\gamma+1}$ ($1\leq\gamma\leq16$), $-C_\delta H_{2\delta}-W$ ($1\leq\delta\leq3$), or $-C_\epsilon F_{2\epsilon}-W$ ($1\leq\epsilon\leq3$)(W=Hal, OH, CN, $CO_2H$, $SO_3H$, SH, $SCH_3$, $SC_2H_5$, or $SO_2Cl$),
- a, c: 1.0<2a+c<3.0, 0<a<1.0, 0<c<2.0,
- $\rho$, $\rho'''$: $0\leq(\rho, \rho''')<2$, and
- $\rho'$: $0\leq\rho'\leq2$.

5. The crosslinked type layered metal phosphonate compound according to claim 2, having an α-type layered structure and a composition represented by the following formula (3):

[Chemical formula 3]

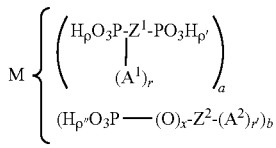

(3)

in which
- M: hexacoordinate metal atom capable of taking a tetra atomic valence,
- $-Z^1-$: (2+r) valent organic group having at least one benzene ring, alkylene chain, or oligo (oxyalkylene) chain,
- $-A^1$: $-(CH_2)_\alpha-SO_3H$, $-(CH_2)_\alpha$-Hal, $-(CH_2)_\alpha-SH$, $-(CH_2)_\alpha-S-R'$, or $-(CH_2)_\alpha-SO_2Cl$ ($0\leq\alpha\leq3$, $-R'=-CH_3$, or $-C_2H_5$),
- r: r=0 to {number of benzene rings in $Z^1$} ×2,
- x: x=0, 1,
- $-Z^2-$: (1+r') valent organic group having at least one benzene ring,
- $-A^2$: $-(CH_2)_\beta-SO_3H$, $-(CH_2)_\beta$-Hal, $-(CH2)_\beta-SH$, $-(CH_2)_\beta-S-R'$, or $-(CH_2)_\beta-SO_2Cl$ ($0\leq\beta\leq3$, $-R'=-CH_3$, or $-C_2H_5$),
- r': r'=0 to {number of benzene rings in $Z^2$} ×2,
- a, b: 1.0<2a+b<3.0, 0<a<1.0, 0<b<2.0,
- $\rho$, $\rho''$: $0\leq(\rho, \rho'')<2$, and
- $\rho'$: $0\leq\rho'\leq2$.

6. A crosslinked type layered metal phosphonate compound in which
   (a) the crosslinked type layered metal phosphonate compound has a two dimensional layered structure in which metal oxide octahedrons having a hexacoordinate metal atom as a central atom (M) and phosphonic acid tetrahedrons are connected by sharing oxygen atoms,
   (b) the crosslinked type layered metal phosphonate compound contains at least one organic diphosphonic acid ingredient in which both ends thereof are connected with different hexacoordinate metal atoms in different layered structures by way of at least one P—O—M bond,
   (c) the crosslinked type layered metal phosphonate compound contains at least one monophosphonic acid ingredient that is bonded with different hexacoordinate metal atoms in the layered structure by way of at least one P—O—M bond,
   (d) at least two or more of the organic diphosphonic acid ingredients and the monophosphonic acid ingredients have a sulfonic group or a group that can be converted into the sulfonic group and the rest of them has no such group,
   (e) the average molecular cross sectional area for the substituent of the organic diphosphonic acid ingredient and the monophosphonic acid ingredient contained in the crosslinked type layered metal phosphonate compound is equal with or less than the free area of one surface phosphonic acid of the two dimensional layered structure, and
   (f) the crosslinked type layered metal phosphonate compound does not contain a fluorine atom bonded with the central atom (M).

7. The crosslinked type layered metal phosphonate compound according to claim 6, wherein the central atom (M) is a hexacoordinate metal atom capable of taking a tetra atomic valence.

8. A process for producing the crosslinked type layered metal phosphonate compound including a reaction step of reacting at least one organic diphosphonic acid or a derivative thereof and at least one monophosphonic acid or a derivative thereof having the following conditions, and a metal source capable of forming an ion of a hexacoordinate metal atom as a central atom (M) of a metal oxide octahedron in the reaction under the presence of a sulfuric acid catalyst:
   (a) the blending ratio of the organic diphosphonic acid or the derivative thereof, the monophosphonic acid or the derivative thereof, and the metal source is such that the molar ratio (M/P ratio) of the central atom (M) to the amount of P contained in the phosphonic group or the derivative thereof is: ⅓<M/P <1.0, and
   (b) the blending ratio of the organic diphosphonic acid or the derivative thereof and the monophosphonic acid or the derivative thereof is such that the average molecular cross sectional area for the substituent of the organic diphosphonic acid ingredient and the monophosphonic acid ingredient constituting the crosslinked type layered metal phosphonate compound is equal with or less than the free area of one surface phosphonic group of the two dimensional layered structure.

9. The process for producing the crosslinked type layered metal phosphonate compound according to claim 8, wherein the organic diphosphonic acid or the derivative thereof and the monophosphonic acid or the derivatives thereof further have the following conditions:
   (c) at least one of the organic diphosphonic acids or the derivative thereof and the monophosphonic acids or the derivative thereof has a sulfonic group or a group that can be converted into the sulfonic group.

10. The process for producing the crosslinked type layered metal phosphonate compound according to claim 8, wherein:
the reaction step is a reaction step of adding and reacting:
   (1) the metal source and
   (2) the remaining ingredient of the organic diphosphonic acids or the derivative thereof and the monophosphonic acids or the derivative thereof, to a stock solution in which at least one of organic diphosphonic acids or the derivative thereof and the monophosphonic acids or the derivative thereof, which has the sulfonic group or the group that can be converted into the sulfonic group is dissolved or dispersed in an aqueous solution of sulfuric acid or a mixed solution of the aqueous solution of sulfuric acid and an organic solvent.

11. The process for producing the crosslinked type layered metal phosphonate compound according to claim 8, wherein the reaction step includes:
- a first reaction step of reacting the organic diphosphonic acid or the derivative thereof and the metal source, and
- a second reaction step of adding the monophosphonic acid or the derivative thereof to the reaction solution obtained by the first reaction step and reacting them under the presence of the sulfuric acid catalyst.

12. A stock solution in which one or more members selected from organic diphosphonic acids or derivatives thereof having a sulfonic group or a group that can be converted into the sulfonic group and monophosphonic acids or derivatives thereof having a sulfonic group or a group that can be converted into the sulfonic group is dissolved or dispersed in an aqueous solution of sulfuric acid or a mixed solution of the aqueous solution of sulfuric acid and an organic solvent.

* * * * *